US008558056B2

(12) United States Patent
Wan et al.

(10) Patent No.: US 8,558,056 B2
(45) Date of Patent: Oct. 15, 2013

(54) LYSM RECEPTOR-LIKE KINASES TO IMPROVE PLANT DEFENSE RESPONSE AGAINST FUNGAL PATHOGENS

(75) Inventors: Jinrong Wan, Columbia, MO (US); Gary Stacey, Columbia, MO (US); Minviluz Stacey, Columbia, MO (US); Xuecheng Zhang, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 13/347,199

(22) Filed: Jan. 10, 2012

(65) Prior Publication Data
US 2012/0110696 A1 May 3, 2012

Related U.S. Application Data

(62) Division of application No. 11/835,328, filed on Aug. 7, 2007, now Pat. No. 8,097,771.

(60) Provisional application No. 60/836,084, filed on Aug. 7, 2006.

(51) Int. Cl.
*A01H 5/00* (2006.01)
*A01H 1/00* (2006.01)
*C12N 15/09* (2006.01)
*C12N 15/82* (2006.01)

(52) U.S. Cl.
USPC ........... 800/279; 800/278; 800/298; 800/312; 800/306; 435/468

(58) Field of Classification Search
None
See application file for complete search history.

(56) References Cited

U.S. PATENT DOCUMENTS

| 2006/0107345 A1* | 5/2006 | Alexandrov et al. ......... 800/278 |
| 2006/0150283 A1 | 7/2006 | Alexandrov et al. |
| 2007/0275464 A1 | 11/2007 | Kaku et al. |

FOREIGN PATENT DOCUMENTS

WO WO 2005003338 1/2005

OTHER PUBLICATIONS

Arrighi, JB et al "The *Medicago truncatula* Lysine Motif-Receptor-Like Kinase Gene Family Includes NFP and New nodule-Expressed Genes" Plant Physiol 142, Sep. 2006 pp. 265-279.
Bulawa, C.E., et al "Attenuated virulence of chitin-deficient mutants of *Candida albicans*" Proc. Natl. Acad. Sci. U.S.A. 92 (Nov. 1995) pp. 10570-10574.
Chisholm, S. T., et al. "Host-Microbe Interactions: Shaping the Evolution of the Plant Immune Response" Cell 124 (Feb. 2006) pp. 803-814.
Clamp M., et al. "The Jalview Java alignment editor" (2004) Bioinformatics 20(3): 426-427.
Day, R.B. et al. "Binding Site for Chitin Oligosaccharides in the Soybean Plasma Membrane" Plant Physiol. (Jul. 2001) 126, pp. 1162-1173.
Eddy, S.R. "Profile hidden Markov models" Bioinformatics (1998) vol. 14, No. 9: pp. 755-763.
Felsenstein, J. "PHYLIP (Phylogeny Inference Package)", Ed 3.6. (2000) University of Washington, Seattle; http://evolution.genetics.washington.edu/phylip/general.html; 1 page.
Gomez-Gomez, L. & Boller, T; "FLS2: An LRR receptor-like kinase involved in the perception of the bacterial elicitor flagellin in *Arabidopsis*"; T. Mol. Cell (2000) 5, pp. 1003-1011.
Goring, D. R., Walker, J. C. "Self-Rejection—A New Kinase Connection" Plant Science 303, pp. 1474-1475 (Mar. 2004).
Ito, Y., Kaku, H., Shibuya, N. "Identification of a high-affinity binding protein for N-acetylchitooligosaccharide elicgtor in the plasma membrane of suspension-cultured rice cells by affinity labeling" Plant J. 12, pp. 347-356 (1997).
Joris, B. "Modular design of the *Enterococcus hirae* muramidase-2 and *Streptococcus faecalis* autolysin" FEMS Microbiol. Lett. 91, pp. 257-264 (1992).
Schmidt, H.A. et al. "Tree-Puzzle: maximum likelihood phylogenetic analysis using quartets and parallel computing" Bioinformatics 18: 502-504 (2002).
Kaku, H. et al. "Plant cells recognize chitin fragments for defense signaling through a plasma membrane receptor" Proc. Natl. Acad. Sci. U.S.A. vol. 103, pp. 11086-11091 (Jul. 2006).
Limpens, E. et al. "LysM Domain Receptor Kinases Regulating Rhizobial Nod Factor-Induced Infection" Science 302, 630-633 (Oct. 2003).
Libault, M., et al. "Identification of 118 Arabidopsis Transcription Factor and 30 Ubiquitin-Ligase Genes Responding to Chitin, a Plant-Defense Elicitor. Molecular Plant-Microbe Interactions", vol. 20, No. 8, 2007, pp. 900-911.
Madsen, Eb; et al. "A receptor kinase gene of the LysM type is involved in legume perception of rhizobial signals" Nature 425 (Oct. 2003) 637-640.
Nürnberger, T. & Kemmerling. B. "Receptor protein kinases—pattern recognition receptors in plant immunity" Trends Plant Sci. vol. 11 No. 11, 519-522 (2006).
Okada, M.,et al. "High-Affinity Binding Proteins for *N*-Acetylchitooligosaccharide Elicitor in the Plasma Membranes from Wheat, Barley and Carrot Cells: Conserved Presence and Correlation with the Responsiveness to the Elicitor" Plant Cell Physiol. 43, 505-512 (2002).
Passarinho, P. et al. "*Arabidopsis chitinases*: A Genomic Survey" The Arabidopsis Book, American Society of Plant Biologists (2002) pp. 1-25.
Radutoiu, S. et al. "Plant recognition of symbiotic bacteria requires two LysM receptor-like kinases" (Oct. 2003) Nature 425: pp. 585-592.
Ramonell, K., et al. "Microarray analysis of chitin elicitation in *Arabidopsis thaliana*" Mol. Plant Pathol. (2002) 3(1): 301-311.

(Continued)

*Primary Examiner* — Medina A Ibrahim
(74) *Attorney, Agent, or Firm* — Dan Cleveland, Jr.; Lathrop & Gage LLP

(57) ABSTRACT

Perception of chitin fragments (chitooligosaccharides) is an important first step in plant defense response against fungal pathogen. LysM receptor-like kinases (LysM RLKs) are instrumental in this perception process. LysM RLKs also play a role in activating transcription of chitin-responsive genes (CRGs) in plants. Mutations in the LysM kinase receptor genes or the downstream CRGs may affect the fungal susceptibility of a plant. Mutations in LysM RLKs or transgenes carrying the same may be beneficial in imparting resistance against fungal pathogens.

16 Claims, 22 Drawing Sheets

(56) References Cited

OTHER PUBLICATIONS

Ramonell K., et al "Loss-of-function mutations in chitin responsive genes show increased susceptibility to the powdery mildew pathogen, *Erysiphe cichoracearum*" )2005) Plant Physiol. 138: 1027-1036.

Shibuya, N., Minami, E. "Oligosaccharide signaling for defence responses in plant" Physiol. Mol. Plant Pathol. 59, 223-233 (2001).

Soulie, M. C. et al., Botrytis cineria virulence is drastically reduced after disruption of chitin synthase class III gene (Bcchs3a) Cellular Microbiol. 8(8), 1310-1321 (2006).

Stacey, G, & Shibuya, N. "Chitin recognition in rice and legumes" (1997) Plant and Soil 194: 161-169.

Stacey, G et al., "Genetics and functional genomics of legume nodulation" Curr. Opin. in Plant. Biol. 9, 110-121 (2006).

Tanabe, S., et al., "Induction of Resistance Against Rice Blast Fungus in Rice Plants Treated with a Potent Elicitor, *N*-Acetylchitooligosaccharide" Biosci. Biotechnol. Biochem. (2006) 70, pp. 1599-1605.

Thompson, J.D., et al. "The Clustal-X windows interface—flexible strategies for multiple sequence alignment aided by quality analysis tools" (1997) Nucleic Acids Research 25: 4876-4882.

Wan, J., et al. "Activation of a mitogen-activated protein kinase pathway in *Arabidopsis* by chitin" (2004) Mol. Plant Pathol. 5(1): 125-135.

Yang, Z. Paml: a program package for phylogenetic analysis by maximum likelihood. (1997) Comput Appl Biosci 13: 555-556.

Zhang, B. et al. "Characterization of Early, Chitin-Induced Gene Expression in *Arabidopsis*" Mol. Plant-Microbe Int. vol. 15, No. 9 (2002) pp. 963-970.

Zhang, X.-C. et al., Molecular Evolution of Lysin Motif-Type Receptor-Like Kinases in Plants; Plant Physiol. 144, 623-636 (Jun. 2007).

Zmasek, C.M. & Eddy, S.R. (2001) ATV: display and manipulation of annotated phylogenetic trees. Bioinformatics 17: 383-384.

PCTUS/2007/075398 Invitation to Pay Additional Fees and Partial Search Report mailed Sep. 25, 2008.

Database Geneseq "Lotus Japonicus NFR1 gene derived 2187bp region", Apr. 7, 2005, 2 pages.

Rosso, M.G. et al., "An *Arabidopsis thaliana* T-DNA mutagenized population (GABI-Kat) for flanking sequence tag-based reverse genetics" Plant Molecular Biol., Sep. 2003, pp. 247-259.

U.S. Appl. No. 11/835,238.

\* cited by examiner

Sequence alignment of plant LysM type receptor-like kinase (LYK) group I

```
MtLYK3    ------------------------------------------------------YTTKEGDYDLIANTYYASLTTVELLKK        28
MtLYK4    ------------------------------------------------------YTTKEGDYDLIANTYYASLTTVELLKK        28
MtLYK2    ------------------------------------------------------YSAKEGDTVDLIANSYYASLTTVELLKK        28
GmNFR1a   ------------------------------------------------------YSASAGDTYDSIAKVTVANLTTVELLRR        28
GmNFR1b   ------------------------------------------------------YSASAGDTYDSIAKVTVANLTTVELLRR        28
LjNFR1a   ------------------------------------------------------YSASKGDTYHTIANLYYANLTTVDLLKR        28
MtLYK1    ------------------------------------------------------YEFHPRETYASIAELTFSNLTNKEWMEK        29
AtLYK1    ---------------------------LRYNSNIKDKRIQMGSRVLVPPCBCOPGDIFLGHNFSYSVRQEDTYERVAISNYANLTTMESLQA    66
GmLYK3    TYITSNLFGRPTSEILKYNPSVILSQTRINVPFSCDCLNGAFLGHTFSYALQHGNTYKIVVEVDFSNLTTEDWVGR              80

MtLYK3    FNSYDPNHIPVKAKINVTVICSCGNSQISKDYGLFVTEYPLRSDDTLAKIATKAGLDEGLIQNFNQDANFSIGSGIVFIP-        107
MtLYK4    FNSYDPNHIPVKAKINVTVICSCGNSQISKDYGLFVTEYPLRSDDTLAKIATKAGLDEGLIQNFNQDANFSIGSGIVFIP-        107
MtLYK2    FNSYDPHIPAKAKVNVTVNCSCGNSQISKDFPGLFITEYPLRTDDTQKIANQSNLDEGLIQSVNSGVNFSNGSGIVFIP-        107
GmNFR1a   FN--DQNGIPANARVNVT---------------------------------------------------------------         44
GmNFR1b   FNSYDQNGIPANATVNVTVNCSCGNSQVSKDYGLFITEYPLRPGNNLHDIANEARLDAQLIQSKNPGVNFSKESGDIVFIP        109
LjNFR1a   FNSYDPKNIPVNAKVNVTVNCSCGNSQVSKDYGLFITEYPLRPGDTLQDIANQSSLDAGLIQSFNPSVN-----------         96
MtLYK1    VN----VPDSVKVNVTVNCSCGDKMVSKDYGLFITEYPLRPEDSLSTARSSGVSADILQRYNPGVN------------           101
AtLYK1    RNPFPATNIPLSATLNVLVNCSCGDESVSKDYGLFVTEYPLRPEDSLGSTARSSGVSADILQRQVNPGVR-----------       134
GmLYK3    VNSYPPNQIPDNVNINVTVNCSCGNRHVSKDYGLFMTEYPLRVGDSLQRVAABAGVPABLLLRYNP----------------     145
```

FIG. 2B

Sequence alignment of plant LysM type receptor-like kinase (LYK) group III

```
GmLYK6   GLATGQDTLMRAN-SVGELQLLPGMELHVPLRCAGPTWEQITNGTEVLITYSVNWGDSIKNIAAPNVAAGNVDANG-PSTQTCHIPPPTVLIP    93
PtLYK3   ---------------------------------------HLIAYMVTWGDSISSIAQLFGVDKQRVLDANK-LSS-SNIIPPFTPLLVP    48
OsLYK1   -PTTCQALMAQNFAPDSLLNPGIRLTVPLRCAGPSPAQAAAQVRLVTEILLGMLDDSETVADRFGADYQAVLPANN-LTD-DSTVYPFTMLVP    91
PtLYK5   ---------------------------------------ELVTEYPLSSDNIPIADRFKVBTKDLIDDANG-MRE-NPLNYPDMLLIP     48
AtLYK2   ----------------------------------------PVGVRDSVSSLAVRFNTTEDATVSANN-KSG--VVPLKP---          36
GmLYK11  ---------------------------------------SNVIRDGDSVESLASRFGVSMDSIEHVNG---IDNP---HVGSLVNIP     42
PtLYK8   ---------------------------------------MLVSYVMKGDTVQSLSSRFGVSMDNIETVNG---IQNPDNVTAGALYVIP    48
AtLYK3   ---------------------------------------NVAMAGHSVQSLSSEFGVSMDRIEBDVNG---ILNLDNITAGDLLVIP       44
OsLYK2   ---------------------------------------NVVQEGNVTSIARRFNTHQDVLAANT----------LLVP              32
PtLYK1   ---------------------------------------IVVEVTVCQHETEDISTRLSSTVGGIQSMNINLIKNPSINVDWLPVP       50
OsLYK3   ---------------------------------------TVMQPCEDVVSALMVAEAANIAASNG--VAGNSIPATQQPVLIP           44
```

FIG. 2E sequence alignment of plant LysM-type extracellular proteins(LysMe)

```
>GmLysMe1     -IYVVREGETLQTISEKC-----GDPYI--VEENPHIHDPDDVFPGLVIKINP
>PtLysMe7     --YVVREGETLNTISEKC-----GDPYI--VEENPHIHDPDDVFPGLVIKITP
>AtLysMe1     ---EVKEGETLQTISEKC-----GDPYI--VEGNPHIHDHDDLFPGLLIRITP
>AtLysMe3     ---IVGEGETLHTIGDKC-----GDPFI--VERNPHIHDPDDVFPGLVLKIAP
>GmLysMe4     -IYVVGEGETLHTISDKC-----GDPFI--VERNPHIHDPDDVFPGLVIKITP
>GmLysMe2     -IYVVGEGETLHTISDKC-----NDPFI--VERNPHIHDPDDVFPGLVIKITP
>GmLysMe3     -IYVVGEGETLHTISDKC-----GDPFI--VEKNPHIHDPDDVFPGLVLKI--
>GmLysMe5     -IYVVGEGETLHTISDKC-----GDPFI--VENNPHIHDP------------
>GmLysMe6     -IYVVGEGETLHTISDKC-----GDPFI--VEKNPHIHDPDDVFPGLVIKITP
>PtLysMe6     --YVVGEGETLHTISDKC-----GDPFI--VEQNPHIHDPDDVFPGLVIKITP
>PtLysMe3     --YVVKEGETLHTISDKC-----GDPFI--VEENPHIHDPDDVYPGLVIKITP
>PtLysMe5     --YVVKEGETLHTISDKC-----DDPFI--VEENPHIHDPDDVFPGLVIKITP
>PtLysMe10    -IYVVGEGETLNTISEKC-----DDPFI--VEQNPHIHDPDDVYPGLVIKI--
>OsLysMe4     EIYVVEEGETLHSISDRC-----GDPYI--LEQNPHVHDPDDVFPGLVIKITP
>AtLysMe2     --YVVGEGDTLHSISEKC-----GDPFI--VERNPHIHDPDDVFPGLLIKLH-
>PtLysMe11    -VVGVASGDTCFTIAQSF--NLTAASFD---AINPNIS-CNALFVGQWLCVAG
>PtLysMe8     --VGAASGDTCFTIAQSF--NLTAASFD---AINPNLN-CTALFVGQWLCV--
>PtLysMe4     --HGVVTGDTCTAVEKQF--DLTANDFK---AINPNLD-CDKLFVGQWLCV--
>OsLysMe2     --HGVQASETCFSVSQSA--GLTQDQFL---AFNPNIN-CAKVFVG-------
>OsLysMe1     --HGVEAGETCDSIARRFHAGLGRAPFFRLVSLNPNIN---------------
>PtLysMe9     --YYVWQGSNLTYISTIF-----NQSITEILRYNPKVPNQDSIRSDTRLNVP-
>OsLysMe3     --YAARPADTLATVADGV---FAGLAFA---DQIRNANPDAPLDPGQKLVVP-
```

FIG. 2F sequence alignment of plant LysM-type non-secratory proteins(LysMn)

```
>AtLysMn1     ----HRICRGDSVTSLAVK-YA-VQVMDIK-RLNN--MMSDHGIYSRDRLL--IP
>GmLysMn1     ---SHHITRGDTVASLAVK-YS-VQVMDIK-RLNN--MMSDHGIYSRERXI--DP
>PtLysMn2     ---SHKIVKGDSVASLAVK-YS-VQVMDIK-RINN--MTSDHGINSRERLL--IP
>PtLysMn1     ---SHKIAREDSVTSLAKK-YS-VQVRDIK-LLNN--MTSDNGIYSMERLL--IP
>OsLysMn1     ----HTVRRGDTVPGIALK-YS-IQVTDIK-RFNN--MMSDHGIYLRERLL--IP
>GmLysMn2     ----EHQVSKLDTLAGVAIK-YG-VEVADIK-RMNG--LATDLQMFALKTLK--IP
>GmLysMn4     ----HQVSKLDTLAGVAIK-YG-VEVADIK-RMNG--LATDLQMFALKTLK--IP
>PtLysMn6     ----EHQVSKRDTLAGVAIK-YG-VEVADVK-RLNG--LSTDLQMFALKTLL--IP
>OsLysMn3     ----HRVGKLDTLAGIAIK-YG-VEVADIK-RLNG--LSTDLQMFAHKTLR--IP
>GmLysMn3     ---DHRVSKFDTLAGVAIK-YG-VEVADIR-KMNN--LVTDHQMFALKTLH--IP
>GmLysMn5     GYIEHHVSKFDTLAGVAIK-YG-VEVADIR-KMNS--LVTDHQMFALKTLH--IP
>AtLysMn2     ----HRISKFDTLAGVAIK-YG-VEVADVK-KMNN--LVTDLQMFALKSLQ--IP
>PtLysMn11    GFIEHPVSKLDTLAGVAIK-YG-VEVADIK-KMNG--LVTDLQMFALKSLQ--IP
>AtLysMn3     ---EHRVSKFDTLAGIAIK-YG-VEVADIT-KLNG--LVTDLQMFALESLR--IP
>OsLysMn2     ----HQVSRMDTLPGLAIK-YG-VEISDIK-RANS--LMTDSQMFAHKMLL--IP
>PtLysMn10    ----IKARKRDTLISVANR-YG-VSASNLA-DWND--LKSSATLHAGQSLVAYLP
>PtLysMn7     ----HDVVRGDTLSAIAKKFYGDANKYPVIFEANKPMLSHPDKIYPGQKLR--IP
>PtLysMn9     ----HVVKEGETLTSISKQ-YG-VSIYSVA-AANKNILD-VDLVFEGQLLN--IP
>PtLysMn8     ----YTVQENDTLTGIAEL-LS-AELTGIE-NLNER-FTRNPNLIDVGWVL-FVP
```

FIG. 2G

Up-regulated Genes (676)

Down-regulated Genes (233)

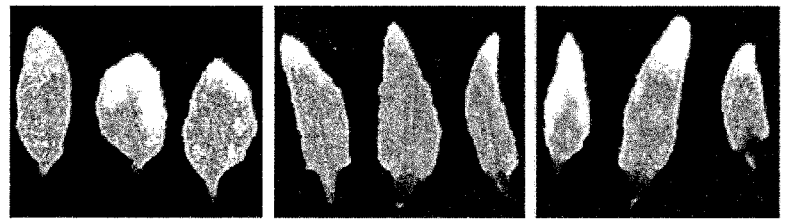
FIG. 13A
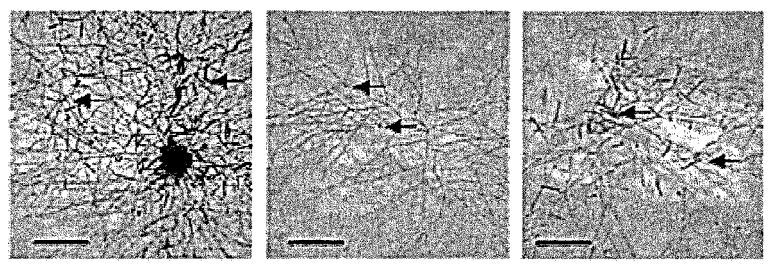
FIG. 13B
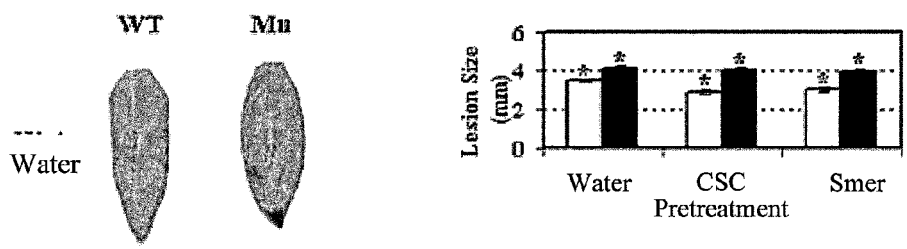
FIG. 13C
FIG. 13D
FIG. 13E
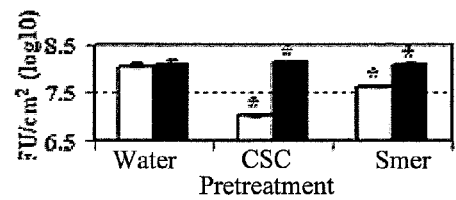
FIG. 13F

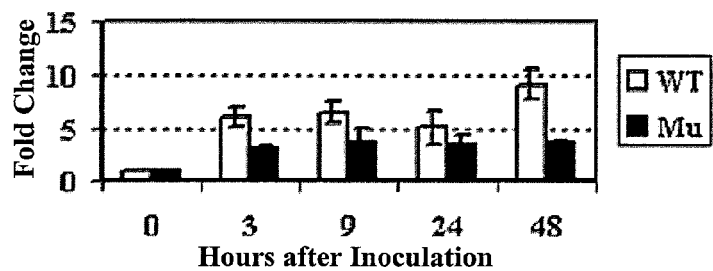
FIG. 14A
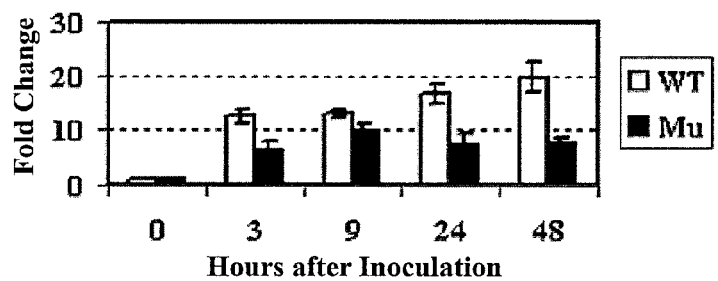
FIG. 14B
FIG. 15

SEQUENCE LISTING

```
<160> NUMBER OF SEQ ID NOS: 215

<210> SEQ ID NO 1
<211> LENGTH: 2205
<212> TYPE: DNA
<213> ORGANISM: Lotus japonicus

<400> SEQUENCE: 1
aagtgtgaca ttagtttcaa gagaaaaata aatgatcaaa acctggtaga gagtcctaga      60
aattcaatgt tctgatttct ttcattcatc tctgctgcca ttttgatttg cacaatgaag     120
ctaaaaactg gtctactttt gttttcatt cttttgctgg ggcatgtttg tttccatgtg     180
gaatcaaact gtctgaaggg gtgtgatcta gctttagctt cctattatat cttgcctggt     240
gttttcatct tacaaaacat aacaaccttt atgcaatcag agattgtctc aagtaatgat     300
gccataacca gctacaacaa agacaaaatt ctcaatgata tcaacatcca atcctttcaa     360
agactcaaca ttccatttcc atgtgactgt attggtggtg agtttctagg gcatgtattt     420
gagtactcag cttcaaaagg agacacttat gaaactattg ccaacctcta ctatgcaaat     480
ttgacaacag ttgatctttt gaaaaggttc aacagctatg atccaaaaaa catacctgtt     540
aatgccaagg ttaatgtcac tgttaattgt tcttgtggga acagccaggt ttcaaaagat     600
```

```
tatggcttgt ttattaccta tcccattagg cctggggata cactgcagga tattgcaaac      660
cagagtagtc ttgatgcagg gttgatacag agtttcaacc caagtgtcaa tttcagcaaa      720
gatagtggga tagctttcat tcctggaaga tataaaaatg gagtctatgt tcccttgtac      780
cacagaaccg caggtctagc tagtggtgca gctgttggta tatctattgc aggaaccttc      840
gtgcttctgt tactagcatt ttgtatgtat gttagatacc agaagaagga agaagagaaa      900
gctaaattgc caacagatat ttctatggcc ctttcaacac aagatgcctc tagtagtgca      960
gaatatgaaa cttctggatc cagtgggcca gggactgcta gtgctacagg tcttactagc     1020
attatggtgg cgaaatcaat ggagttctca tatcaggaac tagcgaaggc tacaaataac     1080
tttagcttgg ataataaaat tggtcaaggt ggatttggag ctgtctatta tgcagaattg     1140
agaggcaaga aaacagcaat taagaagatg gatgtacaag catcaacaga atttctttgt     1200
gagttgaagg tcttaacaca tgttcaccac ttgaatctgg tgcgcttgat tggatactgc     1260
gttgagggat ctctattcct tgtttatgaa catattgaca atggaaactt aggccaatat     1320
ttgcatggtt caggtaaaga accattgcca tggtctagcc gagtacaaat agctctagat     1380
gcagcaagag gccttgaata cattcatgag cacactgtgc ctgtgtatat ccatcgcgat     1440
gtgaaatctg caaacatatt gatagataag aacttgcgtg gaaaggttgc agattttggc     1500
ttgaccaagc ttattgaagt tgggaactcc acactacaaa ctcgtctggt gggaacattt     1560
ggatacatgc ccccagaata tgctcaatat ggtgatattt ctccaaaaat agatgtatat     1620
gcatttggag ttgttctttt tgaacttatt tctgcaaaga atgctgttct gaagacaggt     1680
gaattagttg ctgaatcaaa gggccttgta gctttgtttg aagaagcact taataagagt     1740
gatccttgtg atgctcttcg caaactggtg gatcctaggc ttggagaaaa ctatccaatt     1800
gattctgttc tcaagattgc acaactaggg agagcttgta caagagataa tccactgcta     1860
agaccaagta tgagatcttt agttgttgct cttatgaccc tttcatcact tactgaggat     1920
tgtgatgatg aatcttccta cgaaagtcaa actctcataa atttactgtc tgtgagataa     1980
aggttctcca tgcaaatgca tgtttgttat atatatcttg tagtacaact aagcagacaa     2040
aaagttttgt actttgaatg taaatcgagt cagggtgttt acattttatt actccaatgt     2100
ttaattgcca aaaccatcaa aaagtcctag gccagacttc ctgtaattat atttagcaaa     2160
gttgcagatt ctaagttcag ttttttaaa aaaaaaaa aaaaa                        2205
```

<210> SEQ ID NO 2
<211> LENGTH: 2292
<212> TYPE: DNA
<213> ORGANISM: Lotus japonicus

<400> SEQUENCE: 2

```
ttattgatat actaaaccac aggatatttt attgacaatg tgaatgttcc atattttcaa       60
caatgctgat tccctctgat aaagaacaag ttccttttct ctttccctgt taactatcat      120
ttgttcccca cttcacaaac atggctgtct tctttcttac ctctggctct ctgagtcttt      180
ttcttgcact cacgttgctt ttcactaaca tcgccgctcg atcagaaaag attagcggcc      240 cagactttc atgccctgtt gactcacctc cttcttgtga acatatgtg acatacacag       300 ctcagtctcc aaatcttctg agcctgacaa acatatctga tatatttgat atcagtcctt      360
tgtccattgc aagagccagt aacatagatg cagggaagga caagctggtt ccaggccaag      420
tcttactggt acctgtaact tgcggttgcg ccggaaacca ctcttctgcc aataccctcct    480 accaaatcca gctaggtgat agctacgact ttgttgcaac cactttatat gagaacctta      540
```

-continued

| | |
|---|---:|
| caaattggaa tatagtacaa gcttcaaacc caggggtaaa tccatatttg ttgccagagc | 600 |
| gcgtcaaagt agtattccct ttattctgca ggtgcccttc aaagaaccag ttgaacaaag | 660 |
| ggattcagta tctgattact tatgtgtgga agcccaatga caatgtttcc cttgtgagtg | 720 |
| ccaagtttgg tgcatcccca gcggacatat tgactgaaaa ccgctacggt caagacttca | 780 |
| ctgctgcaac caaccttcca attttgatcc cagtgacaca gttgccagag cttactcaac | 840 |
| cttcttcaaa tggaaggaaa agcagcattc atcttctggt tatacttggt attaccctgg | 900 |
| gatgcacgtt gctaactgca gttttaaccg ggaccctcgt atatgtatac tgccgcagaa | 960 |
| agaaggctct gaataggact gcttcatcag ctgagactgc tgataaacta ctttctggag | 1020 |
| tttcaggcta tgtaagcaag ccaaacgtgt atgaaatcga cgagataatg gaagctacga | 1080 |
| aggatttcag cgatgagtgc aaggttgggg aatcagtgta caaggccaac atagaaggtc | 1140 |
| gggttgtagc ggtaaagaaa atcaaggaag gtggtgccaa tgaggaactg aaaattctgc | 1200 |
| agaaggtaaa tcatggaaat ctggtgaaac taatgggtgt ctcctcaggc tatgatggaa | 1260 |
| actgtttctt ggtttatgaa tatgctgaaa atgggtctct tgctgagtgg ctgttctcca | 1320 |
| agtcttcagg aaccccaaac tcccttacat ggtctcaaag gataagcata gcagtggatg | 1380 |
| ttgctgtggg tctgcaatac atgcatgaac atacctatcc aagaataata cacagggaca | 1440 |
| tcacaacaag taatatcctt ctcgactcga acttcaaggc caagatagcg aatttcgcca | 1500 |
| tggccagaac ttcgaccaac cccatgatgc caaaaatcga tgtcttcgct ttcggggtgc | 1560 |
| ttctgataga gttgctcacc ggaaggaaag ccatgacaac caaggagaac ggcgaggtgg | 1620 |
| ttatgctgtg gaaggatatg tgggagatct ttgacataga agagaataga gaggagagga | 1680 |
| tcagaaaatg gatggatcct aatttagaga gcttttatca tatagataat gctctcagct | 1740 |
| tggcatcctt agcagtgaat tgcacagctg ataagtcttt gtctcgaccc tccatggctg | 1800 |
| aaattgttct tagcctctcc tttctcactc aacaatcatc taaccccaca ttagagagat | 1860 |
| ccttgacttc ttctgggtta gatgtagaag atgatgctca tattgtgact tccattactg | 1920 |
| cacgttaagc aagggaaggt aattcagttt ctcatcaaat tgatcaagat gcactttgtt | 1980 |
| tgcgtggtta ctattacatt tttaactagc tatttgctta tttctctgta tttatttgtc | 2040 |
| agacactgga attgaatatc atatgatgga ggagttgtct gttaatacat gtgctaataa | 2100 |
| caaattcagg caagatagtt aattgcattt gaaatacata tttctgctca gagatggtga | 2160 |
| acatccatgc tccgaagctc atattaagtg tggtagctat tttcttttca tcttttgggg | 2220 |
| gtgaatgcgt gttcatgtaa ctcgtaaggt gttatatatt acagaagtcg tatacgtcgt | 2280 |
| tccaaaaaaa aa | 2292 |

```
<210> SEQ ID NO 3
<211> LENGTH: 2063
<212> TYPE: DNA
<213> ORGANISM: Arabidopsis thaliana

<400> SEQUENCE: 3
```

| | |
|---|---:|
| aaacaaaaaa aacagagacc cttcctctgg ggaatctaag gaagcttcaa aatgaagcta | 60 |
| aagatttctc taatcgctcc gattcttctt ctcttctcat tcttcttcgc cgtggaatct | 120 |
| aagtgcagga ctagctgtcc tttagctcta gcttcgtact atctcgagaa cggaacaaca | 180 |
| ctctccgtca tcaaccaaaa cctcaattct tcaatcgcgc cttacgatca aatcaatttc | 240 |
| gatccaatcc tcaggtacaa cagtaacatt aaagacaaag atagaatcca gatgggctct | 300 |
| agggttcttg tacctttccc ttgcgaatgt caacctggtg atttcctagg gcacaatttc | 360 |

```
agctacagtg ttcgacagga agatacttac gaaagagtcg cgattagtaa ttacgcgaat    420
ctcacgacga tggagtcgtt acaggcgagg aatcctttc cggcgactaa catacctctc     480
tctgcgacgc ttaatgtatt ggtgaattgt tcttgtggtg atgagagtgt ttcgaaagat    540
tttggtttgt ttgttacgta tccgcttcgt cctgaagaca gtctcagttc tattgcgaga    600
tcttccggtg tatcggcgga tattctgcag agatataatc ccggtgttaa ttttaactcc    660
gggaatggaa tcgtttatgt gcctggaaga gatccaaatg gtgcatttcc accattcaaa    720
tcaagtaaac aagatggtgt tggtgctgga gttattgctg gtatagttat aggagtgatt    780
gtggctttgt tgttgatctt gtttatcgta tattatgctt accggaagaa taagtcgaag    840
ggtgattcgt tttcttcttc tattccgttg tctactaagg ctgatcatgc ttcttctact    900
agtctccaaa gtggaggttt gggtggtgcc ggagtgtctc ctggcattgc tgccataagc    960
gtggacaaat ctgttgagtt ttcgttggag gaactagcaa aggctactga taatttcaat   1020
ttgtctttta agattgggca aggtggtttt gggctgtttt actatgcaga gctgagagga   1080
gaaaaagctg cgattaagaa gatggacatg gaggcatcga aacagttctt ggcggaacta   1140
aaagtcttaa cgcgtgtaca tcatgtcaac ctggttcgcc tgattggata ttgtgttgag   1200
ggatcacttt tcttggtgta tgaatatgtt gagaatggta accttggaca acatttacat   1260
gggtcaggac gagaaccatt accgtggact aagagagtgc agattgcact agactcagct   1320
agaggtttag aatatatcca cgagcacacg gttccagttt atgtccatag ggacattaaa   1380
tctgccaata ttttgataga ccagaaattc cgagcaaagg tagcagattt cgggttaaca   1440
aaactgacag aagttggagg ttcagcaact cggggtgcaa tgggtacatt tggttacatg   1500
gcaccagaga ctgtttatgg agaagtgtct gcaaaagtag atgtatatgc atttggagtt   1560
gtcctttacg aattgatttc tgcgaaaggt gcggttgtca aaatgacaga agccgttggt   1620
gaatttagag gccttgttgg tgtgttcgaa gaatcattca aggaaaccga caaagaagaa   1680
gcactacgca agattataga cccgaggctc ggtgatagtt acccgtttga ttcggtatac   1740
aagatggcgg aattagggaa agcatgtaca caagagaatg cgcagctacg tccgagtatg   1800
agatacattg tggttgcttt atccactctc ttttcgtcta ccggaaattg ggatgttgga   1860
aacttccaaa acgaagattt agtcagtctt atgtccggcc ggtagactcg ttttccggtt   1920
tgctgttgtt atatagaaat gattgttttt tggtatgctc acgtatattt tgtctgtcta   1980
tacgaacttt acatgtcaca actcacaagt tgactttat atgattttct ataacgctct    2040
atatgtcaat tattcaacgt ctc                                           2063

<210> SEQ ID NO 4
<211> LENGTH: 1979
<212> TYPE: DNA
<213> ORGANISM: Arabidopsis thaliana

<400> SEQUENCE: 4
tctagaagtc agacatggct gtttcagtta gtaagcagta catgacaagt cttgtagtga     60
tcttgctctt catctcctta tcatctctct ctccaacttc aacttcacac agctgtgacc    120
ctgtcgaaga agaagaagaa gcctcctcct tcggttacgt ttgccactca aacctccaaa    180
agtgccacac tttcgccatt ctcagagcca aacctccctt ctattccctc tcggacctga    240
gtcgccatct tggtctcgac gcagacgacg agtatgttcc gaaaggtcag ttactcttga    300
tcccaataga gtgcaggtgt aatggaagca tctacgaggc cagtctcatt aaaaaattgcg    360
ttaaaggaga caccttcgc tctgtctctc agtctctgca aggcttgacc acctgcctat     420
```

-continued

```
ctatcagaga gaagaatcca catatttccg aagacaagct tggcgacaac attaaactgc      480
gtttggcgat caggtgctct tgtccacaag aaggcgtttc aaacgctagt tttctcgtta      540
cgtatccggt gggcgtccgc gacagcgttt caagcctggc ggttaggttt aacacaacag      600
aggatgccat tgtctctgca aacaacaaat ctggtgtggt tccactcaag cctgctctca      660
tccctcttga tcacaaacca gagaaacaag atcccggaa aagaaatcca tccaagaaga       720
aacggtcaaa gatgaagctc atgatcgctg tgagcagcgc gattgctgga gtttgcggtc      780
ttgtcactct catggtgttt ggttacttac actggaagaa agagacgcag attcaaacgc      840
aaacgcaaaa gtggattagc aacaaagacc ccgagacgcg gcagctgagt ctgagcatcc      900
gaaccacgag tgacaagaaa atctcgtttg aagggtcgca ggacggttcc atcttggatt      960
ctcacaacac cgtcggcacc acaacgcccc gaaaacccgt tctggagatt tacgcgtttg     1020
aagagttaga gaaggccacg gagaatttca gttcaagcaa tcacatcaaa ggttcggttt     1080
atttcggttc gctcaaaggc aaagacttgg ctataaagca agtcaatgca gatgaaatga     1140
aaagattcga tttcgggctt ctcaatgatc agtcacacta ctataaccac aatgtgatta     1200
gggttcttgg aacatgtttt agagaaatcg atcaagattc ttatctggtt ttcgagtatg     1260
caaggaatgg gtccctgtgg gattggattc agaacaaatt ggccatcaag aatcaattca     1320
tcgagtcttg ttactgtttc ttggcatgga acagaggat caagatatgt cacgatgtcg      1380
ccatcgcgtt aaagtatatg catcggatca actacgtcca cggcaacatc aagagcagaa     1440
acatcttctt gaacgaagat ctcagaggta agtcggaaa cttgggatg tcaaagtgcg       1500
taaccaatga attagccaca gaagagaacc ttatagagag ttcactgtct ccagcttctg     1560
acatatttgc ttacgggata atcgtaatgg aggttttgtc tggacaaacc ccagatatgt     1620
tgcttggatt gcaagaagta gagacaacat cccttgggac acaagaaact tttgtttccg     1680
aatggagtag attaagaagg cttctcgggg acaaggaaaa gctgagggaa gtgatggaca     1740
gcacattggg agagagctat tcggttgatt ctgcgtttga atcgcaagt attgcaagag      1800
attgtactgc agaagaagcc gagtcaaggc cgagcgcggt tgagattgca gagagggttt     1860
caagattggt ggatgacgat gaagatgaag aagatgaggc agtaatagat agagagagta     1920
ccttaatttc agagagttca tacaagcctt tggtaaagaa gagtagtata atagattaa      1979
```

<210> SEQ ID NO 5
<211> LENGTH: 2321
<212> TYPE: DNA
<213> ORGANISM: Arabidopsis thaliana

<400> SEQUENCE: 5

```
gctgatttca tctcttctct acttcttcct cttctccatt aaccaaatca accaataccc       60
atttctcaat tcaccatatc ttcatcaaat caagattctt tcttccttaa tccctaaaaa      120
aaaccttctt tcaattctga ttttcactta ggttttctc aatttctact tcacacaatg       180
aatcttacct tctacatctt cttcttaagt cttttaccaa gtttctcatc ttcaaagcca      240
atgaattgct ctgacactac tcgtctctgc agttccttcc ttgctttcaa accaaaccaa      300
aaccaatctt tctctgtaat ccaaagcatg ttcgatgtat taccacaaga cataaccgcc      360
gacatctccg gaggttactt ctttattaaa aagaactgtt cttgtcttac tacgactcat      420
caatacacaa caaacacaac attcacaatc agacaaaacg ttggatacgt ttacaatgtt      480
accgtctctg cttactctgg tctcgcgttt ccaccgaata caactagagc agctcgcgct      540
ggtgcagtgg tttctgttca gcttctttgt ggttgctcta gtggtctctg gaactatctt      600
```

```
atgagctacg ttgctatggc tggagatagt gtacaatctc tctcgagcag atttggtgtt    660
agtatggatc gaattgagga tgttaatggg atcttgaatc ttgataatat cacagctggt    720
gatctccttt atatcccact tgattccgta cctggagagc cttatgagac aagtaagata    780
aatccaccag ctccttctcc tgcgcctgca tcatcattag ctaatggcaa tatctcagat    840
gaccaggtga atcacactgc aaagagtggt agtcatgtgc cttatatatg gattgttggt    900
ggtcttggag ttgtgcttgc acttcttgtt ctgtgcatac ttgtatgtat ctgtttgaga    960
tcatctagtt gcagttccag tgaggaagat ggtaatggac acaacttcca aatccttaga   1020
aaatccggtt tcttttgcgg ttctggtcgg tataactgct gtagatcagg gatttttaga   1080
caaaccaatg gtgaaactca agttgttgct attcctaaag ctcttggtga tggaatgttt   1140
gagatagaga agcctatggt gtttacttat gaagaaattc gtgcggctac ggatgagttt   1200
tcggattcta atcttcttgg tcatggaaac tatggttctg tatactttgg tctacttaga   1260
gaacaggaag ttgctgtcaa aaggatgact gctacaaaaa ctaaagagtt tgcagcagag   1320
atgaaagtgc tttgcaaagt tcatcattcc aatctggtag aattgattgg ttacgctgca   1380
accgttgacg agcttttcgt agtttatgaa tatgtccgaa agggaatgct gaaaagccat   1440
ttgcatgatc ctcagagcaa aggaaatacc ccactttctt ggataatgag gaatcagatt   1500
gcacttgacg cagcaagagg cttggaatat attcatgagc atactaaaac tcattatgtt   1560
caccgagata tcaagacaag caatatttg ctcgacgagg cattcagggc taagatatcg   1620
gattttggac ttgcaaaact cgttgagaaa actggagagg gagaaatatc agtaactaaa   1680
gtagttggta catatggtta tcttgcacca gaatatctaa gcgacggtct tgccacctcg   1740
aaaagtgata tttacgcctt tggtgttgtt cttttcgaaa ttatatccgg aagagaagct   1800
gttataagaa cggaggcgat tggaactaag aatccagaaa gacgtccatt ggcatctatt   1860
atgttagcag tgctaaagaa ctcaccagac tctatgaaca tgtcgagttt gaaggagttt   1920
gttgacccca acatgatgga tttatacccg catgactgtt tgttcaagat tgctacgttg   1980
gcaaagcaat gtgtggatga tgatccgatt ctaagaccaa acatgaagca gtggttata    2040 tcgctctcgc agatactcct gtcttccatt gaatgggaag ccactcttgc tggaaacagc   2100
caagtcttta gtggtctagt ccaaggaaga taaaaacaat aaaaacttag aaccctttct   2160
ttattttcaa tttatgaatg tcgccattgc ctagaagaag cttagtttgt ctaaaccaaa   2220
agatcgttcg cagtctaact aagtagatag ttacagagac aaatctctat atgattattc   2280
ttttggagaa tcaaatgaag agatgtatga gtttatatgc t                       2321

<210> SEQ ID NO 6
<211> LENGTH: 1839
<212> TYPE: DNA
<213> ORGANISM: Arabidopsis thaliana

<400> SEQUENCE: 6
atgatctcgt tttcatttca tctcctcgtc ttcatcctcc taagtctctc ttccttcgca     60
acagcacaac agcctatgt cggaatatca caactgatt gctctgtttc cgacaacaca    120
acctctgttt tcggctactc ttgtaatggt ctcaacaaaa cttgccaagc ttacgtcatt    180
ttccgatcta ctccttcttt ctccaccgtc acctcaatct cttccctctt ctctgtcgac    240
ccatctctcg tctcctccct caatgacgct tcaccttcaa cttctttccc ttctggtcaa    300
caagtcatta tcccttttaac ttgttcttgc accggtgacg attcacaatc caatattaca    360
tacacaatcc aaccaaacga ttcgtatttc gccattgcta cgacactct tcaggggctt    420
```

-continued

| | |
|---|---|
| tcgacatgtc aagctttggc aaaacagaac aatgtttctt ctcaatcttt gtttcctggt | 480 |
| atgaggatcg ttgttccgat ccgttgtgcg tgtcccacgg ctaaacagat caacgaagat | 540 |
| ggcgtgaagt atctgatgag ttatactgtg gttttttgaag acactatcgc gatcatcagc | 600 |
| gatagattcg gggttgagac gagcaagact ttaaaagcta acgaaatgtc ttttgagaat | 660 |
| tctgaagttt tcccttttcac aacaatcctg atcccttttgg tgaatcctcc tgcaaatact | 720 |
| aactctctca ttcctcctcc tcctcctcct cctccacaat cggtttctcc tcctccattg | 780 |
| tcgccggatg gtaggaaatc gaagaagaaa acatgggtct atgctcttgc cggagtacta | 840 |
| ggaggagcat tggttttgag tgtgatcggt gcagccatat tttgcctgtc taagaagaaa | 900 |
| acgaaaacgc aaacgcaaga ggaaacggga aacctcgata gcttcatggg caagaaacca | 960 |
| ccgatgtctg atcaagaatt cgatccgcta atggtttgt caggtatggt ggtagaatcc | 1020 |
| ttaaaagttt acaaatttca cgagctgcaa tcagctacaa gcgatttcac atcgtctagc | 1080 |
| tcgattggag gatcagggta catcggaaaa atcaacggcg atggcgcaat gatcaagaaa | 1140 |
| atcgaaggaa acgcatcgga ggaagtcaac ttattgtcta aactaaacca tcttaacatc | 1200 |
| atccgtctct ctggattctg tttccatgaa ggagattggt acttagtcta cgaacacgct | 1260 |
| tcaaacggaa gcttaagtga atggatccac acgacgaaat cgttactaag cttgacacaa | 1320 |
| aaactacaaa tcgctttgga tatagcaaca gggctaaact atctacacaa cttcgctgat | 1380 |
| cctccatacg ttcacagaga tttgaacagc aacaatgtgt tcctcgacct cgagtttcga | 1440 |
| gcaaagattg gtagtttagg ttcagcaaga tcaacgactg aagatttcgt gttgaccaag | 1500 |
| cacgtggaag gaacaagagg gtacttagct ccggagtatt tggaacatgg tttagtttca | 1560 |
| actaagcttg atgtctatgc ttttggagtt gtcttgttgg agattgttac tggtaaagaa | 1620 |
| gcttctgaat tgaagaaaga gatcgatgaa ggtaaagcta ttgatgagat tttgattcat | 1680 |
| ggaagattgt tacctgaagg attaacaagt tttgttgaga gattagtggt ggattgttta | 1740 |
| aagaaagatc atttgaatcg tccatcgatg gatgaaaatg ttatgtcttt gtctaagatc | 1800 |
| ttggcggcta cgcagaactg ggaagaatcg tcgtactaa | 1839 |

<210> SEQ ID NO 7
<211> LENGTH: 2239
<212> TYPE: DNA
<213> ORGANISM: Arabidopsis thaliana

<400> SEQUENCE: 7

| | |
|---|---|
| gatcagaaca ccacaaaaca tggctgcgtg tacactccac gcgctctcag tcaccttatt | 60 |
| cctccttctc ttctttgccg tgtcaccggc gaaagctcag caaccgtacg tcaacaacca | 120 |
| ccagctcgcc tgcgaggtcc gtgtctacga caacataacc aacggattca catgtaacgg | 180 |
| cccaccttct tgccgctcat acctcacttt ctggtctcaa ccaccgtaca acacggcgga | 240 |
| ctcaatcgca aaactcctca acgtctccgc cgcagagatc caatcaatca acaacctccc | 300 |
| cacagccacc accagaatcc caacccgtga attagtcgtg atcccagcta actgctcctg | 360 |
| ctcctcctcc agcggaggat tttaccaaca caacgccact acaatctct ccggtaacag | 420 |
| aggagatgaa acctattct cagtggctaa cgatacttac caagctttat ccacgtgtca | 480 |
| agccatgatg tcacaaaacc gttacggcga gagacaacta accccggct aaacctcct | 540 |
| tgttcctctc cgatgtgctt gtcccaccgc caaacaaacc accgccggat ttaaatatct | 600 |
| cctgacttac ttagtcgcca tgggagatag tatctccggc atcgccgaga tgttcaacag | 660 |
| cacatccgcc gccataaccg aaggtaacga gcttacatca gacaatatct tcttcttcac | 720 |

```
accggttcta gttcctctca caactgaacc taccaaaatc gttatatctc cgtcgcctcc      780
tcctccaccc gttgttgcta cgccgcctca aacgccagtt gatcctccgg gatcttcttc      840
ttctcacaaa tggatctaca tcggaattgg aatcggagct ggtttgcttc tcttactctc      900
aatcttagct ctctgcttct acaaacgaag gtctaagaag aagtcattac cgtcgtcgtt      960
gccggaggag aacaagctct ttgattcatc aaccaaacaa tctattccca caacaacaac     1020
gactcaatgg tcaatagatt tatccaattc atcagaagct ttcggtttaa aatccgccat     1080
agaatctcta acactataca gattcaacga tcttcaatca gctacttcga atttcagcga     1140
cgaaaacaga atcaaaggct ctgtttatcg cgcgacaatc aacggcgacg atgccgctgt     1200
gaaagtgatc aaaggagatg tttcttcctc tgagatcaat cttttgaaga agctaaatca     1260
ttctaatatc atccgtctct caggtttctg tatccgtgaa ggaacatcgt acctcgtctt     1320
cgagtattca gagaatggat cgatcagtga ttggcttcac tcgtcgggca agaagagttt     1380
gacatggaaa cagagagttg aaatagcaag ggatgtggca gaggcgttag attatctcca     1440
taactatata actccacctc atattcataa gaacttggaa tcaacaaaca tacttctgga     1500
ttctaatttc agagccaaga ttgcgaattt cggtgttgcg aggattcttg atgaaggtga     1560
tcttgatctt cagttaacaa gacatgttga aggaacacaa ggctacttag ctccagagta     1620
tgtggagaat ggagtcatta cttcgaaact agacgtgttt gcttttggag ttgcggttct     1680
tgagcttctt tcggggagag aagcagtaac gatacataag aagaaggaag agaagaagaa     1740
agtggagatg ttgtgtaaag tgataaacag tgtgcttgga ggagaaatg tgagagagaa     1800 gttaaaagag tttatggatc catctctagg gaatgagtat ccgttggagc tggcttacac     1860
catggctcag cttgctaaga gctgtgtcgc aactgatctt aactcgcgtc catctgtcac     1920
tcaggttcta accacgctct caatgatcgt ctcctcctcc atcgattggg agccttctga     1980
tgaccttctt cgttccggct ctcttggcaa ctagttcagt tttttttttc tattggtagt     2040
caataacaag tatttagact ttagataagg accatacggc taaaaagttg agatctaata     2100
agtaccccac tgtgaaacat agtaataaga acatatcata gagaaacttt atttagattt     2160
tgacatgttg cttcagtagt cttttgtatt tcagaaaaaa ataatcattt tcttccaatg     2220
agaagtagaa tcttgagga                                                  2239

<210> SEQ ID NO 8
<211> LENGTH: 1159
<212> TYPE: DNA
<213> ORGANISM: Arabidopsis thaliana

<400> SEQUENCE: 8
atgaacaccg gcggtggcca atacacggat tttccggcgg tggaaactca cggaggacag       60
ttcataagtt acgatatctt cggtagttta ttcgagatca catctaagta tcgtcctccg      120
attataccaa ttggtcgtgg agcttatgga atcgtttgct ctgtgttgga tacggagacg      180
aacgagctag tagcgatgaa gaagatagct aatgcttttg ataatcatat ggatgctaag      240
cgtacgcttc gtgagatcaa gcttcttcgt catcttgatc atgaaaacat tatagctata      300
agagatgttg ttccaccacc actaagaaga cagttcagtg atgtttatat ctctactgaa      360
ttaatggata ctgatcttca tcaaatcatc agatctaacc agagtttatc agaagaacac      420
tgtcagtact tcttgtacca gctacttcga ggactgaagt atatccactc agctaacatt      480
attcataggg atttaaagcc gagcaatctt ctgttgaacg cgaattgcga tttaaagatt      540
tgtgatttcg gtcttgctag acctacttca gagaatgatt ttatgactga gtatgttgtt      600
```

```
acgagatggt atagagcacc tgagcttctg ttgaactctt cagattacac agctgctatt      660
gatgtttggt ctgttggttg tatctttatg gagcttatga atagaaagcc tttgttccct      720
ggtaaagacc atgttcatca aatgcgctta ttgacagagt tgcttggcac accgacagaa      780
tctgatctcg gttttactca caatgaggat gcgaaaagat acatccggca acttcccaac      840
ttcccacgtc agcccttagc taaacttttc tctcatgtta acccaatggc cattgatctt      900
gttgacagaa tgttgacgtt tgaccccaac agaagaatca ctgttgaaca agctctgaat      960
caccagtacc ttgctaaatt gcacgacccg aatgatgagc aatctgtca aaagccattc      1020 tcttttgagt cgaacaaca gcctctggat gaggaacaga taaaagagat gatctaccaa      1080
gaagccatag cactcaatcc aacatacggt tagaagtgca gcagcccgt gaatgcctgg      1140 tattacccaa taaccatcc                                                  1159
```

<210> SEQ ID NO 9
<211> LENGTH: 1219
<212> TYPE: DNA
<213> ORGANISM: Arabidopsis thaliana

<400> SEQUENCE: 9

```
tcagcgctct cttttgtctc ctctgctttt ttctcttctc tcctcagaga ttcgaagctt       60
tttgtctccc ctgagtaacc aaattcaatg gccgacgatt gggatctcca cgccgtagtc      120
agaggctgct cagccgtaag ctcatcagct actaccaccg tatattcccc cggcgtttca      180
tctcacacaa accctatatt caccgtcgga cgacaaagta atgccgtctc cttcggagag      240
attcgagatc tctacacacc gttcacacaa gaatctgtcg tctcttcgtt ttcttgtata      300
aactacccag aagaacctag aaagccacag aaccagaaac gtcctctttc tctctctgct      360
tcttccggta gcgtcactag caaacccagt ggctccaata cctctagatc taaaagaaga      420
aagatacagc ataagaaagt gtgccatgta gcagcagaag cttttaaactc cgatgtctgg      480 gcatggcgaa agtacggaca gaaacccatc aaaggttcac catatccaag aggatactac      540
agatgtagta catcaaaagg ttgtttagcc cgtaaacaag tggagcgaaa tagatccgac      600
ccgaagatgt ttatcgtcac ttacacggcg gagcataatc atccagctcc gacacaccgt      660
aattctctcg ccggaagcac acgtcagaaa ccatccgatc aacagacgag taaatctccg      720
acgaccacta ttgctactta ttcatcgtct ccggtgactt cagccgacga atttgttttg      780
cctgttgagg atcatctagc ggtgggagat cttgacggag aagaagatct gttatctttg      840
tcggatacgt tggttagcga tgatttcttc gatgggttag aggaattcgc agccggagat      900
agcttttccg ggaactcggc tccggcgagt tttgatctct cttggggttgt gaacagtgcc      960 gccactacca ccggaggaat atgattagat tacgacggct tagaatactc ttattaggac     1020
agatttatag gattaaggaa ttattctcgg agcatatgta aaaataggat aaaagaaat      1080 gttctttgtt acttttttc gggttttctt cctattgttt ctaaacatct tagaaaaaat      1140
ttaattgtat attccttaag ctcgatacat cttgtttaac tcgagtacga tttacttatg     1200
gagttatggt ctttgtctc                                                  1219
```

<210> SEQ ID NO 10
<211> LENGTH: 927
<212> TYPE: DNA
<213> ORGANISM: Arabidopsis thaliana

<400> SEQUENCE: 10

```
ggcttatatg gacgaaggag acctagaagc aatagtcaga ggctactccg gctccggaga       60
```

```
cgcgttttcc ggcgaaagtt ccggtacgtt ttcaccttcg ttttgcctac cgatggagac    120
gtctagtttc tacgaaccgg agatggagac aagtggctta gatgagctcg gtgaacttta    180
caaacccttt taccctttct ccacacaaac gatcctcaca agctcggtct ctctccctga    240
agattcaaaa cctttccgag atgacaagaa acaacgatca catggttgtc ttttatccaa    300
cggatcaaga gctgatcata tccgaatttc agaatccaaa tcaaagaaaa gcaagaagaa    360
tcaacagaag agagttgttg agcaagtgaa agaagagaat ctgttgtcgg acgcatgggc    420
gtggcgtaaa tacgggcaga aacccatcaa aggatctcca tacccaagga gttattacag    480
atgcagtagc tcaaaagggt gtttggcaag aaaacaagtc gaaagaaatc ctcaaaaccc    540
ggagaaattc accataacat acactaatga gcacaatcat gaactaccaa cccggagaaa    600
ctcattagcc ggttcgactc gagcaaaaac ttcccaaccc aaaccaacct taaccaaaaa    660
atccgaaaaa gaagttgttt cttcccctac aagtaatcct atgatcccat ccgctgatga    720
atcttctgtt gcggttcaag aaatgagcgt tgcggaaacg agtacgcacc aagcggctgg    780
agcaatcgag ggccgccgct tgagtaacgg tttaccatcg gatttgatgt ccgggagcgg    840
aacttttcca agttttaccg gtgacttcga tgaactattg aatagccaag agttcttcag    900
tgggtattta tggaattact agagagc                                        927
```

`<210>` SEQ ID NO 11
`<211>` LENGTH: 1804
`<212>` TYPE: DNA
`<213>` ORGANISM: Arabidopsis thaliana

`<400>` SEQUENCE: 11

```
aaacttccat ttttcgtatg gctgcttctt ttcttacaat ggacaatagc agaaccagac     60
aaaacatgaa tggttctgct aattggtcac aacaatccgg aagaacatct acttcctctt    120
tggaagatct tgagatacca aagttcagat cttttgctcc ttcttcaatc tctatctctc    180
cttctcttgt ctctccttcc acttgtttca gtccctctct ttttctcgat tcccctgctt    240
ttgtctcctc ctctgctaac gttctagctt ctccaaccac aggagcttta atcacaaacg    300
taactaacca gaaaggtata atgaaggag acaagagcaa caacaacaac tttaacttat    360
tcgatttctc attccacaca caatcatcag gagtttctgc tccgaccaca actacaacta    420
caactacaac tacaacaaca caaacagtt ctatctttca atctcaggaa caacagaaga    480
agaaccagtc agaacaatgg agccaaaccg agactcgtcc aaacaatcaa gctgtatctt    540
acaatggaag agagcaaagg aaaggagagg atggttacaa ttggagaaag tacgacaaa    600 aacaggtgaa aggaagtgag aatcctcgga gttactataa gtgtactttc cctaattgtc    660
caacgaagaa gaaagtggag agatctttgg aaggtcagat cacagagatt gtgtataaag    720
gaagccacaa ccatcctaaa cctcagtcta ctagaagatc ttcttcgtct tcttcgactt    780
ttcattcagc tgtgtacaat gccagttttgg atcataatcg tcaagcttct tctgatcagc    840
ctaattccaa taatagcttt catcagtctg attcctttgg gatgcaacaa gaggataata    900
ctacttctga ttctgttggt gacgatgagt tcgaacaagg ctcatcgatt gtcagcagag    960
acgaagaaga ttgtgggagt gaacctgaag caaagagatg gaaaggggac aatgaaacaa   1020
atggtgggaa tggtggtgga agcaagacag tgagagagcc gagaatcgta gtgcagacaa   1080
cgagtgatat tgacattctt gacgacggtt acagatggag aaaatacggc cagaaagtcg   1140
ttaagggaaa cccaaatcca agaagctact acaagtgcac aaccatcggt tgtccagtga   1200
ggaaacatgt ggagagagca tcacacgaca tgagagcagt aatcacaacc tacgaaggga   1260
```

```
aacacaacca cgatgttcct gcagctcgtg gtagcggtta cgccacaaac agagcaccac    1320
aggattcgtc ttcagtcccg attagaccag ctgctattgc tggtcactcc aactacacta    1380
cttcttctca agcaccatat acacttcaga tgctgcacaa caacaacact aataccgggc    1440
cttttggtta cgccatgaac aacaataaca acaacagcaa ccttcaaacg caacaaaact    1500
ttgttggtgg tggattctct agagcaaagg aagaaccaaa cgaggagacc tcattttcg     1560 attcgtttat gccctgaaga aaaaggaac cagttgttcc ttttttatgt tccttttgta     1620
catttctgcc accaaaggat tttactactt actagttatc ctgcaggata gtaagtcaga    1680
cttctatagt ccatagagaa attttttcat ttgttttttc acacgcctgt aatatgttta    1740
atgtttgtac tttgtaccat agaactagaa cacggaataa aaccaatcaa ttttcagttt    1800
cttc                                                                 1804

<210> SEQ ID NO 12
<211> LENGTH: 1514
<212> TYPE: DNA
<213> ORGANISM: Arabidopsis thaliana

<400> SEQUENCE: 12
aatcctataa cactctcatt ctcatcatat cattcttcaa tctatataac ccattcttaa      60
ttatactcaa cacacattat attttttctga tcatatcatt ctttcagtcc atctatataa    120
ccaattcttg atttatactt aaaacacaca ttatacatct ttctcatcat agtttgtatc    180
aatttcctag agtaaactac ctaaaggaaa aaaaaatct attttgggaa tcatatacta     240
aaaatggaag gaagagatat gttaagttgg gagcaaaaga cattgctaag cgagcttatc    300
aatggatttg atgcggccaa aaagcttcag gcacgactta gagaagctcc gtcgccgtcg    360
tcatcatttt catcaccggc gacggctgtt gctgagacta cgagattct ggtgaagcag     420 atagtttctt cctacgagag atctcttctt ctgctaaact ggtcatcctc accgagcgta    480
caacttattc cgacgccggt tactgtagtc ccggtggcaa atcccggcag tgttccagaa    540
tctccggcat cgataaacgg aagtccgaga agtgaagagt ttgccgatgg aggaggttct    600
agcgagagtc atcatcgcca agattacatt ttcaattcaa agaaaagaaa gatgttacca    660
aagtggtcag aaaaagtgag aataagccca gagagaggct tagaaggacc tcaagatgat    720
gtctttagct ggagaaaata tggtcaaaaa gacatttag gcgccaaatt cccaaggagt     780
tattacagat gcacacatcg tagcacacaa aactgttggg caacgaaaca agtccagaga    840
tcagacgggg atgctacggt tttcgaagtg acgtacagag gaacacacac ttgttcgcag    900
gcgatcacaa gaacaccacc attagcctcg ccggagaagc gacaagacac cagagtcaaa    960
ccagccatta cccaaaagcc aaaggatatt ctcgagagtc ttaaatccaa cttaaccgtt    1020
cgaaccgatg ggcttgatga tggtaaagac gttttctcgt tccctgatac gccgccgttt    1080
tacaattacg gaactatcaa cggcgagttc ggccacgtgg agagttctcc gatcttcgac    1140
gttgttgact ggttcaatcc aacggtcgag attgacacaa ctttccccgc gttttacac     1200 gagtcgattt attattaatt aaaatttgta acagagaaat agatagtaac tagtaagtaa    1260
tgatcagcga gagttaaaac ataaaagtac ttagagtaat ctaacgatgc ataataagga    1320
atgttcaaca ggacttgaac atgatttcaa tactaagaga gatttatcta gctactggta    1380
gtagccgcag acttcttgtt gtaagcttcc acttccttt tgtatgcttc catcagtttt     1440
gcggcctttc cgttgtaaac ttgcttctct tcttcactca attcctgcaa agacgtattc    1500
gcacagatag atta                                                      1514
```

```
<210> SEQ ID NO 13
<211> LENGTH: 22
<212> TYPE: DNA
<213> ORGANISM: Artificial
<220> FEATURE:
<223> OTHER INFORMATION: PCR primer

<400> SEQUENCE: 13
ctcacggagg acagttcata ag                                              22

<210> SEQ ID NO 14
<211> LENGTH: 22
<212> TYPE: DNA
<213> ORGANISM: Artificial
<220> FEATURE:
<223> OTHER INFORMATION: PCR primer

<400> SEQUENCE: 14
gagatcagat tctgtcggtg tg                                              22

<210> SEQ ID NO 15
<211> LENGTH: 23
<212> TYPE: DNA
<213> ORGANISM: Artificial
<220> FEATURE:
<223> OTHER INFORMATION: PCR primer

<400> SEQUENCE: 15
gtaagctcat cagctactac cac                                             23

<210> SEQ ID NO 16
<211> LENGTH: 22
<212> TYPE: DNA
<213> ORGANISM: Artificial
<220> FEATURE:
<223> OTHER INFORMATION: PCR primer

<400> SEQUENCE: 16
accgctagat gatcctcaac ag                                              22

<210> SEQ ID NO 17
<211> LENGTH: 22
<212> TYPE: DNA
<213> ORGANISM: Artificial
<220> FEATURE:
<223> OTHER INFORMATION: PCR primer

<400> SEQUENCE: 17
atggacgaag gagacctaga ag                                              22

<210> SEQ ID NO 18
<211> LENGTH: 22
<212> TYPE: DNA
<213> ORGANISM: Artificial
<220> FEATURE:
<223> OTHER INFORMATION: PCR Primer

<400> SEQUENCE: 18
ccgcttggtg cgtactcgtt tc                                              22

<210> SEQ ID NO 19
<211> LENGTH: 22
<212> TYPE: DNA
<213> ORGANISM: Artificial
<220> FEATURE:
<223> OTHER INFORMATION: PCR primer
```

```
<400> SEQUENCE: 19
ctccgaccac aactacaact ac                                              22

<210> SEQ ID NO 20
<211> LENGTH: 22
<212> TYPE: DNA
<213> ORGANISM: Artificial
<220> FEATURE:
<223> OTHER INFORMATION: PCR primer

<400> SEQUENCE: 20
ggctctctca ctgtcttgct tc                                              22

<210> SEQ ID NO 21
<211> LENGTH: 23
<212> TYPE: DNA
<213> ORGANISM: Artificial
<220> FEATURE:
<223> OTHER INFORMATION: PCR primer

<400> SEQUENCE: 21
cctacgagag atctcttctt ctg                                             23

<210> SEQ ID NO 22
<211> LENGTH: 22
<212> TYPE: DNA
<213> ORGANISM: Artificial
<220> FEATURE:
<223> OTHER INFORMATION: PCR primer

<400> SEQUENCE: 22
agatcggaga actctccacg tg                                              22

<210> SEQ ID NO 23
<211> LENGTH: 30
<212> TYPE: DNA
<213> ORGANISM: Artificial
<220> FEATURE:
<223> OTHER INFORMATION: PCR primer

<400> SEQUENCE: 23
gactaagaga gaaagtaaga gataatccag                                      30

<210> SEQ ID NO 24
<211> LENGTH: 30
<212> TYPE: DNA
<213> ORGANISM: Artificial
<220> FEATURE:
<223> OTHER INFORMATION: PCR primer

<400> SEQUENCE: 24
cagcctttga tttcaatttg catgtaagag                                      30

<210> SEQ ID NO 25
<211> LENGTH: 29
<212> TYPE: DNA
<213> ORGANISM: Artificial
<220> FEATURE:
<223> OTHER INFORMATION: PCR primer 1

<400> SEQUENCE: 25 caccettgcg tagagagttt actgatgtc                                       29

<210> SEQ ID NO 26
<211> LENGTH: 29
<212> TYPE: DNA
```

```
<213> ORGANISM: Artificial
<220> FEATURE:
<223> OTHER INFORMATION: PCR primer

<400> SEQUENCE: 26
gttgacgagg atattgagga agttgtctg                                    29

<210> SEQ ID NO 27
<211> LENGTH: 29
<212> TYPE: DNA
<213> ORGANISM: Artificial
<220> FEATURE:
<223> OTHER INFORMATION: PCR primer

<400> SEQUENCE: 27
tcaccttgct ggttctggtt ctggttctg                                    29

<210> SEQ ID NO 28
<211> LENGTH: 29
<212> TYPE: DNA
<213> ORGANISM: Artificial
<220> FEATURE:
<223> OTHER INFORMATION: PCR primer

<400> SEQUENCE: 28 tctgatagggg gtgcaacccc atcttcttc                                   29

<210> SEQ ID NO 29
<211> LENGTH: 29
<212> TYPE: DNA
<213> ORGANISM: Artificial
<220> FEATURE:
<223> OTHER INFORMATION: PCR primer

<400> SEQUENCE: 29
agttgtggtt cagaccacca gtgacattg                                    29

<210> SEQ ID NO 30
<211> LENGTH: 29
<212> TYPE: DNA
<213> ORGANISM: Artificial
<220> FEATURE:
<223> OTHER INFORMATION: PCR primer

<400> SEQUENCE: 30
accccattga gtttccaaac cctgatgag                                    29

<210> SEQ ID NO 31
<211> LENGTH: 29
<212> TYPE: DNA
<213> ORGANISM: Artificial
<220> FEATURE:
<223> OTHER INFORMATION: PCR primer

<400> SEQUENCE: 31
cccatcaaaa gaaccaacca caacaagag                                    29

<210> SEQ ID NO 32
<211> LENGTH: 29
<212> TYPE: DNA
<213> ORGANISM: Artificial
<220> FEATURE:
<223> OTHER INFORMATION: PCR primer

<400> SEQUENCE: 32
atccgcacgc acttgaacca tgtattgtg                                    29
```

```
<210> SEQ ID NO 33
<211> LENGTH: 29
<212> TYPE: DNA
<213> ORGANISM: Artificial
<220> FEATURE:
<223> OTHER INFORMATION: PCR primer

<400> SEQUENCE: 33
aaggttcgta aacgatggct gatgctgag                                           29

<210> SEQ ID NO 34
<211> LENGTH: 29
<212> TYPE: DNA
<213> ORGANISM: Artificial
<220> FEATURE:
<223> OTHER INFORMATION: PCR primer

<400> SEQUENCE: 34
accttgatct tcatgctgct aggagcaag                                           29

<210> SEQ ID NO 35
<211> LENGTH: 760
<212> TYPE: DNA
<213> ORGANISM: Arabidopsis thaliana

<400> SEQUENCE: 35
ataacacaac aataaccatt atcaacttag aaaaatgaat tttactggct attctcgatt         60
tttaatcgtc tttgtagctc ttgtaggtgc tcttgttctt ccctcgaaag ctcaagatag        120
cccacaagat tatctaaggg ttcacaacca ggcacgagga gcggtaggcg taggtcccat        180
gcagtgggac gagaggggttg cagcctatgc tcggagctac gcagaacaac taagaggcaa      240
ctgcagactc atacactctg gtgggcctta cggggaaaac ttagcctggg gtagcggtga       300
cttgtctggc gtctccgccg tgaacatgtg ggttagcgag aaggctaact acaactacgc       360
tgcgaacacg tgcaatggag tttgtggtca ctacactcaa gttgtttgga gaaagtcagt      420
gagactcgga tgtgccaaag tgaggtgtaa caatggtgga accataatca gttgcaacta      480
tgatcctcgt gggaattatg tgaacgagaa gccatactaa tgaagtaatg atgtgatcat      540
gcatacacac gtacataaag gacgtgtata tgtatcagta tttcaataag gagcatcata      600
tgcaggatgt atcaatattt atcaaataat acaaataaga gctgagatta cgagaatcta      660
tttaaattaa aagttacata cttaattatt atagttatat atgtaaaata tgtggccttt      720
ttaaaagtta cataattaat tattatagtt aatgtctttc                             760

<210> SEQ ID NO 36
<211> LENGTH: 28
<212> TYPE: DNA
<213> ORGANISM: Artificial
<220> FEATURE:
<223> OTHER INFORMATION: PCR primer

<400> SEQUENCE: 36
aacacgtgca atggagtttg tggtcact                                            28

<210> SEQ ID NO 37
<211> LENGTH: 28
<212> TYPE: DNA
<213> ORGANISM: Artificial
<220> FEATURE:
<223> OTHER INFORMATION: PCR primer 2

<400> SEQUENCE: 37
```

```
accattgtta caccctcactt tggcacat                                           28
```

<210> SEQ ID NO 38
<211> LENGTH: 438
<212> TYPE: DNA
<213> ORGANISM: Arabidopsis thaliana

<400> SEQUENCE: 38

```
acacaacaca tacatctata cattgaaaac aaaatagtaa taatcatcat ggctaagttt   60
gcttccatca tcacccttat cttcgctgct cttgttctct ttgctgcttt cgacgcaccg  120
gcaatggtgg aagcacagaa gttgtgcgag aagccaagtg ggacatggtc aggggtttgc  180
ggaaacagta atgcatgcaa gaatcagtgc attaaccttg aaggagccaa acatggatca  240
tgcaactatg tcttcccagc acacaagtgt atctgttacg tcccatgtta aatctaccaa  300
taatctttgg tgctaaatcg tgtgtatttt acataaaata agtctctgtc actctatgag  360
taacttatg acatgcatat ttctgtttta atgtttattt tcccgttgtt gttacaataa  420
tataaaaata atttatgt                                                438
```

<210> SEQ ID NO 39
<211> LENGTH: 29
<212> TYPE: DNA
<213> ORGANISM: Artificial
<220> FEATURE:
<223> OTHER INFORMATION: PCR primer

<400> SEQUENCE: 39

```
agtgcattaa ccttgaagga gccaaacat                                     29
```

<210> SEQ ID NO 40
<211> LENGTH: 29
<212> TYPE: DNA
<213> ORGANISM: Artificial
<220> FEATURE:
<223> OTHER INFORMATION: PCR primer

<400> SEQUENCE: 40

```
aacagataca cttgtgtgct gggaagaca                                     29
```

<210> SEQ ID NO 41
<211> LENGTH: 30
<212> TYPE: DNA
<213> ORGANISM: Artificial
<220> FEATURE:
<223> OTHER INFORMATION: PCR primer

<400> SEQUENCE: 41

```
tggccattga tcttgttgac agaatgttga                                    30
```

<210> SEQ ID NO 42
<211> LENGTH: 29
<212> TYPE: DNA
<213> ORGANISM: Artificial
<220> FEATURE:
<223> OTHER INFORMATION: PCR primer

<400> SEQUENCE: 42

```
tcgtgcaatt tagcaaggta ctggtgatt                                     29
```

<210> SEQ ID NO 43
<211> LENGTH: 29
<212> TYPE: DNA
<213> ORGANISM: Artificial
<220> FEATURE:

<223> OTHER INFORMATION: PCR primer

<400> SEQUENCE: 43
tttaggcgcc aaattcccaa ggagttatt                                29

<210> SEQ ID NO 44
<211> LENGTH: 29
<212> TYPE: DNA
<213> ORGANISM: Artificial
<220> FEATURE:
<223> OTHER INFORMATION: PCR primer

<400> SEQUENCE: 44
tctggacttg tttcgttgcc caacagttt                                29

<210> SEQ ID NO 45
<211> LENGTH: 28
<212> TYPE: DNA
<213> ORGANISM: Artificial
<220> FEATURE:
<223> OTHER INFORMATION: PCR primer

<400> SEQUENCE: 45
ggtattctta ccttgaagta tcctattg                                 28

<210> SEQ ID NO 46
<211> LENGTH: 28
<212> TYPE: DNA
<213> ORGANISM: Artificial
<220> FEATURE:
<223> OTHER INFORMATION: PCR primer

<400> SEQUENCE: 46
ctcattgtag aaagtgtgat gccagatc                                 28

<210> SEQ ID NO 47
<211> LENGTH: 29
<212> TYPE: DNA
<213> ORGANISM: Artificial
<220> FEATURE:
<223> OTHER INFORMATION: PCR primer

<400> SEQUENCE: 47
agaatatatc cacgagcaca cggttccag                                29

<210> SEQ ID NO 48
<211> LENGTH: 29
<212> TYPE: DNA
<213> ORGANISM: Artificial
<220> FEATURE:
<223> OTHER INFORMATION: PCR primer

<400> SEQUENCE: 48
gacgaaaaga gagtggataa agcaaccac                                29

<210> SEQ ID NO 49
<211> LENGTH: 25
<212> TYPE: DNA
<213> ORGANISM: Artificial
<220> FEATURE:
<223> OTHER INFORMATION: PCR primer

<400> SEQUENCE: 49
cccatttgga cgtgaatgta gacac                                    25

<210> SEQ ID NO 50

```
<211> LENGTH: 28
<212> TYPE: DNA
<213> ORGANISM: Artificial
<220> FEATURE:
<223> OTHER INFORMATION: PCR primer

<400> SEQUENCE: 50
atgaagctaa agatttctct aatcgctc                                         28

<210> SEQ ID NO 51
<211> LENGTH: 27
<212> TYPE: DNA
<213> ORGANISM: Artificial
<220> FEATURE:
<223> OTHER INFORMATION: PCR primer

<400> SEQUENCE: 51
gaaatgcacc atttggatct cttccag                                          27

<210> SEQ ID NO 52
<211> LENGTH: 1249
<212> TYPE: DNA
<213> ORGANISM: Arabidopsis thaliana

<400> SEQUENCE: 52
atatcatttt tcacagaatc atagaaaaat caagaaaatg tctgaatcaa ggagcttagc      60
ctcaccacca atgttgatga ttcttctcag ccttgtaata gcttccttct caaccacac     120 agctggacaa tcggagtat gctacgggat gctaggcgat accttgccaa gtccatcgga     180
cgttgtggct ctttacaaac aacaaaacat ccagcgaatg cggctctacg ccctgaccc     240 aggcgctctt gccgctctcc gtggctctga catcgagctc atcctcgacg ttcccagttc    300
agatcttgaa cgtctcgcct ccagtcaaac ggaggccgac aagtgggttc aagaaaacgt    360
tcagagctac agagatggtg tcagattccg gtacatcaac gttggaaatg aggtgaaacc    420
ctcagttggg gggttttctct acaagcaat gcagaacatc gagaacgcgg tttctggagc    480
agggcttgaa gtcaaggtct caacagctat agccactgac accaccactg atacgtctcc    540
tccgtctcaa ggaaggttca gggatgagta taagagcttt ctcgaaccag tgataggttt    600
cttggcaagc aagcaatctc ccttgctcgt gaatctctac ccttacttca gctacatggg    660
agacacggcc aacatccatc tagactacgc tctgttcacc gcccagtcca ctgttgataa    720
cgatccaggg tactcatacc aaaacctatt cgacgcaaat ctcgactcgg tttatgcagc    780
attggagaaa tcaggggcg gatcgttgga aatcgtggtg tcgagaccg gttggcccac     840 agagggagca gtcgggacga gtgtggaaaa cgcaaagact tatgttaaca atttgataca    900
acatgtgaag aatggatcac cgagaaggcc agggaaagct atagagactt atatattcgc    960
tatgttcgat gagaataaga aggaaccaac gtatgagaag ttttgggga ctgtttcatcc    1020 agatcgacag tctaagtatg aagttaattt caactaatcc ttagagactt gtgggctttt   1080
tatgtaagcg tatttaaaaa ttgggaactt gttgtagtaa taggaataa ttaatgcgct    1140 ttcagcgtgt agtatgttgt tatttttaag gttataaatg agctgcaagc ataaataagg   1200
aaaaaaaata gcatgggcct ataggcccaa taataaaaca agcttgctt                1249

<210> SEQ ID NO 53
<211> LENGTH: 617
<212> TYPE: PRT
<213> ORGANISM: Arabidopsis thaliana

<400> SEQUENCE: 53
```

```
Met Lys Leu Lys Ile Ser Leu Ile Ala Pro Ile Leu Leu Leu Phe Ser
1               5                   10                  15

Phe Phe Phe Ala Val Glu Ser Lys Cys Arg Thr Ser Cys Pro Leu Ala
                20                  25                  30

Leu Ala Ser Tyr Tyr Leu Glu Asn Gly Thr Thr Leu Ser Val Ile Asn
            35                  40                  45

Gln Asn Leu Asn Ser Ser Ile Ala Pro Tyr Asp Gln Ile Asn Phe Asp
50                  55                  60

Pro Ile Leu Arg Tyr Asn Ser Asn Ile Lys Asp Lys Asp Arg Ile Gln
65                  70                  75                  80

Met Gly Ser Arg Val Leu Val Pro Phe Pro Cys Glu Cys Gln Pro Gly
                85                  90                  95

Asp Phe Leu Gly His Asn Phe Ser Tyr Ser Val Arg Gln Glu Asp Thr
            100                 105                 110

Tyr Glu Arg Val Ala Ile Ser Asn Tyr Ala Asn Leu Thr Thr Met Glu
            115                 120                 125

Ser Leu Gln Ala Arg Asn Pro Phe Pro Ala Thr Asn Ile Pro Leu Ser
130                 135                 140

Ala Thr Leu Asn Val Leu Val Asn Cys Ser Cys Gly Asp Glu Ser Val
145                 150                 155                 160

Ser Lys Asp Phe Gly Leu Phe Val Thr Tyr Pro Leu Arg Pro Glu Asp
                165                 170                 175

Ser Leu Ser Ser Ile Ala Arg Ser Ser Gly Val Ser Ala Asp Ile Leu
            180                 185                 190

Gln Arg Tyr Asn Pro Gly Val Asn Phe Asn Ser Gly Asn Gly Ile Val
            195                 200                 205

Tyr Val Pro Gly Arg Asp Pro Asn Gly Ala Phe Pro Pro Phe Lys Ser
210                 215                 220

Ser Lys Gln Asp Gly Val Gly Ala Gly Val Ile Ala Gly Ile Val Ile
225                 230                 235                 240

Gly Val Ile Val Ala Leu Leu Leu Ile Leu Phe Ile Val Tyr Tyr Ala
                245                 250                 255

Tyr Arg Lys Asn Lys Ser Lys Gly Asp Ser Phe Ser Ser Ser Ile Pro
            260                 265                 270

Leu Ser Thr Lys Ala Asp His Ala Ser Ser Thr Ser Leu Gln Ser Gly
            275                 280                 285

Gly Leu Gly Gly Ala Gly Val Ser Pro Gly Ile Ala Ala Ile Ser Val
290                 295                 300

Asp Lys Ser Val Glu Phe Ser Leu Glu Glu Leu Ala Lys Ala Thr Asp
305                 310                 315                 320

Asn Phe Asn Leu Ser Phe Lys Ile Gly Gln Gly Gly Phe Gly Ala Val
                325                 330                 335

Tyr Tyr Ala Glu Leu Arg Gly Glu Lys Ala Ala Ile Lys Lys Met Asp
            340                 345                 350

Met Glu Ala Ser Lys Gln Phe Leu Ala Glu Leu Lys Val Leu Thr Arg
            355                 360                 365

Val His His Val Asn Leu Val Arg Leu Ile Gly Tyr Cys Val Glu Gly
370                 375                 380

Ser Leu Phe Leu Val Tyr Glu Tyr Val Glu Asn Gly Asn Leu Gly Gln
385                 390                 395                 400

His Leu His Gly Ser Gly Arg Glu Pro Leu Pro Trp Thr Lys Arg Val
                405                 410                 415

Gln Ile Ala Leu Asp Ser Ala Arg Gly Leu Glu Tyr Ile His Glu His
            420                 425                 430
```

Thr Val Pro Val Tyr Val His Arg Asp Ile Lys Ser Ala Asn Ile Leu
            435                 440                 445

Ile Asp Gln Lys Phe Arg Ala Lys Val Ala Asp Phe Gly Leu Thr Lys
        450                 455                 460

Leu Thr Glu Val Gly Gly Ser Ala Thr Arg Ala Met Gly Thr Phe
465                 470                 475                 480

Gly Tyr Met Ala Pro Glu Thr Val Tyr Gly Glu Val Ser Ala Lys Val
                485                 490                 495

Asp Val Tyr Ala Phe Gly Val Val Leu Tyr Glu Leu Ile Ser Ala Lys
            500                 505                 510

Gly Ala Val Val Lys Met Thr Glu Ala Val Gly Glu Phe Arg Gly Leu
        515                 520                 525

Val Gly Val Phe Glu Glu Ser Phe Lys Glu Thr Asp Lys Glu Glu Ala
    530                 535                 540

Leu Arg Lys Ile Ile Asp Pro Arg Leu Gly Asp Ser Tyr Pro Phe Asp
545                 550                 555                 560

Ser Val Tyr Lys Met Ala Glu Leu Gly Lys Ala Cys Thr Gln Glu Asn
                565                 570                 575

Ala Gln Leu Arg Pro Ser Met Arg Tyr Ile Val Val Ala Leu Ser Thr
            580                 585                 590

Leu Phe Ser Ser Thr Gly Asn Trp Asp Val Gly Asn Phe Gln Asn Glu
        595                 600                 605

Asp Leu Val Ser Leu Met Ser Gly Arg
    610                 615

<210> SEQ ID NO 54
<211> LENGTH: 1872
<212> TYPE: DNA
<213> ORGANISM: Glycine max

<400> SEQUENCE: 54
atggaactca aaaagggtt acttgtgttc tttttgctgc tggagtgtgt tgttacaat      60 gtggaatcca gtgtgtgaa gggatgtgat gtagctttcg cttcctacta tgtcagtccg     120
gatttaagct tagaaaatat agcgcggttg atggaatcaa gcattgaagt tataatcagc    180
ttcaatgaag acaatatatc gaatggttat ccgctatcct tttacagact caatattcca    240 ttccctgtg actgtattgg tggtgagttt ctggggcatg tgtttgagta ctcagcttct     300
gcaggtgaca cctatgattc gattgcgaaa gtgacatacg ccaatctcac caccgttgag    360
cttttgcgga ggttcaatgg ctatgatcaa aatggtatac ctgcaaatgc cagggttaat    420
gtcacggtca attgttcttg tgggaacagc caggtttcaa aagattatgg gatgtttatt    480
acctatccac tcaggcctgg gaataatttg catgatattg ccaatgaggc tcgtcttgat    540
gcacagttgc tgcagcgtta caatcctggt gtcaatttca gcaaagagag tgggactgtt    600
ttcattccag gaagagatca acatggagac tatgttccct gtacccgag aaaaacaggt    660 cttgctaggg gtgctgcagt tggaatatct atagcaggaa tatgcagtct tctattatta    720
gtaatttgct tatatggcaa gtacttccag aagaaggaag gagagaaaac taaattgcca    780
acagaaaatt ctatggcgtt ttcaactcaa gatggtacgg tctctggaag tgcagaatat    840
gaaacttcag gatccagtgg gactgctagt gctactggcc tcacaggcat atggtggca    900 aaatcaatgg agttctcata tcaagaacta gccaaggcta caaataactt tagcttggag   960
aataaaattg tcaaggtgg atttggagct gtctattatg cagaactgag aggcgagaaa  1020
actgcaatta agaagatgga tgtgcaagca tcgacagaat ttctttgcga gttgaaggtc  1080

```
ttaactcacg ttcatcactt taatctggta cagcatcctt caaacaaccc caagcatgtg    1140
cgcttgattg gatattgtgt tgagggatcc ctttccttg tatatgaata tattgacaat     1200
ggaaacttag gccaatattt gcatggtaca gggaaagatc ctttgccatg gtctggtcga    1260
gtgcaaattg cgctagattc agcaagaggc cttgaatata ttcacgagca cactgtgcct    1320
gtgtatatcc atcgtgatgt aaaatcagca aatatattaa tagacaagaa catccgtgga    1380
aaggttgcag attttggctt gaccaaactt attgaagttg gaggctccac acttcacact    1440
cgtcttgtgg gaacatttgg atacatgcca ccagaaatg ctcaatatgg tgacattct      1500 ccaaaagtag atgtatatgc ttttggagtg gttctttatg aacttatttc tgcaaagaat    1560
gctgttctaa agacaggtga atctgttgct gaatcaaagg ccttgtagc tttgtttgaa     1620 gaagcactta atcagagtaa tccttcagaa agtattcgca aactggtgga tcctaggctt    1680
ggcgaaaact atccaattga ttcagttctc aagattgctc aacttgggag gcttgtaca    1740 agagataacc cactactacg cccgagtatg aggtctatag ttgttgctct catgacactt    1800
tcatcaccta ctgaggattg cgacacttcc tacgaaaatc agactctcat aaatctactg    1860
tctgtgagat ga                                                        1872

<210> SEQ ID NO 55
<211> LENGTH: 1860
<212> TYPE: DNA
<213> ORGANISM: Glycine max

<400> SEQUENCE: 55
atggaactca aaaatggtt actgttcttt ttgttgctgg agtatgtttg ttgcaatgcg       60
gagtctaagt gtgtgaaggg atgtgatgta gctttagctt catactatgt tagtccaggg    120
tatttactct tggaaaatat aacgcgcttg atggaatcaa ttgttctgtc caattctgat    180
gttataatct acaacaaaga caaatattc aatgaaaatg tgctagcatt ttccagactc     240
aatattccat tccctgtgg ctgtatcgat ggtgagtttc tggggcatgt gtttgagtac     300
tcagcttctg caggtgacac ctatgattcg attgcgaaag tgacatatgc caatctcacc    360
actgttgagc ttttgcggag gttcaacagt tatgatcaaa atggtatacc tgcaaatgcc    420
acggttaatg tcacggtcaa ttgttcttgt gggaacagcc aggtttcaaa agattatggg    480
ctgtttatta cctatctact caggcctggg aataatttgc atgatattgc caacgaggct    540
cgccttgatg cacagttgct acagagttac aatcctggtg tcaatttcag caaagagagt    600
ggggatattg ttttcattcc aggaaaagat caacatggag attatgttcc cttgtacct    660 agaaaaacag caggtcttgc tacgagtgct tcagttggaa taccaatagc aggaatatgc    720
gttcttctat tagtaatttg catatatgtc aagtacttcc agaagaagga aggagagaaa    780
gctaaattgg caacagaaaaa ttctatggcg tttttcaactc aagatgtctc tggaagtgca    840
gaatatgaaa cttcaggatc cagtgggact gctagtacta gtgcaactgg ccttacaggc    900
attatggtgg caaaatcaat ggagttctca tatcaagaac tagccaaggc tacaaataac    960
ttcagcttgg agaataaaat tggtcaaggt ggatttggaa ttgtctatta tgcagaactg   1020
agaggcgaga aaactgcaat caagaagatg acgtgcaag catcaacaga atttctttgc    1080
gagttgaagg tcttaactca tgttcatcac ttgaatctgg tgcgcttgat tggatattgt   1140 gttgagggt ctcttttcct tgtatatgaa tatattgaca atggaaactt aggccaatat    1200
ttgcatggta cagggaaaga tccttttccta tggtctagcc gagtgcaaat tgcactagat    1260
tcagcaagag gccttgaata tattcacgag cacactgtgc cagtgtatat ccatcgtgat    1320
```

| | |
|---|---|
| gtaaaatctg caaatatatt aatagacaaa aacttccgtg gaaaggttgc agattttggt | 1380 |
| ttgaccaaac ttattgaagt tggaggttcc acacttcaaa ctcgtcttgt gggaacattt | 1440 |
| ggatacatgc caccagaata tgctcaatat ggtgacattt ctccaaaagt agatgtatat | 1500 |
| gcttttggag ttgttcttta tgaacttatt tctgcaaaga atgctgtcct aaagacagta | 1560 |
| gaatctgttg ctgaatcaaa gggccttgta gctttgtttg aagaagcact taatcagagt | 1620 |
| aatccttcag aaagtattcg caaactggtg gatcctaggc ttggagaaaa ctatccaatc | 1680 |
| gattcagttc tcaagattgc tcaacttggg agagcttgta caagagataa cccactacta | 1740 |
| cgcccgagta tgaggtctat agttgttgct ctcttgacac tttcatcacc tactgaggat | 1800 |
| tgctatgatg acacttccta cgaaaatcag actctcataa atctactgtc tgtgagatga | 1860 |

<210> SEQ ID NO 56
<211> LENGTH: 1803
<212> TYPE: DNA
<213> ORGANISM: Glycine max

<400> SEQUENCE: 56

| | |
|---|---|
| atggaacaca gtttcagatt accagttttc ttcttgttat gtgcctctat agcgttcagt | 60 |
| gcagaatcca agtgtagcag gggttgtgat ttagctctag cttcctacta tctatcacaa | 120 |
| ggtgacttga catatgtatc aaagcttatg gaatctgagg ttgtttcaaa acctgaagat | 180 |
| attctcagct acaacactga caccataaca aacaaagacc tgttgcctgc ctctatcaga | 240 |
| gtgaacgttc cattcccttg tgactgcatt gatgaagagt tcttggcca tacttttcaa | 300 |
| tacaacctta caacaggaga cacttatttg tccattgcca ctcagaacta ctctaatttg | 360 |
| accactgctg agtggttgcg gagcttcaac agatatttac cagctaatat tcctgatagt | 420 |
| gggactctta atgtcaccat taactgttcc tgtgggaata gtgaagtttc aaggattat | 480 |
| ggattgttca tcacgtaccc tcttagacct gaggattctt tgcagtcgat tgccaacgag | 540 |
| actggcgttg atcgtgactt gctggttaag tacaacccgg gtgtaaattt tagccaaggg | 600 |
| agtggtctgg tttatattcc aggaaaaggt cttgcgggtg gtgttattgc tggaatatct | 660 |
| attggagtag taacaggact tctgctattg gcattttgtg tgtatgttac atattaccga | 720 |
| agaaagaagg tatggaagaa ggattttgctc tcagaagaat ccaggaagaa ctctgctaga | 780 |
| gttaagaatg tccctctttc agatgaagcc tctggtgatt cggctgcaga aggtggtact | 840 |
| aacaccattg cattagggt gaacaaatca gcagagtttt catatgagga actagccaat | 900 |
| gccacaaata acttcagttt ggctaataaa attggtcaag tggttttgg ggtagtctat | 960 |
| tatgcagagc tgaatggaga gaaagctgca ataaaaaaga tggacataca agcaacaaga | 1020 |
| gaatttcttg cggaattgaa agtgttgaca catgttcatc acttgaacct ggtgcgcttg | 1080 |
| attggatatt gtgttgaggg ctccctttt cttgtctatg agtacattga gaatggcaac | 1140 |
| ttaggacaac atctacgtaa atcaggtttc aatcctttgc catggtctac ccgagttcaa | 1200 |
| attgctctgg attcagccag aggtcttcaa tacattcatg agcatacggt acctgtatat | 1260 |
| atccatcgtg acataaagtc ggaaaacatt ttaatagaca aaaacttcgg tgcaaaggtt | 1320 |
| gcagactttg gattaaccaa gttgattgat gttggaagtt catcacttcc cactgttaat | 1380 |
| atgaagggca catttggtta catgccacca gaatatgcat atggcaatgt ttctcccaaa | 1440 |
| atagatgtct atgcttttgg agttgttctt tatgaactaa tttctggtaa agaagcattg | 1500 |
| agcagaggtg gtgtctctgg tgctgaacta aagggccttt ttgatgaagt atttgatcag | 1560 |
| caagatacca cagaaggtct taaaaaactg gtggatccta ggcttggaga taactaccca | 1620 |

-continued

| attgattcag tttgcaagat ggcacaactt gctagagcat gcacagagag cgatccacaa | 1680 |
| caacgtccaa atatgagttc tgttgtggtt actctcacag cacttacttc aactactgag | 1740 |
| gattgggata ttgcttccat cattgaaaat ccaactcttg caaatctaat gtctggtaaa | 1800 |
| taa | 1803 |

<210> SEQ ID NO 57
<211> LENGTH: 1740
<212> TYPE: DNA
<213> ORGANISM: Glycine max

<400> SEQUENCE: 57

| atgaccacac acccaactac aaaatcaaaa ccaccccatg ttttcttcct tctcttaatt | 60 |
| cagttattga tttcgattac aagagtcaaa ggtagttgcg ttactggctg caaccttgct | 120 |
| ttagcttcct attacttagg aacggcaca aacctcactt acattagcaa cctcttcgga | 180 |
| aggccaacat cggagattct aaaatacaac ccaagtgtta agaacccaaa cgtgattctt | 240 |
| agccaaacac ggatcaacgt gccctttcg tgtgactgct tgaacggtgc gttttgggg | 300 |
| cacacttttct cgtacgcgat ccaacacgga aacacgtaca agatagttgc cgaggttgat | 360 |
| ttctcgaacc tcacgacgga ggattgggtt ggcagggtca acagttaccc gccgaatcag | 420 |
| atacccgaca acgtgaacat caacgtcacc gttaactgtt cctgcggaaa ccgacacgtg | 480 |
| tccaaggatt atgggctgtt catgacgtac ccgcttcggg tcggtgacag cttacagcgg | 540 |
| gttgcggccg aagccggcgt gccggcgag ctgctgctga ggtacaaccc cacggcggat | 600 |
| ttcggtgctg ggaatggact cgtgtttgtg ccggctaaag ttgaagacca gtgcacattg | 660 |
| cacctctgga tgaccctagg gccagccctg gttgtcttct ggaaatctgg tgggatgatt | 720 |
| tgtaagggtt gggggcactc cttgcaccct tatcctatta tgtatttcca ttttcattta | 780 |
| ctatacacaa atggtccaag cacaaagact caacatatga aaaatggaaa cttttccacca | 840 |
| atgcagttga tcaggaat atctagtgga gccattgctg gcatagctgt tggaggagct | 900 |
| gttgggtct taattttggc acttcttcta tatgttggac tacgcagaag aaggaaagtg | 960 |
| gctgaggtat cccttctccc agtcccagga gcatctgaag atcagtgtag tccactccaa | 1020 |
| ctccatcatg gtattggttg tggaagcagc ttggacaagg catctgaatc ttctgttgta | 1080 |
| gcctctccaa ggttgacagg gattacagtg gacaagtcag tggagttccc atatgaggag | 1140 |
| ctagacaagg ctactgatgg ctttagtgcg gctaatataa ttggtcgagg tggctttgga | 1200 |
| tctgtttact atgctgagct ccggaatgag gtgaggttaa taggatattg tgttgagggc | 1260 |
| tccttatttt tggtttatga gtacattgag aacggcaatt taagtcaaca tttgcgaggc | 1320 |
| tcagggaggg atccgttaac atgggcagct cgagttcaaa ttgcccttga tgcagcaaga | 1380 |
| ggattggaat acatccatga gcacactgtt cctgtctaca tccatagaga tattaaatca | 1440 |
| gcaaacattt tgatagacaa aaactttcgt gcaaagtttg aagaagttct tggtctgtca | 1500 |
| gatccaaaag tagatcttcg tcaacttatt gaccctacac ttggtgacaa ctaccctctt | 1560 |
| gactcggtat ttaaggtgtc tcagcttgcc aaagcatgta cacatgagaa ccctcaactt | 1620 |
| aggccaagca tgagatcaat tgtagttgcc ttaatgacac tttcatctgc aactgaggat | 1680 |
| tgggatgttg gctccttcta tgaaaaccaa gctttggtgc acctaatgtc tggaaggtag | 1740 |

<210> SEQ ID NO 58
<211> LENGTH: 1902
<212> TYPE: DNA
<213> ORGANISM: Glycine max

<400> SEQUENCE: 58

```
atggatctct ttcccttcat ccccatcatc attttcacac tattgatcca caacttctct      60
ctgattctgg ggcagcaacc ttacattggt ttaggcacag tagcgtgccc aagaaggggt     120
aacaaaaatt ctatccgtgg ttacacttgc aatggtgcaa accatagctg ccaaagttac     180
ctcaccttca gatctcaacc catctacaac tctgtcaaga caatatcaac tttgttgggt     240
tctgacccat cccagcttgc taaaataaac tcagtttcca tgaatgacac ctttgaaaca     300
aacaagttgg ttattgttcc ggtcaactgt tcctgtgcag gtgagtatta tcaaacaaac     360
acatcctatg agttccataa ttcagaaact tacttcttga ttgccaacaa tacttttgag     420
ggcctcacaa catgccaagc tttggagaac caaaaccaca ccctgcaaa catataccct      480
ggtagaaggc ttttagtgcc tcttagatgt gcttgtccca caagaatca aactgagaaa      540
ggcatcaggt acctcctaag ttacttggta aactggggtg attctgtttc attcattagt     600
gagaaatttg gtgtcaactt tatgaccact cttgaagcta atacttac tctcacccaa       660
gccacgatct atcccttac cacaattcta gttcccttc atgacaagcc ctcaagttct       720
caaactgttt cgccaactcg gcgcactcca ccacctctc ctccctcttc tgatcatagc      780
tcaaacaaaa catgggtgta tgtagttgtt ggggttgttg tgggagctat tgccttaata    840
tcggttctct gtgctgtcat tttcttcaca cgctatcgca aaaatagaaa gaaagatgac    900
tcagtggtag tagggtccaa gagttttgag gcaattgagg aaaaaccaga agtgaaagtg    960
aatgaaaaat tgtcagagat catatctggc atagctcagt ctttcaaagt gtataatttt   1020
gaggaactac agcgtgcaac agataacttt agtcctagca gctggatcaa agggtctgtt   1080
tatcgcggtg tgattaacgg tgatttggct gcaattaaaa ggatagaagg agatgtgtca   1140
aaagagatag agatactgaa caaaatcaac cattccaatg ttatacgcct ttccggggtt   1200
agcttccacg agggggttg gtaccttgtt tatgagtatg ccgctaatgg ggacttgagt   1260
gaatggatct acttccacaa cgtgaatggg aaatttctga gttggacgca gagaatgcag   1320
attgcattgg atgtggccac aggacttgac tatcttcaca gtttcacttc tcctcctcat   1380
atccacaagg atataaacag cagtaacatt cttctggatg gtgatttcag gggaaaggtc   1440
acgaatttaa gccttgctag gtgtttggaa ggaggggacg atcaacttcc cgcgacgagg   1500
cacattgttg ggacaagagg ctacatggct ccagagtatt tggaaaatgg tcttgtgtct   1560
acaaagcttg atgtgtatgc atttggggta cttatgctgg aaatggtcac tggaaaagag   1620
gttgctgcta ttttaactga agatgagaca aaattgtcac atgttttaag tggcatactt   1680
ggtgaggaaa gtggcaagga gatgttgaag gagtttgtgg atccctcttt gggagaaat   1740
tgtccattgg aacttgctat gtttgtgatt gaaatgattg ataattgcat aaagacagat   1800
ccggcaagtc gccctagtgt gcatgagatt gtgcaatcta tgtcaagaac cctgaagtct   1860
tcactgagtt gggaaaggtc aatgaatgtc ccacgaaatt aa                       1902
```

<210> SEQ ID NO 59
<211> LENGTH: 1797
<212> TYPE: DNA
<213> ORGANISM: Glycine max

<400> SEQUENCE: 59

```
atggctgtct ctttcccctt tcttcctctc cactctcaga ttctttgtct tgtgatcatg      60
ttgttttcca ctaatattgt agctcaatca caacaggaca atagaacaaa ctttcatgc      120
ccttctgatt caccgccttc atgtgaaacc tatgtaacat acattgctca gtctccaaat    180
```

```
tttttgagtc taaccaacat atccaatata tttgacacaa gcccttatc cattgcaaga    240 gccagtaact tagagcctat ggatgacaag ctagtcaaag accaagtctt actcgtacca    300
gtaacctgtg gttgcactgg aaaccgctct tttgccaata tctcctatga gatcaaccaa    360
ggtgatagct tctactttgt tgcaaccact tcatacgaga atctcacgaa ttggcgtgca    420
gtgatggatt taaaccccgt tctaagtcca aataagttgc caataggaat ccaagtagta    480
tttcctttat tctgcaagtg cccttcaaag aaccagttgg acaaagagat aaagtacctg    540
attacatacg tgtggaagcc cggtgacaat gtttcccttg taagtgacaa gtttggtgca    600
tcaccagagg acataatgag tgaaaacaac tatggtcaga actttactgc tgcaaacaac    660
cttccagttc tgatcccagt gacacgcttg ccagttcttg ctcgatctcc ttcggacgga    720
agaaaaggcg gaattcgtct tccggttata attggtatta gcttgggatg cacgctactg    780
gttctggttt tagcagtgtt actggtgtat gtatattgtc tgaaaatgaa gactttgaat    840
aggagtgctt catcggctga aactgcagat aaactacttt ctggagtttc aggctatgta    900
agtaagccta ccatgtatga aactgatgcg atcatggaag ctacaatgaa cctcagtgag    960
cagtgcaaga ttggggaatc agtgtacaag gcaaacatag agggtaaggt tttggcagta   1020
aaaagattca aggaagatgt cacggaagag ctgaaaattc tgcagaaggt gaatcatggg   1080
aatctggtga aactaatggg tgtctcatca gacaatgatg gaaactgttt tgtggtttat   1140
gaatacgctg aaaatgggtc tcttgatgag tggctattct ccaagtcttg ttcagacaca   1200
tcaaactcaa gggcatccct tacatggtgt cagaggataa gcatggcagt ggatgttgcg   1260
atgggtttgc agtacatgca tgaacatgct tatccaagaa tagtccacag ggacatcaca   1320
agcagtaata tccttcttga ctcgaacttt aaggccaaga tagcaaattt ctccatggcc   1380
agaactttta ccaaccccat gatgccaaag atagatgtct ttgcatttgg ggtggttctg   1440
attgagttgc ttaccggaag gaaagccatg acaaccaagg aaaatggtga ggtggtcatg   1500
ctgtggaagg acatttggaa gatctttgat caagaagaga atagagagga gaggctcaaa   1560
aaatggatgg atcctaagtt agagagttat tatcctatag attacgctct cagcttggcc   1620
tccttggcgg tgaattgtac tgcagataag tctttgtcca gaccaaccat tgcagaaatt   1680
gtccttagcc tctcccttct cactcaacca tctcccgcaa cattggagag atccttgact   1740
tcttctggat tggatgtaga agctactcaa attgtcactt ccatagcagc tcgttga     1797

<210> SEQ ID NO 60
<211> LENGTH: 1800
<212> TYPE: DNA
<213> ORGANISM: Glycine max

<400> SEQUENCE: 60
atggctgtct tcttttcctt tcttccgctc cgttctcaga ttctttgtct tgtacttatg     60 ttgttttca ctaatattgt agctcaatca caacagacca atgaaacaaa cttttcatgc    120
ccttctgatt caccaccgcc ttcatgtgaa acctatgtaa catacattgc tcagtctcca    180 aatttttga gtctaaccag catatccaat atatttgaca caagtccttt atccattgca    240
agagcaagta acttagagcc tgaagacgac aagctgatcg cagaccaagt cttactgata    300
ccagtaacct gtggttgcac tggaaaccgt tctttcgcca atatctccta tgagatcaac    360
ccaggtgata gcttctactt tgttgcaacc acttcatacg agaatctcac gaattggcgt    420
gtagtgatga atttaaaccc cagtctaagt ccaaatacgt tgccaatagg aatccaagta    480
gtatttcctt tattctgcaa gtgtccttca agaaccagt tggacaaagg gataaagtac    540
```

```
ctgattacat acgtgtggca gcccagtgac aatgtttccc ttgtaagtga aaagtttggt    600
gcatcaccag aggacatatt gagtgaaaac aactatggtc agaactttac tgctgcaaac    660
aaccttccag ttctgatccc agtgacacgc ttgcctgttc ttgctcaatc tccttcagat    720
gtaagaaaag gcggaattcg tcttccagtt ataattggta ttagcttggg atgcacgcta    780
ctggtcgtgg ttttagcagt attactggtg tatgtatact gtctgaaaat taagagtttg    840
aataggagtg cttcatcagc tgaaactgca gataaactac tttctggagt ttcaggctat    900
gtaagtaagc ctaccatgta tgaaactgat gcgatcatgg aagctaccat gaacctcagt    960
gagcagtgca agattgggga atcagtgtac aaggcaaaca tagagggtaa ggttttggca   1020
gtaaaaagat tcaaggaaaa tgtcacagag gagttgaaaa ttctgcagaa ggtgaatcat   1080
ggaaatctgg tgaaattaat gggtgtctcg tcagacaatg atggaaattg ttttgtggtt   1140
tatgaatatg ctcaaaatgg atctcttgat gagtggctat tctacaagtc ttgttcagac   1200
acatcagact caagggcctc ccttacatgg tgtcagagga taagcatagc agtggatgtt   1260
gcaatgggtt tgcagtacat gcatgaacat gcatatccaa gaatagtcca cagggacatc   1320
gcaagcagca atatccttct tgactcaaac ttcaaggcca agatagcaaa tttctccatg   1380
gccagaactt ttaccaaccc cacgatgcca aagatagatg tctttgcatt tggggtggtt   1440
ctgatagagt tgcttactgg taggaaagcc atgacaacca aggaaaatgg tgaggtagtt   1500
atgctgtgga aggacatttg gaagatcttt gatcaagaag agaatagaga ggagaggctc   1560
aaaaaatgga tggatcctaa gttagagagt tattatccta tagattatgc tctcagcttg   1620
gcctccttgg cagtgaattg tactgcagat aagtctttgt ccagatcaac cattgcagaa   1680
attgtcctta gcctctccct tctcactcaa ccatctcccg tgacattgga gagatccttg   1740
acttcttctg gattagatgt agaagctact caaattgtca cttccatagc agctcgttga   1800

<210> SEQ ID NO 61
<211> LENGTH: 1794
<212> TYPE: DNA
<213> ORGANISM: Glycine max

<400> SEQUENCE: 61
atggggcctt caccttcctt cctttacact tgcaatggct tcaacaaaac ctgcatgtcc     60
ttcctcatct tcaaatccaa acctcctttc aactccataa ctacaatctc caacctcaca    120
tcatcaaacc cagaagagct tgcaagaatc aatgatgtca ctgtgctcaa agtgttttca    180
actgggaaag aggtgattgt cccctttgaac tgttcttgtt taactaggga atattaccaa    240
gctgaaacca atatgtatt ggggcaatcc ccaacatatt tcacggtggc aaatgatact    300
tttgagggtt tgaccacttg tgatacctc atgcgtgcta attcatatgg tgaacttgat    360
ttgcttcctg gcatggaact gcacgtgcca ctcagatgtg cttgtcctac atggcatcag    420
atcacaaatg gcaccaagta tttgctgaca tactcagtga actgggtgta tagcattaaa    480
aatattgctg caaggttcaa tgtagcagca ggtaatgtgg tcgatgccaa tggttttttcc    540
acacaaacac aaactatttt tccattcaca actgtactaa ttcctttgcc aagtgaacct    600
gtgagttcaa tggccataat tgtcaatggt ccaccagctg tgtcacctct tcctgtttgc    660
agctcagaaa agtgcaactc aaggaggaaa ctttacattg ttattgccac cactgggggt    720
tccatgctgg ttctttgtgt tgtcttattt gggggttttc tgtgcagaaa gagatcagca    780
aggttcatta agagaggtga gcaaagtgag aaagcaaaga agttgtcttc ggaagatatc    840
cgcggcaaga tagccatcat tgaacatcac tccaaggtgt acaagtttga ggaaatagag    900
```

```
gaggccactg aaaactttgg ttcaaagaat agaattaaag gttctgtgtt tcgtggagta    960
ttcggtaaag agaaaaacat attggctgtc aagaaaatga gaggagatgc atccatggaa   1020
gtgaatttgc tggaaaggat caatcatttc aacctgataa aactgcaagg ttactgtgaa   1080
aatgatggtt tccctatct tgtttatgag tttatggaaa atggctcttt gagagaatgg    1140
ctaagcagaa acaggtcgaa ggagcaccag agtttggcat ggaggatcct gattgctctg   1200
gatgttgcca atggtcttca gtatcttcac aacttcacag aaccttgcta tgtgcacagg   1260
aacataaaca gtggaaacat tctactgaac agagatctaa gggccaagat agcaaacttt   1320
gctcttgttg aagaatcaga agtaaaata acttctggtt gtgccgcatc acatgtcgtg    1380
aaatcgaggg ttatacggc tccggagtat ctggaggcag ggatggtcac taccaaaatg    1440
gacgttttg ccttcggagt ggtgctgttg gaattgatca cgggtaaaga ttctgttacc    1500
ctacacgatg aagagaagt gatgcttcat gcaatcatag taaatctcat tggtaaagag   1560
aatttagaag agaaggtgag tttgttcatt gatccttgcc tcactgtcac tggaaacagt   1620
gagatagtat gtgctcccca gctagttaaa cttggtctgg catgcttgat ccaagaacca   1680
gcagagagac caaccatggt agaggtagtc tctagccttat tgaaaatata tacaagttat   1740
atggagcaaa taataccacc tagcatcagc aacagtccta gcatggagag gtga         1794

<210> SEQ ID NO 62
<211> LENGTH: 1905
<212> TYPE: DNA
<213> ORGANISM: Glycine max

<400> SEQUENCE: 62
atgcatctct ttcccttcat ccccataatc attttcacac tattgatcca caacttctct     60
ctgattctgg ggcagcaacc ttatattggt ttaggcacag tagcgtgtcc aagaagggggt  120
aacaaaaatt ctatccgagg ttacacttgc aatggtgcaa accatagctg ccaaagttac   180
ctcaccttca gatctcaacc catttacaac tctgtcaaga caatatcaac tttgttgggt   240
tctgacccat cccagcttgc taaaataaac tcagtttcca tgaatgacac ctttgagaca   300
aacaagttgg tgattgttcc ggtcaactgt tcctgttcag gtgagtatta tcaaacaaac   360
acatcctatg tgttccagaa ttcagaaact tacttgttga ttgctaacaa cacttttgag   420
ggcctcacaa catgtcaagc tttggagaac caaaaccaca ccctgcaaa catataccc    480
ggtagaagac tttagtgcc ctcagatgt gcttgtccca caagaaccaa accaagaaa    540
ggcatcaggt acctcttgag ttacttggtg aactggggtg attctgtttc attcattagt   600
gagaaatttg tgtcaactt tatgtctact cttgaagcta ataccttac tctcacacaa    660
gccatgatct atccctttac gacaattta gttccccttc atgacaagcc ctcaagttct   720
caaaccgttt cgccaactca acgcattagt ccaccaccct cacctccctc ttctgatcat   780
agctcaaaca aaacatgggt gtatgtagtt gttggggttg ttgtgggagc tattgcctta   840
acatcggttc tctgtgctgt cattttctc aaacgctatc gcaaaaatag aaacaaagat   900
gactcattgg tggcagtgcc taagagtttt gaggcaattg aggaaaaacc tcaagtgaaa   960
gtgaatgaaa aattgtcaga gaacatatct ggcatagctc agtctttcaa agtgtataac  1020
tttgaggaac tacagcgtgc aacagataac tttagtccta gcagctggat caagggtct   1080
gtttatcgcg gtgtgattaa tggtgatttg gctgcaatta aaagataga aggagatgtg   1140
tcaaaagaga tagagatact gaacaaaatc aaccatacca cgttatacg cctttctgga   1200
gttagcttcc atgagggtcg ttggtacctt gttatgtgt atgctactaa tgggacttg    1260
```

```
agtgaatgga tctacttcaa caacgtggac gggaagtttt tgagttggac tcaaagaatg    1320
caaattgcat tggatgtggc aacaggactt gactatcttc acagtttcac ttctcctcct    1380
cacatccaca aggatattaa cagcagtaac attcttctgg atggtgattt caggggaaag    1440
gtcgcgaatt taagccttgc taggtgtttg aaggagggg atgatcaatt tcccacgacg     1500
aggcacattg ttgggacaag aggctacatg gctccagagt atttggaaaa tggtcttgtg    1560
tccacaaagc ttgacgtata tgcatttggg gtactgatgc tggaaatggt cactggaaaa    1620
gaggtcgctg ctattttaac tgaagatgag acaaaattgt cacatgtttt aagtggcata    1680
cctggtgaga gaagtggcaa ggagtggttg aaggagtttg tggatccctc tttgggagag    1740
aattgtccat ggaacttgc tatgtttgtg attgaaatga ttgatgattg cataaagaca     1800
gatccagcaa gtcgccctag tgtgcatgag attgtgcaat ctctttcaag aacagtgaac    1860
tcttcactga gttgggaaag gtcaatgaat gtcccacgaa attaa                    1905

<210> SEQ ID NO 63
<211> LENGTH: 1992
<212> TYPE: DNA
<213> ORGANISM: Glycine max

<400> SEQUENCE: 63
atggccacaa tccagtgcgc cacaaccacc ctaatactgt tactcctcct cctcctcatc      60
ataccaagat ccaattccca acaagagtac gtaaacaaca gcaactaga ctgcaacaac      120 gaatacaact ccacaaaggg taacctctgc aacagtctcc cgtcatgcac ctcctacctc     180
accttcaagt cctccccgcc ggaatacacc acccccgccg ccatctcctt cctcctcaac     240
tccactccgg ccctcatcgc cgccgccaac aacatcaccg acgtccagac cctcccggcc     300
gacaccctcg tcaccgtccc cgtcaactgc tcctgctccg gcccctacta ccagcacaac     360
gcctcctaca ccatcaaagt ccaaggcgaa acctacttct ccatcgccaa caacacctac     420
caggccctca ccacgtgtca ggccctcgag cttcaaaaca ccgtcggcat gcgcgacctc     480
ctcaagggtc agaacctcca cgtgcctctc aggtgcgcgt gtcccacgca gaagcagcgc     540
gaggcagggt tcaagtactt gctcacttac ttggtttctc aaggagaatc ggtttccgcc     600
attggagata tcttcggtgt cgacgaacag agcattctcg acgccaacga gctttctact     660
tcttccgtta tttctactt cacgccgatt tcggttcctt tgaaaacaga gccaccggtt     720
acaataccga gagcagcgat tccccggag gattccccgt cgccgccgct gccgcctgct     780
ccggcggggg acggagattc cgactcttcc aagaaatggg tcattgtcgg aatcgtggtt     840
ggggttgttg tgttgcttat tttaggtgct gctctgtttt acctctgttt ctatcggcgg     900
cggcggcggg tggaacaccc tccgccgccg ccttcagcga aggctttctc gggctctacc     960
accacgaagg cgactattcc gacgacgcag tcgtggtctc tttcctcgga aggggttcgt    1020
tacgcgattg aatcgttgag tgtgtacaag ttcgaggagt gcagaaggc tacggggttc     1080 ttcggcgaag agaacaagat caagggttct gtttataggg cttctttcaa gggtgattat    1140
gccgcggtga agattctcaa aggtgatgtg tcgggtgaga ttaaccttct caggaggatt    1200
aaccacttca acattataag gttgtcgggt ttctgtgtct acaaaggtga cacctatctt    1260
gtgtacgagt tcgcggagaa tgattctctt gaggattggc ttcacagtgg tagcaagaag    1320
tacgagaatt ctacatctct gagttgggtg cagagggttc atattgctca tgatgttgct    1380
gacgcactta actaccttca taactatact agtcctcctc acgtacacaa gaatttgaag    1440
agtgggaacg tgcttttgga tggcaatttt agggctaaag tttcgaattt gggattggca    1500
```

| | |
|---|---|
| agagctgtgg aggatcacgg ggatgatggg gggtttcaat tgacaaggca tgtggtgggg | 1560 |
| actcatgggt acatggcacc tgagtacatt gagaatggtt tgattactcc aaagatggat | 1620 |
| gttttttgcgt ttgggggttgt gcttttggag cttctttcgg ggagagaagc tgttgttggt | 1680 |
| ggagaccaga atggatctgg ggagaagatg ctgtcggcaa ctgtgaatca cgtgcttgaa | 1740 |
| ggagagaatg ttagagagaa acttagaggt ttcatggatc caaatttgag agatgaatat | 1800 |
| cccttggaac tggcttattc catggccgaa cttgccaaac tctgtgttgc tcgtgacctc | 1860 |
| aatgcaaggc cacagatttc tgaagctttc atgattttgt ctaagattca atcctccacg | 1920 |
| ttggattggg atccgtctga cgagcttgaa cggtctagat ctgttggcca aatctctgat | 1980 |
| agcagcagat ag | 1992 |

<210> SEQ ID NO 64
<211> LENGTH: 1854
<212> TYPE: DNA
<213> ORGANISM: Glycine max

<400> SEQUENCE: 64

| | |
|---|---|
| atgcatcagt tcttctctgc tgtcttcctc ttcctcctcc ttccactttg cagcaacgct | 60 |
| caaacagcac gacaagcgaa caacacgggc ttcacgtgca acttcacacg cacgtgcacg | 120 |
| tcctacgcct tctaccgggc caccgccccc aacttcaccg acctggcctc catcggcgac | 180 |
| ctcttctcgg tgagccgcct catgatatca accccatcca acatctcctc ttcttccctc | 240 |
| aacacccctt tactcccaaa tacacccctc ttcgtcccct taacctgctc ctgcaacccc | 300 |
| gtcaacgcct ccttcggctc cctctcctac gccaacatct cctacaccat caaccccggc | 360 |
| gacaccttct tcttagtctc caccatcaag ttccagaacc tcaccacttt ccctccgtt | 420 |
| gaagtcgtca accccaccct cctcgccacc aacctctcca tcggccagga caccatcttc | 480 |
| cccatcttct gcaaatgccc cccaacagc caaggaacaa attacatgat ctcctacgtc | 540 |
| gtccaacccg aggataacat gtcgtcaata gcttcaactt tcggtgctga agaacagtcc | 600 |
| atcattgacg ccaacggcgg tgagacaact ctacatgact atgacaccat tttcgtgccc | 660 |
| gtggcgcggc tgccggctct gtcgcagccc gcggtggttc ctcccgcgcc gccgccagta | 720 |
| attgggagca ataatgatga taggacaggg actgttagag ggttgggggt tggattgggg | 780 |
| attgtggggt tgttgttgat tttggtgagt ggggtttggg tgtacagaga ggttgttgtg | 840 |
| atgaagggag tggtgagaga tgatgaggag aagaatgtgt atttggagg gaaagcggag | 900 |
| ggtaagaatt tggatgtcaa gttgatggct aatgtgtctg attgtttgga taagtatagg | 960 |
| gttttttggga ttgatgagct ggtggaggcc actgatgggt ttgatcagag ttgcttgatt | 1020 |
| caggggtcgg tgtacaaagg cgaaattgat gggcatgtct ttgccatcaa gaagatgaag | 1080 |
| tggaatgcct atgaggaact caagatcttg cagaaggtaa accatgggaa tctagtgaag | 1140 |
| ttggagggat tttgcataga cccagaagaa gcaaattgct atctagtcta tgaatatgta | 1200 |
| gagaatggat ctctatactc atggctgcat gagggcaaaa aagaaaagtt gagctggaaa | 1260 |
| ataaggctaa gaatagccat tgacattgcc aatggtctcc aatacatcca cgagcacaca | 1320 |
| aggccacggg ttgtgcacaa agacatcaag agcagcaaca ttctcttgga ctccaacatg | 1380 |
| agagccaaaa ttgccaattt tgggcttgca agtctggaa tgaatgccat taccatgcac | 1440 |
| attgtgggaa cacagggcta tattgcccct gaatatcttg ctgatggtgt ggtctctaca | 1500 |
| aagatggatg tgttcgcatt tggggttgtg ttgcttgaat taatttctgg gaaggaagtc | 1560 |
| attaacgagg agggaaatct cttgtgggca agtgccatca aaacctttga agtggacaat | 1620 |

| | |
|---|---|
| gagcaagaga agacaaggag gctgaaggaa tggttggaca aggatatttt aagggagaca | 1680 |
| ttctcaatgg aaagtttgat gggtgctctc accgttgcaa ttgcttgctt gcatagagac | 1740 |
| ccgtctaaga ggcccagcat aatggatatc gtctatgcac tgagtaaaag tgaagatatg | 1800 |
| ggctttgata tttccgatga tgggattggt tccccacggg tgatagctag gtga | 1854 |

<210> SEQ ID NO 65
<211> LENGTH: 2055
<212> TYPE: DNA
<213> ORGANISM: Glycine max

<400> SEQUENCE: 65

| | |
|---|---|
| atgatcattg catttcacat gaaggctttg gtcttttttcc tttggctgtt tgtcccctca | 60 |
| ttgggcaaag acttgctaag ctgtgagaca acttcacctg atgcctctgg ctaccattgc | 120 |
| attgaaaatg tgtcacagaa ccaatgtgag acatttgcac tcttttttaac aaactcttac | 180 |
| tactcctctc tctccaacct cacctcttat ttgggactaa acaagtttgt catagcacaa | 240 |
| gcaaatggtt tctctgcaga cactgagttc ctctcccagg atcagcctct actggtacct | 300 |
| attcattgta aatgcatagg tggcttctct caggctgagt taaccaaaac taccgtcaaa | 360 |
| ggagagagct tctatggcat tgctcaatca ctagagggat tgacaacttg caaggctatt | 420 |
| agggacaaca accctggtgt gtcaccttgg aatcttgatg acaaagtgag attggttgtt | 480 |
| ccattgagat gttcctgccc atttttcatct caagttagac cacaaccaaa gcttctgctt | 540 |
| tcttatccag taagtgaagg tgatactatt tccaatttgg cctcaaagtt caatattact | 600 |
| aaagaagcta ttgtttatgc taataacata tcatcacaag gccttaggac tagaagtagt | 660 |
| cttgcacccct ttacctctat tctcattcca cttaatggta agcctatcat tggtcctttg | 720 |
| gttaagccca aggaacccga ttctggcaat caaacaacca gcatcccagt gacaagtcca | 780 |
| cacaagaaat caccaatgtg gaagactgaa ttgtgcattg gcctagctgg ggttgcactt | 840 |
| ggagtctgca ttgcttttgc tgccgccttt ttcttcatca gattgaaaca caagaaggag | 900 |
| gaagagaatt catgcaaaga aggggacttg gagctgcaat atctgaacca agtgtgaga | 960 |
| accacctcaa ctagtgacaa gaaagtttca tttgaagggt ctcaggatgc tcttgatgtg | 1020 |
| aaaatcgtgg acgccctgcc gcggaagttg ttgctggata catacaccat gaagatgtg | 1080 |
| agaaaagcaa ctgaagattt cagctcaagc aatcacattg aagggtcagt gtatcacggt | 1140 |
| cgtctgaacg ggaagaacat ggcaatcaaa gggacaaagg cagaagtagt gtcaaagata | 1200 |
| gatcttggcc ttttccatga tgcacttcac catcatccca acatactcag gcttcttgga | 1260 |
| actagcatgt tagagggga gcagcaagaa gagtcatttt tagttttttga gtatgccaaa | 1320 |
| aatggttcat tgaaagattg gctccatggt ggattagcca tcaagaacca attcattgct | 1380 |
| tcctgctact gtttcctgac ttggagccaa aggctcagga tctgccttga tgtggccggt | 1440 |
| gccttgcagt atatgcacca tgttatgaat ccaagctatg tgcatagaaa tgtaaagagc | 1500 |
| aggaacatct ttttggatga agaaatttggt gccaagatag ggaattttgg tatggcaggt | 1560 |
| tgtgttgaga atgacactga ggaccctcaa ttctattcca ccaaccctgc ctcttggagt | 1620 |
| cttggttatt tggcacctga atatgtgcac caaggtgtaa tttccccaag tgttgatatc | 1680 |
| tttgcttatg gggtggtttt gttggaagtt ttgtccggtc aaacaccat aagcaggccc | 1740 |
| aatgagaagg gagaaggaag catttggctt acagatamma tcaggtccat tttggtgtca | 1800 |
| gaaaatgtga atgaactaag ggattggata gacagtgcat tgggggagaa ctattcattt | 1860 |
| gatgcagctg tgacacttgc caacattgca agagcttgtg tggaggaaga ttcctctttg | 1920 |

| agaccaagtg caagggaaat tgttgagaag ctatcaagat tggtggagga attaccacaa | 1980 |
| ggggaaaatg acatgttaat gtgtgaaagc tctagcaaac ctctggtgaa ggcagtggaa | 2040 |
| aacaatgttg aataa | 2055 |

<210> SEQ ID NO 66
<211> LENGTH: 2340
<212> TYPE: DNA
<213> ORGANISM: Glycine max

<400> SEQUENCE: 66

| atgaactgca ccgacacaag tcgtgttttgc acttctttct tggccttttaa gcctcatcaa | 60 |
| aaccaaacct tggctgtgat acaaagcatg tttgatgtgt tgcccggtga gatcaccgtt | 120 |
| gaaggcaatg gctgggatta tatattcatc aggaaaaact gttcttgtgc tgctggtatg | 180 |
| aagaagtatg tgtctaacac cacactcact gtgaaatcca atggaggatt tgagcatgat | 240 |
| ttggtgatgg aagcctatga caggcttgct ctcttgccca acaccacgac gcgttggcca | 300 |
| agagaaggcg gtatcatatc tctgagcttg ttctgtagtt gctctagtgg actgtggaac | 360 |
| tatctgatga gctatgtcat cagagatggg gacagtgttg aatcactagc aagcaggttt | 420 |
| ggggttagta tggatagcat tgagacagtg aatggcattg acaatcctac tgttggttct | 480 |
| ctcgtttata tacctttgaa ttcggttcct ggtgagtctt accacttgat gaatgatact | 540 |
| cctccagctc caacccctttc gccgtctgtt ataattttt cagctgacca agtcaaccag | 600 |
| aaggctcatg taccccatga atggatcata ggaggtttag gggttggtct tgctctgata | 660 |
| atattaacca ttattgtgtg tgtggcccta agatcaccca attgtttggt tgaagccgga | 720 |
| aataatgcaa aagattcttc aggaaagatc tctaataagt tctatgtttt tggaaatcca | 780 |
| agtttgttttt gtggatgtgt caaacctgtg gaccagaagc aaactgatgg tgaatccagc | 840 |
| agtcaccaaa ttaccggtac caaaacatca actctaatac ctgacatgtt ggacatggat | 900 |
| aagcctgtag ttttttcata tgaagaaatt tttttcttcaa ctgatggttt ctctgattca | 960 |
| aatctacttg gcacagaac atatggctct gtttactatg gtctcctcgg tgaccaggaa | 1020 |
| gttgctatta aagaatgac atctactaaa actaaagaat ttatgtcaga ggtaaaagtt | 1080 |
| ctgtgcaagg ttcatcatgc taatctggta gaattgatcg gctatgcggt tagccatgat | 1140 |
| gagttttttcc ttatttatga atttgctcag aaaggttcac tcagcagcca tttgcatgat | 1200 |
| cctcaaagta agggtcattc acctcttttct tggatcacaa gggtccagat tgcacttgat | 1260 |
| gctgctaggg gccttgaata catacacgag catacaaaaa ctcgttacgt ccatcaagat | 1320 |
| atcaagacaa gcaacatttt acttgatgct tcctttagag ccaagatatc agattttggg | 1380 |
| ttagcaaaac ttgtaggtaa aacaaatgag ggagaaaccg cagcaaccaa agttgtaaat | 1440 |
| gcatatggat atcttgctcc agaatacttg agcaatggcc ttgcaacgac caaaagtgat | 1500 |
| gtctatgcat ttggtgttgt tcttttttgag attatatcag ggaaggaagc cattattcaa | 1560 |
| acacaaggcc ctgaaaaacg atcattggca tctattatgt tggcagttct taggaactca | 1620 |
| cctgataccg tgagcatgtc aagcacgaga aacctcgttg atcctattat gatggatatg | 1680 |
| tatccccatg attgtgtata aagatggcc atgctggcaa agcaatgtgt ggatcaggat | 1740 |
| cctgtattac gccctgatat gaaacaagtt gtgatttccc tctcacaaac cctgttgtct | 1800 |
| tctgttgagt gggaagccac tcttgctggg aacagccagt tgaaactggt gaaacattgg | 1860 |
| tacaaggcta aggcttactt gacaaggtgg atcaaaagat cttctggaat aaaggacggc | 1920 |
| ccaattatca atcaagagaa cgtccccttt ttgccaagga atggcaacag attcttcctc | 1980 |

```
cagaatgtgg agacaatcat agacaatgtg agagggggtac ttctccttca tcctttgata    2040
caccacgcgg ctaagaacaa tgattcaagg aaagcttttt gggttttgac ggagtccctg    2100
agaggaaccg aacttgcagt tgcaggtgga ggagacacca cagcggggaa tggaactccg    2160
ttcacaagct tctgcccggg aacttggatt tccaccaatg aacttcccat gttttctccc    2220
acagtcaccc gccacggagg aaaggataac tttagagacg gaaactctga atgcgaccag    2280
tgtcatatgg gctatcctat ggcccattta gcgcactcac aacccatggg ctcatgctag    2340
```

<210> SEQ ID NO 67
<211> LENGTH: 1809
<212> TYPE: DNA
<213> ORGANISM: Lotus japonicus

<400> SEQUENCE: 67

```
atggaaccaa aattaacgtt ttcactttcg ttcttgttaa cgttgttgtc cccatttgca      60
gaatcaaagt gcatcaaagg ttgtgattta gctctagctt catactacca atggagtggt     120
tcaaacctca cctatatctc aaagatcatg gagtctcaga ttctttcaaa accacaagac     180
attgtcacct acaacaaagg caaaagaaac tttggtgttt tctccacaag ggttaacgtt     240
ccatttcctt gtgattgcat caatggtgag ttttttgggtc acacgtttga gtaccagctt     300
cagccagagg agacatacac aacagttgca agtgaaacgt tttccaattt gactgttgat     360
gtgtggatgc aagggtttaa catttatcca ccgaccaata ttcctgattt gctgtgttg      420
aatgttactg ttaattgttc ttgtgggaat agtgaggttt ctaaggatta tgggttgttt     480
atcacgtatc cgcttagaat tgaggatagt ttgcagtcca ttgcggaaga gatgaagctt     540
gaggctgagt tgctgcagag gtacaatcct ggtgtgaatt tcagccaagg aagtggcctg     600
gttttcattc ctggaaaagg cttttcaggc ggggttattg ctggaatatc tgttggagta     660
ctagttgggc ttttgttagt tgcattttgt gtgtatacta acatctgca aaagaaaaaa      720
gcattggaga aaaaattgat cttggatgat tccacagtta actctgctca agttagtaat     780
gattctggtg gcattatgat ggacaaatca cgcgagttct catataaaga actagccgat     840
gccacaaata actttagcgt ggctaataga attggtgaag gtggtttttgg aacagtttac     900
tatgcagatc tgagtggcga gacaatacca gaaggcaata atgcgaaaca atcaagagcc     960
actgacaata aaactgccat caagaagatg aacatgctcg catcgagaga atttcttgct    1020
gaagtgaaag tcttagctaa tgttcatcac ttgaacctgg tacggttgat tggatactgc    1080
attgagggtt ctctcttcct tgtatatgaa tacattgaca atggaaactt aaaacaaagt    1140
ttgcatgatt tagaaagaga gccttttgcca tggtctacta gggtgcaaat tgctttggat    1200
tcagccagag ctcttgaata cattcacgag catacagtgc atgtgtatat tcatcgtgac    1260
ataaagtcgg aaaatatttt actagacaat agcttccatg caaaggttgc agattttgga    1320
ttgtccaagc tggttcaagt tggaaattcg attggttctt ctgttaatat gatgaagggt    1380
acatttggtt acatgccacc agaatatgca cgtggtgttg tctctccttc tcccaaaata    1440
gatgtttatg cctttggagt tgttctttat gaacttattg ctgctaaaga agctgtaatc    1500
agggatggtg ctcaatctaa gggcctcgta gcattgtttg atgaagtttt gggtaatcag    1560
ctagatccta gggaaagtct tgtaagtttg gtggatccta ggcttcaaga taactactca    1620
attgactcag tttgcaagat ggcacaactt gccaaagtgt gcacagagcg tgatccaacg    1680
ggacgtccaa gtatgagatc tgttatggtt gctctaatga cacttagttc tacaactcaa    1740
agttgggaca ttgcatcctt ctatgaaaat ccagctcttg taaatcgaat gtcgggaaga    1800
``` ttggagtag 1809

<210> SEQ ID NO 68
<211> LENGTH: 1794
<212> TYPE: DNA
<213> ORGANISM: Lotus japonicus

<400> SEQUENCE: 68

```
atggaatcta gggttctttc agaacctgaa gatattatca actacaacca agaccatgtt    60
aggaacccag atgtattaca ggttcacacc agggttaacg ttccattccc ttgtgattgt   120
atcaatggcg agtttttagg tcatatattt cggcatgagt ttcatgaagg ggacacctat   180
ccatccgttg caggcacggt cttttccaat ttgaccaccg atgcgtggtt gcaaagcacg   240
aacatttatg gaccaacctc gattcctgtt ttagcgaagg ttgatgtcac ggttaactgt   300
tcctgtgggg acatcaaggt ttccaaggat tatgggttgt tcatcacata cccacttaga   360
gctgaggata ctttggagtc cattgcagaa gaggcgaagc ttcaaccgca cttgctgcag   420
aggtacaacc cgggtgtgga tttcagccgc ggaaatggtc tggtttttat tccggggaag   480
gatgaaaatg gagtttatgt tcccttgcac attagaaaag caggtctaga tagggtagtt   540
gcaggagtat ccataggagg tacatgtggg cttctgttat ttgcactttg tatatatatg   600
agatactttc ggaagaagga aggagaagag gctaaatttc caccaaaaga atctatggag   660
ccttcaattc aagatgatag taaaattcat cctgctgcca atggaagtgc tggctttaaa   720
tatattatga tggatagatc atcagagttt tcatatgaag aacttgccaa tgccacaaat   780
gacttcaatt tggctaataa aattggtcaa ggtggtttcg gagaggtcta ctatgctgag   840
ctgagaggcg agaaagttgc tatcaagaag atgaagatcc aagcatcacg ggaatttctt   900
gctgaattga agtcttaac aagtgttcat cacctgaact tggtacgctt gattggatat   960
tgcgttgaga gatctctctt tcttgtctac gaatacatgg acaatggaaa tttaagccaa  1020
catttacgcg agtcagagag agaactgatg acatggtcta ccaggttgca aattgcactg  1080
gatgtagcga gaggccttga atacattcat gactatacag tgcctgtgta tatccaccgg  1140
gacattaaac cagataatat tttattaaat aaaaacttca atgccaaggt tgcagatttt  1200
gggctaacca agctgactga catagaaagt tctgcaatta acactgatca tatggcaggc  1260
acatttggtt acatgccgcc agaaaatgca cttggacgtg tttctcgcaa gatagatgtt  1320
tatgcatttg gagttgttct ttatgaatta atttctgcca agaagctgt ggtcgagata  1380
aaggagtcat ctacagagct caaaagcctt gaaattaaga ctgatgaacc tagtgttgag  1440
tttaagagcc ttgtagcttt gtttgatgaa gttattgacc atgagggaa tcccattgaa  1500
ggtcttagaa aactggtgga tccgaggctt ggagagaact actcaattga ttccattcgt  1560
gagatggctc aacttgccaa agcttgcaca gaccgagatc caaaacaacg tccaccaatg  1620
agatctgttg tggttgttct aatggcttta aattctgcta ctgatgatag gatgagtcat  1680
gctgaggggg aaaatctgat tatgaaggc attcagaaaa attcagggaa ttgttattgt  1740
ggagagacag gctctcgaaa tcctgagagg agatatagcc tctcaaaaac ctga        1794
```

<210> SEQ ID NO 69
<211> LENGTH: 1902
<212> TYPE: DNA
<213> ORGANISM: Lotus japonicus

<400> SEQUENCE: 69

```
atgcattgct ttcccttcac ccttatcttc ctttccaccc tcttcatctt cttcaccttc    60
```

```
cctatcactc tagctcagca accttacatt ggtttagcca ccaatgcgtg ccctcgccgg      120
ggaaactcaa attccatccg cggctacact tgcaacggcg gcagtgcaaa tcacacttgc      180
caagcttacc tcaccttcag aactcaaccc atttacaact ctgtctacac aatttccact      240
ctgttatcct ctgacgcacg ccacctagct gaaacaatgt cagtctcaca aacaccacc       300 ttcgaaacaa acaagcttgt aatcgttcct gttcaatgtt cttgtgctgg tgagtattac      360
caggcaaaca catcatatgc atttcagaac acagacaccc ccttttcgat tgctaacaac      420
acttttgaag gcctcacaac atgtcaagct ttgatgcatg agaatcacaa ccctggtcat      480
ctataccttg gtagagaact cacagttcct cttagatgtg cttgtcccac taagaatcaa      540
acagagaaag gaatcaagta cctcttgagt tatcttgtga attggggaga ttctatttca      600
gtcatcagtg agaaatttgg tgtcagctgt aataacactc ttgaagctaa ttcccttttct      660 ctcacaaaag ccaaaattta ccctttacc acacttttag tacccctta tgataagccc       720 tccaattcac aaaccatttt gcaatctcaa ccatcttcaa cctcatcttc accaccaccc      780
tcttcttcca cacatcaaag ctcaaacaaa acgtggttgt atgtagttgt tggaggagtt      840
tttgccttaa ttgttctcac tgctgtcatt ttctgcatac actatcacaa gggtaggaag      900
aaagatgatt ctttgagtca attgactgtg tctgagagtt ttgaaaacca acaattaggg      960
aaggaaatga agaaggaga tggaaaattg tcagagttca tacatggcat agctcaatct     1020
ttcaaagtgt acagctttga ggaaatacag cgtgcaacaa ataatttgaa ttcaagcagt     1080
ttgataaaag gttctgttta tcgcggtgtt atgaatggtg atttggttgc aattaagaaa     1140
acagaaggag atgtatcaaa agagatacaa attctgaaca aggtgaacca ttctaatgtt     1200
atacgtctct ctggggttag cttcaacgag ggtcaatggt accttgttta tgagtatgct     1260
gctaatggac ccttgagtga gtggattttc tttgggaagt ttctgagttg gactcagaga     1320
atacagattg cactggatgt ggccatagga cttgactatc ttcatagttt cacttctcct     1380
cctcacatcc acaaggatct gaagagtagt aatattcttc tggacagtga tttccgagca     1440
aagattgcaa atttaagcct tgcaaggtct gtgaaaggag tggatgagga tgatcaattt     1500
ctcgcgacaa ggaatattgt tgggacaaga ggttacatgg ctccagagta tttggaaaat     1560
gggcttgtat ccacaaagct tgatgtgtat gcatttgggg tactgatgct ggaaatcctc     1620
acaggaaaag aggttgctgc tatttagca gaagataata ataagaattt gtcaggcgtt      1680
ttaagtgctg tacttggtga ggaaaggctg aaggagttta tggatccctc tcttcaatca     1740
aattatccat ttgaacttgc tatgtttgtg tttgaaatta tagttggttg catagagaaa     1800
gatccagcta gtcgcccttc catgcaggag attgtaccaa ctctttcaag aaccatgaac     1860
tcttcattga gttgggaaat gtcagtgaac atctcaggat ag                        1902
```

<210> SEQ ID NO 70
<211> LENGTH: 3861
<212> TYPE: DNA
<213> ORGANISM: Lotus japonicus

<400> SEQUENCE: 70

```
atggcttctc taactcatcc tctatgtgtt ctccttactc taatggctgc agcttcattt       60
gcaagtgtgt tttcccttga gtttcatccc aaaacaactt acatggaacc ttttaactgc      120
tctacaaaga tcagaacatg caattccttg ctctaccaca taagcatcgg tctcaaggtc      180 gaagaaaatag cccgctttta ctcggttaat ctctcccgaa tcaagccaat aactcgcggt      240
accaagcaag attaccttgt ctcagtgcct tgtacttgca gaaacaccaa tggccttaat      300
```

-continued

```
ggatatttct atcatacatc ctacaaggtt aaggttaatg acagttttgt ggatattcag      360
aacctgttct atagtggaca agcttggcct gtgaatgaag atttggtggt tccaaatgag      420
actatgacaa tacatattcc ttgtgggtgt tcagaaagtg gctctcaaat tgtcgtcaca      480
tacacagttc aaaggaatga tacaccatta tcaattgctc ttttgctaaa tgctacggtt      540
gaaggcatgg tgagtgtgaa ctcagttatg gctccgaatc ccacattcat agatgttggt      600
tgggtgttat atgttcccaa ggagttgaat ccaatttccc atggaaaaga aaataaacac      660
aagctggaga aaattattgg catcttagcg ggtgtgatat tactttcaat tattaccttg      720
atcattctta tcgtcaggag aaatagatcc tatgaaacct gcaaagatga tccacgcgct      780
atctcaaaaa gatcaatcgg caaaagaact agttccttaa tgaaccgcga ctttcacaaa      840
gaatacatgg aagatgcgac atcatttgac tcagaaagac cagtaattta tactcttgag      900
gagattgaac aagctactaa tgacttcgat gaaactcgaa ggattggagt cggtggatat      960
ggaacagtgt attttggagt gttagggag aaggtatgga ttatggaaat cccacctaca     1020
ttctttaatg gtcctcccca tgctagcatt tcttttcat gctgcaacaa agcattgaag     1080
aataatagct attttgattt tcaggaggtt gctataaaga gatgaaatc taacaaatcc      1140 aaagaattct atgcagaact caaggccttg tgtaagatcc atcacattaa cattgtggag     1200
ttattaggat atgccagcgg agatgaccac ctttacttgg tgtatgagta tgtgcccaat     1260
ggatctctca gtgaacatct tcatgatccc ttactgaaag tctgcaacgt tggtcctacc     1320
gtttgtttgt taatggagga ggtttacgtg atggtcact tagctgatgt ggaagttgaa     1380
ttagagagag aaagagacca gcaactgatt cagccttctt cctcgcctct agggactcgt     1440
tcgttcttta tctcttcctt ttcgctaaat ctcaagcttc gaaacatctt cctcacggtg     1500
ctctgttttt taaggaggaa gagggtagaa gatgaccgtt gcaggtctca cgtgcaactc     1560 acgtgttcc ctctctcttc agtccttctt tctctctcca attggacatc cacaaatcta     1620
aattgtggta ctggaacagg tcaccagcct ctttcttggt gtgctaggat tcaaattgca     1680
ctggattcag caaaaggtat tgaatacata catgattaca caaaagcaca gtatgtgcac     1740
cgcgatataa agactagtaa tattcttctt gatgagaagc tcagagcaaa ggtagcagat     1800
tttgggcttg caaagctagt agaacgaacc aatgatgaag aattcatagc aacaaggctt     1860
gttggaacac caggctatct tccaccagaa tctctaaagg agcttcaagt gacagtaaaa     1920
actgatgtat ttgcatttgg ggtggttatg ttagagttga taacagggaa acgtgcacta     1980
tttcgtgaca accaagaagc caacaatatg agatcacttg ttgcagttgt taaccaaata     2040
tttcaagaag ataaccctga gactgcttta gaagttaccg tggatgggaa tctacaacgt     2100
agctatccta tggaagatgt ctacaatatg gcagaactat cacactggtg cttgcgcgaa     2160
aatccggtgg acaggcctga aatgagtgag atcgttgtga aattgtcaaa gattataatg     2220
tcctcgatag agtgggaagc atcacttggc ggagacagcc aagtcttcag cgggtttaag     2280
caatatctga agcaaagtcc cacactgacc aaaacaatgg gcaagcaggt tttaggttca     2340
cgcaaaggga gcataaagct cacaaagacg gtctttgaag ttttgcttga gtgtaagcat     2400
gggaagagca gtcctcgtcc tcttccttct ccctattctt tcaacaccgt gacgctcgtt     2460
gatctgattg gaaattggga tccagctcca gcagcaatgg caggggcagc ttctgctctg     2520
ttcctcctcg acatcaaagg ccgcgtcctc atctggcgcg actaccgcgg cgacgtcacc     2580
gccctcgacg ccgaacgctt cttcaccaag ctcatcgaaa acaggctga tgcgcagtct     2640 caagatccgg ttgtccacga taacggtatc agctacatgt tcgttcagca cagcaatgtt     2700
```

-continued

| | |
|---|---|
| tacctcatga tagccaccag acaaaactgc aatgccgcta gcctcctctt cttcctccat | 2760 |
| cgagtagtcg acgtttttaa gcattatttt gaagaattgg aagaggaatc acttagggat | 2820 |
| aactttgtcg ttgtgtatga actgcttgat gaaattatgg actttggcta ccctcagtac | 2880 |
| actgaggcga agattcttag tgagtttatc aagaccgatg cttatagaat ggaagttacg | 2940 |
| cagagacctc ccatggctgt gactaatgcc gtgtcttggc gcagtgaagg gataagctac | 3000 |
| aagaaaaatg aggtagctgt taggaaaagt gaagaatgcg tactggtttt cttggatgtg | 3060 |
| gtggagagtg tgaacatact tgtcaatagc aatggacaaa taattagatc tgatgttgtt | 3120 |
| ggggctctca agatgagaac ttatttgagt ggtatgcctg agtgtaaact tggcttaaat | 3180 |
| gatagagtat tattagaggc gcaaggtaga acaaccaaag gaaaggcgat agacttggaa | 3240 |
| gacatcaaat ttcaccagta cggttgcttg actttcttgt ctttactaac tgatcagtta | 3300 |
| gagtgtgtcc gtttggctcg atttgaaaat gatcgaacaa tttccttcat accacctgat | 3360 |
| ggagcatttg atttgatgac atacaggctc agtacacagg ttaagccatt aatttgggtg | 3420 |
| gaagcaactg ttgaaaagca ttctaaaagt cggattgaga taatggtaaa agctagaagt | 3480 |
| caatttaagg aacgtagcac tgccacaaat gttgagattg agttgcctgt gcctgttgat | 3540 |
| gcaatgaatc caaatgttcg aacttcaatg ggatctgcag catatgcacc tgaaaaagat | 3600 |
| gcattaatct ggaaaattcg atccttccct ggaggcaagg agtatatgtt aagagcagag | 3660 |
| tttcgtcttc ccagtataac agctgaggaa gcaacccctg agagaaaagc tcctatacgt | 3720 |
| gtgaaatttg aaatacccta ttttactgtt tctggaatac aggtaagata tttgaagatt | 3780 |
| attgagaaaa gtgggtatca ggctcttccg tgggtgagat acataacaat ggctggagag | 3840 |
| tatgaactaa ggcttatttta a | 3861 |

<210> SEQ ID NO 71
<211> LENGTH: 1773
<212> TYPE: DNA
<213> ORGANISM: Medicago truncatula

<400> SEQUENCE: 71

| | |
|---|---|
| atgaaaccaa tcaaattcat attgtcactt ttacttatgt tgctggcctc ctctagtgca | 60 |
| gaatcaaaat gtagcaaaac ttgtgactta gctttagcat cctattatat atgggaaggt | 120 |
| acaaacttga catatatttc aaacatcatg caatccaatg ttgtttcaaa acctctagat | 180 |
| attttcagct acaatactga tactctacca aacctagata tgctccgttt ttcttcaaga | 240 |
| ctgaatgttc cattcccttg tgattgcatt aatgacgagt ttcttggtca cacgttttg | 300 |
| tacgagtttc acccaagaga gacctatgct tccattgctg agttgacttt tagcaatttg | 360 |
| accaataaag agtggatgga aaggtcaat gttcctgatt ctgtgaaggt taatgttact | 420 |
| gttaactgtt cctgtggaga caaaatggtt tccaaggatt atggtttgtt cataacatat | 480 |
| cctcttagtt ctgaggacac tttggagtcc attgcgaagc atacaaaagt taagcctgag | 540 |
| ttgctacaga agtacacccc tggtgtgaat ttcagcaaag gaagtgggct ggtttttatt | 600 |
| ccagggaaag ataaaaatgg agtttatgtt cccttgcccc acggaaaagc aggtcattta | 660 |
| gctaggagtt tagctactgc tgtcggagga acatgcacgg ttctgttatt agcaattagt | 720 |
| atatatgcta tatactttcg aaataagaat gcaaggagt ctaaattgcc atcaaaatat | 780 |
| attgtggtgg acaaatcacc taaattttca tacgaagaac tagccaatgc tactgataaa | 840 |
| ttcagcttgg ctaacaaaat tggtcaaggt ggttttggtg aagtctacta tggagagccg | 900 |
| agaggcaaga aaactgcaat aaaaaagatg aagatgcaag caacaaggga atttcttgct | 960 |

```
gaactgaaaa tcttaacaag agttcaccac tgcaacctgg tacacttgat tggatattgt   1020
gttgagggat ctctattcct tgtttatgaa tacatcgaca atggaaactt aagccaaaat   1080
ctacatgatt cagagagagg accgatgacg tggtctacca ggatgcaaat tgctctggat   1140
gtagcaagag gccttgaata cattcatgag cattcagtgc ctgtatacat ccatcgcgac   1200
atcaaatcag ataatatttt attaaatgaa aactttactg gaagattgc agattttgga    1260 ttaaccaggc ttactgattc tgcaaattca acagataaca ctcttcatgt ggctggcaca   1320
tttggttaca tgccacctga aaatgtatat ggacgtattt ctcgcaagat agatgtatat   1380
gcttttggag ttgttcttta tgaactaatt tctgctaaac cagctgtgat caagatcgat   1440
aaaaccgagt tcgagagcga gattaggacc aatgaatcta ttgatgaata caagagcctt   1500
gtagctttgt ttgatgaagt tattgatcaa aagggagatc ctattgaagg tctaagaaat   1560
ctggtggatc caaggctaga agataattat tcaattgatt ccattagcaa gatggcaaag   1620
cttgccaggg cttgcttaaa ccgagatccg aaacgtcgtc caacaatgag agctgttgtg   1680
gtttctctaa tgacacttaa ttctacaatt gatgatggaa gtaggtcagc cagtgcagca   1740
ttgagtactg ttatggagca tgactcgaaa tga                                1773

<210> SEQ ID NO 72
<211> LENGTH: 1863
<212> TYPE: DNA
<213> ORGANISM: Medicago truncatula

<400> SEQUENCE: 72
atgaatctca aaatggatt actattgttc attctgtttc tggattgtgt ttttttcaaa     60
gttgaatcca aatgtgtaaa agggtgtgat gtagctttag cttcctacta tattatacca    120
tcaattcaac tcagaaatat atcaaacttt atgcaatcaa agattgttct taccaattcc    180
tttgatgtta aatgagcta caatagagac gtagtattcg ataaatctgg tcttatttcc     240
tatactagaa tcaacgttcc gttcccatgt gaatgtattg gaggtgaatt ctaggacat     300 gtgtttgaat atcaacaaa agaaggagac gattatgatt taattgcaaa tacttattac    360
gcaagtttga caactgttga gttattgaaa aagttcaaca gctatgatcc aaatcatata    420
cctgttaagg ctaagattaa tgtcactgta atttgttcat gtgggaatag ccagatttca    480
aaagattatg gcttgtttgt tacctatcca ctcaggtctg atgatactct tgcgaaaatt    540
gcgaccaaag ctggtcttga tgaagggttg atacaaaatt tcaatcaaga tgccaatttc    600
agcataggaa gtgggatagt gttcattcca ggaagagatc aaaatggaca ttttttttcct   660 ttgtattcta gaacaggtat tgctaaggg tcagctgttg gtatagctat ggcaggaata    720
tttggacttc tattatttgt tatctatata tatgccaaat acttccaaaa gaaggaagaa    780
gagaaaacta aacttccaca aacttctagg gcattttcaa ctcaagatgc ctcaggtagt    840
gcagaatatg aaacttcagg atccagtggg catgctactg gtagtgctgc cggccttaca    900
ggcattatgg tggcaaagtc gacagagttt acgtatcaag aattagccaa ggcgacaaat    960
aatttcagct tggataataa aattggtcaa ggtggatttg agctgtcta ttatgcagaa     1020 cttagaggcg agaaaacagc aattaagaag atggatgtac aagcatcgtc cgaatttctc   1080
tgtgagttga aggtcttaac acatgttcat cacttgaatc tggtgcggtt gattggatat   1140
tgcgttgaag ggtcactttt cctcgtatat gaacatattg acaatggaaa cttgggtcaa   1200
tatttacatg gtataggtac agaaccatta ccatggtcta gtagagtgca gattgctcta   1260 gatttcagcca gaggcctaga atacattcat gaacacactg tgcctgttta tatccatcgc   1320
```

```
gacgtaaaat cagcaaatat attgatagac aaaaatttgc gtggaaaggt tgctgatttt    1380
ggcttgacca aacttattga agttggaaac tcgacacttc acactcgtct tgtgggaaca    1440
tttggataca tgccaccaga atatgctcaa tatggcgatg tttctccaaa aatagatgta    1500
tatgcttttg gcgttgttct ttatgaactt attactgcaa agaatgctgt cctgaagaca    1560
ggtgaatctg ttgcagaatc aaagggtctt gtacaattgt ttgaagaagc acttcatcga    1620
atggatcctt tagaaggtct tcgaaaattg gtggatccta ggcttaaaga aaactatccc    1680
attgattctg ttctcaagat ggctcaactt gggagagcat gtacgagaga caatccgcta    1740
ctacgcccaa gcatgagatc tatagttgtt gctcttatga cactttcatc accaactgaa    1800
gattgtgatg atgactcttc atatgaaaat caatctctca taaatctgtt gtcaactaga    1860
tga                                                                 1863

<210> SEQ ID NO 73
<211> LENGTH: 1875
<212> TYPE: DNA
<213> ORGANISM: Medicago truncatula

<400> SEQUENCE: 73
atgaatctca aaatggatt actattgttc attctgtttc tggattgtgt tttttttcaaa     60 gttgaaacca atgtgtaaa agggtgtgat gtagctttag cttcctacta tattatgcca    120
tcaattcaac tcataaatgt atcaaacttt atacaatcaa agattgttct taccaattcc    180
tttgatgtta taatgagcta caatagagtc gtagtattcg ataaatctgg tcttatttcc    240
tatactagaa tcaacgttcc gttcccatgt gaatgtattg gaggtgaatt tctaggacat    300
gtgtttgaat atacaacaaa agaaggagac gattatgatt taattgcaaa tacttattat    360
gcaagtttga caactgttga gttattgaaa aagttcaaca gctatgatcc aaatcatata    420
cctgttaagg ctaagattaa tgtcactgta atttgttcgt gtgggaatag ccagatttca    480
aaagattttg gcttgtttgt tacctatcca ctcaggtctg atgatactct tgcgaaaatt    540
gcgaccaaag ctgatcttga tgaagggttg ttacaaaatt tcaatcaaga tgccaatttc    600
agcaaaggaa gtgggatagt gttcattcca ggaagagatg aaaatggagt ttatgttccc    660
ttgccctcta gaaaagcagg tcacttagct agaagtttag ttgctgctgg aatatgtatt    720
cgaggagtat gcatggttct gctattagca atttgtatat atgttagata cttcgcaag    780 aagaatggag aagagtctaa attgccacca gaagattcta tgtcaccttc aactaaagat    840
ggtgataaag atagctatag tgatactaga tccaaatata tattggtgga caaatcacca    900
aagttctcat acaaagtact agccaatgct acagagaact tcagtttggc taaaaaaatt    960
ggtcaaggtg gttttggtga ggtctactat ggagtgctgg gaggcaagaa agttgcaatc   1020
aagaagatga agacgcaagc aacaagagaa tttctttctg aactgaaagt cttaacaagt   1080
gttcgtcact taaacctggt acacttgatt ggatattgtg ttgagggatt tctatttctt   1140
gtgtatgaat acatggaaaa tggaaactta agccaacatc tacataattc agagaaagaa   1200
ctgatgacct tgtctagaag gatgaaaatt gctctggatg tagcaagagg ccttgagtat   1260
attcatgatc attcggtgcc tgtatatatc catcgtgaca taaaatcaga taatatttta   1320
ttaaataaaa acttcaatgg gaagattgca gattttggat taaccaagct gactaatatc   1380
gcaaattcaa cagataacac taatcacatg gcaggcacat ttggttacat gccgcccgaa   1440
aatgcatacg ggcgtatttc tcgcaagatg gatgtgtatg cttttggagt tgttctttat   1500
gagctaattt ctgctaaagc agccgtgatc atgatcgata aaaacgagtt cgagagccat   1560
```

```
gagattaaga ccaatgaatc tactgatgag tacaagagcc ttgtagcttt gtttgatgaa    1620
gttatggatc aaaagggaga tcctatagaa ggtctaagaa agctggtgga tccaaggcta    1680
ggagataact attcaattga ttccattagc aagatggcaa agcttgccaa ggcttgcata    1740
aaccgagatc cgaaacaacg tccaaaaatg agagatgttg tggtttctct tatgaaacta    1800
atttctacta ttgatgatga aagtaggaca gatagcgcag agttgagtct tgatgtggag    1860
catgattcaa attga                                                     1875

<210> SEQ ID NO 74
<211> LENGTH: 1773
<212> TYPE: DNA
<213> ORGANISM: Medicago truncatula

<400> SEQUENCE: 74
atggtttctt cctttttca tacactcata ttcttttctg ccacccatat cctacttcaa      60
ttgccacaag ccaatggaaa aaacttctca tgtactttga attcctctcc ttcatgtgac    120
acatatgttg catactttgc taactctcca aactttttaa ccctcacagc catatctgat    180
atatttgaca ccagtcctca atccattgca agagcaagca acataaaaga tgaaaatatg    240
aacctcattc atggccaact tttgcttata cctataactt gtggttgcaa tggaaatgga    300
aactactctt ttgccaatat ctcacactta atcaaagaaa gtgaaagtta ctattatctt    360
tcgaccattt cgtatcagaa tctcactaat ggcagacag tggaagattc aaaccctaat     420
ctgaatccat atttgttgaa ataggcacc aaaataaaca tccctttgtt ttgtaggtgc     480
ccttcaaact attttgcaaa agggatagag tatctcatta cttatgtttg gcagcctaat    540
gataatctta cacttgtagc ttccaagctt ggtgcatcac caaaggacat aatcacagca    600
aatacaaaca actttggtca aaacttcact gttgcaatca accttccagt ttttattcct    660
gtgaaaaact taccagctct ttctcaatca tactattctt caagtgaaag aaagagaatc    720
aatcattttt ctattataat ttccattggt atatgtctag gatgcactat tctgatttca    780
ctattattat tactttttta tgtttattgt ttaaggaaga gaaaggcttg tgagaataag    840
tgtgtgcctt ctgtggagat aacagataag ttaatttccg aagtttcaaa ttatgtaagt    900
aagccaacag tgtatgaagt tggtatgatt atgaaagcta ccatgaacct taatgaaatg    960
tgtaagatag ggaaatcagt gtacaaagct aaaatagatg gtttggtttt ggctgtgaaa   1020
aatgtaaagg acatatcac agtcacagaa gagttgatga ttttacaaaa ggtaaatcat   1080
gcaaatctag tgaaactagt aggtgtctct tcaggatatg atggaaatca ctttcttgta   1140
tatgaatatg ctgaaaatgg atctctttat aactggttat tatctgagtt ttgcactctt   1200
agttggagtc agaggttaag catagcagtt gatattgcaa tagggctgca atacttgcat   1260
gaacacacac aaccatgtat agtccatagg aacatcaaat caagtaacat tcttcttgac   1320
tcaaaattta aggccaagat agcaaatttt tctgttgcaa gaactacaaa gaatcctatg   1380
ataacaaaag ttgatgtttt aggttatgga atggttctga tggagctaat aacaggaaag   1440
aagtttttgt cgtatagcga acatagcgag gtgaatatgt tgtggaaaga ttttaagtgt   1500
gtgtttgata cagaacaaaa gagagaagaa attgttagaa gatggatgga tcctaagtta   1560
gggaggtttt ataatgttgt tgaagctctt agtttattca ctttggcagt gaattgcata   1620
gaagaacaac ctttgttaag accaactatg ggagaagttg ttcttagtct ttctcttctc   1680 actcaacccct ctcctacttt gttagaggtg tcttggactt atggattaga gtagaggtt    1740 gctgaaatgg ttactcccat catagctcgt tga                                 1773
```

<210> SEQ ID NO 75
<211> LENGTH: 2313
<212> TYPE: DNA
<213> ORGANISM: Medicago truncatula

<400> SEQUENCE: 75

| | | | | | |
|---|---|---|---|---|---|
| atgaatacct | tggatcttaa | actacacctc | aaaattgaag | tgcaactcat | caaactcatg | 60 |
| aagtttcttt | atctttacat | tctcttatgt | atgttacctt | actcaatcaa | ctgccaacag | 120 |
| atattactta | acaccactgt | cactgattgc | tcaggcaccc | cttcagcacc | aaaaggatac | 180 |
| ctatgcaata | gtcctcaaaa | ctcatgcaat | tcattcttaa | ctttcaggtc | aaaaccttct | 240 |
| tatgacaacc | ctacaagtat | tgcttacctt | cttggctcag | aagcatcgac | atagcctca | 300 |
| atcaacaaca | tctcaagaaa | tgaaaaactt | ccaaccaata | aaacaatcat | tgtccctatc | 360 |
| ttgtgctcat | gttctggaaa | tatctaccaa | cataacactc | cttacactgt | ccaaaaaggt | 420 |
| gatacatact | ttcacttggt | aaatgaaact | taccaaagcc | tcacaacatg | tcaagctttg | 480 |
| aagggtcaga | attattatgc | ttctgaaaac | attgcaattg | gtgccgaggt | aacagttcca | 540 |
| gtactttgtg | cttgtcctac | aacaacacag | atggcgaaag | gatcacttc | cttgctggtt | 600 |
| tacatagtga | actatggtga | aactgttaag | tctataggag | aggcttatgg | tgttgatgaa | 660 |
| caaagcatat | tagaggcaaa | tgagttgcaa | ccaagtgaaa | acagaagtgt | gattctcttt | 720 |
| gcgttgacac | cgatattact | tcctcttaga | ggcaagagct | gcaagagga | tcctgatagt | 780 |
| ttctactgta | cttgttctca | gggaaggcta | gcagatggaa | gttgtaatga | atcccatggt | 840 |
| caaaagtttc | ctgccaagtt | ggttgctgca | ttaggtgttg | gtattggtgc | aggcttctg | 900 |
| gtattgtttc | tgcttagtta | caggttatat | caatacataa | agaaaaagag | agcgagtatt | 960 |
| cgtaaggaaa | agttattcag | gcaaaacggt | ggttacttgt | acaagagaa | gttatcatca | 1020 |
| tatggaaatg | gagaaatggc | aaagcttttt | acagcagagg | agctccaaag | agcaacagat | 1080 |
| gactacaacc | aaagtaggtt | tcttggtcaa | ggcggctatg | gcacagtgta | caaggaatg | 1140 |
| ctaccagatg | gaaccatagt | cgcagttaaa | aagtcaaaac | accttgacag | aaaccaaata | 1200 |
| gaaacgtttg | tcaacgaagt | agtcatctta | tctcagatca | accacaggaa | cattgtcaaa | 1260 |
| cttttaggtt | gttgtcttga | gacagaaact | ccattacttg | tctatgaata | cattcacagc | 1320 |
| ggaactcttt | cccaacatat | ccatgggaaa | gaccgtgatt | catcccttc | atgggaaagt | 1380 |
| cgccttagaa | ttgcatgtga | ggttgccgga | gcagtgacat | atatgcattt | ctcagcttct | 1440 |
| attccaatct | tccatagaga | cataaaacca | agtaacatac | tcctagacaa | taactatagt | 1500 |
| gccaaagtgt | ctgattttgg | aacatctaga | tcaatcccat | tagataagac | tcatttaacc | 1560 |
| acagcagtag | gaggtacttt | tgggtacatg | gatcctgaat | attttcagtc | aagtcaattt | 1620 |
| acagataaga | gtgatgtata | tagttttcggc | gtggtgcttg | ttgagcttat | aaccggtaga | 1680 |
| aagccaataa | cattcaatga | tgaagatgag | ggtcagaata | tgacggcaca | tttcatttca | 1740 |
| gtgatgaagg | aaaaccaact | tcctcaaatt | ttagataacg | cattggttaa | tgaagcaagg | 1800 |
| aaagatgaca | ttctagctat | tgcaaatctt | gcaatgagat | gtttgagact | taatggtaag | 1860 |
| aaaagaccaa | caatgaaaga | ggtttcaatg | gaattagaag | cactaagaaa | ggaaatatct | 1920 |
| accaacataa | caccccctac | actgtcaaaa | aaaggtgatt | cctattatca | cttggtaaat | 1980 |
| ggtacttacc | aaagaaagcc | tcacgccatg | tcaggctacg | aagggtcaga | attactatgc | 2040 |
| ttctgtgaaa | acatttcaat | tgatgttgag | ctcacatttg | atcaaggaga | cagagggttg | 2100 |
| ggactcctta | agttcttggt | cagcagttgt | ggaagcagga | tagagatatc | tagaatcacc | 2160 |

```
attgatagag attcctgggt aattcttatc aagattcaag attgtgtatc agagaactct    2220
ggcttggaac ttttgttcca gccatttgag tgtccgtttt cactatgtta tccccgtgaa    2280
gcagtttctc acccacatgt gtcaaacaat tag                                 2313

<210> SEQ ID NO 76
<211> LENGTH: 2040
<212> TYPE: DNA
<213> ORGANISM: Medicago truncatula

<400> SEQUENCE: 76
atggaacttt acaactacat tcttcacttc acagttctgt tcctatgcat gttttctcag      60
ttattcaact gccagcaagt atacctcaat aacactgtct ttgactgcac taacccctct     120
actgtaccaa aaggatacct ctgcaatggc cttaaaaaat catgtacttc cttttagtt      180 ttcaagtcaa aacctctcta tgataaccct acaaaaattg cctaccttct tcgctctgaa     240
gcatcagcca tagcctcaat caataagatc ccttaaatg aaaagattcc ttcaaataaa      300
tcaatcattg tcccagtctt ttgttcatgt gatggaaata tctaccagca tagtacatct     360
tactctgtaa agcagaatga tacttactat gagttggtaa agaaaactta ccaaggcctt     420
acaacctgcc aggcattgat gggtcagaac tactatgctc ctgtctcaat tcaacttgat     480
gctgagctca cagttccaat actatgtgct tgtcccacag caaacctgac ggcaaaaggg     540
gttacctcct tactcgttca catggtgaac tatggtgaaa cggttaagtc gataggagaa     600
gcttatggtt tgatgaaca tagtatgcga gaggccaatg agttgtcagg ctgcaaagt      660 gcaaacagca gtgtgatcct cttttgcatcg acgcctatac tagttcctct gagacgcaag     720
aattgtaaag agaactcaga tagattctat tgcaaatgtt ccgaggcact acatggagat     780
gaaagctcca agggggatcta ctgtgacgaa tctcctagac gaaaagttcc tgcaaaattg     840
gttgctgcct caggtatggg aattggtaca gtcttactgt gtttgtttct tttgagttgc     900
aaattatatc aacacataaa gaaaaggaga gcaagtactc ataaggaaaa gttattcagg     960
caaaacggtg gttacttgtt acaagagaag ttatcatctt atggaaatgg agaaatggca    1020
aagcttttta cggcagaaga gctgcaaaga gcaacagata actacaaccg gagtagattt    1080
cttggtcaag gtggctatgg cacggtgtac aaaggaatgt taccagatgg aaccatagtt    1140
gcagttaaaa agtcaaaaga actagaaagg aaccagatag agacttttgt caatgaagtg    1200
gtcatcttgt cacagatcaa ccacaggaat attgtcaaac tcttaggctg ttgtcttgaa    1260
acagaaactc cattactagt ttatgaattt attcccaacg gaactctttc ccaacatata    1320
catatgaaag accaagagtc ctccctttca tgggaaaacc gcctaagaat tgcatgtgaa    1380
gttgctggag cagtggcata tatgcatttt tcggcttcta ttccaatctt ccacagagac    1440
ataaaaccca caaacatact actagacagt aactttagtg ccaaggtatc tgattttggg    1500
acatcaagat caataccact agataagact cacctaacca catttgtagg tggaacttac    1560
gggtacatag atcctgaata tttccagtcc aatcaattca ctaataagag tgatgtatac    1620
agtttcgggg tcgtgcttgt agagctcata accagtagaa agcctatttc attctatgat    1680
gaagatgacg gtcagaattt gattgcacat ttcatttcag tgatgaagga gaaccaagtt    1740
tctcaaatta tagatgctag actgcaaaag gaagcaggga agacaccat tcttgccatt    1800 tcaagtcttg caaggagatg cttgagactt aatcataaga aaagaccaac aatgaaagaa    1860
gtttcagcag aattagaaac actaagaaag gcacaaagtt cttttgaaat caaccatgat    1920
catgattctt catcaagtga tgaagaatca tttgggcacg gaattaatga atcaacagac    1980
```

```
caagagtcca aagaggaaag caatttattt tccttacaaa tagaatccgc gtccttctga    2040
```

<210> SEQ ID NO 77
<211> LENGTH: 1914
<212> TYPE: DNA
<213> ORGANISM: Medicago truncatula

<400> SEQUENCE: 77

```
atgcatctct ttcccttcat cccttttttc attttcaatc tcttcttctt cttcttcgtc      60
agcaacatct ccatcatcct aggacaacaa ccttatattg gtttagcaac aaatgcatgt     120
ccacgaaaag gcgattcaaa atcaatccga ggttacacat gtaacggcaa aactcaaaca     180
tgccaagcat acctcacctt cagaactcaa ccaatttact cctcagtttc aacaatatca     240
tcattactag gctcaaatcc atctcaactc gccgaaataa actccgtttc tttaaacgaa     300
acattcgaaa caaacaaaat ggtaattgtt cctgtcaatt gttcttgttc tggtaactat     360
tatcaagcaa atacatccta tgtttttcaa aacacagaca cttattttat agttgctaac     420
aacacttttg aaggactttc aacatgtcaa gctttgatgc atgaaaatca taatcctggt     480
gatgtatatc ctggtagaaa actacttgtt cctcttagat gtgcttgtcc tacaaagaat     540
caaactcaga aaacataaa gtatcttttg agttatttgg ttgattgggg tgattctgtt     600
tcattcatta gtgataaatt tggtgttaac tttagaacca ctcttgaagc taatacactt     660
tctttaacac aatctacaat ttatcccttt acaacacttc ttgttcctct ttttgataag     720
ccctcaagtt ctcaaattca aacacatcat tctccttcat catccccacc tttatcttct     780
tcttcttcga ccgacaaaaa atcgaaaaaa acttgggttt atgttgttgt tggagtactt     840
ggaggagttg taattgtagc tttaatatta ttttttatatg ctttcatttc cttcaaaaag     900
ggtaaaaaga aaatgatttt ttggtgagt gtttctgaaa gtactatttt tgaggaaaaa     960
gagaaaccaa tgaagaaaga agatgaaaaa ttgtctgaga ttatatgtgg tatagctcaa    1020
tctttcaaag tgtatgattt tgaggaaatt aaggttgcaa ctgataattt tagtccaagt    1080
tgtcgggtta aaggaactgt ttatcgcggc cttattaaag gcgatttggc tgcgattaag    1140
aagacagaag gagatgtttc aaaagagata caaattctaa acaaagttaa ccattccaat    1200
gttattcgtc tttccggtgt tagcttcaat caaggacatt ggtaccttgt ttatgagtat    1260
gctgctaatg gagcattaag tgattggtta ttttctaaca aaaaaatgga tgatggaaat    1320
attctgagtt ggattcggag aataaagatt gcattagatg tggcaatagg agttgaatat    1380
cttcatagtt tcacttctcc tccacatatt cataaggatc taaagtgtag taacatactt    1440
cttgatagtg attttaaagc aaaggttgca aatttaaggc atgtaaggtg tgtggaagaa    1500
gttgaaaatg atgaagaatt tgttgctaca agacatattg ttgggacaag aggttacatg    1560
gctcctgagt atttggaaaa tggtcttgtt tctacaaagc ttgatgtgta tgcatttggt    1620
attttgatgt tggaaattat tacaggaaaa gaggttggtt ttatgatatc aaaagataat    1680
gagaatttgt tggatgtttt gagtggaata cttggtgaga aaagtggtga tgagaagttg    1740
aaggagttta tggatccttc attgcaagga aattatccat ttgaacttgc tatgtttgtg    1800
attgaaatta ttcagaattg ttttaaacaag gatccaggaa atagacctgc tatggatgag    1860
attgtaccag ttttgtcaag aacattgaat tcttcattga gttgggaaat gtaa          1914
```

<210> SEQ ID NO 78
<211> LENGTH: 1788
<212> TYPE: DNA
<213> ORGANISM: Medicago truncatula

```
<400> SEQUENCE: 78
atgtctgcct tctttcttcc ttctagttct catgctcttt tcttgtcct catgttgttt      60 tttctcacta acatctcagc tcaaccacta tatataagtg aaacaaactt tacatgccct    120
gtggattctc ctccttcatg tgaaacctat gtagcataca gagctcagtc tccaaatttt    180
ttgagcctat ctaacatatc tgatattttt aatttgagtc ctttacgcat tgcaaaagcc    240
agtaacatag aagccgagga taagaagctg attccagatc aactgttact agtacctgta    300
acttgtggtt gcactaaaaa tcactctttc gcgaatatca cctactcaat caagcaaggt    360
gacaacttct tcatactttc aatcacttca taccagaatc tcaccaatta tcttgaattt    420
aaaaatttca accccaatct aagtccaact ctattgccac tagacaccaa agtttcagtc    480
cctttattct gcaagtgccc ttcaaagaat caattgaaca aaggaataaa gtatcttatt    540
acttatgtgt ggcaggataa tgacaatgtt acccttgtta gttcaaagtt tggtgcatca    600
caagttgaaa tgttagctga aaacaatcat aacttcactg cttcaaccaa ccgttcagtt    660
ttgatccctg tgacaagttt accaaaactt gatcaaccat cttcaaatgg aagaaaaagc    720
agcagtcaaa atctggctct tataattggt atcagcctag gaagtgcttt tttcatttta    780
gttttaacac tatcacttgt gtacgtatat tgtctcaaaa tgaagagatt gaatagaagt    840
acttcatcgt ccgagactgc agataagtta ctttcaggtg tttcaggtta tgtaagcaag    900
ccaacaatgt atgaaattga tgcaatcatg gaaggtacaa cgaatctgag tgacaattgt    960
aagattggtg aatcagttta caaggctaat atagatggta gagttttagc agtgaaaaaa    1020
atcaaaaaag atgcttcaga ggagctgaaa attctgcaga aggtaaacca tggaaatctt    1080
gtgaaactaa tgggtgtgtc ttctgacaat gatggaaact gttttctggt ctatgagtat    1140
gctgaaaatg gatcacttga agagtggttg ttctcggaat cttcgaaaac ttcaaactcg    1200
gtggtttcgc ttacatggtc tcagagaata accattgcca tggatgttgc aatcggtctg    1260
caatacatgc atgaacatac ttatccacga ataatccaca gagacatcac aacaagtaat    1320
atccttcttg gctcaaattt taaggccaag atagcgaatt cgggatggc tagaacttca    1380 accaactcaa tgatgccgaa aattgatgtt ttcgcttttg gggtggttct aatagagttg    1440
ttaactggca agaaagctat gacaactaaa gaaaatggtg aggttgttat tctgtggaag    1500 gattttttgga agatttttga tcttgaaggg aatagagaag agaggttaag aaaatggatg    1560
gatcctaagt tagagagttt ttatcctata gataatgctc taagtttggc ttctttggca    1620
gtaaattgca ctgctgataa atcattgtct agaccaacca ttgcagaaat tgttctttgt    1680
ctttctcttc tcaaccaacc atcatctgaa ccaatgttag aaagatcctt gacatctggt    1740
ttagatgctg aagctactca tgttgttact tctgtaatag ctcgttaa                 1788

<210> SEQ ID NO 79
<211> LENGTH: 1653
<212> TYPE: DNA
<213> ORGANISM: Oryza sativa

<400> SEQUENCE: 79
atgtccaagc atggtttcct gttcttcctc ctcttctttg tgcaacacct tcacaccatc       60
atctctttgc ttgattcacc tggaggaagc ttagcatcac ttccagaatg gcagcccatg    120
ccatgcaagt ctgtatctgt caacccctta tgcagctcat acctctatgt caccccagaa    180
gggcgcaatt tgtccaaagt agcctctgat ttcagtggga atgcatctct tttccagcgg    240
atcacacggc tctctggttc agaggacttg ctggtgaatg tgccgtgtgt gtgcgaagcg    300
```

```
atcaatgcca ccatgactgg tctcttccat gacactaact acagggtgaa ggatggcgat      360
atgggtgaca ttatcaacag caagactttc agtgggctcg cgttgaatgt tggtgatggt      420
cagatcctgc acaaagaaga gaagttgatc attcaccttc catgtggatg ctcctcgaca      480
gcgccagagg gagtgttgtc ttatgcagtt caggatggag ataccttggg caacatcgca      540
agcttgttca gatcgagttg gaaagatatc ttggatttga acccaagagt cgcaaatcct      600
gatttcataa agccaggatg gatcttgttt atcccgatgg gagttgctgg tccttctaac      660
aagaaaattg atccattcca aacagagagg cctgtgattt tcagcttgag agcaattgaa      720
gatgctacat ctaattttga tgagaagagg aagattggtg agggaggata tggaagtgtc      780
tacctcggtt tcataggaac acacgaaata gcagtcaaga gatgaaagc aagcaaatca       840 aaggagttct ttgctgagtt gaaagtgctg tgcaaaatac atcacataaa tgtggttgaa      900
ttgattggtt atgctgctgg ggatgatcat ctttacctcg tttatgagta tgtccagaat      960
ggatcgctta gtgaacatct ccatgatcct ttgctgaaag gccaccaacc tctatcatgg     1020
actgcaagaa cacagatagc aatggactct gcacgtggta ttgaatacat ccatgatcat     1080
acaaagacct gctatgtgca ccgtgacatc aaaaccagca atattctgct agacaatggt     1140
ctacgagcta aagttgcaga tttcggcttg gtcaagctcg ttcagcgtag tgatgaagat     1200
gaatgtctgg caactcgttt ggttggaacg ccaggctacc ttccaccaga atcagttctt     1260
gagcttcaca tgactaccaa atccgatgtg tatgcattcg gagtagttct tgcagagctt     1320
attactggtc tccgtgcact tgtacgggac aacaaggaag ctaacaagac aaaatctcta     1380
atctcaatca tgaggaaagc attcaaacca gaagatctgg agagttccct ggagacaatt     1440
gtagatccct acctgaagga caattacccc atagaagaag tttgcaagtt ggcaaacatt     1500
tcgatgtggt gcctcagtga ggatccactg caccgccctg aaatgaggga ggttatgccg     1560
attttggctc aaattcatat ggcttccata gagtgggaag catcactcgg aggcgatggt     1620
gaagtcttca gtggcgtttc caatggtaga tga                                  1653

<210> SEQ ID NO 80
<211> LENGTH: 2004
<212> TYPE: DNA
<213> ORGANISM: Oryza sativa

<400> SEQUENCE: 80
atgtcgatgc tgccgcgctt cctcctcctc gtcgtgctgc tcgcggtgcc gatgacggcg       60
gcgcagcagc agtacgaggc caacgcgcag ggcgactgct acaccgacaa cggcagctcc      120
gtcctcggct acacctgcgg caccgccgcc tccccgccgc cgccgccatg cacggcctac      180
ctcaccttcc gctccgcccc accgagctac gcctccccga tcaccgtctc ctacctcctc      240
aacgccagcg tccccgccgt cgccgccgcc aactccgtcc cggtctcgcc tccggtcgcc      300
cgcgacggcc tcctcctcgt ccccgtcccc tgcgcctgca ccgccgccgg gtactaccag      360
cacgacgccg gctacgtcat ccagttcgac gacgagacct acttcgtcat ggcgaacgac      420
acgtaccagg ggctcacgac gtgccaggcg ctcatggcgc agaacccggc gcacgacagc      480
ctcgacctct acccgggaat cagactcacc gtgccgctgc gctgcgcgtg cccgtcgccg      540
gcgcaggccc ccgccggcgt gaggtaccta gtgacgtacc tcctcggctg ggacgacgac      600
tcgtccaccg tcgccgaccg cttcggcgcc gactaccagg ccgttctctt cgccaacaac      660
ctcaccgacg actccacggt gtatcccttc accacgatgc ttgtcccgct caagcatcgg      720
cccaagcccg acgtgacggt cttgccggag ccggggcctc cttctccggc tccggctccg      780
```

```
gcagtgtcag ctccgccgcc gccggcggtg ccttccagcg aatcgggcag tgggaggtgg      840
aagaaatcct ttcgcggtag gtgtatcggc attggagttg gtgttgggtt cgccgttctt      900
gcgtctggtg ctctgcttgc tctgttcttg ctacggcgtc ggtggcggtg gcgtggcaac      960
ggcgagcttc acgatgtgcc gttggctccg gataaggagg gagcgaaggc gacgccgccg     1020
ccgtggatgc tgccgacgac ggtggcggac gtcgacgtgc gcgatgccgt gggatcgatg     1080
gccgtgtacg agtacggcga gctggagcgg gtgacggccg ggttcgcgga ggagcggcgc     1140
atcggggact cgtcggtcta ccgcgcggtg atcaacggcg acgtcgcggc ggcggtgaag     1200
cgcgtcgccg gcgacgtggg cgccgaggtg agcgtcctgg gacgcgtcag ccactcgtgc     1260
ctcgtccgcc tgttcggcct ctgcgtgcac cgcggcgaca cgtacctggt gttcgagctc     1320
gccgagaacg gcgcgctcag cgactggatc cgcggcgaca acggcggccg cgccctctcg     1380
tggaggcagc ggatgcaggc ggcgctcgac gtggccgacg ggctcaacta cctccacaac     1440
tacaccaggc cgccctacgt gcacaagaac ctcaagagca gcaacgtcct cctcgacgcc     1500
gacttccgcg ccaaggtctc caacttcggc ctggcgcgca ccgtcgccgg cgccggcggg     1560
cagatgacgt cgcgcgtcgt gggtacgcag gggtacatgg cgccggagta cctggagcac     1620
gggctgatcg ggcctcacct cgacgtgttc gccttcggtg tcgtcctgct cgagctcctg     1680
tccgggaagg aggcagcgcc tgcgcgagac ggcggcgagg gtggcgatgg cgaagcattg     1740
gcgttgctgc tgtgggagga agcggagggg cagctggtgg tcgacggcga cgatgacgac     1800
gcgcggggca aggtggcggc gttcatggac tcccggttgc gtggcgacta cccgtcggag     1860
gtggctctcg cgatggctgc gctggcgctg cggtgcgtcg cgcgggagcc ccgcgcgcgg     1920
ccgtcgatgg tggaggtgtt cctctcgctc tcggcgttgc acggcacaac gttggattgg     1980 gcccccccatg caaccctgag ttga                                           2004
```

<210> SEQ ID NO 81
<211> LENGTH: 1893
<212> TYPE: DNA
<213> ORGANISM: Oryza sativa

<400> SEQUENCE: 81

```
atgccgccg gcgcgcgagc aagacgcatc gccgcactcg acctgatctt cctcgtgttt       60
ctccggctcg ccagcgcgta tcaacgacca tccgacgcgc atatcaactg catcgacagc     120
ttctgtctcg gcggctacac ctgcagcgaa accaccgcca ccacgtcctg caccgcctac     180
ctcaccttcc gctccgaccc cccgctctcc gtcgcctacc tcctcaacgc gacgccctcc     240
gccgtcgccg ccgccaactc tgtccccctc gccgtctccc ccgtcgacgg cacgcagctc     300
ctcctcgtcc ctgtccccctg ctcctgcaac cgggccaccg gctactacca acacaacacc     360
acctacgcca ttcaggaact tgatacctcc ttcctcatcg ccaataacac gttccagggg     420
ctcacgacgt accaaagcat catcgccaat aaccctgcaa gcgaagctat gtctccagtg     480
atcaacggcc cctcgccgt gccgctccgc tgcgcgtgcc cctctgcgac tacgggacga     540
ataaacaatc tgctgacgta cgtggtccag gagggggaca acgtgaccag catcgcgcgc     600
agattcaact ctacgcacgg cgacgtgctt gccgccaaca cgttgttggt cccgctcgtc     660
cacccgccgc attcgcgagt ggtgctcgcg aatactacta ttacttccac gactccgccg     720
gaatctcaga aattttacgt gtcgagtccc tgcagcaatg gcttgctggc tggcttgggt     780
atcggcgtcg gatgcggcgt ctctgcgtgg gctgccgttc ttgctgtgtt cttgctatgg     840
cgtcgaaggc ggcggcgccc cgtcggcgac agctcaggca tggccaggga gacccccctg     900
```

```
gtagcggctg tgcgtggcgc ggtggagact ctggctgcct acagctacgc ggacatcgag      960
acggcgacgg cggggttcgc ggaggagcgg agagtggccg ccggatcgtc ggtgtaccgc     1020
gcggtgatca acggcgaggc tttcgcggtg aaacgcgtgg ccgccggcgg cgacgacgtg     1080
cgcggtgagg tcgacgtcct cggccgcgtc aaccactccg gcctcgtccg gctccggggc     1140
ctgtgcgcga acggagacga cacctacctg gtgctcgagt cgccgagaa cggcgcgctc      1200 agcgagtggc ttcaccccgg cagcgcagcc gcgtgtctcc gccgtgtcct cggctggaag     1260
cagcgcgttc tggtggcgct cgacgtcgcg ggtgggctca actacctgca ccacttcacc     1320
aaccctccct acgtgcacaa gaatctcaac agcggcaacg tcctcctcga cgcgaacctc     1380
cgcgcgaagg tctcgagcct cgggttcgcg cgcgccgtgg ccgtcgccgt cgcagccgga     1440
gacgacagca tcgccctgat gacacaccac gtcgtgggca cccacggtta cctggcgccg     1500
gagtacctgg agcacggcct gatcagtccc aagctcgacg tgttcagctt cggtgtcatc     1560
cagctcgagc tcttgtccgg gaagacgcg gcgtttgtca ccgacgatga cgggcagaac     1620
atgctgctgt ggcaggcggc ggacgggctc gtcgacggcg atggcgcatg gttcaagctg     1680
agggcgttca tggaccctca gctgcaaggc cactacccga tcggtgtcgc gtccgcggtg     1740
gccgcgctgg ccgttcggtg cgtggcgcgg gagccacggg cgcggccttc catggaggag     1800
gtgttcgtca cgctctcagc ggtgtacaac ctcacggttg attgggatcc tcagaattac     1860
agcgcatcag cttctatggt cctcggtagg tag                                  1893

<210> SEQ ID NO 82
<211> LENGTH: 2070
<212> TYPE: DNA
<213> ORGANISM: Oryza sativa

<400> SEQUENCE: 82
atggcggaaa ctccacgccg aatccgccgc ggcggcgccg ggctctcgct cgtcgtcgtc       60
gccctcctcc tcgccgtcgc ggcgagggcg cagcaggagt acgaggcgaa ccagcagaac      120
gcctgctacg ccaccaacgc gagctccacc ctcggctaca cctgcaacgc cacctccgcc      180
tccgccgccg ccgcggcgcc ctgcgacgcg tacctggtgt tccgctcctc cccgcccctc      240
tacgcctccg ctgtctccat ctcctacctc ctcaacgtcg ccgccgccgc cgtcgccgac      300
tccaacgccg tcgacccggt cgcccccgtc gccgccgacc gcctcgtgct cgcgcccgtg      360
ccgtgcggct gctccccggg cggctactac cagcacaacg cctcccacac catccgcgac      420
accggcgtcg agacctactt catcatcgcc aacctcacct accagggcct ctcgacgtgc      480
caggctctca tcgcgcagaa tccccctccac gacagccgcg gcctcgtcgc cggcgacaac      540
ctcaccgtcc cgctccgctg cgcctgcccc tcgccgccgc aggccgccgc gggcgtcaag      600
cacatggtca cctacctcgt cacctggggc gacaccgtct ccgccatcgc cgcgcggttc      660
cgcgtcgacg cgcaggaggt gctcgacgcc aacacgctca ccgagagctc catcatatac      720
cccttcacca cgctgctggt cccgctcaag aacgcgccca cgccggacat gctcgcgccg      780
ccggcccagg cgccgccgcc ccccgcgccc gccgccgcgc gggcgcagcc gccgcctggt      840
gggtcgggca gcgggaaggg agtcgccgtt ggggtaggcg tcggttgcgg cgttcttgcg      900
ttggcgggtg tctttggctt gctgttcttc tgtctccggc ggcgacgcgg cgttgggaa       960 gaaagtgttc gtccggggaa ggtggtcggc gacgtgtcct cttcggcgga gtacggcgcc     1020
ctggcatcgg gaagcagac gacgacggca acctcgatgt cgtcgctgtc gcggcgagg      1080 tcgctgatgg cgagcgaagt gcgcgaggcg ttggagtcgc taacggtgta caagtactcg     1140
```

```
gagctggaga aggccacggc ggggttctcg gaggagcgga gggtgcccgg caccgccgtg    1200
taccgcggcg tgttcaacgg cgatgcggcg gcggtgaagc gtgtttccgg cgacgtgagc    1260
ggcgaggtcg gcatcctgaa gcgcgtgaac cactgcagcc tgatccgcct ctccggcctc    1320
tgcgtccacc gcggcgacac ctacctcgtc ttcgagtacg ccgagaacgg cgcgctcagc    1380
gactggctcc acggcggcga cgccgccacc ggcgtcctgg ggtggaggca gcgcgtgcag    1440
gtggcgttcg acgtcgccga cgggctcaac tacctccacc actacaccaa cccgccatgt    1500
gtgcacaaga acatcaagag cagcaacatc ctcctcgacg ccgacctcca cggcaagatg    1560
tccagcttcg ggctagcccg cgcgctcccc gcgggcgacg gcgccgccgc cgccgccgcg    1620
cagctgacgc gccacgtcgt gggcacccag ggctacctct ccccggagta cctcgagcac    1680
ggcctcatca cgcccaagct cgacgtgttc gccttcgggc tcgtcctcct cgagctcctc    1740
tccggcaagg aggcggcgtc ctccggcgac ggcgagaacg gcgaggcgct gctgctgtgg    1800
gagtccgcgg cggaggcgct cgtcgacggc ggcggcgagg acgcggggag caacgtcgcg    1860
gcgttcatgg acccgcggct tggcggcgac tacccgctcg acctggccat ggccgtggcg    1920
tcgctggcgg cgcggtgcgt ggcgaggcag cccgccgcgc ggccggccat ggacgaggtg    1980
ttcgtctcgc tcgcggcggt gtacggctcc acggtggact ggaaccccct ggatcacggc    2040
aactccgggt cgtcgctgat tgggaggtag                                     2070

<210> SEQ ID NO 83
<211> LENGTH: 1875
<212> TYPE: DNA
<213> ORGANISM: Oryza sativa

<400> SEQUENCE: 83
atggaacaca agggtttgtg catcctcgcc gtcgtcatcg ccttccagct cgccggcggg    60
gaggccgtca ccgatgccac tgcccgggca cgtcgcttcg cctgtaacgt gtcggcgccg    120
tgcgacacgt tcgtcgtgta ccggacgcag tcgccggggt tcctcgacct cggcaacatc    180
tcggacctgt tcggcgtgag ccgggcgctg atcgccagcg ccaacaagct gaccaccgag    240
gacggggtgc tcctgccggg gcagccgctg ctcgtgccgg tcaagtgcgg ctgcacgggc    300
gcgcgctcct tcgccaacgt cacgtacccc atcggcctc gcgacacctt cttcgggctc    360
gccgtcaccg cgttcgagaa cctcaccgac ttcgtcctcg tcgaggagct caacccggcg    420
gcggaggcga ccaggctgga gccgtggcag gaggtcgtcg tgccgctctt ctgccggtgc    480
ccgacgcggg aggagctcag cgccgggtca cggctcctcg tcacctacgt gtggcagccc    540
ggggacgacg tgtccgtggt gagcgcgctg atgaacgcct ccgctgccaa catcgccgcg    600
tcgaacggcg tcgcgggcaa ctccaccttc gcgacggggc agcccgtgct gatcccggtg    660
tcgcagccgc cgcgttttcc ttccgctgacc tacggtgcca tcgccgccga tcccggagcg    720
ggcaagcacc gccacggcat catcgtggcg acgagcatcg cggggtcttt cgtcgcgtgc    780
gccgtgctgt gcacggcgat cttggcgtac cggaggtacc gcaagaaggc gccggtgcca    840
aagcacgtca gcccgaagct ttcttggacc aagagcctga acagattcga cagcaatagc    900
tccattgctc gcatgatcaa tggaggggac aagctgctca ccagcgtgtc gcagttcatc    960
gacaaaccga tcatctttag agaggaggaa atcatggaag cgacgatgaa cttggacgaa    1020
cagtgcaagc tcgcagctc gtattaccgc gcgaaccttg aaagggaggt gttcgcggtg    1080
aagccggcga aggcaacgt tgccggggag ctgaggatga tgcagatggt gaaccacgcc    1140
aacctgacca agctggccgg catatccatc ggcgcggacg gcgactacgc cttcctcgtg    1200
```

-continued

| | |
|---|---|
| tacgagttcg ccgagaaggg ctcgcttgac aagtggctgt accagaagcc gccgtgctcg | 1260 |
| cagccgtcgt cgagctccgt ggcaactctg tcgtgggacc agaggctggg catcgcgctg | 1320 |
| gacgtcgcga acggcttgct ctacctgcac gagcacacgc agccgagcat ggtgcacggc | 1380 |
| gacgtccgtg cccggaacat cctcctcacc gcgggcttca gggcgaagct gtccaacttc | 1440 |
| tccctggcca agccggccgc catggtcgac gcggcggcga cgagcagcga cgtgttcgcg | 1500 |
| ttcgggctgc tcctcctcga gctcctctcc gggaggaggg cggtggaggc gcgcgtcggg | 1560 |
| gtggagatcg gcatgctgcg gacggagatc cgcaccgtgc tggacgccgg cggggacaag | 1620 |
| agggcggcga agctgaggaa gtggatggac ccgaccctcg gcggtgagta cggcgtggac | 1680 |
| gcggcgctca gcttggccgg catggcgagg gcgtgcaccg aggaggacgc ggcgcggcgg | 1740 |
| cccaagatgg ccgagatcgc gttcagcctc tcggtgctcg acagccgct gtccgtctcc | 1800 |
| gacgcgttcg agaggctatg gcagcccagc tcggaggaca gcatcgggat gggaacgag | 1860 |
| gtggcagcta gatag | 1875 |

<210> SEQ ID NO 84
<211> LENGTH: 2055
<212> TYPE: DNA
<213> ORGANISM: Oryza sativa

<400> SEQUENCE: 84

| | |
|---|---|
| atggcgcaat cgcgttcaca cgccatggcc gcgttcgcct tcgtcgtcgt cttcctcctc | 60 |
| tccggcgcgc cggagcccg gtcgcagcag ccgtacggct cgcaggtggc cgactgcccc | 120 |
| aacaagcaca acgacaccgg cctcctgggc tacttctgca gcagcggcgg cggcggcggc | 180 |
| ggcgcgccgt cgtcgtcgtc gtcgtcgtgc cagacctacc tcaccttcca cgccacgccg | 240 |
| cgctaccccg acctcgccgc catcgcgtcg ctcctcggcg ccgacgcgtc cagcctcgcc | 300 |
| gccgcgaact ccgcggcgtt gcccaccgcg gcgctcgcgc cggcgccaa ggtgctcgtc | 360 |
| ccggcgacct gctcctgcac gggcgccgcc tactaccagc ggaacgcgac gtacgtggcg | 420 |
| gtcgccggcg acacgctgct ggtgatcgcg aacgacacgt ccagggcct gtccacgtgc | 480 |
| caggcggtgc aggagcaggc cctcggcgac gcgccggcga ggtcgctcct ggcggggcag | 540 |
| cgcgtcaccg tgccgctccg gtgcgcgtgc ccgagcgccg cccaggccgc cgccggcgtg | 600 |
| aggtacctgg tgacgtacct ggtcgacgag ttcgacgagg tgggcgccat cgctgcgagg | 660 |
| ttcggcgtcg acgccgggaa catctcggcg ccaacgaga tggccattac tgacaccata | 720 |
| tacccttca caacgctgct catccccgtc aagtccaagc ccgacgtgtc gcagctccgg | 780 |
| tcgccgccgc cgccgcctcc tccgccgccg gcggcgcctg ctccgaccac gaaccgcaag | 840 |
| aaccacaccg gagtctacgt cggcatcggt gcggccgccg tggctgttct cgccgtggtc | 900 |
| accgccgttg tggctgccct tgctgtgagg gcgaggaggc agcgacggcg agccaccgcc | 960 |
| gctgtcgccc ccgccggagg caagggcggt aaaggcaacg acaaggcgtc gccggcgttc | 1020 |
| accggcggcg aggtgtccgt gtcgatcagc gaggcgttct cgggcctctc gacatcaag | 1080 |
| tcctccctga aggtgttcac ctacgcggag ctcgcgcgg cgaccgacgg cttcagcccg | 1140 |
| gaccgccgcg tcggcgggtc ggtgtaccgc gccgtgttca acggcgacgc ggccgccgtg | 1200 |
| gaggtcgtgg accgggacgt gtcggcggag gtggagatca tgaggaagat caaccacctc | 1260 |
| aaccttgtca ggctcatcgg cctctgccac caccgcgggc ggtggtacct cgtctcggag | 1320 |
| tacgccgagc acggcacgct ccgcgaccgc ctcctcgccg gcggcggcgc gccgccgctg | 1380 |
| agctggtcgc agcgcgtgca ggtggccctc gacgtcgccg aggggctccg ctacctgcac | 1440 |

```
gggtacacgc ggccgccgta cgtgcacatg gacgtcagca gcgacagcgt cctcctcgcc    1500
ggcggcgccg acctccgcgg caagctccgc aacttcggcg gcgccaggt catccgcggg     1560 ggcggcggcg aggcgttcac gatgacgagc aacatcgccg gacgcgcgg gtacacggcg     1620 ccggagtacc tggagcacgg cgtcgtgtcg cccaaggccg acgtgtactc cctcggcgtc    1680
gtgctcctgg agctcgtcac cggcaagggc gtcgacgagc tggaggccga cggcgccggc    1740
gacccgttcg ccggcatgaa cgcgctggcc ggagacctcg acggcggcag cgaagacgac    1800
gcggcggtga cgaggagaat ggaggagttc ttggacccgg cgatggcggc gaccgggagc    1860
agctgcccgc gcgaggccgt ggcgatgatg gtgaagctga tcgagaggtg cgtccgccgc    1920
gacgcggcgg cgcggccggg aatgggggag gtggcgcagc atctgctgat gttgcacggc    1980
gtctccggcg acggctggca cagctcgctg gagcactacc ggagctccgg cggcgacggc    2040
ggcgaacagc catag                                                     2055
```

<210> SEQ ID NO 85
<211> LENGTH: 1680
<212> TYPE: DNA
<213> ORGANISM: Populus sp.

<400> SEQUENCE: 85

```
atgacttccc acaatttcct tcttggtctc ctgatcactt taatggcaac cctagtagct     60
ttaggttttg cctctgatga ctccaccaat tcaccaaata tgtacccatt tacttgctct    120
gattctgaag acatcaaaat tgtaatgcc tcactgtacc ataccaacta cgacagctta    180
cagaaagaac agcttgcttc catttatggt gtcagcccag ctcagatcat ttctatttcc    240
tatgcaagcc gacaagacta tcttgtaacg gtaccttgct cgtgcaaaaa tatcaatggc    300
actgttggat acttctatga tgcaatccac aacgtaagtc aaggagaact gttttctaat    360
gtttcagctc agatttttaa tgggcaagct tggtgggttg aagatgaagc gtggttgttt    420
aatccaagaa ataatttctc catgcatctc ttgtgtgggt gtacaaaaag caaatcccaa    480
attgtggtaa catatactgt tcagcagcat gacacattat cagatatttc aaccaggcta    540
tcatctacag taggtggcat acagagcatg aacataaatc tgattaagaa cccaagttcc    600
ataaatgtgg attgggtgct gtttgttccc atggacagta accggcctc tggaaaagga    660 tcaggaaggg gacacaaatg gataataatc gtcggcatac tatcttctct gacagcactt    720
tcaatcatca cattggtaat cctccttctt tggagaaaag gatgccgaca gaacagcgag    780
gaggacttga aacctgtacc caaaagcatg agcacgaaca gagcattttc cttgcagagt    840
ctgtacaagg gaagtaacga agatgggaca gcttttgaat cagaaaaacc agtcgtcttt    900
agtctagaag agattgaaga ggctacaaaa gctttgaca aaacgaagaa atcggagag     960 ggtggatatg gatgtgtgta ccatggatta ttgcgaggac aggaggttgc agtaaagaag    1020
atgagatcaa acaaatccca tgagtttttt gcagagctca aggtcttatg taagatccat    1080
cacataaatg tggtggaact tctgggttat gccggtggag atgatcactt ctacttgatt    1140
tatgagtatg ttcgaaatgg gtcacttagt gatcaccttc acgatccatt gctaaaaggt    1200
caccagccac tctcttggac agcaagagca cagattgccc ttgatgctgc aaagggaatt    1260
gaatacatcc atgaccacac caaagcacgc tatgtgcaca gagatataaa gacaagtaac    1320
attctactcg atgagggact gcgagcaaag gttgcagatt ttggattggc aaagcttgtt    1380
gaacgaacga gtgatgaaga tttaatagca acacgactgg tctacaaaat ttttgaagat    1440
aaagatccag agactgcttt agcagatgtc atcgacaaaa atctccgcaa cagctacccc    1500
```

| | |
|---|---|
| atggaggatg tctacaagat ggcagaaatt gctgactggt gtttgagcga agaagcaatt | 1560 |
| aatagaccag agatgcgaga agtagttcaa aaattatcta tgatcgtagt gtcctcagta | 1620 |
| gagtgggagg cttcactggg agggagcagc atatttagtg gggttttaa tggaagatga | 1680 |

<210> SEQ ID NO 86
<211> LENGTH: 1797
<212> TYPE: DNA
<213> ORGANISM: Populus sp.

<400> SEQUENCE: 86

| | |
|---|---|
| atggcaattt ctttgctctc ttccttttc actcaagctc tatttttctt ggttcttgta | 60 |
| ttttctcca cctatgtcac agcacaagct ccacccggca caaatttttc atgccctgtt | 120 |
| gattcaccga cctcatgtcc tactatatt agttaccttg cccagccacc agattttttg | 180 |
| gacctcggaa agatttctca tctatttggg atcagtcgta cgctaatagc aagtgccagt | 240 |
| aacctggtgt ctgaggacac cccatttatt ccaaatcaac tcttgcttgt acctatacgt | 300 |
| tgtggttgca ctggtagcca atcttttgtc aatatcacct accaaatcca gcaaggtgat | 360 |
| agcatctact cggtttcaac tatttcattt gagaacctca cccgttggca agaggtggaa | 420 |
| gctttgaacc gcagtctgac tccaaccctc ttgcatgctg gtgacgaggt tatatttcct | 480 |
| ctgttctgta agtgcccttc aaggactcat ttggagaatg ggattgaaca tctcattact | 540 |
| tatgtgtggc aacctggtga tgatctcaag aaagtagctg ctatgcttaa tgcatctgaa | 600 |
| cgtaatattg tgattgaaaa aactatgat aactttaatg ctgcagtcta taccccgata | 660 |
| gtgatccctg tgtccaagtt accagttctc tctcaaccat acctcactcc tgaaagaaga | 720 |
| ggatctaagc atctttggat tgtcattgtt gctgcaagca tagcaagcac ttttttttacc | 780 |
| tgtcctttgg ttgcttttct gatccacaag cgttgttcat ataaggcaac caaagctttg | 840 |
| gatcgtactg gttcctgttt ggagaccagc gatctgcttc caggggtttt aggttgtctg | 900 |
| gacaagtcaa tcatttatga ggttaaagca attatggagg gaaccatgga tctacacgaa | 960 |
| cactacaaga taggaggatc agtatatagg gccaacatca atggctgtgt cttagcagtg | 1020 |
| aagaaaacca aggatgatgt cacggaagag ctaaagattt tgcagaaagt cagtcatgca | 1080 |
| aatctggtga actaatggg gatgtcatct gaatctgata gagaaggcaa tcgcttcttg | 1140 |
| gtctatgaat atgcagaaaa cgggtcactg gacaagtggt tgcatcccaa gtctgaatct | 1200 |
| tcctcaagct ccgtgggttt cctcacttgg aagcaaagga tgcaagtagc actagatgtg | 1260 |
| gccaacggcc tgcaatactt gcatgaacat actcaaccaa gaaccgttca caaggatatt | 1320 |
| cgaacgagta atattcttct cgattccaca tttcgggcaa agatagcaaa tttctcaatg | 1380 |
| gctagagctg ccacagactc gatgatgcct aaagatgatg tatttgattt tggagttgtt | 1440 |
| ttgttagagt tgctttctgg aaagaaggcc atggtaacca agaaaaagg cgagattgtt | 1500 |
| ctgttgtgca gggaaataaa agatgtcttg gaaatggaag agaaaagaga ggagaggtta | 1560 |
| agaaagtgga tggatcccaa cttggagaga ttttatccca ttgatagtgc catgagcttg | 1620 |
| gcaaccttgg ctaggttgtg cacactggaa aagtcttcag aaaggccaag catggcagag | 1680 |
| attgtctttta acctcacagt tctcacccag tcatctccag agacattaga aaggtggact | 1740 |
| tctgaggtgg aaacgaaga ttttactcgg ctcgtcagcc ctgtcacagc tcgttga | 1797 |

<210> SEQ ID NO 87
<211> LENGTH: 1965
<212> TYPE: DNA
<213> ORGANISM: Populus sp.

<400> SEQUENCE: 87

```
atggactttc ttctactgta tctgtatgtg gtgctgctgc tctcaccagc actggtacaa      60
gggcaacaaa cctatgtagc caaccaccaa ctggactgct acaacaatgc cttcaatgaa     120
acgaccaagg gatttctgtg caacggagtt caatcatcat gccaatccta cctcaccttc     180
cgatctatgc ctccctacaa ttctcctgtc cttattgcct atctcttagg cgtcccacaa     240
tccgccactc gcatcgcctc catcaataac ctctcctctg acactgccac tattcccacc     300
aacacccagg tcgtggttcc agtcaactgc tcctgttatg cccgtcaata ttaccagcac     360
aattccacct atcagctcaa ggacaaatcc gaaacctact cagcgtggc caacaacacc      420
taccaaggcc tcaccacatg ccagtccttg atgtctcaga tccctacgg cgatcggaat      480
ctgtcactcg gtctcactct ccaaataccc ctgaggtgtg cttgcccaac ttccaaccag     540
aatgcttcag ggatcaacca cttgctcacc tacatggtca cttggggcga ttccatctct     600
tccattgccc agctgtttgg cgttgacaag cagagggtac ttgatgcaaa caagctgtct     660
tcctccaata tcattttccc cttcactccg attctggttc ctctgcccac tgagcccacc     720
aaaattgaac agccatcggc agcccctccg cctgccgcac catctccgca gactcccaat     780
gtttccgttg ggggctcttc cgatcacaaa gccttgtatg tgggtgttgg gataggagct     840
gctttcctca ttctttttatt tgctgcgttt ggatttctgt tttggcaccg caaatctcgt     900
aagcaacaga gcctgtctc cacttcagaa cccgaaacgc tgccatcagt ctctactgat      960
ttcactgtac tcccagtctc caacaacaaa tcttggtctc tctcttctca tgacgcccga    1020
tatgctattg agtccttgac tgtctacaaa tacgaggact acaagtggc caccgggtac     1080
ttcgcccaag ctaatctgat caagggctcg gtttataggg gatctttcaa gggtgacaca    1140
gccgcagtca aggttgtgaa aggagatgtc tccagcgaga tcaacatttt gaagatgatc    1200
aatcactcca acgtcatcag gctctctggt ttctgcttac atgagggcaa cacttacctt    1260
gtttatgagt acgccgacaa tggctctctc actgattggc ttcactctaa caacatatac    1320
cgaattcttg cttggaagca gagagttcgg attgcctacg atgtggctga tgccctcaat    1380
taccttcaca actacaccaa cccgtcctat atccataaga acttgaagac cagcaacatt    1440
cttttggatg ccaacttgag agccaaggtt gctaatttcg gcttggcaag aacactggaa    1500
aatggccaag atggtggact gcaactgaca agacatgtgg taggcactca aggttatttg    1560
gcccccgagt acatcgagaa tggagttatc accccgaaat tagatgtttt tgctttcggg    1620
gttgtgatgt tggagctctt atctgggaag gaagcagctg ctacagctat tgacaagatt    1680
gcaggagacg acttgctctc tgtaatgata atgcgtgtgc ttgaggggga caatgtgaga    1740
gagaaactct ctgccttcct ggacccttgc ctaagagacg agtaccctt ggatctagct     1800
ttctcaatgg cccaactggc taaaagctgt gtcgagcatg atctcaatac acgaccttca    1860
atgcctcaag ttttcatgat gttgtccaag atcctctcgt cttcgttgga ctgggatcca    1920
tccgatgagc tcaatcgatc taggtctata gacagtggca ggtag                    1965
```

<210> SEQ ID NO 88
<211> LENGTH: 1575
<212> TYPE: DNA
<213> ORGANISM: Populus sp.

<400> SEQUENCE: 88

```
atgttcttgc aacaccatca tattagcact agcatttcct ctgcaaacat cacatatacc      60
atcgaggcag gcaacacttt ctacattgtc tcgactaaat acttccaaaa ccttacgacc     120
```

```
taccagtctg ttgagctttt caaccctaca cttatcccgg aactactcga cataggagta    180
gaggtgatct ttccaatatt ttgcaagtgt cctcatcaaa cccagttgca aaacaaggtg    240
aattatctgg tatcttatgt gtttcagcct tctgataact tatcttcagt tgcttcaaca    300
tttggagttg aaacacaatc tattgttgat gttaatggca ataacatcca gccttatgat    360
accatattcg ttccagtcaa tcaacttcca caactggcac aacctacagt agttgttcct    420 tctgggcgc cgcccctga aagacagag aggaaggtg tgattatagg attagcagtt        480
gggctaggaa ttgctgggct tttactggtc ttggtaagtg gggtttggtt ttatagagag    540
ggtgtgttga agaagagaag agatgttgag aaagttgagg agaagcgtag gatgcagttg    600 aatggggaa gtaaagggtt gaaggatata aagtgagtt tgatggcaga tgtttcagat      660
tgcttggata agtacagggt ctttaagatt gatgaactga agaagctac taacgggttc     720 agtgaaaatt gcttgattga aggatctgtg tttaaggggt ccataaatgg agagacctat    780
gccatcaaga agatgaagtg gaatgcctgt gaggagctca agatattgca gaaggtaaac   840
catggcaact tggtgaagct agagggcttt tgcatagacc ccgaggatgc aaattgctat   900
ctggtctatg agttcgtaga cagtggctct ctacattcgt ggttgcatcg caacgagaaa   960
gaaaaactaa gctggaaaac aaggttacgc gttgcaattg atgttgcaaa tggtctccaa   1020
tacatccatg agcacactag gccaagggtt gtgcacaaag acattaaaag cagcaatatc   1080
ctcttggact ccagcatgag agccaaaatt gccaactttg gactagcaaa acaggctgc    1140 aacgccataa caatgcacat tgttggcact caaggctaca ttgcgcctga atatttagct   1200
gatggtgtgg tgtcaacgag aatggatgtt ttctcttttg gtgtggtttt gcttgagcta   1260
atctcaggaa gagaagcaat tgatgaagaa ggcaaggttt tgtgggcaga agctattgga   1320
gttctggaag gaaatgttga agagaggagg aaggtaaaga gattgacagc atggatggac   1380
aaggttcttt tagaggagtc atgctcaatg gagagtgtaa tgaatacaat ggctgttgca   1440
attgcttgct tgcatagaga tccatcaaag aggcctagca tggtggatat tgtctatgcc   1500
ttgtgcaaga gcgatgattt gttttttgac atctcagaag acggattgtc aaaccctcag   1560
gtaatggcaa gataa                                                    1575
```

<210> SEQ ID NO 89
<211> LENGTH: 1830
<212> TYPE: DNA
<213> ORGANISM: Populus sp.

<400> SEQUENCE: 89

```
atggcaaact tctttctcag tttgctcact ctcagttttc tcacttcata tgctaatgct    60
caacaaaact actcgaagga ttcagcacta gactgcaacg ccaatgatga tgcaggacca   120
tcctctgcat ttctttacac ctacaatggc caggaccaat cttgccaggc ctttctgatc   180
ttcaaatctc aaccttcttt taactcggtg ccttcaatct cagcccttac gtcggcaaac   240
caagaagagc tggcaagaat caacaatgtt acaaggctat cagagttccc taccaacaat   300
gaggtgattg ttcctgtaaa ttgttttttgt tttggccaat attccaggc caacactaca    360 attcaggtca cgactactcg tggaacctac tatgtcatag cgaatgaaac ttacgaggga   420
ttatctactt gtgctcgct taagcatttg aatatacatg gtgaatatga tttgttgcct    480
ggtgaggaac tgcaagtacc acttcgatgt gcttgcccta caacgaatca atgataaga   540 ggaacaaagt atctagtgac ttacctctt agctcagatg ataacattcc tgatattgct   600
gacagattca agtaagcac caaggatata cttgatgcaa atggtatgga agaaaatcca   660
```

```
actctttatc ctgatacaac aattctcata cctctgccta ctcaacctac aagttcacaa      720
acaataattc acagcaaccc aaacatttct cctccatcag ctttgagtcc tagaaataga      780
ggatcaaaga aaaacatta tgagtctgct gggcttgctg cagcttgctc tttgctagtc       840
atcagtatca ttacagctgt cgttttctc tcttgcaaaa agacaagaga aaggtttct        900 gggagaggta gagaaagaaa acaggcagtg ccagaagaca ttcgtgtcga aattgcaagc      960
tatgagcaag ttttaaaagt cttcaaattc gaagaggtaa ggaaagctac tgaaaatctc     1020
agttcagaaa gtagaataaa tggctctgtg tatcgtggag agtttggtgg ggagatctta     1080
gctgtcaaga agatgagtag agatgtaaca aaggaagtga acattttgaa gaggatcaac     1140
cacttcaatt tgattaagct tgaaggtgta tgcgaaaatc gtggctgttt ctaccttgtt     1200
ttggagtata tggaaaatgg gtcccttaga gagtggctgt cctgtaaaaa gttcgaagaa     1260
actggaaatt gggcacagag aattcagatt gctctggatg ttgctaatgg actttactat     1320
cttcacagct tcaccgaacc tgcctatgtg cacaaggaca tcaaaagcag caatgttctg     1380
ttaaacggca atctaagggc caagattgca aatttcagtc ttgcgagagc agcgacaagc     1440
gctgccatga caaaacatgt tgtgggctct ataggttaca tggcgcctga gtacgtacgg     1500
gaaggacaag tgaccccca gattgatgtt tatgcttttg gagtcatttt gctggaactg     1560
atcacaggga aagatgctgt tttcacacag gatggcaggg aagccctcct ttcaacggaa     1620
atatttccta tcatggagaa taaaaaccct gaagttgagc tggatttctt tgtcgatcct     1680
gctctaaaag gaagttgtgg aacaaacttc gcattatgct tggctaaagt aagcgtagcc     1740
tgcttgatga agaaccagc aaggagacct agtatggagg aagtggtatc agttctgttg     1800
aaaattcagg caaatgtaca gaaatcataa                                      1830

<210> SEQ ID NO 90
<211> LENGTH: 1913
<212> TYPE: DNA
<213> ORGANISM: Populus sp.

<400> SEQUENCE: 90
atgagcttcc gttctgttgt ttctcctttt gctctcttca ttctttattg ctgttctttg       60
attcaagctc agcagcctta cgtggggaaa ggtacaacaa aatgttcaaa cacagaaaat      120
tccgctctgg ggtattcttg caatggcctg aacaagagtt gccaagctta tctgatcttc      180
agatcccaac ctccttacag tactgttgcc tccatatcta ctcttttggg ttcagaccca      240
tctcagctct ctcaaataaa ttcagtttct gagactacat catttccaac aaaccagttg      300
gtgctggttc ctgtcaactg ctcatgttca ggcgattatt tcaggcaaa cgcatcttat       360 attgttcaat caggtaacac tccttttcttg attgctaata acacttatca aggcctctca     420
acctgtcaag ctatccggaa tgaaaaaggt acacgaactg tcaatatatt tgctggtgaa     480
acactcactg ttcctcttag atgtgcctgt cctacaaaga accagagtga tttaggtatc      540
aggtatctgt taagttactt agtcacatgg ggcgatacag tttcaattgc tggtgtacga      600
tttggtgcag atatcgggag agctcttgaa gctaatgaaa tcagtgagaa aaatcccacg     660
atttacccct tcacaacact cctaattcct ttaaaaaacc caccaacaag ttcacaaact      720
gtagtgccac cgccacctcc agcttcacct tcaccttcac ctccatcacc gtctccaaac      780
tccgacaaaa gcgcaaacaa acatggatt tatgttttcg ttggggctgt tggaggaatt      840
gttcttacac tagtcattgg aaccattatt ttccttcatgc tcttccgaaa aagtaagaag     900
caaccgggtc caattatcgt gtcacaaagc tttgaggcac atgagaaacc actcaacagg     960
```

| | |
|---|---|
| aagttggatg aagaacctca ggatttgtta gagagtgttt atagcatagc tcaatccatc | 1020 |
| aaagtctaca actatgaaga tctgaaagct gcaacagata acttcagtcc cagttttgg | 1080 |
| atcaaaggt ctgttttcg tggcctaatc aatggtgatt tcgctgccat taagaagatg | 1140 |
| aacggagacg tgtccaagga gatagattta ttgaataaga tcaaccactc taatctaatt | 1200 |
| cgcctctccg gtgtttgttt caatgatggg cattggtacc tggtttacga gtatgctgcc | 1260 |
| aatggaccctt tgagtgattg gatttatgtt agcagtaacg aaggaaagtt tttgaaatgg | 1320 |
| acacaaagga tacagattgc tacgatgta gctacagggc ttaactatct gcatagtttt | 1380 |
| actaactatc ctcatgtcca caaggatata aagagcagca acatacttct tgataaagat | 1440 |
| ttaagggcta agattgcgaa cttttccctg gcaaggtcaa cagatgggcc ggaaggtgaa | 1500 |
| tttgcattga caaggcacat cgttgggact aaaggttaca tggctcccga gtacttggaa | 1560 |
| aatggtatta tctgtacaaa acttgatgtc tatgcatttg gaattctcac actggagata | 1620 |
| atgactggga aagaagttgc tgctttatac agagaggaaa acagggagct atctgatgtt | 1680 |
| ttaaatggtg ttcttttctga ggaaggtggg ctggaggaga gtctgagtca acttattgat | 1740 |
| ccttcaatgc aagggaatta tccttcagga ctcgccgttt taatggtcag attgattgat | 1800 |
| agttgcttga acaaaaatcc agcaggtcgc ccagccatgg atgaaatcgt gcagtctctc | 1860 |
| tcaggaattt tgattacttc tctggcctgg gaattgtcaa acaacacatc tag | 1913 |

<210> SEQ ID NO 91
<211> LENGTH: 2043
<212> TYPE: DNA
<213> ORGANISM: Populus sp.

<400> SEQUENCE: 91

| | |
|---|---|
| atgggcatgg ttccacttat cagtaagctc tactttggag ctttcgcctt tatattaatc | 60 |
| tgtttacttg tctctgcact tggacagaac ttgttgagct gccagacaac atctccagat | 120 |
| gcttctggct accattgtaa cagtaacgga ttgcaggatc agtgcaagac atttgctatt | 180 |
| cttcacacta gctcatactt ctcatctctt tccaacttaa gcttttattt gggcttagat | 240 |
| cggtttgtga tcgcggcaac aaacggcttt tctgccaaca ctgagtttct gccgaaagat | 300 |
| cagccttgc tgataccgat tgactgcaaa tgcaatggtg gcttctttca ggctcttgtg | 360 |
| acgaaaacta ccatcaaagg ggagagtttt tacagcattt ctaagtcact ggagggacta | 420 |
| acaacctgca aagccattcg agagaagaac ccaggtatct caccggagaa tctaaatggt | 480 |
| aaagttcagt tacaggtacc cttgagatgt gcttgtccat cctctactga agtcattcta | 540 |
| gcaactagac tattgctttc ttatccggta agtgctggcg acacaatctc gaaccttgct | 600 |
| attaagttca atactactcc agaagctatt acatccgcaa ataacagatc attgacaacc | 660 |
| tttaaaccca caagccttgt acctcttaca tctcttttga taccactagg tggcaagcct | 720 |
| accctcggtc ccctttgcaaa acctaatgaa cccaatttgc atattcctgc aagtagcctt | 780 |
| ccagtgatca atccacataa gaaaaggtcc aagatgtgga ggattggtgt ttatattgct | 840 |
| gttactggag ctgtagttgg agtaagcatt gctattgcag cagcttttctt ggtgatccaa | 900 |
| ttgaagaaga agaagcaagt tttaagcaag gaggcagata cggagcttca gcagcttagt | 960 |
| ttaagtgtaa gaactacaag tgacaagaaa gtctcattcg atgactcaca aaatcatttt | 1020 |
| gatagtcaga tcactgacac cacacccggt aaggtgttta tggagactta cactgtagag | 1080 |
| gagctcaaaa gagcaaccga ggacttcaat tcaagcaatc aaatcgaagg ttctgtgtat | 1140 |
| catggtcgtc tcaatgggaa gaacttggca ataaagcgcg tgcaaccaga aactatttca | 1200 |

| | |
|---|---|
| aaagttgagc ttgggctttt tcaagatgca actcaccatc atccaaacat aatcagagtg | 1260 |
| gtgggaacat gtttgagtga aggtcctgat tcattttttgg tttttgagta cgctaaaaat | 1320 |
| ggatctttga aggattggct tcatgggggga ctggccatga agaaccaatt cattgcctcc | 1380 |
| tgctactgtt tcctaacgtg gaatcagagg ctgaagatat gtcttgatgt agcagtggcc | 1440 |
| ctacaatata tgcaccatat catgcaccct agctatgttc atagaaacat caagagccgg | 1500 |
| aacatcttcc tcgatgaaga attcaatgcg aagataggaa atttcggcat ggcagggtgt | 1560 |
| gttgaagatg ataccaagga gccagacttt aattcaacca accctgcctc ctggagcctt | 1620 |
| ggatacttgg ctcctgaggc tcatcaaggt gtagtttcct ctagcacaga tatattttct | 1680 |
| tttggggtgg ttctgatgga ggttctatct ggacaaacac cgataacaag gcctaacgac | 1740 |
| aacggagaag ggagcatttg gctgtcgaag aaaatcaagt ccattttgct atcagaaaat | 1800 |
| gcggatgagc tgagagaatg gattgacagt gcaatggggg agaattactc atttgatgag | 1860 |
| gctgccactt tggccaatat tgcacgagct tgcacagaag aagacccttc tttgagacca | 1920 |
| acttctggtg aaatcgttga aaagctgttg agattggtgg aagaatccac agaaggagag | 1980 |
| cagatactaa tctgtgaaag ctcttgcaaa cctctagtca agtcaactgc aacaagtgtt | 2040 |
| taa | 2043 |

<210> SEQ ID NO 92
<211> LENGTH: 1902
<212> TYPE: DNA
<213> ORGANISM: Populus sp.

<400> SEQUENCE: 92

| | |
|---|---|
| atgaactgta cggacactac acgactgtgc acatcgtttt tggcctttaa accccaggag | 60 |
| aacctaactc tagcaatgat tcaaagcatg tttgatgtgt taccccaaga tgtgaccaga | 120 |
| gaaggcaatg gccatggcta catattcatc aagaagaact gctcttgttt gtccaaggac | 180 |
| aaagtctatg tgactaactc tacatataca gtgaaattca gtgggggtta tgtttatgac | 240 |
| atcgtgatca atgcttatga cgggcttgct ttccttgccca acacaacaag acaagcaaag | 300 |
| gttggtgctg ttgtgtcatt gaggttgttc tgtgggtgtt caagtgggtt gtggaattat | 360 |
| ttggtgagtt atgtgatgaa ggaaggagat actgttcagt ccttgtctag tcgatttggt | 420 |
| gttagtatgg ataatattga acagtgaat gggattcaga atcctgataa tgttacagct | 480 |
| ggtgcgctgt attatattcc tctgaattca gttcccgggg aaccttatcc cttggagaat | 540 |
| gataatcctc ctgctcctgt tcctgcacct ccggatgaca ttttctcagc aaatattcca | 600 |
| acaattcaca aggctcgtgt accatatgga tggatcatag ggggtcttgg gatcggtctt | 660 |
| gcactgattg tattatgtat aattatttgt gtgtctctta agtcctcaag ttgcttatct | 720 |
| gaatctcgag gaagtcacgc caagcctcct gatggcaaga tttctcaaaa gtttcatatt | 780 |
| cttcgcaagc aaagcttttg ttgtacttct agaaggtcca tctgctgcaa atctgtagac | 840 |
| tggaagcaaa caaatgggga gtctagcagc caccagatta ctatacctaa aggtctagca | 900 |
| actgatgtat tgatgagaa gcctgtggtt tttacatacg aagaaattct tttttgcaact | 960 |
| gatgaatttt tggattctag tcttcttggt catggaacat atggttctgt gtattatggt | 1020 |
| caccttcatg accaggaagt tgctattaag agaatgactc tacaaaaac taagaatttt | 1080 |
| atggctgaga tgaaaatcct gtgcaaggtc catcatacaa atctggtaga attgattggc | 1140 |
| tacgcagcta gtgatgcaga gctcttccgtg atctatgaat atgcacagaa gggttcactt | 1200 |
| agaagtcatt tacatgatcc ccaaaataag ggtcatacac cactttcatg gatcatgcgg | 1260 |

```
gtccagattg cacttgatgc agctagaggc ctggagtaca tccatgagca cactaaaaca    1320
cactatgtcc accgggatat caagacaagc aacatcttac ttgatggttc cttcagggcc    1380
aagatttcag attttggatt ggcaaaactg gttggcaaaa caggcgaggg agaagctaca    1440
gcaacaaaag ttgttggtac atatggttat ctagcaccag aatacttgag tgatggcctt    1500
gccacaacca agagtgatgt ttatgcattt ggtgtcgttc tttttgagat catatctggg    1560
aaggaagcca taataagaac tgaaggtgcg gttacaaaaa atcctgaaag acgttcactg    1620
gcatctacta tgctagcagc tcttaggaac acacctgact ccatgagcat gtcaagcttg    1680
aaagacctca ttgatcctaa tatgatggat ttatatcccc atgattgtgt attcaagttg    1740
gccatgctag caaagcaatg tgtggatgag atcccatcc tacggcctga catgaagcaa    1800
gttgtgattt ccctgtcaca aattgtttta tcctccattg agtgggaagc aactcttgct    1860
gggaacagcc aagttttcag tggtcttgtc aaggaaggt ag                       1902
```

<210> SEQ ID NO 93
<211> LENGTH: 1953
<212> TYPE: DNA
<213> ORGANISM: Populus sp.

<400> SEQUENCE: 93

```
atgaacccgg gtccaggatt tcatgcgttg caagttttag agattatatc aggtttagga     60
ggttttctcg ggtttacttg ttctttgatt caagctcagc aaccatatgt agggaaagct    120
acgacaaatt gttccaacac ggaaaattct gctcttgggt attcttgcaa cgccctaaac    180
aagagctgcc aagcttatct catcttcaga tcccagcctc cttacaacac tgttgcctcc    240
atatctaccc ttttgggatc tgacccatct cagctctctg aagtaaattc agtttctgag    300
accacatcat tcccatcaaa ccagttggtg atagttccag taaactgctc atgttcaggc    360
gagtactctc aggcaaacgc atcttatatt gttcaaccga acgatactct tttcttgatt    420
gctaataaca cctatcaagg cctctcaacc tgtcaagctc tccagaatca aaaaactacg    480
cgaactgacg atatacttag cggtgaaaca ctcactgttc ctcttagatg tgcctgtccc    540
acaaagaacc agagtgattt aggtataagg tatctcttaa gttacttagt cacaccggga    600
gatgacgttc cagctattag tgaacaattt ggcgcagcta ctgggagaac tctcgaggct    660
aatggactcc ctgagcaaaa tcccaccatt tttcccttca caacactcct aattccttta    720
caaagcacgc aacaagttc tcaaactgta gtgccaccac cacctccagc ttcatcttca    780
ccaccatcac catctccaaa ccctgaaaaa agctcaaaga aacatggct ttatgttgtg    840 gttgggggttg ttggaggaat tgctcttaca atagtcattg gaaccattat tttcttcatg    900
ttgtcccgta aaagtaagaa gcaacccggt ccagttatcg aatcgcaaag ctttgaggca    960
catgagaaac cactcaacaa gaagttggat gaagaatctc aggagttttt cgagagtata   1020
tccgctatag ctcaatccat caaagtctac aagtttgaag atctgaaagc tgcaactgat   1080
aacttcagtc ctagctgttg gatcaaaggg tctgtttatc gtggcctaat caatggtgac   1140
tttgctgcca ttaagaagat gaatggagac gtgtctaaag agtagaatt gttgaataag   1200 atcaaccatt ctaatctaat tcgcctctcc ggtgtttgtt tcaatgatgg tcattggtac   1260
ctggtttacg agtatgctgc tagtggacaa ttgagtgatt ggatttatga tagaagcaat   1320
gaagggaagt ttttaaattg gacaaaaaga atacagattg cttccgatgt cgccacggga   1380
cttaattatc tacatagttt cactaactat ccgcatgtcc acaaggatat aaagagcagc   1440
aacattcttc ttgacagtga tttaagggct aaaattgcaa acttttccct ggcaaggtca   1500
```

-continued

| | |
|---|---|
| acaggtgacc aggatgatga atttgttttg acaaggcaca ttgttgggac aaaaggttac | 1560 |
| atggctcctg agtacttgga aaatggagtt gtctcctcaa agcttgatgt ctatgcattt | 1620 |
| gggattctca ctctggagat aattaccggg aaagaagttg ctgctttaca cagtgaggaa | 1680 |
| agcaggaact tatcagatgt tttaaatggt gctctatctg aggtagatgg gcaggaggag | 1740 |
| agtttgaagc aactcattga tccttcactg catgagaact atccttcagg acttgctgtt | 1800 |
| ttagtggtca gattgattga tagttgctta aacaaaaacc caggagatcg cccgaccatg | 1860 |
| gatgaaatcg tgcagtctct ctcaagaatt ttgactactt cgctggcctg ggaattgtct | 1920 |
| agcaatgtat ctggctacca tatctctagt tag | 1953 |

<210> SEQ ID NO 94
<211> LENGTH: 1878
<212> TYPE: DNA
<213> ORGANISM: Populus sp.

<400> SEQUENCE: 94

| | |
|---|---|
| atgacatcca atcccatct agtcttctct ctcctcttt ttatctatta cagtactatc | 60 |
| ctccaccatt tgcaagccca accaagcacc caaggattca cctgcacagc caatcagagt | 120 |
| tcctttccat gccaaaccta tgccttctac cgagctacag ctcctaactt ccttgacctt | 180 |
| tcctcaatcg gtgaccttt tcggttagc cgccttatga tatcaaaacc aagtaacatc | 240 |
| tcctctccag cctctcctct catccccaat caaccctgt tgtccctt atcatgttct | 300 |
| tgcaacacca tgaatggcac tagtatctcc tttgcaaaca tcacatatac cataaagcca | 360 |
| aatgacactt tctaccttgt ctcaactgaa tacttcggaa accttactac ctaccagtct | 420 |
| gttcaacttg ttaaccctac gcttatcccc acactactcc aaataggagt agaagtgatc | 480 |
| tttccaatat tttgcaagtg tcctaatcaa actcaattgc aaaacaaggt gaattatctg | 540 |
| gtatcttatg tgtttcagcc ttctgataac ttatcatcag ttgcttcaac atttggagtc | 600 |
| gaaacacaat ctattgtgga tgctaatggc aataacatac agccttttga taccatattc | 660 |
| ataccagtaa atcaacttcc acaactggca caacctacgg ttttccttc tttggcgcct | 720 |
| tctgggaaga ctcagaggaa aggtttgatc ataggattag cagttggact aggaattgcc | 780 |
| gggcttttgt tggtcttggt aagcggggtt tgtttttta gagacggtgt attgaagaag | 840 |
| agacgggatt ttgagagaga tgatcaggag aagcagagga tgcagttcaa tggaggaagg | 900 |
| aaagggttga aggatataga agtgaatttg atggcagatg tttcagattg cttggataag | 960 |
| tacagggtct ttaagattga tgaactgaaa gaagctactg atgagttcgg tgagaattgc | 1020 |
| ttgattgaag gatctgtgtt taaagggtcc ataaatggag agacctatgc catcaagaag | 1080 |
| atgaagtgga atgcttgtga ggagctcaag atattgcaga aggtaaacca tggcaacttg | 1140 |
| gtgaagctag aaggcttttg catagaccct gaggatgcaa attgctatct ggtctacgag | 1200 |
| tacatcgaca atggctctct gcattcgtgg ttgcatggta acgagaaaga aaaactaagc | 1260 |
| tggaaaacaa ggttacgcat tgcaattgac gttgcaaatg gtctccaata catccatgag | 1320 |
| cacactaggc caagggttgt acacaaagac attagaagca gcaacattct tctagactcg | 1380 |
| agcatgagag ccaaaattgc caactttgga ctagcaaaat caggctacaa tgccataaca | 1440 |
| atgcacattg tcggcaccca aggctacatt gcacctgaat atttagctga cggtgtggtg | 1500 |
| tcaacaagaa tggatgtttt tctcatttggt gtggttttgc ttgagctaat ctcaggcaaa | 1560 |
| gaagcaattg acgaagaagg caaggttttg tgggcagaag ctagtggaat tttgcaggga | 1620 |
| aatgttgaag agaggaaggt gaagagattg acaccatgga tggataaggt tctattagag | 1680 |

| | |
|---|---|
| cagtcatgct taatggagag tgtaatgaat gcaatggttg ttgcaattgc ttgcttgcat | 1740 |
| agagatccat caaagaggcc cagcatggtg gatattgttt atgccttgtg taagaccgat | 1800 |
| gatctgtttt ttgacatctc agaagacgta ttgtcagacc ctcaggcatc tttagcctat | 1860 |
| gggcgtactc cttttttaa | 1878 |

<210> SEQ ID NO 95
<211> LENGTH: 1728
<212> TYPE: DNA
<213> ORGANISM: Populus sp.

<400> SEQUENCE: 95

| | |
|---|---|
| atggcaatat ctttgctccc tttcttttcc acacaagctc ttcttctctt gatcctttta | 60 |
| ttttcctcca catatgtcac ctcacaagca ccacctgcct caaacttttc atgtcctgtt | 120 |
| gattcaccta ccacatgctc tacatatttc acttaccttg cccagccacc aaatttcttg | 180 |
| gacctcggaa acatttctga tctatttggg gtcagtcgta aggaaatagc aactgcaagc | 240 |
| aacctggagt ctgaggacac cccattattt ccaaatcaac ttttgcttgt acctaaacct | 300 |
| tgtggttgca caggtaaccg gtcttttgcc aacataactt accaaatcca gcaaggtgaa | 360 |
| agcttctact tggttttcgac tacttcattt gagaacctca cccgttggca agaggtggaa | 420 |
| gctttgaacc ccagtctgac tccaacccte ttgcatgctg tgacaaggt tatatttcct | 480 |
| ttgttctgta agtgcccttc aaatactcat ttggagagcg gaattgctta tctcattact | 540 |
| tatgtgtggc aacctagtga tgatctcacg aaagttgctg ctaaacttaa tgcctctgaa | 600 |
| cgtaacattg tgattgaaaa caactatgtg aactttactg ctgcagtcta cctcccggta | 660 |
| ttgatccctg tgtcccagtt gccagttctc tctcaaacta agcttttga tcgcactgga | 720 |
| tcttgtttgg agaccggcga tctcattcaa acaaaggaac ttacaaaact ggagagtttt | 780 |
| gaggcaaaga tcacaccaga tgagctgctt ccagggttt caggatatct gagcaagccg | 840 |
| atcatttatg aggttaaaga gatcatggag ggcacgatgg atctaaatga acattataag | 900 |
| atacgaggat cagtatatag ggccaaaatc aatggccggg tcttggcagt gaagaaaacc | 960 |
| aaggatgatg tcacagaaga actaaagatt ttgcagaaag tcagtcatgc aaatctggtt | 1020 |
| aaactaatgg ggatgtcatc tggatttgac agagaaggaa atcgcttctt ggtctatgaa | 1080 |
| tatgcagaaa atgggtcgct ggaaaaatgg ttgcatccca cctctgaatc ttcctcaagc | 1140 |
| tctgcgggtt tcctcacttg gagtcaaagg ttacatgtag cactagatgt ggccaatggc | 1200 |
| ctgcaataca tgcatgaaca cactcaacca agcatcgttc acaaggatat tcgaacaact | 1260 |
| aatattcttc tcgattccac atttcgggcg aaaatagcaa atttctcaat ggctagacct | 1320 |
| gccacagact cattgatgcc aaaagttgat gtatttgatt atggagttgt tttgttacaa | 1380 |
| ttgctttctg gaaagaaggc catggtaacc aaagaaaatg gcgagattgt tctgctgtgc | 1440 |
| aaggaaatca agccgtcttt ggaaattgaa gagaaaagag aagagagtct aagaaagtgg | 1500 |
| atggatccct gcttggagag gttttatccc attgatagtg ctctgagctt ggcaaccttg | 1560 |
| gcaaggttgt gcactctgga ggagtcttca gaaaggccaa gcatggcaga aattgtcttc | 1620 |
| aacctcacag ttctcactca gtcacctcct gagacatttg aaagatggac atctgggatg | 1680 |
| gaaacagaag attttactcg actcatcagc cctgtcacag ctcgttga | 1728 |

<210> SEQ ID NO 96
<211> LENGTH: 21
<212> TYPE: DNA
<213> ORGANISM: Artificial

<220> FEATURE:
<223> OTHER INFORMATION: PCR primer

<400> SEQUENCE: 96
agctattcgc agttcccaaa t                    21

<210> SEQ ID NO 97
<211> LENGTH: 21
<212> TYPE: DNA
<213> ORGANISM: Artificial
<220> FEATURE:
<223> OTHER INFORMATION: PCR primer

<400> SEQUENCE: 97
cagagacgaa ccttgaggag a                    21

<210> SEQ ID NO 98
<211> LENGTH: 21
<212> TYPE: DNA
<213> ORGANISM: Artificial
<220> FEATURE:
<223> OTHER INFORMATION: PCR primer

<400> SEQUENCE: 98
aagaacatcc gtggaaaggt t                    21

<210> SEQ ID NO 99
<211> LENGTH: 21
<212> TYPE: DNA
<213> ORGANISM: Artificial
<220> FEATURE:
<223> OTHER INFORMATION: PCR primer

<400> SEQUENCE: 99
aatgttccca caagacgagt g                    21

<210> SEQ ID NO 100
<211> LENGTH: 21
<212> TYPE: DNA
<213> ORGANISM: Artificial
<220> FEATURE:
<223> OTHER INFORMATION: PCR primer

<400> SEQUENCE: 100
tgacatatgc caatctcacc a                    21

<210> SEQ ID NO 101
<211> LENGTH: 21
<212> TYPE: DNA
<213> ORGANISM: Artificial
<220> FEATURE:
<223> OTHER INFORMATION: PCR primer

<400> SEQUENCE: 101
gtgacattaa ccgtggcatt t                    21

<210> SEQ ID NO 102
<211> LENGTH: 21
<212> TYPE: DNA
<213> ORGANISM: Artificial
<220> FEATURE:
<223> OTHER INFORMATION: PCR primer

<400> SEQUENCE: 102
gatccacaac aacgtccaaa t                    21

```
<210> SEQ ID NO 103
<211> LENGTH: 21
<212> TYPE: DNA
<213> ORGANISM: Artificial
<220> FEATURE:
<223> OTHER INFORMATION: PCR primer

<400> SEQUENCE: 103
atggaagcaa tatcccaatc c                                              21

<210> SEQ ID NO 104
<211> LENGTH: 21
<212> TYPE: DNA
<213> ORGANISM: Artificial
<220> FEATURE:
<223> OTHER INFORMATION: PCR primer

<400> SEQUENCE: 104
taacggtgac gttgatgttc a                                              21

<210> SEQ ID NO 105
<211> LENGTH: 21
<212> TYPE: DNA
<213> ORGANISM: Artificial
<220> FEATURE:
<223> OTHER INFORMATION: PCR primer

<400> SEQUENCE: 105
gttgtcgagg ttgatttctc g                                              21

<210> SEQ ID NO 106
<211> LENGTH: 21
<212> TYPE: DNA
<213> ORGANISM: Artificial
<220> FEATURE:
<223> OTHER INFORMATION: PCR primer

<400> SEQUENCE: 106
agatgtgctt gtcccacaaa g                                              21

<210> SEQ ID NO 107
<211> LENGTH: 21
<212> TYPE: DNA
<213> ORGANISM: Artificial
<220> FEATURE:
<223> OTHER INFORMATION: PCR primer

<400> SEQUENCE: 107
cagaatcacc ccagtttacc a                                              21

<210> SEQ ID NO 108
<211> LENGTH: 21
<212> TYPE: DNA
<213> ORGANISM: Artificial
<220> FEATURE:
<223> OTHER INFORMATION: PcR primer

<400> SEQUENCE: 108
accgctcttt tgccaatatc t                                              21

<210> SEQ ID NO 109
<211> LENGTH: 21
<212> TYPE: DNA
<213> ORGANISM: Artificial
<220> FEATURE:
<223> OTHER INFORMATION: PCR primer

<400> SEQUENCE: 109
```
aacggggttt aaatccatca c                                               21

<210> SEQ ID NO 110
<211> LENGTH: 21
<212> TYPE: DNA
<213> ORGANISM: Artificial
<220> FEATURE:
<223> OTHER INFORMATION: PCR primer 1

<400> SEQUENCE: 110
catggccaga acttttacca a                                               21

<210> SEQ ID NO 111
<211> LENGTH: 21
<212> TYPE: DNA
<213> ORGANISM: Artificial
<220> FEATURE:
<223> OTHER INFORMATION: PCR primer

<400> SEQUENCE: 111
gttgtcatgg ctttcctacc a                                               21

<210> SEQ ID NO 112
<211> LENGTH: 21
<212> TYPE: DNA
<213> ORGANISM: Artificial
<220> FEATURE:
<223> OTHER INFORMATION: PCR primer 1

<400> SEQUENCE: 112
tgatctccta cgtcgtccaa c                                               21

<210> SEQ ID NO 113
<211> LENGTH: 21
<212> TYPE: DNA
<213> ORGANISM: Artificial
<220> FEATURE:
<223> OTHER INFORMATION: PCR primer

<400> SEQUENCE: 113
gcgtcaatga tggactgttc t                                               21

<210> SEQ ID NO 114
<211> LENGTH: 21
<212> TYPE: DNA
<213> ORGANISM: Artificial
<220> FEATURE:
<223> OTHER INFORMATION: PCR primer

<400> SEQUENCE: 114
cctctctctc caacctcacc t                                               21

<210> SEQ ID NO 115
<211> LENGTH: 21
<212> TYPE: DNA
<213> ORGANISM: Artificial
<220> FEATURE:
<223> OTHER INFORMATION: PCR primer

<400> SEQUENCE: 115
ctgatcctgg gagaggaact c                                               21

<210> SEQ ID NO 116
<211> LENGTH: 21
<212> TYPE: DNA
<213> ORGANISM: Artificial

```
<220> FEATURE:
<223> OTHER INFORMATION: PCR primer 1

<400> SEQUENCE: 116
ttcggttcct ggtgagtctt a                                              21

<210> SEQ ID NO 117
<211> LENGTH: 21
<212> TYPE: DNA
<213> ORGANISM: Artificial
<220> FEATURE:
<223> OTHER INFORMATION: PCR primer

<400> SEQUENCE: 117
tcatggggta catgagcttt c                                              21

<210> SEQ ID NO 118
<211> LENGTH: 26
<212> TYPE: DNA
<213> ORGANISM: Artificial
<220> FEATURE:
<223> OTHER INFORMATION: PCR primer

<400> SEQUENCE: 118
tggcatcact cagtaccttt caacag                                         26

<210> SEQ ID NO 119
<211> LENGTH: 28
<212> TYPE: DNA
<213> ORGANISM: Artificial
<220> FEATURE:
<223> OTHER INFORMATION: PCR primer

<400> SEQUENCE: 119
acccaaagca tcaaataata agtcaacc                                       28

<210> SEQ ID NO 120
<211> LENGTH: 20
<212> TYPE: DNA
<213> ORGANISM: Artificial
<220> FEATURE:
<223> OTHER INFORMATION: PCR primer

<400> SEQUENCE: 120
catgagcatt cagtgcctgt                                                20

<210> SEQ ID NO 121
<211> LENGTH: 21
<212> TYPE: DNA
<213> ORGANISM: Artificial
<220> FEATURE:
<223> OTHER INFORMATION: PCR primer

<400> SEQUENCE: 121
tgcagaatca gtaagcctgg t                                              21

<210> SEQ ID NO 122
<211> LENGTH: 23
<212> TYPE: DNA
<213> ORGANISM: Artificial
<220> FEATURE:
<223> OTHER INFORMATION: PCR primer

<400> SEQUENCE: 122
tgctaagggt tcagctgttg gta                                            23
```

```
<210> SEQ ID NO 123
<211> LENGTH: 24
<212> TYPE: DNA
<213> ORGANISM: Artificial
<220> FEATURE:
<223> OTHER INFORMATION: PCR primer

<400> SEQUENCE: 123
aaatgcccta gaagtttgtg gaag                                          24

<210> SEQ ID NO 124
<211> LENGTH: 20
<212> TYPE: DNA
<213> ORGANISM: Artificial
<220> FEATURE:
<223> OTHER INFORMATION: PCR primer

<400> SEQUENCE: 124
cgcaagatgg atgtgtatgc                                               20

<210> SEQ ID NO 125
<211> LENGTH: 20
<212> TYPE: DNA
<213> ORGANISM: Artificial
<220> FEATURE:
<223> OTHER INFORMATION: PCR primer

<400> SEQUENCE: 125
catggctctc gaactcgttt                                               20

<210> SEQ ID NO 126
<211> LENGTH: 25
<212> TYPE: DNA
<213> ORGANISM: Artificial
<220> FEATURE:
<223> OTHER INFORMATION: PCR primer

<400> SEQUENCE: 126
cactcatatt cttttctgcc accca                                         25

<210> SEQ ID NO 127
<211> LENGTH: 23
<212> TYPE: DNA
<213> ORGANISM: Artificial
<220> FEATURE:
<223> OTHER INFORMATION: PCR primer

<400> SEQUENCE: 127
tgcaatggat tgaggactgg tgt                                           23

<210> SEQ ID NO 128
<211> LENGTH: 20
<212> TYPE: DNA
<213> ORGANISM: Artificial
<220> FEATURE:
<223> OTHER INFORMATION: PCR primer

<400> SEQUENCE: 128
ggaaatggag aaatggcaaa                                               20

<210> SEQ ID NO 129
<211> LENGTH: 20
<212> TYPE: DNA
<213> ORGANISM: Artificial
<220> FEATURE:
<223> OTHER INFORMATION: PcR primer

<400> SEQUENCE: 129
```
cgccttgacc aagaaaccta                                        20

<210> SEQ ID NO 130
<211> LENGTH: 20
<212> TYPE: DNA
<213> ORGANISM: Artificial
<220> FEATURE:
<223> OTHER INFORMATION: PCR primer

<400> SEQUENCE: 130
ggcattgatg ggtcagaact                                        20

<210> SEQ ID NO 131
<211> LENGTH: 20
<212> TYPE: DNA
<213> ORGANISM: Artificial
<220> FEATURE:
<223> OTHER INFORMATION: PcR primer

<400> SEQUENCE: 131
tgcaaagagg atcacactgc                                        20

<210> SEQ ID NO 132
<211> LENGTH: 25
<212> TYPE: DNA
<213> ORGANISM: Artificial
<220> FEATURE:
<223> OTHER INFORMATION: PCR primer

<400> SEQUENCE: 132
ctcttcttct tcttcttcgt cagca                                  25

<210> SEQ ID NO 133
<211> LENGTH: 24
<212> TYPE: DNA
<213> ORGANISM: Artificial
<220> FEATURE:
<223> OTHER INFORMATION: PCR primer

<400> SEQUENCE: 133
ggtatgcttg gcatgtttga gttt                                   24

<210> SEQ ID NO 134
<211> LENGTH: 20
<212> TYPE: DNA
<213> ORGANISM: Artificial
<220> FEATURE:
<223> OTHER INFORMATION: PCR primer

<400> SEQUENCE: 134
ggttgttctc ggaatcttcg                                        20

<210> SEQ ID NO 135
<211> LENGTH: 20
<212> TYPE: DNA
<213> ORGANISM: Artificial
<220> FEATURE:
<223> OTHER INFORMATION: PCR primer

<400> SEQUENCE: 135
atgcatgtat tgcagaccga                                        20

<210> SEQ ID NO 136
<211> LENGTH: 24
<212> TYPE: DNA
<213> ORGANISM: Artificial

```
<220> FEATURE:
<223> OTHER INFORMATION: PCR primer

<400> SEQUENCE: 136
tttcactctt ggtgtgaagc agat                                    24

<210> SEQ ID NO 137
<211> LENGTH: 25
<212> TYPE: DNA
<213> ORGANISM: Artificial
<220> FEATURE:
<223> OTHER INFORMATION: PcR primer

<400> SEQUENCE: 137
gacttccttc acgatttcat cgtaa                                   25

<210> SEQ ID NO 138
<211> LENGTH: 20
<212> TYPE: DNA
<213> ORGANISM: Artificial
<220> FEATURE:
<223> OTHER INFORMATION: PCR primer

<400> SEQUENCE: 138
atggcgatat gggtgacatt                                         20

<210> SEQ ID NO 139
<211> LENGTH: 20
<212> TYPE: DNA
<213> ORGANISM: Artificial
<220> FEATURE:
<223> OTHER INFORMATION: PCR primer

<400> SEQUENCE: 139
tccacatgga aggtgaatga                                         20

<210> SEQ ID NO 140
<211> LENGTH: 20
<212> TYPE: DNA
<213> ORGANISM: Artificial
<220> FEATURE:
<223> OTHER INFORMATION: PCR primer

<400> SEQUENCE: 140
gttcttgcgt ctggtgctct                                         20

<210> SEQ ID NO 141
<211> LENGTH: 19
<212> TYPE: DNA
<213> ORGANISM: Artificial
<220> FEATURE:
<223> OTHER INFORMATION: PCR primer

<400> SEQUENCE: 141
ctccttatcc ggagccaac                                          19

<210> SEQ ID NO 142
<211> LENGTH: 20
<212> TYPE: DNA
<213> ORGANISM: Artificial
<220> FEATURE:
<223> OTHER INFORMATION: PCR primer

<400> SEQUENCE: 142
atggaggagg tgttcgtcac                                         20
```

```
<210> SEQ ID NO 143
<211> LENGTH: 20
<212> TYPE: DNA
<213> ORGANISM: Artificial
<220> FEATURE:
<223> OTHER INFORMATION: PCR primer

<400> SEQUENCE: 143
ccgaggacca tagaagctga                                              20

<210> SEQ ID NO 144
<211> LENGTH: 20
<212> TYPE: DNA
<213> ORGANISM: Artificial
<220> FEATURE:
<223> OTHER INFORMATION: PcR primer

<400> SEQUENCE: 144
catggtcacc tacctcgtca                                              20

<210> SEQ ID NO 145
<211> LENGTH: 20
<212> TYPE: DNA
<213> ORGANISM: Artificial
<220> FEATURE:
<223> OTHER INFORMATION: PCR primer

<400> SEQUENCE: 145
tatgatggag ctctcggtga                                              20

<210> SEQ ID NO 146
<211> LENGTH: 20
<212> TYPE: DNA
<213> ORGANISM: Artificial
<220> FEATURE:
<223> OTHER INFORMATION: PCR primer

<400> SEQUENCE: 146
gttcatcgac aaaccgatca                                              20

<210> SEQ ID NO 147
<211> LENGTH: 20
<212> TYPE: DNA
<213> ORGANISM: Artificial
<220> FEATURE:
<223> OTHER INFORMATION: PCR primer

<400> SEQUENCE: 147
taatacgagc tgccgagctt                                              20

<210> SEQ ID NO 148
<211> LENGTH: 20
<212> TYPE: DNA
<213> ORGANISM: Artificial
<220> FEATURE:
<223> OTHER INFORMATION: PCR primer

<400> SEQUENCE: 148
gtgacgagga gaatggagga                                              20

<210> SEQ ID NO 149
<211> LENGTH: 20
<212> TYPE: DNA
<213> ORGANISM: Artificial
<220> FEATURE:
<223> OTHER INFORMATION: PCR primer

<400> SEQUENCE: 149
```
ctcgatcagc ttcaccatca                                         20

<210> SEQ ID NO 150
<211> LENGTH: 29
<212> TYPE: PRT
<213> ORGANISM: Medicago truncatula

<400> SEQUENCE: 150

Thr Tyr Pro Ile Arg Ser Glu Asp Thr Leu Glu Ser Ile Ala Lys Gly
1               5                   10                  15

Ala Glu Ile Glu Ala Glu Leu Ile Gln Arg Tyr Asn Pro
            20                  25

<210> SEQ ID NO 151
<211> LENGTH: 30
<212> TYPE: PRT
<213> ORGANISM: Medicago truncatula

<400> SEQUENCE: 151

Ile Thr Tyr Pro Leu Arg Pro Glu Asp Ser Leu Glu Leu Ile Ser Asn
1               5                   10                  15

Lys Tyr Glu Ile Asp Ala Glu Leu Ile Gln Lys Tyr Asn Pro
            20                  25                  30

<210> SEQ ID NO 152
<211> LENGTH: 107
<212> TYPE: PRT
<213> ORGANISM: Medicago truncatula

<400> SEQUENCE: 152

Tyr Ser Ala Lys Glu Gly Asp Thr Tyr Asp Leu Ile Ala Asn Ser Tyr
1               5                   10                  15

Tyr Ala Ser Leu Thr Thr Val Glu Leu Leu Lys Lys Phe Asn Ser Tyr
            20                  25                  30

Asp Gln Asp His Ile Pro Ala Lys Ala Lys Val Asn Val Thr Val Asn
        35                  40                  45

Cys Ser Cys Gly Asn Ser Gln Ile Ser Lys Asp Tyr Gly Leu Phe Ile
    50                  55                  60

Thr Tyr Pro Leu Arg Thr Asp Thr Leu Gln Lys Ile Ala Asn Gln
65                  70                  75                  80

Ser Asn Leu Asp Glu Gly Leu Ile Gln Ser Tyr Asn Ser Gly Val Asn
                85                  90                  95

Phe Ser Asn Gly Ser Gly Ile Val Phe Ile Pro
            100                 105

<210> SEQ ID NO 153
<211> LENGTH: 46
<212> TYPE: PRT
<213> ORGANISM: Populus sp.

<400> SEQUENCE: 153

Tyr Thr Val Gln Glu Asn Asp Thr Leu Thr Gly Ile Ala Glu Leu Leu
1               5                   10                  15

Ser Ala Glu Leu Thr Gly Ile Glu Asn Leu Asn Glu Arg Phe Thr Arg
            20                  25                  30

Asn Pro Asn Leu Ile Asp Val Gly Trp Val Leu Phe Val Pro
        35                  40                  45

<210> SEQ ID NO 154
<211> LENGTH: 112

<212> TYPE: PRT
<213> ORGANISM: Populus sp.

<400> SEQUENCE: 154

```
Ile Ser Ser Ala Asn Ile Thr Tyr Thr Ile Glu Ala Gly Asn Thr Phe
1               5                   10                  15

Tyr Ile Val Ser Thr Glu Tyr Phe Gln Asn Leu Thr Thr Tyr Gln Ser
            20                  25                  30

Val Glu Leu Phe Asn Pro Thr Leu Ile Pro Glu Leu Ile Asp Ile Gly
        35                  40                  45

Val Glu Val Pro Ile Phe Cys Lys Cys Pro Asn Gln Thr Gln Leu Gln
    50                  55                  60

Asn Lys Val Asn Tyr Leu Val Ser Tyr Val Phe Gln Pro Ser Asp Asn
65                  70                  75                  80

Leu Ser Ser Val Ala Ser Thr Phe Gly Val Glu Thr Gln Ser Ile Val
                85                  90                  95

Asp Val Asn Gly Asn Asn Ile Gln Pro Tyr Asp Thr Ile Phe Val Pro
            100                 105                 110
```

<210> SEQ ID NO 155
<211> LENGTH: 116
<212> TYPE: PRT
<213> ORGANISM: Pisum sativum

<400> SEQUENCE: 155

```
Arg Tyr Phe Ala Asn Phe Thr Tyr Thr Ile Lys Leu Gly Asp Asn Tyr
1               5                   10                  15

Phe Ile Val Ser Thr Thr Ser Tyr Gln Asn Leu Thr Asn Tyr Val Glu
            20                  25                  30

Met Glu Asn Phe Asn Pro Asn Leu Ser Pro Asn Leu Ile Pro Pro Glu
        35                  40                  45

Ile Lys Val Val Pro Leu Phe Cys Lys Cys Pro Ser Lys Asn Gln
    50                  55                  60

Leu Ser Lys Gly Ile Lys His Leu Ile Thr Tyr Val Met Gln Ala Asn
65                  70                  75                  80

Asp Asn Val Thr Arg Val Ser Ser Lys Phe Gly Ala Ser Gln Val Asp
                85                  90                  95

Met Phe Thr Glu Asn Asn Gln Asn Phe Thr Ala Ser Thr Asn Val Pro
            100                 105                 110

Ile Leu Ile Pro
        115
```

<210> SEQ ID NO 156
<211> LENGTH: 107
<212> TYPE: PRT
<213> ORGANISM: Populus sp.

<400> SEQUENCE: 156

```
Tyr Thr Val Gln Lys Asp Asp Gly Leu Phe His Ile Ala Ala Glu Val
1               5                   10                  15

Phe Ser Gly Leu Val Thr Tyr Gln Glu Ile Ala Ala Val Asn Asn Ile
            20                  25                  30

Ser Asp Val Asn Leu Ile Lys Val Gly Gln Lys Leu Leu Ile Pro Leu
        35                  40                  45

Phe Cys Asn Cys Asp Asp Val Asp Gly Val Lys Val Val His Tyr Gly
    50                  55                  60

His Val Val Glu Ala Gly Ser Ser Leu Glu Leu Ile Ala Gln Glu Tyr
65                  70                  75                  80
```

```
Gly Thr Ser Thr Asp Thr Leu Val Lys Leu Asn Gly Val Asn Asp Ser
                85                  90                  95

Ser Leu Leu Ala Gly Gln Val Leu Asp Val Pro
            100                 105
```

<210> SEQ ID NO 157
<211> LENGTH: 110
<212> TYPE: PRT
<213> ORGANISM: Populus sp.

<400> SEQUENCE: 157

```
Tyr Thr Val Gln Lys Asp Asp Gly Leu Tyr His Ile Ala Ala Glu Val
1               5                   10                  15

Phe Ser Gly Leu Val Thr Tyr Gln Glu Ile Ala Ala Val Asn Asn Asn
                20                  25                  30

Val Thr Asp Val Asn Leu Ile Glu Val Gly Gln Glu Leu Met Ile Pro
            35                  40                  45

Leu Pro Cys Ser Cys Asp Asp Val Asp Gly Val Lys Val Val His Tyr
        50                  55                  60

Gly His Val Val Glu Ala Gly Ser Ser Leu Glu Phe Ile Ala Gln Glu
65                  70                  75                  80

Tyr Gly Thr Ser Arg Asn Thr Ile Met Lys Leu Asn Gly Ile Ala Asn
                85                  90                  95

Gly Ser Ser Leu Leu Ala Gly Gln Leu Ser Leu Leu Val Ser
            100                 105                 110
```

<210> SEQ ID NO 158
<211> LENGTH: 108
<212> TYPE: PRT
<213> ORGANISM: Populus sp.

<400> SEQUENCE: 158

```
Tyr Thr Val Gln Pro Asp Asp Gly Leu Tyr Tyr Ile Ala Asn Asn Val
1               5                   10                  15

Phe Met Gly Leu Leu Ala His Gln Arg Ile Gln Gln Val Asn Arg Ile
                20                  25                  30

Glu Asn Pro Asn Val Ile Tyr Val Gly Gln Glu Leu Trp Ile Pro Leu
            35                  40                  45

Pro Cys Ser Cys Glu Glu Val Glu Gly Glu Arg Val Val His Tyr Ala
        50                  55                  60

His Leu Val Glu Glu Gly Ser Thr Val Glu Glu Ile Ala Glu Lys Phe
65                  70                  75                  80

Gly Thr Thr Asn Asp Thr Leu Tyr Arg Leu Asn Gly Ile Thr Asn Asn
                85                  90                  95

Ser Gln Leu Ile Ala Ala Thr Ala Phe Asp Val Pro
            100                 105
```

<210> SEQ ID NO 159
<211> LENGTH: 107
<212> TYPE: PRT
<213> ORGANISM: Arabidopsis thaliana

<400> SEQUENCE: 159

```
Thr Ile Lys Lys Asp Asp Ile Leu Ser Phe Val Ala Thr Glu Ile Phe
1               5                   10                  15

Gly Gly Leu Val Thr Tyr Glu Lys Ile Ser Glu Val Asn Lys Ile Pro
                20                  25                  30

Asp Pro Asn Lys Ile Glu Ile Gly Gln Lys Phe Trp Ile Pro Leu Pro
```

```
                35                  40                  45
Cys Ser Cys Asp Lys Leu Asn Gly Glu Asp Val Val His Tyr Ala His
        50                  55                  60

Val Val Lys Leu Gly Ser Ser Leu Gly Glu Ile Ala Ala Gln Phe Gly
 65                  70                  75                  80

Thr Asp Asn Thr Thr Leu Ala Gln Leu Asn Gly Ile Ile Gly Asp Ser
                85                  90                  95

Gln Leu Leu Ala Asp Lys Pro Leu Asp Val Pro
            100                 105

<210> SEQ ID NO 160
<211> LENGTH: 110
<212> TYPE: PRT
<213> ORGANISM: Glycine max

<400> SEQUENCE: 160

Pro Leu Tyr Arg Ile Lys Lys Gly Asp Thr Leu Tyr Tyr Ile Ala Thr
 1               5                  10                  15

Thr Thr Phe Ala Gly Leu Met Lys Trp Pro Gln Ile Gln Val Ala Asn
            20                  25                  30

Asn Ile Ala Asn Ala Asn Asn Ile Thr Thr Gly Asp Met Leu Tyr Ile
        35                  40                  45

Pro Leu Pro Cys Ser Cys Asp Glu Val Gly Gly Lys Ser Val Val His
 50                  55                  60

Tyr Ala His Leu Val Ala Pro Gln Ser Thr Val Glu Gly Ile Ala Glu
 65                  70                  75                  80

Glu Phe Gly Tyr Tyr Gln Gln Ile Leu Leu Asn Leu Asn Gly Ile Ser
                85                  90                  95

Asp Pro Lys Asn Leu Gln Ala Gly Gln Ile Leu Asp Val Pro
            100                 105                 110

<210> SEQ ID NO 161
<211> LENGTH: 108
<212> TYPE: PRT
<213> ORGANISM: Oryza sativa

<400> SEQUENCE: 161

Tyr Val Val Gln Pro Gln Asp Gly Leu Asp Ala Ile Ala Arg Asn Val
 1               5                  10                  15

Phe Asn Ala Phe Val Thr Tyr Gln Glu Ile Ala Ala Ala Asn Asn Ile
            20                  25                  30

Pro Asp Pro Asn Lys Ile Asn Val Ser Gln Thr Leu Trp Ile Pro Leu
        35                  40                  45

Pro Cys Ser Cys Asp Lys Glu Glu Gly Ser Asn Val Met His Leu Ala
 50                  55                  60

Tyr Ser Val Gly Lys Gly Glu Asn Thr Ser Ala Ile Ala Ala Lys Tyr
 65                  70                  75                  80

Gly Val Thr Glu Ser Thr Leu Leu Thr Arg Asn Lys Ile Asp Asp Pro
                85                  90                  95

Thr Lys Leu Gln Met Gly Gln Ile Leu Asp Val Pro
            100                 105

<210> SEQ ID NO 162
<211> LENGTH: 109
<212> TYPE: PRT
<213> ORGANISM: Populus sp.

<400> SEQUENCE: 162
```

Tyr Lys Thr Arg Pro Ser Asp Thr Leu Ser Thr Ile Ala Asp Ser Ile
1               5                   10                  15

Tyr Ala Gly Leu Val Ser Ala Asp Gln Ile Lys Glu Ala Asn Ser Ile
            20                  25                  30

Asp Asp Pro Ser Val Leu Asp Val Gly Gln Ser Leu Val Val Pro Leu
            35                  40                  45

Pro Cys Thr Cys Phe Asn Gly Thr Asp Asn Ser Leu Pro Ala Ile Tyr
50                  55                  60

Leu Ser Tyr Val Val Lys Glu Val Asp Thr Leu Ala Ala Ile Ala Ala
65                  70                  75                  80

Arg Tyr Ala Thr Thr Leu Thr Asp Ile Met Asn Val Asn Ala Met Gly
                85                  90                  95

Ser Val Ala Ile Met Ala Gly Asp Ile Leu Ala Val Pro
                100                 105

<210> SEQ ID NO 163
<211> LENGTH: 110
<212> TYPE: PRT
<213> ORGANISM: Populus sp.

<400> SEQUENCE: 163

His Tyr Lys Thr Arg Pro Ser Asp Thr Leu Ser Thr Ile Ala Asp Ser
1               5                   10                  15

Ile Tyr Ala Gly Leu Val Ser Ala Asp Gln Ile Lys Glu Ala Asn Ser
            20                  25                  30

Ile Asp Asp Pro Ser Val Ile Asp Val Gly Gln Ser Leu Val Val Pro
            35                  40                  45

Leu Pro Cys Thr Cys Phe Asn Gly Thr Asp Asn Ser Leu Pro Ala Ile
50                  55                  60

Tyr Leu Ser Tyr Val Val Lys Glu Val Asp Thr Leu Ala Ala Ile Ala
65                  70                  75                  80

Ala Arg Tyr Ala Thr Thr Leu Thr Asp Ile His Asn Val Asn Ala Met
                85                  90                  95

Gly Ser Val Ala Ile Met Ala Gly Asp Ile Leu Ala Val Pro
                100                 105                 110

<210> SEQ ID NO 164
<211> LENGTH: 110
<212> TYPE: PRT
<213> ORGANISM: Populus sp.

<400> SEQUENCE: 164

His Tyr Lys Thr Arg Pro Ser Asp Thr Leu Ser Ser Ile Ala Asp Ser
1               5                   10                  15

Ile Tyr Ala Gly Leu Val Ser Ala Asp Gln Ile Lys Glu Ala Asn Ser
            20                  25                  30

Ile Asp Asp Pro Ser Val Ile Asp Val Gly Gln Ser Leu Val Val Pro
            35                  40                  45

Leu Pro Cys Thr Cys Phe Asn Gly Thr Asp Asn Ser Leu Pro Ala Ile
50                  55                  60

Tyr Leu Ser Tyr Val Val Lys Glu Val Asp Thr Leu Ala Ala Ile Ala
65                  70                  75                  80

Ala Arg Tyr Glu Thr Thr Leu Thr Asp Ile Met Asn Val Asn Ala Met
                85                  90                  95

Gly Ser Ala Ala Ile Lys Ala Gly Asp Ile Leu Ala Val Pro
                100                 105                 110

```
<210> SEQ ID NO 165
<211> LENGTH: 79
<212> TYPE: PRT
<213> ORGANISM: Glycine max

<400> SEQUENCE: 165

Ser Asp Pro Ser Val Ile Asp Val Gly Gln Asn Leu Val Val Pro Leu
1               5                   10                  15

Pro Cys Thr Cys Phe Asn Gly Ser Asp Asn Ser Leu Pro Ala Ile Tyr
            20                  25                  30

Leu Ser Tyr Val Val Arg Pro Val Asp Thr Leu Ala Ala Ile Ala Ala
        35                  40                  45

Arg Tyr Phe Thr Thr Leu Thr Asp Leu Met Asn Val Asn Ala Met Gly
    50                  55                  60

Ser Tyr Ala Ile Asn Asp Gly Asp Ile Leu Ala Val Pro Ile Pro
65                  70                  75

<210> SEQ ID NO 166
<211> LENGTH: 100
<212> TYPE: PRT
<213> ORGANISM: Glycine max

<400> SEQUENCE: 166

His Tyr Arg Thr Arg Pro Ser Asp Thr Leu Ser Ser Ile Ala Asn Ser
1               5                   10                  15

Ile Tyr Gly Gly Leu Val Ser Pro Asp Gln Leu Arg Glu Ala Asn Ser
            20                  25                  30

Ile Gly Asp Asp Pro Ser Val Ile Asp Val Gly Leu Asn Leu Val Val
        35                  40                  45

Pro Leu Pro Cys Thr Cys Phe Asn Glu Ser Asp Asn Ser Leu Pro Ser
    50                  55                  60

Ile Tyr Leu Ser Tyr Val Val Gln Pro Ile Asp Thr Leu Ala Ala Ile
65                  70                  75                  80

Ala Ala Arg Tyr Phe Thr Thr Phe Thr Asp Ile His Asn Val Asn Asp
                85                  90                  95

Met Gly Thr Thr
            100

<210> SEQ ID NO 167
<211> LENGTH: 100
<212> TYPE: PRT
<213> ORGANISM: Arabidopsis thaliana

<400> SEQUENCE: 167

Gly Ser Ile Ala Asp Ser Val Tyr Gly Gly Leu Val Ser Ala Glu Gln
1               5                   10                  15

Ile Gln Glu Ala Asn Ser Val Asn Asp Pro Ser Leu Ile Asp Val Gly
            20                  25                  30

Thr Ser Leu Val Ile Pro Leu Pro Cys Ala Cys Phe Asn Gly Thr Asp
        35                  40                  45

Asn Ser Leu Pro Ala Val Tyr Leu Ser Tyr Val Val Lys Glu Ile Asp
    50                  55                  60

Thr Leu Val Gly Ile Ala Arg Arg Tyr Ser Thr Thr Ile Thr Asp Leu
65                  70                  75                  80

Met Asn Val Asn Ala Met Gly Ala Pro Asp Val Ser Ser Gly Asp Ile
                85                  90                  95

Leu Ala Val Pro
            100
```

<210> SEQ ID NO 168
<211> LENGTH: 108
<212> TYPE: PRT
<213> ORGANISM: Arabidopsis thaliana

<400> SEQUENCE: 168

Lys Thr Arg Thr Ser Asp Thr Leu Gly Ser Ile Ala Asp Ser Val Tyr
1               5                   10                  15

Gly Gly Leu Val Ser Pro Glu Gln Ile Gln Val Ala Asn Ser Glu Thr
            20                  25                  30

Asp Leu Ser Val Leu Asp Val Gly Thr Lys Leu Val Ile Pro Leu Pro
        35                  40                  45

Cys Ala Cys Phe Asn Gly Thr Asp Glu Ser Leu Pro Ala Leu Tyr Leu
    50                  55                  60

Ser Tyr Val Val Arg Gly Ile Asp Thr Met Ala Gly Ile Ala Lys Arg
65                  70                  75                  80

Phe Ser Thr Ser Val Thr Asp Leu Thr Asn Val Asn Ala Met Gly Ala
                85                  90                  95

Pro Asp Ile Asn Pro Gly Asp Ile Leu Ala Val Pro
            100                 105

<210> SEQ ID NO 169
<211> LENGTH: 109
<212> TYPE: PRT
<213> ORGANISM: Glycine max
<220> FEATURE:
<221> NAME/KEY: misc_feature
<222> LOCATION: (76)..(76)
<223> OTHER INFORMATION: Xaa can be any naturally occurring amino acid

<400> SEQUENCE: 169

Ile Tyr Thr Val His Ala Ala Asp Thr Leu Ala Ser Ile Ser Glu Gly
1               5                   10                  15

Tyr Gly Gly Leu Val Ser Ala Glu Gln Ile Lys Ile Val Asn Ala Ile
            20                  25                  30

Asn Ala Thr Asn Pro Leu Thr Tyr Arg Gly Thr Leu Val Ile Pro Leu
        35                  40                  45

Pro Cys Thr Cys Phe Asp Asn Val Asn Asn Gly Gly Asn Ala Ile Tyr
    50                  55                  60

Met Ser Tyr Val Val Gln Arg Arg Glu Ser Leu Xaa Ser Ile Ala Thr
65                  70                  75                  80

Lys Phe Gly Thr Thr Val Ser Asp Leu Glu Thr Val Asn Gly Phe Gly
                85                  90                  95

Glu Ala Thr Val Asp Pro Gly Asp Ile Leu Ser Ile Pro
            100                 105

<210> SEQ ID NO 170
<211> LENGTH: 45
<212> TYPE: PRT
<213> ORGANISM: Glycine max

<400> SEQUENCE: 170

Ile Tyr Val Val Arg Glu Gly Glu Thr Leu Gln Thr Ile Ser Glu Lys
1               5                   10                  15

Cys Gly Asp Pro Tyr Ile Val Glu Glu Asn Phe His Ile His Asp Phe
            20                  25                  30

Asp Asp Val Phe Pro Gly Leu Val Ile Lys Ile Asn Pro
        35                  40                  45

```
<210> SEQ ID NO 171
<211> LENGTH: 44
<212> TYPE: PRT
<213> ORGANISM: Medicago truncatula

<400> SEQUENCE: 171

Tyr Val Val Arg Glu Gly Glu Thr Leu His Thr Ile Ser Glu Lys Cys
1               5                   10                  15

Gly Asp Pro Phe Ile Val Glu Glu Asn Phe His Ile His Asp Phe Asp
            20                  25                  30

Asp Val Phe Pro Gly Leu Val Ile Lys Ile Asn Pro
        35                  40

<210> SEQ ID NO 172
<211> LENGTH: 44
<212> TYPE: PRT
<213> ORGANISM: Populus sp.

<400> SEQUENCE: 172

Tyr Val Val Arg Glu Gly Glu Thr Leu Asn Thr Ile Ser Glu Lys Cys
1               5                   10                  15

Gly Asp Pro Tyr Ile Val Glu Glu Asn Phe His Ile His Asp Phe Asp
            20                  25                  30

Asp Val Phe Pro Gly Leu Val Ile Lys Ile Thr Pro
        35                  40

<210> SEQ ID NO 173
<211> LENGTH: 45
<212> TYPE: PRT
<213> ORGANISM: Glycine max

<400> SEQUENCE: 173

Ile Tyr Val Val Gly Glu Gly Glu Thr Leu Phe Thr Ile Ser Asp Lys
1               5                   10                  15

Cys Asn Asp Pro Phe Ile Val Glu Arg Asn Phe His Ile His Asp Phe
            20                  25                  30

Asp Asp Val Phe Pro Gly Leu Val Ile Lys Ile Thr Pro
        35                  40                  45

<210> SEQ ID NO 174
<211> LENGTH: 45
<212> TYPE: PRT
<213> ORGANISM: Glycine max

<400> SEQUENCE: 174

Ile Tyr Val Val Gly Glu Gly Glu Thr Leu His Thr Ile Ser Asp Lys
1               5                   10                  15

Cys Gly Asp Pro Phe Ile Val Glu Arg Asn Phe His Ile His Asp Phe
            20                  25                  30

Asp Asp Val Phe Pro Gly Leu Val Ile Lys Ile Thr Pro
        35                  40                  45

<210> SEQ ID NO 175
<211> LENGTH: 44
<212> TYPE: PRT
<213> ORGANISM: Populus sp.

<400> SEQUENCE: 175

Tyr Val Val Gly Glu Gly Glu Thr Leu His Thr Ile Ser Asp Lys Cys
1               5                   10                  15

Gly Asp Pro Phe Ile Val Glu Gln Asn Phe His Ile His Asp Phe Asp
            20                  25                  30
```

```
Asp Val Phe Pro Gly Leu Val Ile Lys Ile Thr Pro
            35                  40

<210> SEQ ID NO 176
<211> LENGTH: 43
<212> TYPE: PRT
<213> ORGANISM: Glycine max

<400> SEQUENCE: 176

Ile Tyr Val Val Gly Glu Gly Glu Thr Leu His Thr Ile Ser Asp Lys
1               5                   10                  15

Cys Gly Asp Pro Phe Ile Val Glu Lys Asn Phe His Ile His Asp Phe
            20                  25                  30

Asp Asp Val Phe Pro Gly Leu Val Leu Lys Ile
            35                  40

<210> SEQ ID NO 177
<211> LENGTH: 45
<212> TYPE: PRT
<213> ORGANISM: Glycine max

<400> SEQUENCE: 177

Ile Tyr Val Val Gly Glu Gly Glu Thr Leu His Thr Ile Ser Asp Lys
1               5                   10                  15

Cys Gly Asp Pro Phe Ile Val Glu Lys Asn Phe His Ile His Asp Phe
            20                  25                  30

Asp Asp Val Phe Pro Gly Leu Val Ile Lys Ile Thr Pro
            35                  40                  45

<210> SEQ ID NO 178
<211> LENGTH: 32
<212> TYPE: PRT
<213> ORGANISM: Glycine max

<400> SEQUENCE: 178

Ile Tyr Val Val Gly Glu Gly Glu Thr Leu His Thr Ile Ser Asp Lys
1               5                   10                  15

Cys Gly Asp Pro Phe Ile Val Glu Asn Asn Phe His Ile His Asp Phe
            20                  25                  30

<210> SEQ ID NO 179
<211> LENGTH: 44
<212> TYPE: PRT
<213> ORGANISM: Populus sp.

<400> SEQUENCE: 179

Tyr Val Val Lys Glu Gly Glu Thr Leu His Thr Ile Ser Asp Lys Cys
1               5                   10                  15

Gly Asp Pro Phe Ile Val Glu Glu Asn Phe His Ile His Asp Phe Asp
            20                  25                  30

Asp Val Tyr Pro Gly Leu Val Ile Lys Ile Thr Pro
            35                  40

<210> SEQ ID NO 180
<211> LENGTH: 44
<212> TYPE: PRT
<213> ORGANISM: Populus sp.

<400> SEQUENCE: 180

Tyr Val Val Lys Glu Gly Glu Thr Leu His Thr Ile Ser Asp Lys Cys
1               5                   10                  15
```

```
Asp Asp Pro Phe Ile Val Glu Glu Asn Phe His Ile His Asp Phe Asp
            20                  25                  30

Asp Val Phe Pro Gly Leu Val Ile Lys Ile Thr Pro
            35                  40
```

<210> SEQ ID NO 181
<211> LENGTH: 43
<212> TYPE: PRT
<213> ORGANISM: Populus sp.

<400> SEQUENCE: 181

```
Ile Tyr Val Val Gly Glu Gly Glu Thr Leu Asn Thr Ile Ser Glu Lys
1               5                   10                  15

Cys Asp Asp Pro Phe Ile Val Glu Gln Asn Phe His Ile His Asp Phe
            20                  25                  30

Asp Asp Val Tyr Pro Gly Leu Val Ile Lys Ile
            35                  40
```

<210> SEQ ID NO 182
<211> LENGTH: 43
<212> TYPE: PRT
<213> ORGANISM: Arabidopsis thaliana

<400> SEQUENCE: 182

```
Ile Val Gly Glu Gly Glu Thr Leu His Thr Ile Gly Asp Lys Cys Gly
1               5                   10                  15

Asp Pro Phe Ile Val Glu Arg Asn Phe His Ile His Asp Phe Asp Asp
            20                  25                  30

Val Phe Pro Gly Leu Val Leu Lys Ile Ala Pro
            35                  40
```

<210> SEQ ID NO 183
<211> LENGTH: 46
<212> TYPE: PRT
<213> ORGANISM: Oryza sativa

<400> SEQUENCE: 183

```
Glu Ile Tyr Val Val Glu Glu Gly Glu Thr Leu His Ser Ile Ser Asp
1               5                   10                  15

Arg Cys Gly Asp Pro Tyr Ile Leu Glu Gln Asn Phe His Val His Asp
            20                  25                  30

Phe Asp Asp Val Phe Pro Gly Leu Val Ile Lys Ile Thr Pro
            35                  40                  45
```

<210> SEQ ID NO 184
<211> LENGTH: 43
<212> TYPE: PRT
<213> ORGANISM: Arabidopsis thaliana

<400> SEQUENCE: 184

```
Tyr Val Val Gly Glu Gly Asp Thr Leu His Ser Ile Ser Glu Lys Cys
1               5                   10                  15

Gly Asp Pro Phe Ile Val Glu Arg Asn Phe His Ile His Asp Phe Asp
            20                  25                  30

Asp Val Phe Pro Gly Leu Leu Ile Lys Leu His
            35                  40
```

<210> SEQ ID NO 185
<211> LENGTH: 43
<212> TYPE: PRT
<213> ORGANISM: Arabidopsis thaliana

```
<400> SEQUENCE: 185

Glu Val Lys Glu Gly Glu Thr Leu Gln Thr Ile Ser Glu Lys Cys Gly
1               5                   10                  15

Asp Pro Tyr Ile Val Glu Gly Asn Phe His Ile His Asp His Asp
            20                  25                  30

Leu Phe Pro Gly Leu Leu Ile Arg Ile Thr Pro
        35                  40

<210> SEQ ID NO 186
<211> LENGTH: 45
<212> TYPE: PRT
<213> ORGANISM: Populus sp.

<400> SEQUENCE: 186

His Val Val Lys Glu Gly Glu Thr Leu Thr Ser Ile Ser Lys Gln Tyr
1               5                   10                  15

Gly Val Ser Ile Tyr Ser Val Ala Ala Ala Asn Lys Asn Ile Leu Asp
            20                  25                  30

Val Asp Leu Val Phe Glu Gly Gln Ile Leu Asn Ile Phe
        35                  40                  45

<210> SEQ ID NO 187
<211> LENGTH: 49
<212> TYPE: PRT
<213> ORGANISM: Populus sp.

<400> SEQUENCE: 187

His Asp Val Val Arg Gly Asp Thr Leu Ser Ala Ile Ala Lys Lys Phe
1               5                   10                  15

Tyr Gly Asp Ala Asn Lys Tyr Pro Val Ile Phe Glu Ala Asn Lys Phe
            20                  25                  30

Met Leu Ser His Phe Asp Lys Ile Tyr Pro Gly Gln Lys Leu Arg Ile
        35                  40                  45

Phe

<210> SEQ ID NO 188
<211> LENGTH: 43
<212> TYPE: PRT
<213> ORGANISM: Populus sp.

<400> SEQUENCE: 188

Val Gly Ala Ala Ser Gly Asp Thr Cys Phe Thr Ile Ala Gln Ser Phe
1               5                   10                  15

Asn Leu Thr Ala Ala Ser Phe Asp Ala Ile Asn Phe Asn Leu Asn Cys
            20                  25                  30

Thr Ala Leu Phe Val Gly Gln Trp Leu Cys Val
        35                  40

<210> SEQ ID NO 189
<211> LENGTH: 46
<212> TYPE: PRT
<213> ORGANISM: Populus sp.

<400> SEQUENCE: 189

Val Val Gly Val Ala Ser Gly Asp Thr Cys Phe Thr Ile Ala Gln Ser
1               5                   10                  15

Phe Asn Leu Thr Ala Ala Ser Phe Asp Ala Ile Asn Phe Asn Ile Ser
            20                  25                  30

Cys Asn Ala Leu Phe Val Gly Gln Trp Leu Cys Val Ala Gly
        35                  40                  45
```

<210> SEQ ID NO 190
<211> LENGTH: 43
<212> TYPE: PRT
<213> ORGANISM: Populus sp.

<400> SEQUENCE: 190

His Gly Val Val Thr Gly Asp Thr Cys Ile Ala Val Glu Lys Gln Phe
1               5                   10                  15

Asp Leu Thr Ala Asn Asp Phe Leu Ala Ile Asn Phe Asn Leu Asp Cys
            20                  25                  30

Asp Lys Leu Phe Val Gly Gln Trp Leu Cys Val
        35                  40

<210> SEQ ID NO 191
<211> LENGTH: 45
<212> TYPE: PRT
<213> ORGANISM: Glycine max

<400> SEQUENCE: 191

Glu His Gln Val Ser Lys Leu Asp Thr Leu Ala Gly Val Ala Ile Lys
1               5                   10                  15

Tyr Gly Val Glu Val Ala Asp Ile Lys Arg Met Asn Gly Leu Ala Thr
            20                  25                  30

Asp Leu Gln Met Phe Ala Leu Lys Thr Leu Lys Ile Phe
        35                  40                  45

<210> SEQ ID NO 192
<211> LENGTH: 46
<212> TYPE: PRT
<213> ORGANISM: Glycine max

<400> SEQUENCE: 192

His Gln Val Ser Lys Leu Asp Thr Leu Ala Gly Val Ala Ile Lys Tyr
1               5                   10                  15

Gly Val Glu Val Ala Asp Ile Lys Arg Met Asn Gly Leu Ala Thr Asp
            20                  25                  30

Leu Gln Met Phe Ala Leu Lys Thr Leu Lys Ile Pro Leu Pro
        35                  40                  45

<210> SEQ ID NO 193
<211> LENGTH: 45
<212> TYPE: PRT
<213> ORGANISM: Populus sp.

<400> SEQUENCE: 193

Glu His Gln Val Ser Lys Arg Asp Thr Leu Ala Gly Val Ala Ile Lys
1               5                   10                  15

Tyr Gly Val Glu Val Ala Asp Val Lys Arg Leu Asn Gly Leu Ser Thr
            20                  25                  30

Asp Leu Gln Met Phe Ala Leu Lys Thr Leu Leu Ile Pro
        35                  40                  45

<210> SEQ ID NO 194
<211> LENGTH: 44
<212> TYPE: PRT
<213> ORGANISM: Oryza sativa

<400> SEQUENCE: 194

His Arg Val Gly Lys Leu Asp Thr Leu Ala Gly Ile Ala Ile Lys Tyr
1               5                   10                  15

```
Gly Val Glu Val Ala Asp Ile Lys Arg Leu Asn Gly Leu Ser Thr Asp
            20                  25                  30

Leu Gln Met Phe Ala His Lys Thr Leu Arg Ile Pro
        35                  40
```

<210> SEQ ID NO 195
<211> LENGTH: 47
<212> TYPE: PRT
<213> ORGANISM: Glycine max

<400> SEQUENCE: 195

```
Asp His Arg Val Ser Lys Phe Asp Thr Leu Ala Gly Val Ala Ile Lys
1               5                   10                  15

Tyr Gly Val Glu Val Ala Asp Ile Arg Lys Met Asn Asn Leu Val Thr
            20                  25                  30

Asp His Gln Met Phe Ala Leu Lys Thr Leu His Ile Phe Leu Pro
        35                  40                  45
```

<210> SEQ ID NO 196
<211> LENGTH: 50
<212> TYPE: PRT
<213> ORGANISM: Glycine max

<400> SEQUENCE: 196

```
Gly Tyr Ile Glu His His Val Ser Lys Phe Asp Thr Leu Ala Gly Val
1               5                   10                  15

Ala Ile Lys Tyr Gly Val Glu Val Ala Asp Ile Arg Lys Met Asn Ser
            20                  25                  30

Leu Val Thr Asp His Gln Met Phe Ala Leu Lys Thr Leu His Ile Phe
        35                  40                  45

Leu Pro
    50
```

<210> SEQ ID NO 197
<211> LENGTH: 44
<212> TYPE: PRT
<213> ORGANISM: Arabidopsis thaliana

<400> SEQUENCE: 197

```
His Arg Ile Ser Lys Phe Asp Thr Leu Ala Gly Val Ala Ile Lys Tyr
1               5                   10                  15

Gly Val Glu Val Ala Asp Val Lys Lys Met Asn Asn Leu Val Thr Asp
            20                  25                  30

Leu Gln Met Phe Ala Leu Lys Ser Leu Gln Ile Phe
        35                  40
```

<210> SEQ ID NO 198
<211> LENGTH: 50
<212> TYPE: PRT
<213> ORGANISM: Populus sp.

<400> SEQUENCE: 198

```
Gly Phe Ile Glu His Pro Val Ser Lys Leu Asp Thr Leu Ala Gly Val
1               5                   10                  15

Ala Ile Lys Tyr Gly Val Glu Val Ala Asp Ile Lys Lys Met Asn Gly
            20                  25                  30

Leu Val Thr Asp Leu Gln Met Phe Ala Leu Lys Ser Leu Gln Ile Phe
        35                  40                  45

Leu Pro
    50
```

<210> SEQ ID NO 199
<211> LENGTH: 45
<212> TYPE: PRT
<213> ORGANISM: Arabidopsis thaliana

<400> SEQUENCE: 199

Glu His Arg Val Ser Lys Phe Asp Thr Leu Ala Gly Ile Ala Ile Lys
1               5                   10                  15

Tyr Gly Val Glu Val Ala Asp Ile Thr Lys Leu Asn Gly Leu Val Thr
            20                  25                  30

Asp Leu Gln Met Phe Ala Leu Glu Ser Leu Arg Ile Phe
        35                  40                  45

<210> SEQ ID NO 200
<211> LENGTH: 44
<212> TYPE: PRT
<213> ORGANISM: Glycine max
<220> FEATURE:
<221> NAME/KEY: misc_feature
<222> LOCATION: (41)..(41)
<223> OTHER INFORMATION: Xaa can be any naturally occurring amino acid

<400> SEQUENCE: 200

Ser His His Ile Thr Arg Gly Asp Thr Val Ala Ser Leu Ala Val Lys
1               5                   10                  15

Tyr Ser Val Gln Val Met Asp Ile Lys Arg Leu Asn Asn His His Ser
            20                  25                  30

Asp His Gly Ile Tyr Ser Arg Glu Xaa Ile Asp Phe
        35                  40

<210> SEQ ID NO 201
<211> LENGTH: 44
<212> TYPE: PRT
<213> ORGANISM: Arabidopsis thaliana

<400> SEQUENCE: 201

His Arg Ile Cys Arg Gly Asp Ser Val Thr Ser Leu Ala Val Lys Tyr
1               5                   10                  15

Ala Val Gln Val His Asp Ile Lys Arg Leu Asn Asn His His Ser Asp
            20                  25                  30

His Gly Ile Tyr Ser Arg Asp Arg Leu Leu Ile Phe
        35                  40

<210> SEQ ID NO 202
<211> LENGTH: 45
<212> TYPE: PRT
<213> ORGANISM: Populus sp.

<400> SEQUENCE: 202

Ser His Lys Ile Val Lys Gly Asp Ser Val Ala Ser Leu Ala Val Lys
1               5                   10                  15

Tyr Ser Val Gln Val His Asp Ile Lys Arg Ile Asn Asn His Thr Ser
            20                  25                  30

Asp His Gly Ile Asn Ser Arg Glu Arg Leu Leu Ile Phe
        35                  40                  45

<210> SEQ ID NO 203
<211> LENGTH: 45
<212> TYPE: PRT
<213> ORGANISM: Populus sp.

<400> SEQUENCE: 203

```
Ser His Lys Ile Ala Arg Glu Asp Ser Val Thr Ser Leu Ala Lys Lys
1               5                   10                  15

Tyr Ser Val Gln Val Arg Asp Ile Lys Leu Leu Asn Asn His Thr Ser
                20                  25                  30

Asp Asn Gly Ile Tyr Ser Met Glu Arg Leu Leu Ile Phe
            35                  40                  45

<210> SEQ ID NO 204
<211> LENGTH: 44
<212> TYPE: PRT
<213> ORGANISM: Oryza sativa

<400> SEQUENCE: 204

His Thr Val Arg Arg Gly Asp Thr Val Phe Gly Ile Ala Leu Lys Tyr
1               5                   10                  15

Ser Ile Gln Val Thr Asp Ile Lys Arg Phe Asn Asn His Ser Asp
                20                  25                  30

His Gly Ile Tyr Leu Arg Glu Arg Leu Leu Ile Phe
            35                  40

<210> SEQ ID NO 205
<211> LENGTH: 46
<212> TYPE: PRT
<213> ORGANISM: Populus sp.

<400> SEQUENCE: 205

Ile Lys Ala Arg Lys Arg Asp Thr Leu Ile Ser Val Ala Asn Arg Tyr
1               5                   10                  15

Gly Val Ser Ala Ser Asn Leu Ala Asp Trp Asn Asp Leu Lys Ser Ser
                20                  25                  30

Ala Thr Leu His Ala Gly Gln Ser Leu Val Ala Tyr Leu Phe
            35                  40                  45

<210> SEQ ID NO 206
<211> LENGTH: 45
<212> TYPE: PRT
<213> ORGANISM: Populus sp.

<400> SEQUENCE: 206

Tyr Tyr Val Trp Gln Gly Ser Asn Leu Thr Tyr Ile Ser Thr Ile Phe
1               5                   10                  15

Asn Gln Ser Ile Thr Glu Ile Ile Arg Tyr Asn Phe Lys Val Pro Asn
                20                  25                  30

Gln Asp Ser Ile Arg Ser Asp Thr Arg Leu Asn Val Phe
            35                  40                  45

<210> SEQ ID NO 207
<211> LENGTH: 112
<212> TYPE: PRT
<213> ORGANISM: Oryza sativa

<400> SEQUENCE: 207

Tyr Ser Ala Arg Pro Ala Asp Thr Leu Ala Ser Val Ala Asp Val Val
1               5                   10                  15

Phe Ala Gly Lys Ala Ser Ala Asp Gln Ile Arg Arg Ala Asn Gly Leu
                20                  25                  30

Ser Ala Glu Asp Pro Asp Ala Pro Leu Asp Ala Gly Ala Thr Leu Val
            35                  40                  45

Val Pro Leu Pro Cys Ala Cys Phe Asn Ser Thr Asp Asn Asn Leu Pro
        50                  55                  60
```

```
Ala Val Tyr Leu Ser Tyr Val Val Arg Val Gly Asp Thr Val Gln Ser
 65                  70                  75                  80

Ile Ala Ala Thr His Ala Thr Thr Val Thr Asp Ile Ser Asn Val Asn
                 85                  90                  95

Ala Met Gly Ser Pro Ile Val Ala Pro Gly Asp Ile Leu Ala Ile Pro
            100                 105                 110
```

<210> SEQ ID NO 208
<211> LENGTH: 112
<212> TYPE: PRT
<213> ORGANISM: Oryza sativa

<400> SEQUENCE: 208

```
Tyr Ala Ala Arg Pro Ala Asp Thr Leu Ala Thr Val Ala Asp Gly Val
  1               5                  10                  15

Phe Ala Gly Leu Ala Phe Ala Asp Gln Ile Arg Asn Ala Asn Ala Val
                 20                  25                  30

Ala Ser Ala Asp Pro Asp Ala Pro Leu Asp Pro Gly Gln Lys Leu Val
             35                  40                  45

Val Pro Leu Pro Cys Val Cys Phe Asn Ser Ser Asp Asn Asn Leu Pro
 50                  55                  60

Ala Val Tyr Leu Ser Tyr Val Val Gln Val Gly Asp Thr Val Pro Ala
 65                  70                  75                  80

Ile Ala Ala Ser Tyr Glu Thr Thr Val Thr Asp Val Met Asn Val Asn
                 85                  90                  95

Ala Met Gly Ser Pro Ile Ala Ala Pro Gly Asp Ile Leu Ala Ile Pro
            100                 105                 110
```

<210> SEQ ID NO 209
<211> LENGTH: 112
<212> TYPE: PRT
<213> ORGANISM: Oryza sativa

<400> SEQUENCE: 209

```
Tyr Val Ala Arg Pro Gly Asp Thr Leu Ala Ser Val Ala Ser Ser Val
  1               5                  10                  15

Tyr Gly Gly Leu Thr Thr Pro Asp Trp Ile Ser Asp Ser Asn Gly Ile
                 20                  25                  30

Leu Gly Ala Lys Pro Asp Ala Val Asp Ala Gly Thr Thr Leu Phe
             35                  40                  45

Val Pro Leu His Cys Ala Cys Phe Gly Gly Val Asp Asn Gly Leu Pro
 50                  55                  60

Ala Val Tyr Leu Thr Tyr Val Ala Gly Lys Gly Asp Thr Val Ala Ala
 65                  70                  75                  80

Val Ala Gln Arg Tyr Arg Thr Thr Ala Thr Asp Leu Met Ser Val Asn
                 85                  90                  95

Asp Met Ala Thr Pro Glu Leu Ala Ala Gly Asp Ile Ile Val Val Pro
            100                 105                 110
```

<210> SEQ ID NO 210
<211> LENGTH: 107
<212> TYPE: PRT
<213> ORGANISM: Oryza sativa

<400> SEQUENCE: 210

```
His Ile Ile Gln Ile Asn Asp Asn Met Ser Tyr Ile Ala Ala Gln Phe
  1               5                  10                  15

Asp Asp Phe Val Thr Tyr Gln Glu Ile Ala Ala Ala Ser Asn Ile Ser
                 20                  25                  30
```

Asn Pro Asp Phe Leu Glu Val Gly Gln Glu Leu Trp Ile Pro Leu Pro
            35                  40                  45

Cys Ser Cys Asp Gln Val Glu Gly Asn Asn Val Thr His Phe Ala Tyr
    50                  55                  60

Lys Val Arg Ala Ala Asp Asn Val Ser Lys Ile Ala Ala Arg Phe Gly
65                  70                  75                  80

Val Lys Glu Ser Thr Leu Leu Lys Ile Asn Gly Ile Thr Asp Pro Lys
                85                  90                  95

Asn Leu Thr Gln Gly Gln Ile Leu Asp Val Pro
            100                 105

<210> SEQ ID NO 211
<211> LENGTH: 108
<212> TYPE: PRT
<213> ORGANISM: Oryza sativa

<400> SEQUENCE: 211

Tyr Arg Ile Arg Ala Gly Asp Thr Leu Asp Ala Ile Ala Arg Gly Val
1               5                   10                  15

Phe Ala Gly Leu Val Thr Tyr Gln Asp Ile Ala Ala Asn Asn Val
                20                  25                  30

Ser Asp Pro Asn Lys Ile Ala Val Gly Gln Glu Leu Trp Ile Pro Val
            35                  40                  45

Pro Cys Ser Cys Asp Pro Val Ala Gly Gln Pro Val Val His Tyr Thr
    50                  55                  60

Tyr Val Val Pro Pro Gly Ala Ser Val Ala Ala Ile Ala Gln Asp Phe
65                  70                  75                  80

Ala Thr Thr Glu Ala Thr Val Leu Ala Leu Asn Arg Met Pro Asp Ala
                85                  90                  95

Lys Ser Leu Leu Ala Gly Gln Val Leu Asp Val Pro
            100                 105

<210> SEQ ID NO 212
<211> LENGTH: 38
<212> TYPE: PRT
<213> ORGANISM: Oryza sativa

<400> SEQUENCE: 212

His Gly Val Gln Ala Ser Glu Thr Cys Phe Ser Val Ser Gln Ser Ala
1               5                   10                  15

Gly Leu Thr Gln Asp Gln Phe Leu Ala Phe Asn Pro Asn Ile Asn Cys
                20                  25                  30

Ala Lys Val Phe Val Gly
            35

<210> SEQ ID NO 213
<211> LENGTH: 36
<212> TYPE: PRT
<213> ORGANISM: Oryza sativa

<400> SEQUENCE: 213

His Gly Val Glu Ala Gly Glu Thr Cys Asp Ser Ile Ala Arg Arg Phe
1               5                   10                  15

His Ala Gly Leu Gly Arg Ala Pro Phe Phe Arg Leu Val Ser Leu Asn
                20                  25                  30

Pro Asn Ile Asn
            35

```
<210> SEQ ID NO 214
<211> LENGTH: 44
<212> TYPE: PRT
<213> ORGANISM: Oryza sativa

<400> SEQUENCE: 214

Tyr Ala Ala Arg Pro Ala Asp Thr Leu Ala Thr Val Ala Asp Gly Val
1               5                   10                  15

Phe Ala Gly Leu Ala Phe Ala Asp Gln Ile Arg Asn Ala Asn Pro Asp
            20                  25                  30

Ala Pro Leu Asp Pro Gly Gln Lys Leu Val Val Pro
        35                  40

<210> SEQ ID NO 215
<211> LENGTH: 42
<212> TYPE: PRT
<213> ORGANISM: Oryza sativa

<400> SEQUENCE: 215

His Gln Val Ser Arg Met Asp Thr Leu Pro Gly Leu Ala Ile Lys Tyr
1               5                   10                  15

Gly Val Glu Ile Ser Asp Ile Lys Arg Ala Asn Ser Leu Met Thr Asp
            20                  25                  30

Ser Gln Met Phe Ala His Lys Met Leu Leu
        35                  40
```

LYSM RECEPTOR-LIKE KINASES TO IMPROVE PLANT DEFENSE RESPONSE AGAINST FUNGAL PATHOGENS

This application is a divisional application of U.S. patent application Ser. No. 11/835,328 filed Aug. 7, 2007, now U.S. Pat. No. 8,097,771 which claims priority to U.S. provisional patent application Ser. No. 60/836,084 filed on Aug. 7, 2006. Both of the aforementioned applications are incorporated herein by reference.

GOVERNMENT INTERESTS

This work was funded in part by a grant from the United States Department of Energy, Energy Biosciences Program, Office of Basic Energy Sciences (grant number DE-FG02-02ER15309). The United States government may have certain rights in the invention disclosed herein.

SEQUENCE LISTING

This application is accompanied by a sequence listing that accurately reproduces the sequences described herein.

BACKGROUND

This disclosure relates to the use of molecular genetic technology involving LysM receptor kinase family genes and the expression or nonexpression thereof to modulate plant defense responses, especially against fungal pathogens.

Fungal disease causes significant agricultural losses in the United States and other parts of the world. Control of these pathogens is particularly difficult, often requiring treatment of entire fields with biocidal compounds. Although effective, increasing concern about the environmental and economic costs of such treatments require the need for alternative control methods.

*Phakopsora pachyrhizi* is a fungus that causes a rust disease of soybean (*Glycine max*), also known as Asian Soybean Rust. The pathogen has spread from Asia to all other soybean production regions in the world, and is reported to have arrived in the United States in the fall of 2004. At present, there is no known durable resistance available in any soybean varieties. *Uromyces appendiculatus* is a fungus that causes rust on bean (*Phaseolus vulgaris*). Breeders are working to identify genes in bean that can be manipulated for rust resistance. United States soybean producers have anticipated the arrival of *P. pachyrhizi*, the fungus that causes soybean rust, since its reported occurrence in Brazil. The arrival of *P. pachyrhizi* in the U.S. in late 2004 ended the anticipation, and farmers must now respond to the potential annual occurrence of this new disease. Farmer concerns have been based on reports of losses ranging from 10 to 80% in other regions of the world when control measures were not successfully implemented.

As rust-inducing fungi, *U. appendiculatus* and *P. pachyrhizi* belong to the order Uredinales, within the class Basidiomycetes. *U. appendiculatus* produces five spore stages on a single host plant. *P. pachyrhizi* reproduces predominantly by uredospores on a single host plant. Uredospores are responsible for rapid spread of the fungus. *P. pachyrhizi* can infect dozens of legume species, in addition to soybean.

Uredospores of *U. appendiculatus* penetrate through foliar stomatal openings. *P. pachyrhizi* differs in that germinated uredospores penetrate directly through the leaf epidermal cell layer. Typically, a uredospore that lands on a leaf surface germinates to produce an infection pad (appressorium) that adheres to the surface. In both species, the appressorium produces a hyphal peg that penetrates the plant. After penetration, each fungus develops thread-like structures (hyphae) that grow inter-cellularly through leaf tissues. The hyphae enter host cells without killing them. There, they produce spherical structures (haustoria) that extract nutrients from the living leaf cells. Soon after infection each fungus forms uredia that produce additional spores.

Soybean producers are particularly concerned because no durable, natural resistance to rust has been discovered after testing more than 18,000 soybean varieties. The pathogen, *P. pachyrhizi* can potentially infect any cultivar produced. In anticipation of the arrival of the rust pathogen, a great deal of research has been conducted to identify effective fungicides, and emergency governmental clearance for application to soybean has been obtained. Traditional screening and breeding methods have identified no major resistance genes to the aforementioned pathogens, and particularly in the case of *U. appendiculatus* and *P. pachyrhizi*.

Fungicides will likely be the front-line of defense against these and other fungal pathogens for many years until new resistance genes or other forms of resistance are identified. Fungicides have not traditionally been used in most soybean production. Consequently, there is limited information concerning the costs of this disease management practice and its likely economic viability. Widespread use of fungicides may also raise environmental concerns. These concerns have led to variable estimates of the acreage in Missouri and other states that may be shifted from soybean to alternative crops.

To protect soybean farmers and to ensure that soybean production meets increasing market demand, it is imperative that alternatives to fungicides be developed as rapidly as possible. Biotechnology-based approaches for defense against plant diseases are more preferable due to the minimal use of chemicals and the relative ease of deployment.

Chitin is a polymer of N-acetyl-D-glucosamine, found in fungal cell walls, insect exoskeletons, and crustacean shells. It has been hypothesized that plant chitinases can degrade chitin in the fungal cell walls to directly affect the viability of the invading fungal pathogen and to release short fragments (chitooligosaccharides) that can act as a general elicitor of plant innate immunity pathways. See e.g., Shibuya et al., 2001 and Stacey et al., 1997. In support of the above hypothesis, purified chitooligosaccharides have been shown to induce various defense responses in plants or cultured cells, such as induction of defense related genes and synthesis of phytoalexin. Shibuya et al., 2001 and Ramonell et al., 2005.

More particularly, chitooligosaccharides have been shown to induce a large number of genes (including many defense-related genes), and mutations in selected chitooligosaccharide-responsive genes or chitin-responsive genes (CRGs) have been shown to increase the susceptibility of a plant to certain fungal pathogens. See Ramonell et al., 2002; and Ramonell et al., 2005. Taken together, these studies suggest that plants possess a specific system to recognize chitooligosaccharides which, in turn, activate defense genes. See generally, Day et al., 2001; Zhang et al., 2002; Wan et al., 2004; Kaku et al., 2006; and Libault et al., 2007.

Previous work has reported chitin recognition in rice and legumes. Stacey, G. and N. Shibuya, Plant and Soil 194: 161-169 (1997) The ability of *Arabidopsis thaliana* to recognize and respond to chitin has also been reported. A variety of genes have been shown to respond to chitin treatment. See e.g., Ramonell et al. Microarray analysis of chitin elicitation in *Arabidopsis thaliana*. Mol. Plant Pathol. 3 (1): 301-311 (2002) and Zhang et al., Characterization of Early, Chitin- Induced Gene Expression in *Arabidopsis* Mol. Plant-Microbe Int. 15: 963-970 (2002) and Wan et al., Activation of a potential mitogen-activated protein kinase pathway in *Arabidopsis* by chitin. Mol. Plant Pathol. 5(1): 125-135 (2004).

More specifically, chitin binding sites or proteins have been previously identified in membrane preparations of a variety of plant cells. Day et al., 2001; Ito et al., 1997; and Okada et al, 2002. More recently, a LysM domain-containing protein (CEBiP) has been shown to be involved in the binding and recognition of chitooligosaccharides in rice. Kaku et al., 2006. The LysM motif was originally identified in bacterial enzymes that degrade cell wall component peptidoglycan, which is structurally similar to chitin. Joris, 1992. Since CEBiP lacks a significant intracellular domain, it likely functions as part of a chitin receptor complex. Kaku et al., 2006. However, no such chitin receptor complexes have been identified.

SUMMARY

The present disclosure overcomes the problems outlined above and advances the art by providing methods to confer fungal resistance to plants. This disclosure addresses a new biotechnology-based approach to generate rust resistant soybean and to confer rust resistance upon soybean plants. The technology also involves the development and/or deployment of defense peptides against fungal pathogen, such as the Asian soybean rust fungus. The technology similarly applies to other pathogens in plants, such as the field bean (*Phaseolus vulgaris*) rust pathogen, *Uromyces appendiculatus*.

It is hereby disclosed a number of LysM-containing receptor like kinases ("LysM RLKs") in soybean, as well as in other legume or non-legume plants. The lysine motif (LysM) domain is an ancient and ubiquitous protein module that binds peptidoglycan and structurally related molecules. A genomic survey in a large number of species spanning all kingdoms reveals that the combination of LysM and receptor kinase domains is present exclusively in plants. Table 1 lists a number of genes encoding LysM containing proteins from both prokaryotes and eukaryotes, along with their accession numbers from GenBank or other databases.

TABLE 1

LysM family genes in prokaryotes and eukaryotes

| LysM motif | kingdom | domain | | species name | sources | accession number |
|---|---|---|---|---|---|---|
| >AGRT52b | Bacteria | Proteobacteria | alpha-proteobacteria | *Argobacterium_tumefaciens*_C58 | UniProt/TrEMBL | Q8UEQ5 |
| >ANASP1 | Bacteria | Cyanobacteria | | *Nostoc*_PCC | UniProt/TrEMBL | Q8YRU0 |
| >BACAN1a | Bacteria | Firmicutes | | *Bacillus_anthracis* | UniProt/TrEMBL | Q81WS5 |
| >BACAN2b | Bacteria | Firmicutes | | *Bacillus_anthracis* | UniProt/TrEMBL | Q81Y89 |
| >BACAN7 | Bacteria | Firmicutes | | *Bacillus_anthracis* | UniProt/TrEMBL | Q81SZ3 |
| >BORPE5 | Bacteria | Proteobacteria | Beta-proteobacteria | *bordetella_pertussis* | UniProt/TrEMBL | Q7W0R5 |
| >BORPE6 | Bacteria | Proteobacteria | Beta-proteobacteria | *bordetella_pertussis* | UniProt/TrEMBL | Q7VY72 |
| >BRAJA1 | Bacteria | Proteobacteria | alpha-proteobacteria | *Bradyrhizobium_japonicum* | UniProt/TrEMBL | Q89Y08 |
| >BRAJA2 | Bacteria | Proteobacteria | alpha-proteobacteria | *Bradyrhizobium_japonicum* | UniProt/TrEMBL | Q89XF2 |
| >BURPS1 | Bacteria | Proteobacteria | Beta-proteobacteria | *Burkholderia_pasudomallei*_1710b | UniProt/TrEMBL | Q63LR7 |
| >BURPS4 | Bacteria | Proteobacteria | Beta-proteobacteria | *Burkholderia_pasudomallei*_1710b | UniProt/TrEMBL | Q63TI4 |
| >BURPS6a | Bacteria | Proteobacteria | Beta-proteobacteria | *Burkholderia_pasudomallei*_1710b | UniProt/TrEMBL | Q63V96 |
| >CHLAU2 | Bacteria | Chloroflexi | | *Chloroflexus_aurantiacus* | UniProt/TrEMBL | Q3E5J5 |
| >ECOLI6 | Bacteria | Proteobacteria | Gama-proteobacteria | *Escherichia_coli* | UniProt/TrEMBL | P75954 |
| >PELCD5a | Bacteria | Proteobacteria | Delta-proteobacteria | *Pelobacter_carbinolicus*_DSM | UniProt/TrEMBL | Q3A2X4 |
| >RALSO3 | Bacteria | Proteobacteria | Beta-proteobacteria | *Ralstonia_solanacearum* | UniProt/TrEMBL | Q8Y0H0 |
| >RALSO6 | Bacteria | Proteobacteria | Beta-proteobacteria | *Ralstonia_solanacearum* | UniProt/TrEMBL | Q8XZ88 |
| >RHOPA4 | Bacteria | Proteobacteria | Alpha-proteobacteria | *Rhodopseudomonas_palustris* | UniProt/TrEMBL | Q379H8 |
| >SALCH2 | Bacteria | Proteobacteria | Gama-proteobacteria | *Salmonella_choleraesuis* | UniProt/TrEMBL | Q5J4C2 |
| >SALCH5 | Bacteria | Proteobacteria | Gama-proteobacteria | *Salmonella_choleraesuis* | UniProt/TrEMBL | Q57QE0 |
| >STRCO4 | Bacteria | Firmicutes | Actinobacteridae | *Streptomyces_coelicolor* | UniProt/TrEMBL | Q9ACX5 |
| >VIBCH4 | Bacteria | Proteobacteria | Gama-proteobacteria | *Vibrio_cholerae* | UniProt/TrEMBL | Q9KNA7 |
| >VIBCH5a | Bacteria | Proteobacteria | Gama-proteobacteria | *Vibrio_cholerae* | UniProt/TrEMBL | Q9KV14 |
| >WOLSU1a | Bacteria | Proteobacteria | Epsilon-proteobacteria | *wolinella_succinogenes* | UniProt/TrEMBL | Q7M7V0 |
| >WOLSU1b | Bacteria | Proteobacteria | Epsilon-proteobacteria | *wolinella_succinogenes* | UniProt/TrEMBL | Q7M7V0 |
| >CAEEL1 | Eukaryota | Metazoa | Nematoda | *Caenorhabditis_elegans* | UniProt/TrEMBL | P90882 |
| >CAEEL6 | Eukaryota | Metazoa | Nematoda | *Caenorhabditis_elegans* | UniProt/TrEMBL | Q93715 |
| >CHLRE1 | Eukaryota | Chlorophyta | | *Chlamydomonas_reinhardtii* | UniProt/TrEMBL | Q9M5B9 |
| >DICDI2 | Eukaryota | Mycetozoa | Dictyosteliida | *Dictyostelium_discoideum* | UniProt/TrEMBL | Q54BF7 |
| >DROME10 | Eukaryota | Metazoa | Chordata | *Drosophila_melanoqaster* | UniProt/TrEMBL | Q9V4P7 |
| >DROME9 | Eukaryota | Metazoa | Chordata | *Drosophila_melanoqaster* | UniProt/TrEMBL | Q9VNA1 |
| >HUMAN1 | Eukaryota | Metazoa | Chordata | *Homo_sapiens* | UniProt/TrEMBL | Q5TF95 |
| >HUMAN7 | Eukaryota | Metazoa | Chordata | *Homo_sapiens* | UniProt/TrEMBL | Q7Z3D4 |
| >MOUSE5 | Eukaryota | Metazoa | Chordata | *Mus_musculus* | UniProt/TrEMBL | Q99LE3 |
| >MOUSE9 | Eukaryota | Metazoa | Chordata | *Mus_musculus* | UniProt/TrEMBL | Q6DFV7 |
| >XENLA5 | Eukaryota | Metazoa | Chordata | *Xenopus_laevis* | UniProt/TrEMBL | Q5BJ38 |
| >AtLYK1b | Eukaryota | Viridiplantae | Streptophyta | *Arabidopsis_thaliana* | TAIR | At2g21630 |
| >AtLYK1c | Eukaryota | Viridiplantae | Streptophyta | *Arabidopsis_thaliana* | TAIR | At2g21630 |
| >AtLYK2 | Eukaryota | Viridiplantae | Streptophyta | *Arabidopsis_thaliana* | TAIR | At3g01840 |
| >AtLYK3 | Eukaryota | Viridiplantae | Streptophyta | *Arabidopsis_thaliana* | TAIR | At1g51940 |
| >AtLYK4a | Eukaryota | Viridiplantae | Streptophyta | *Arabidopsis_thaliana* | TAIR | At2g23770 |
| >AtLYK4b | Eukaryota | Viridiplantae | Streptophyta | *Arabidopsis_thaliana* | TAIR | At2g23770 |
| >AtLYK4c | Eukaryota | Viridiplantae | Streptophyta | *Arabidopsis_thaliana* | TAIR | At2g23770 |
| >AtLYK5a | Eukaryota | Viridiplantae | Streptophyta | *Arabidopsis_thaliana* | TAIR | At2g33580 |
| >AtLYK5c | Eukaryota | Viridiplantae | Streptophyta | *Arabidopsis_thaliana* | TAIR | At2g33580 |
| >AtLYP1b | Eukaryota | Viridiplantae | Streptophyta | *Arabidopsis_thaliana* | TAIR | At1g21880 |
| >AtLYP2a | Eukaryota | Viridiplantae | Streptophyta | *Arabidopsis_thaliana* | TAIR | At1g77630 |
| >AtLYP3a | Eukaryota | Viridiplantae | Streptophyta | *Arabidopsis_thaliana* | TAIR | At2g17120 |
| >AtLYP3b | Eukaryota | Viridiplantae | Streptophyta | *Arabidopsis_thaliana* | TAIR | At2g17120 |

TABLE 1-continued

LysM family genes in prokaryotes and eukaryotes

| LysM motif | kingdom | domain | species name | sources | accession number |
|---|---|---|---|---|---|
| >AtLysMe1 | Eukaryota | Viridiplantae | Streptophyta | Arabidopsis_thaliana | TAIR | At3g52790 |
| >AtLysMe2 | Eukaryota | Viridiplantae | Streptophyta | Arabidopsis_thaliana | TAIR | At4g25433 |
| >AtLysMe3 | Eukaryota | Viridiplantae | Streptophyta | Arabidopsis_thaliana | TAIR | At5g62150 |
| >AtLysMn1 | Eukaryota | Viridiplantae | Streptophyta | Arabidopsis_thaliana | TAIR | At1g55000 |
| >AtLysMn2 | Eukaryota | Viridiplantae | Streptophyta | Arabidopsis_thaliana | TAIR | At5g08200 |
| >AtLysMn3 | Eukaryota | Viridiplantae | Streptophyta | Arabidopsis_thaliana | TAIR | At5g23130 |
| >GmLYK10b | Eukaryota | Viridiplantae | Streptophyta | Glycine_max | this study | GmW2080D08.12 |
| >GmLYK10c | Eukaryota | Viridiplantae | Streptophyta | Glycine_max | this study | GmW2080D08.12 |
| >GmLYK11 | Eukaryota | Viridiplantae | Streptophyta | Glycine_max | this study | GmW2042I24.15 |
| >GmLYK2 | Eukaryota | Viridiplantae | Streptophyta | Glycine_max | this study | GmW2098N11.15 |
| >GmLYK4b | Eukaryota | Viridiplantae | Streptophyta | Glycine_max | this study | GmW2095P01.22 |
| >GmLYK4c | Eukaryota | Viridiplantae | Streptophyta | Glycine_max | this study | GmW2095P01.22 |
| >GmLYK8a | Eukaryota | Viridiplantae | Streptophyta | Glycine_max | this study | GmW2098N11.2 |
| >GmLYK8b | Eukaryota | Viridiplantae | Streptophyta | Glycine_max | this study | GmW2098N11.2 |
| >GmLYK9b | Eukaryota | Viridiplantae | Streptophyta | Glycine_max | this study | GmW2069O12.22 |
| >GmLYK9c | Eukaryota | Viridiplantae | Streptophyta | Glycine_max | this study | GmW2069O12.22 |
| >GmLYP1b | Eukaryota | Viridiplantae | Streptophyta | Glycine_max | TIGR | |
| >GmLYP2a | Eukaryota | Viridiplantae | Streptophyta | Glycine_max | TIGR | |
| >GmLYP2b | Eukaryota | Viridiplantae | Streptophyta | Glycine_max | TIGR | |
| >GmLYP3a | Eukaryota | Viridiplantae | Streptophyta | Glycine_max | TIGR | |
| >GmLYP3b | Eukaryota | Viridiplantae | Streptophyta | Glycine_max | TIGR | |
| >GmLysMe1 | Eukaryota | Viridiplantae | Streptophyta | Glycine_max | TIGR | |
| >GmLysMe2 | Eukaryota | Viridiplantae | Streptophyta | Glycine_max | TIGR | |
| >GmLysMe3 | Eukaryota | Viridiplantae | Streptophyta | Glycine_max | TIGR | |
| >GmLysMe4 | Eukaryota | Viridiplantae | Streptophyta | Glycine_max | TIGR | |
| >GmLysMn1 | Eukaryota | Viridiplantae | Streptophyta | Glycine_max | TIGR | |
| >GmLysMn2 | Eukaryota | Viridiplantae | Streptophyta | Glycine_max | TIGR | |
| >GmLysMn3 | Eukaryota | Viridiplantae | Streptophyta | Glycine_max | TIGR | |
| >GmNFR1ab | Eukaryota | Viridiplantae | Streptophyta | Glycine_max | this study | |
| >GmNFR1ac | Eukaryota | Viridiplantae | Streptophyta | Glycine_max | this study | |
| >GmNFR5aa | Eukaryota | Viridiplantae | Streptophyta | Glycine_max | this study | |
| >GmNFR5ab | Eukaryota | Viridiplantae | Streptophyta | Glycine_max | this study | |
| >GmNFR5ac | Eukaryota | Viridiplantae | Streptophyta | Glycine_max | this study | |
| >MtLYK10a | Eukaryota | Viridiplantae | Streptophyta | Medicago_truncatula | Medicago truncatula sequencing resources | AC148994_13 |
| >MtLYK10b | Eukaryota | Viridiplantae | Streptophyta | Medicago_truncatula | Medicago truncatula sequencing resources | AC148994_13 |
| >MtLYK10c | Eukaryota | Viridiplantae | Streptophyta | Medicago_truncatula | Medicago truncatula sequencing resources | AC148994_13 |
| >MtLYK12b | Eukaryota | Viridiplantae | Streptophyta | Medicago_truncatula | Medicago truncatula sequencing resources | AC126779_3 |
| >MtLYK12c | Eukaryota | Viridiplantae | Streptophyta | Medicago_truncatula | Medicago truncatula sequencing resources | AC126779_3 |
| >MtLYK13a | Eukaryota | Viridiplantae | Streptophyta | Medicago_truncatula | Medicago truncatula sequencing resources | AC126779_4 |
| >MtLYK13b | Eukaryota | Viridiplantae | Streptophyta | Medicago_truncatula | Medicago truncatula sequencing resources | AC126779_4 |
| >MtLYK3b | Eukaryota | Viridiplantae | Streptophyta | Medicago_truncatula | Gene Bank | AY372402 |
| >MtLYK3c | Eukaryota | Viridiplantae | Streptophyta | Medicago_truncatula | Gene Bank | AY372402 |
| >MtLYK9a | Eukaryota | Viridiplantae | Streptophyta | Medicago_truncatula | Medicago truncatula sequencing resources | AC148241_11 |
| >MtLYK9b | Eukaryota | Viridiplantae | Streptophyta | Medicago_truncatula | Medicago truncatula sequencing resources | AC148241_11 |
| >MtLYK9c | Eukaryota | Viridiplantae | Streptophyta | Medicago_truncatula | Medicago truncatula sequencing resources | AC148241_11 |

TABLE 1-continued

LysM family genes in prokaryotes and eukaryotes

| LysM motif | kingdom | domain | | species name | sources | accession number |
|---|---|---|---|---|---|---|
| >OsLYK2b | Eukaryota | Viridiplantae | Streptophyta | Oryza_sativa | TIGR | LOC_Os06g41980 |
| >OsLYK2c | Eukaryota | Viridiplantae | Streptophyta | Oryza_sativa | TIGR | LOC_Os06g41980 |
| >OsLYK3 | Eukaryota | Viridiplantae | Streptophyta | Oryza_sativa | TIGR | LOC_Os06g41960 |
| >OsLYK4b | Eukaryota | Viridiplantae | Streptophyta | Oryza_sativa | TIGR | LOC_Os02g09960 |
| >OsLYK4c | Eukaryota | Viridiplantae | Streptophyta | Oryza_sativa | TIGR | LOC_Os02g09960 |
| >OsLYK5a | Eukaryota | Viridiplantae | Streptophyta | Oryza_sativa | TIGR | LOC_Os03g13080 |
| >OsLYK5c | Eukaryota | Viridiplantae | Streptophyta | Oryza_sativa | TIGR | LOC_Os03g13080 |
| >OsLYK6a | Eukaryota | Viridiplantae | Streptophyta | Oryza_sativa | TIGR | LOC_Os11g35330 |
| >OsLYK6b | Eukaryota | Viridiplantae | Streptophyta | Oryza_sativa | TIGR | LOC_Os11g35330 |
| >OsLYK6c | Eukaryota | Viridiplantae | Streptophyta | Oryza_sativa | TIGR | LOC_Os11g35330 |
| >OsLYP1b | Eukaryota | Viridiplantae | Streptophyta | Oryza_sativa | TIGR | LOC_Os03g04110 |
| >OsLYP2a | Eukaryota | Viridiplantae | Streptophyta | Oryza_sativa | TIGR | LOC_Os09g37600 |
| >OsLYP2b | Eukaryota | Viridiplantae | Streptophyta | Oryza_sativa | TIGR | LOC_Os09g37600 |
| >OsLYP3a | Eukaryota | Viridiplantae | Streptophyta | Oryza_sativa | TIGR | LOC_Os06g10660 |
| >OsLYP3b | Eukaryota | Viridiplantae | Streptophyta | Oryza_sativa | TIGR | LOC_Os06g10660 |
| >OsLYP5b | Eukaryota | Viridiplantae | Streptophyta | Oryza_sativa | TIGR | LOC_Os02g53000 |
| >OsLYP6a | Eukaryota | Viridiplantae | Streptophyta | Oryza_sativa | TIGR | LOC_Os11g34570 |
| >OsLYP6b | Eukaryota | Viridiplantae | Streptophyta | Oryza_sativa | TIGR | LOC_Os11g34570 |
| >OsLysMe1 | Eukaryota | Viridiplantae | Streptophyta | Oryza_sativa | TIGR | LOC_Os01g57390 |
| >osLysMe2 | Eukaryota | Viridiplantae | Streptophyta | Oryza_sativa | TIGR | LOC_Os01g57400 |
| >OsLysMe3 | Eukaryota | Viridiplantae | Streptophyta | Oryza_sativa | TIGR | LOC_Os04g48380 |
| >OsLysMn1 | Eukaryota | Viridiplantae | Streptophyta | Oryza_sativa | TIGR | LOC_Os03g49250 |
| >OsLysMn2 | Eukaryota | Viridiplantae | Streptophyta | Oryza_sativa | TIGR | LOC_Os06g51360 |
| >PtLysMe4 | Eukaryota | Viridiplantae | Streptophyta | Populus_trichocarpa | DOE JGI | EUGENE3.00051310 |
| >PtLysMe8 | Eukaryota | Viridiplantae | Streptophyta | Populus_trichocarpa | DOE JGI | EUGENE3.00070396 |
| >PtLysMe9 | Eukaryota | Viridiplantae | Streptophyta | Populus_trichocarpa | DOE JGI | EUGENE3.00110096 |
| >PtLysMe11 | Eukaryota | Viridiplantae | Streptophyta | Populus_trichocarpa | DOE JGI | EUGENE3.00070285 |

In comparison to the LysM proteins in other kingdoms, plant LYK proteins possess unique features: (1) the combination of LysM and kinase domains exists exclusively in the plant lineage; (2) plant LYK proteins have no more than three LysM motifs; (3) if more than two LysM motifs exist within a single plant LYK protein, they are always distinct from each other at the protein sequence level; and (4) the LysM domain sequences in plant LYK proteins are highly diversified due to different combinations of heterogenous LysM motifs. Based on the sequence phylogenies, LysM motifs (named LYKa, LYKb, and LYKc from the N to the C terminus) in plant LYK proteins largely fall into five clades (FIG. 1A). This distribution of LysM motifs was found in all six plant species studied (i.e. LysM motifs from dicots and rice are clustered together in each clade, suggesting that the diversification event of plant LysM motifs predated the divergence of monocot and dicot plants).

The LysM motifs from non-kinase plant LysM proteins have also been investigated. These sequences have been retrieved using BLAST searches against genomic sequence databases of Arabidopsis, rice, and poplar and EST sequences of soybean. Based on their subcellular localization predictions and domain arrangements, non-kinase plant LysM proteins may be further categorized into three subgroups, including LysM-type receptor-like proteins (LYPs), extracellular LysM proteins (LysMe), and nonsecretory intracellular LysM proteins (LysMn; FIG. 1B). This grouping will be helpful in understanding the nature of each LysM protein and providing insightful clues to the biological functions.

FIG. 1B illustrates the general domain structure of different LysM containing proteins. As shown in FIG. 1B, LysM RLKs (also referred to as "LYK") typically possess one or more LysM domains, a transmembrane domain and a kinase domain. The LysM domain is known for its capability to bind chitin. The transmembrane domain may serve to anchor the LysM RLKs in the membrane of the cells, whereas the kinase domain extends into the cytoplasm where it may phosphorylate specific substrates in the cell. In one embodiment, it is conceivable that the transmembrane domain of an LYK may be replaced with a different transmembrane domain from another LYK, or from another transmembrane protein.

As shown in FIG. 1 and FIG. 2, LysM domains in plants are highly diversified and that at least six distinct types of LysM motifs exist in plant LysM kinase proteins, which are shown as Types I-V and VII in FIG. 1B. Five additional types of LysM motifs exist in non-kinase plant LysM proteins, designated as Types VI, VIII-XI as shown in FIG. 1B. See also Zhang et al., Plant Physiol. 144, 623-636 (2007), which is hereby expressly incorporated by reference. FIG. 2 shows sequence alignment of representative LysM domains. FIG. 2A shows an alignment of 93 LysM-containing proteins in plants. Shaded areas indicate conserved residues in FIG. 2. FIG. 2B is an alignment of LysM domains from the LYK Group I, which contains LysM motif Types II and IV. FIG. 2C is an alignment of LysM domains from the LYK Group II, which contains LysM motif Types I, II and V. FIG. 2D is an alignment of LysM domains from the LYK Group III, which contains LysM motif Type VII. FIG. 2E is an alignment of LysM domains from the LYP group, which typically contains LysM motif Types VI and VII, or VI and VIII. See also FIG. 1B. FIG. 2F is an alignment of LysM domains from the LysMe group, which typically contains LysM motif Types IX or X. FIG. 2G is an alignment of LysM domains from the LysMn group, which typically contains LysM motif Type XI.

As predicted by Pfam, LYP proteins have exactly two LysM motifs and LysMe and LysMn proteins have only one LysM motif. Sequence alignments show that, among the 11 types of LysM motifs, motif sequences of LysMn (the motif within LysMn proteins, LysM motif type XI), one group of LysMe (the motif within LysMe proteins, LysM motif type X), and one group of LYPb (the second motif from the N terminus within LYP proteins, LysM motif VII) are extremely conserved. In these motifs, the amino acid identities averaged across the alignments are 91% for LysMe (type X), 86% for LysMn (type XI), and 75% for LYP (type VII). LysMn motif sequences always start with a His and end with a Pro. Similarly, LYPb motif sequences always end with a Pro. LYKa motifs are seven to 10 residues shorter.

In one aspect of this disclosure, soybean plants may be made resistant to soybean rust where no durable resistance is currently available. Certain soybean strains may be susceptible to rust diseases because they lack a functional signaling pathway that can perceive the existence of chitin or pass such a signal into the plant cell. Other strains may lack certain functional chitin responsive proteins and thus are not capable of mounting successful defenses against the invaders. It is hereby disclosed a methodology whereby a transgene encoding a component of the chitin signaling pathway may be introduced into a plant, such as a soybean plant. Expression of the transgene may enhance the perception of chitin by the transgenic plant, augment subsequent signaling that leads to gene activation inside the cells, and/or increase the capability of effector proteins in fighting the fungal pathogens.

In another aspect, mutations may be identified, induced or introduced into a plant, such as soybean, in order to obtain a mutant plant that have enhanced chitin perception or response. Certain mutations in LysM RLKs may enhance recognition of chitin by plant cells, whereas some other mutations in LysM RLKs may abolish chitin recognition. Similar situations may apply to other protein involved in fungal defense, including but not limited to the CRGs. The polynucleotide sequences disclosed herein may aid identification, mapping and/or genetic analysis of such mutants.

In one embodiment, a transgenic plant may be prepared by identifying in a plant one or more genes that contain a LysM receptor kinase family gene with a level of expression that is regulated by treatment of the plant with chitin. Such a plant may then be transformed with one or more LysM receptor kinase genes. The resulting transgenic plant may be challenged with chitin, its derivatives, or a pathogen to confirm an enhanced plant defense response, if desired.

The same general techniques disclosed herein may be employed in plants other than soybean to help create strains that are resistant to fungal infection. Different plants may be used to effect the transformation, such as soybean, *Arabidopsis thaliana*, or others. For instance, genes identified in one species may be introduced into another species in order to obtain transgenic plants that have enhanced fungal defense.

In another embodiment, a gene which belongs to the LysM receptor kinase family may be knocked out. Alternatively, a LysM receptor kinase family gene may be overexpressed. The resultant mutant plants may exhibit improved plant defense responses when challenged with chitin or its derivatives, for example, by spraying the leaves with chitin, or when challenged with a chitin-expressing organism.

In another embodiment, the LysM receptor kinase family gene may be any genes having a coding sequence that has 70%, 80%, 90%, 95%, 99%, or 100% sequence identity to any one of the polynucleotides of SEQ ID Nos. 1-7 and 54-95. In another embodiment, the LysM receptor kinase family gene may be any genes having a coding sequence that has 70%, 80%, 90%, 95%, 99%, or 100% sequence identity to the polynucleotides of SEQ ID No. 6 (AtLyk4).

BRIEF DESCRIPTION OF THE DRAWINGS

FIG. 1 illustrates the eleven distinct types of LysM motifs in plants. (A) The evolutionary relationships of plant LysM motifs. (B) Subcellular localization and LysM domain structures of LysM proteins in plants.

FIG. 2 shows a sequence comparison of various plant LysM sequences that were obtained by computerized searching. FIG. 2A shows an alignment of 93 LysM-containing proteins: MtLYK10 (SEQ ID No. 75), MtLYK11 (SEQ ID No. 76), MtLysMe2 (SEQ ID No. 150; HtLYK1 (SEQ ID No. 71); MtLysHe1 (SEQ ID No. 151); AtLYK1 (SEQ ID No. 3); GmLYK2 (SEQ ID No. J6); HtLYK3 (SEQ ID No. 72); HtLYK4 (SEQ ID No. 73); HtLYK2 (SEQ ID No. 152); LjNFR1a (SEQ ID No. 1); PtLysHn8 (SEQ ID No. 153); PtLYK1 (SEQ ID No. 85); GmLYK8 (SEQ ID No. 63); PtLYK3 (SEQ ID No. 87); AtLYK5 (SEQ ID No. 5); GmLYK6 (SEQ ID No. 61); GmLYK4 (SEQ ID No. 58); HtLYK12 (SEQ ID No. 77); PtLYK6 (SEQ ID No. 90); PtLYK9 (SEQ ID No. 93); AtLYK4 (SEQ ID No. 6); OsLYK1 (SEQ ID No. 79); PtLYK5 (SEQ ID No. 89); GnLYK10 (SEQ ID No. 65); PtLYK7 (SEQ ID No. 91); AtLYK2 (SEQ ID No. 4); OsLYK2 (SEQ ID No. 80); PtLYP1 (SEQ ID No. 154); PtLYK4 (SEQ ID No. 88); PtLYK10 (SEQ ID No. 94); GmLYK9 (SEQ ID No. 64); GnNFR5a (SEQ ID No. 59); LjNFR5 (SEQ ID No. 2); PsSYH10 (SEQ ID No. 155); HtLYK13 (SEQ ID No. 78); HtLYK9 (SEQ ID No. 74); PtLYK2 (SEQ ID No. 86); OsLYK3 (SEQ ID No. 81); AtLYK3 (SEQ ID No. 5); PtLYK8 (SEQ ID No. 92); GnLYK11 (SEQ ID No. 66); PtLYP2 (SEQ ID No. 156); PtLYP3 (SEQ ID No. 157); PtLYP6 (SEQ ID No. 158); AtLYP3 (SEQ ID No. 159); GmLYP1 (SEQ ID No. 160); OsLYP1 (SEQ ID No. 161); PtLYP7 (SEQ ID No. 162); PtLYP5 (SEQ ID No. 163); PtLYP4 (SEQ ID No. 164); GmLYP4 (SEQ ID No. 165); GmLYP2 (SEQ ID No. 166); AtLYP2 (SEQ ID No. 167); AtLYP2 (SEQ ID No. 168); GmLYP3 (SEQ ID No. 169); GmLysHe1 (SEQ ID No. 170); MtLysH16 (171); PtLysHe7 (SEQ ID No. 172); GmLysHe2 (SEQ ID No. 173); GmLysHe4 (SEQ ID No. 174); PtLysHe6 (SEQ ID No. 175); GmLysHe3 (SEQ ID No. 176); GmLysHe6 (SEQ ID No. 177); GmLysHe5 (SEQ ID No. 178); PtLysHe3 (SEQ ID No. 179); PtLysHe5 (SEQ ID No. 180); PtLysMe10 (SEQ ID No. 181); AtLysHe3 (SEQ ID No. 182); OsLysHe4 (SEQ ID No. 183); AtLysHe2 (SEQ ID No. 184); AtLysHe1 (SEQ ID No. 185); PtLysHn9 (SEQ ID No. 186); PtLysHn7 (SEQ ID No. 187); PtLysHe8 (SEQ ID No. 188); PtLysMe11 (SEQ ID No. 189); PtLysHe4 (SEQ ID No. 190); GmLysHn2 (SEQ ID No. 191); GmLysHn4 (SEQ ID No. 192); PtLysHn6 (SEQ ID No. 193); OsLysHn3 (SEQ ID No. 194); GmLysHn3 (SEQ ID No. 195); GmLysHn5 (SEQ ID No. 196); AtLysHn2 (SEQ ID No. 197); PtLysMn11 (SEQ ID No. 198); AtLysHn3 (SEQ ID No. 199); GmLysHn1 (SEQ ID No. 200); AtLysHn1 (SEQ ID No. 201); PtLysHn2 (SEQ ID No. 202); PtLysHn1 (SEQ ID No. 203); OsLysHn1 (SEQ ID No. 204); PtLysMn10 (SEQ ID No. 205); and PtLysHe9 (SEQ ID No. 206). FIG. 2B is an alignment of LysM domains from the following proteins: MtLYK3 (SEQ ID No. 72), MtLYK4 (SEQ ID No. 73), MtLYK2 (SEQ ID No. 152), GmNFR1a (SEQ ID No. 54; GmNFR1b (SEQ ID No. 55); LjNFR1a (SEQ ID No. 1); MtLYK1 (SEQ ID No. 71); AtLYK1 (SEQ ID No. 3); GmLYK3 (SEQ ID No. 57); MtLYK3 (SEQ ID No. 72); MtLYK4 (SEQ ID No. 73); MtLYK2 (SEQ ID No. 152); GmNFR1a (SEQ ID No. 54); GmNFR1b (SEQ ID No. 55); LjNFR1a (SEQ ID No. 1); MtLYK1 (SEQ ID No. 71); AtLYK1 (SEQ ID No. 3); and GmLYK3 (SEQ ID No. 57). FIG. 2C is an alignment of LysM domains from GmNFR5a (SEQ ID No. 59); LjNFR5 (SEQ ID No. 2); MtLYK9 (SEQ ID No. 74); PtLYK2 (SEQ ID No. 86); GmLYK10 (SEQ ID No. 65); PtLYK7 (SEQ ID No. 91); AtLYK5 (SEQ ID No. 7); GmLYK8 (SEQ ID No. 63); MtLYK10 (SEQ ID No. 75); MtLYK11 (SEQ ID No. 76); LjLYK4 (SEQ ID No. 69); MtLYK12 (SEQ ID No. 77); GmLYK4 (SEQ ID No. 58); PtLYK6 (SEQ ID No. 90); PtLYK9 (SEQ ID No. 93); AtLYK4 (SEQ ID No. 6); PtLYK10 (SEQ ID No. 94); PtLYK4 (SEQ ID No. 88); GmLYK9 (SEQ ID No. 62); MtLYK13 (SEQ ID No. 78);

PsSYM10 (SEQ ID No. 155); PtLYK11 (SEQ ID No. 95); GmNFR5b (SEQ ID No. 60); GmNFR5a (SEQ ID No. 59); LjNFR5 (SEQ ID No. 2); MtLYK9 (SEQ ID No. 74); PtLYK2 (SEQ ID No. 86); GmLYK10 (SEQ ID No. 65); PtLYK7 (SEQ ID No. 91); AtLYK5 (SEQ ID No. 7); GmLYK8 (SEQ ID No. 63); MtLYK10 (SEQ ID No. 75); MtLYK11 (SEQ ID No. 76); LyLYK4 (SEQ ID No. 69); MtLYK12 (SEQ ID No. 77); GmLYK4 (SEQ ID No. 58); PtLYK6 (SEQ ID No. 90); PtLYK9 (SEQ ID No. 93); AtLYK4 (SEQ ID No. 6); PtLYK10 (SEQ ID No. 94); PtLYK4 (SEQ ID No. 88); GmLYK9 (SEQ ID No. 64); MtLYK13 (SEQ ID No. 78); PsSYM10 (SEQ ID No. 155); PtLYK11 (SEQ ID No. 95); and GmNFR5b (SEQ ID No. 60). FIG. 2D is an alignment of LysM domains from GmLYK6 (SEQ ID No. 61); PtLYK3 (SEQ ID No. 87); OsLYK1 (SEQ ID No. 79); PtLYK5 (SEQ ID No. 89); AtLYK2 (SEQ ID No. 4); GmLKY11 (SEQ ID No. 66); PtLYK8 (SEQ ID No. 92); AtLYK3 (SEQ ID No. 5); OsLYK2 (SEQ ID No. 80); PtLYK1 (SEQ ID No. 85); OsLYK3 (SEQ ID No. 81). FIG. 2E is an alignment of LysM domains from AtLyP1 (SEQ ID No. 167); AtLYP2 (SEQ ID No. 168); PtLYP5 (SEQ ID No. 163); PtLYP7 (SEQ ID No. 162); PtLYP4 (SEQ ID No. 164); GmLYP4 (SEQ ID No. 165); GmLYP2 (SEQ ID No. 166); OsLYP3 (SEQ ID No. 207); OsLYP5 (SEQ ID No. 208); OsLYP4 (SEQ ID No. 209); GmLYP3 (SEQ ID No. 169); OsLYP1 (SEQ ID No. 161); OsLYP6 (SEQ ID No. 210); OsLYP2 (SEQ ID No. 211); PtLYP2 (SEQ ID No. 156); PtLYP3 (SEQ ID No. 157); AtLYP3 (SEQ ID No. 159); GmLYP1 (SEQ ID No. 160; PtLYP6 (SEQ ID No. 158); and PtLYP1 (SEQ ID No. 154). FIG. 2F is an alignment of LysM domains from GMLYSMe1 (SEQ ID No. 170); PtLysMe7 (SEQ ID No. 172); AtLysMe1 (SEQ ID No. 185); AtLysMe3 (SEQ ID No. 182); GmLysMe4 (SEQ ID No. 174); GmLysMe2 (SEQ ID No. 173); GmLysMe3 (SEQ ID No. 176); GmLysMe5 (SEQ ID No. 178); GmLysMe6 (SEQ ID No. 177); PtLysMe6 (SEQ ID No. 175); PtLysMe3 (SEQ ID No. 179); PtLysMe5 (SEQ ID No. 180); PtLysMe10 (SEQ ID No. 181); OsLysMe4 (SEQ ID No. 183); AtLysMe2 (SEQ ID No. 184); PtLysMe11 (SEQ ID No. 189); PtLysMe8 (SEQ ID No. 188); PtLysMe4 (SEQ ID No. 190); OsLysMe2 (SEQ ID No. 212); OsLysMe1 (SEQ ID No. 213); PtLysMe9 (SEQ ID No. 206); OsLysMe3 (SEQ ID No. 214). FIG. 2G is an alignment of LysM domains from AtLYSMn1 (SEQ ID No. 201); AtLysMn1 (SEQ ID No. 201); GmLysMn1 (SEQ ID No. 200); PtLysMn2 (SEQ ID No. 202); PtLysMn1 (SEQ ID No. 203); OsLysMn1 (SEQ ID No. 204); GmLysMn2 (SEQ ID No. 191); GmLysMn4 (SEQ ID No. 192); PtLysMn6 (SEQ ID No. 193); OsLysMn3 (SEQ ID No. 194); GmLysMn3 (SEQ ID No. 195); GmLysMn5 (SEQ ID No. 196); AtLysMn2 (SEQ ID No. 197); PtLysMn11 (SEQ ID No. 198); AtLysMn3 (SEQ ID No. 199); OsLysMn2 (SEQ ID No. 215); PtLysMn10 (SEQ ID No. 205); PtLysMn7 (SEQ ID No. 187); PtLysMn9 (SEQ ID No. 186); and PtLysMn8 (SEQ ID No. 153).

FIG. 3 presents experimental results showing enhanced expression of the defense genes PR1 and PR-2 in the LysM receptor kinase mutant L3.

Figure 7A:
Figure 7B:

FIG. 7 shows disruption of the AtLysM RLK1 gene expression by the T-DNA insertions. WT=Wild-type Col-0; Mu=AtLysM RLK1 mutant. Actin-2 was used as an internal control.

Figure 8:
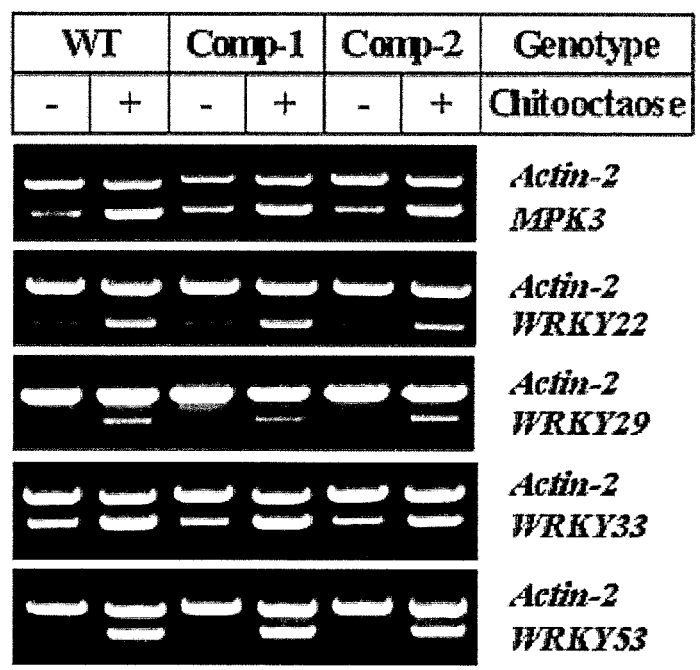

FIG. 8 shows restoration of CRGs in the AtLysM RLK1 mutant by the ectopic expression of the AtLysM RLK1 gene. Actin-2 serves as an internal control.

Figure 9:
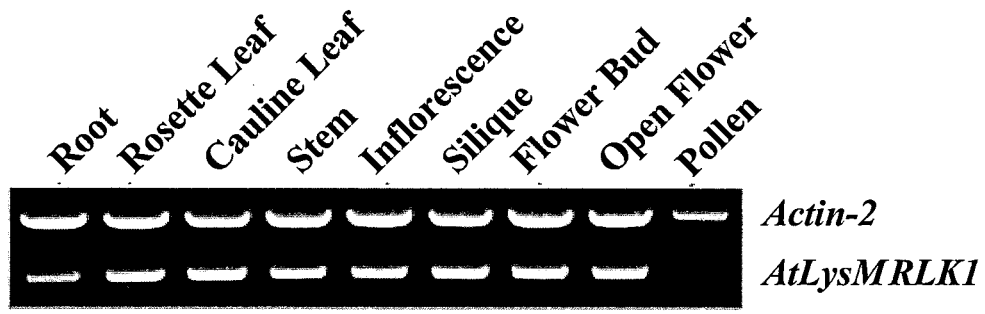

FIG. 9 shows the tissue expression pattern of the AtLysM RLK1 gene. Actin-2 serves as an internal control.

Figure 10:
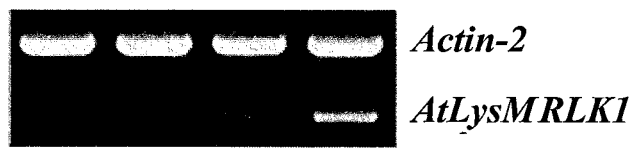
Figure 10:

FIG. 10 shows that AtLysM RLK1 is induced by chitooligosaccharides, but not by the flagellin-derived flg22 peptide.

FIG. 11 shows that the T-DNA insertions in the AtLysM RLK1 gene block the induction of virtually all CRGs.

Figure 12:
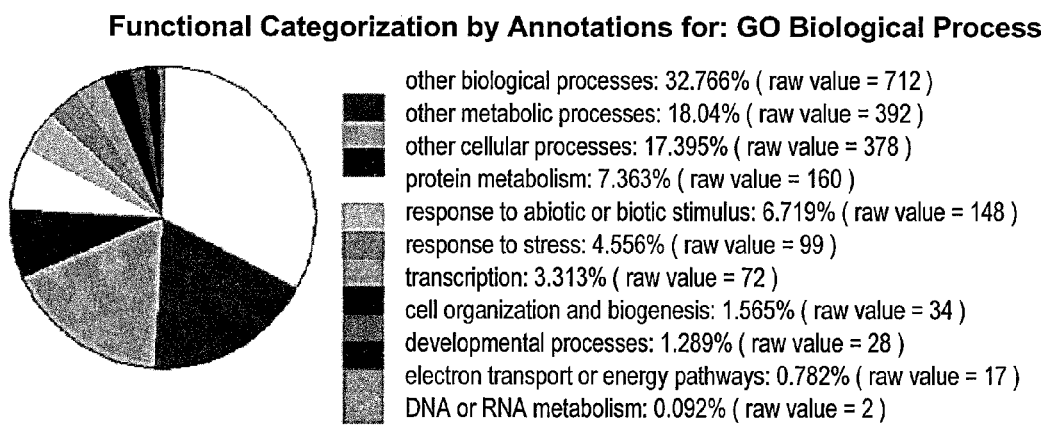

FIG. 12 shows the functional categorization by annotations of 909 CRGs-GO Biological Process.

FIG. 13 shows that the AtLysM RLK1 mutant is more susceptible to fungal pathogens than wild-type plants and that exogenously applied chitooligosaccharides enhances resistance in the wild-type plants, but not in the mutant.

FIG. 14 shows that the selected CRGs are still induced in the AtLysM RLK1 mutant by a fungal pathogen, but to a reduced level.

FIG. 15 shows that mutations in the legume Nod signal receptor genes NFR1 and NFR5 do not affect the induction of the selected CRGs in *Lotus japonicus*.

Figure 16A:
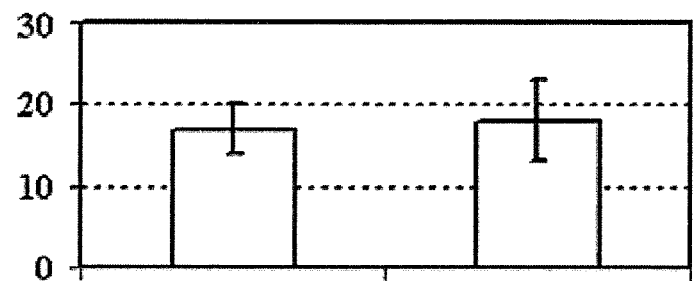
Figure 16B:
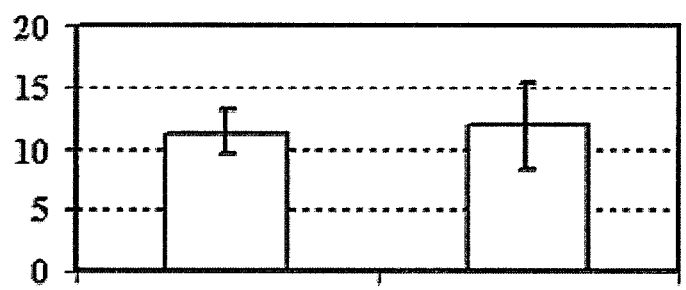
Figure 16C:
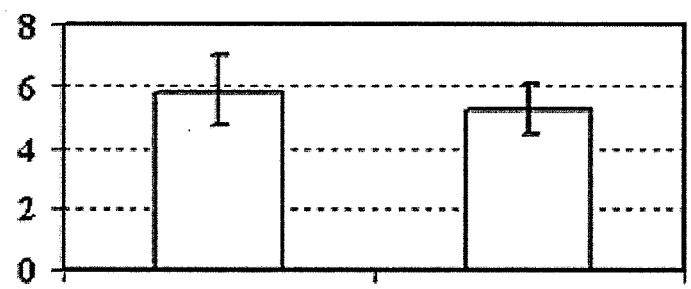

FIG. 16 shows that the mutation in the AtLysM RLK1 gene does not affect other defense-related pathways.

Figure 17:
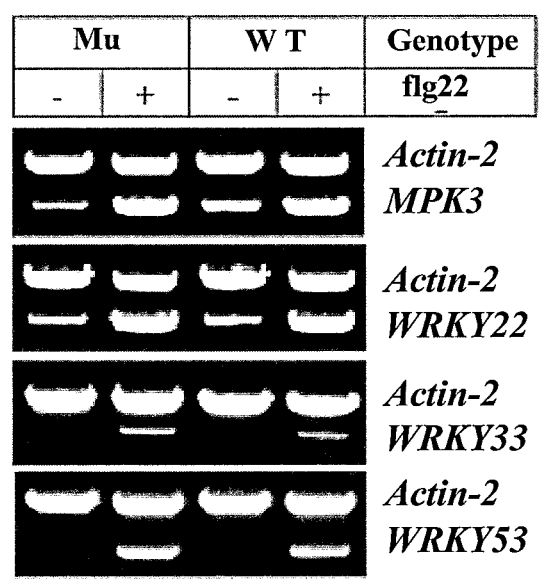

FIG. 17 shows that the AtLysM RLK1 mutation does not block the induction of flagellin-responsive genes.

Figure 18:
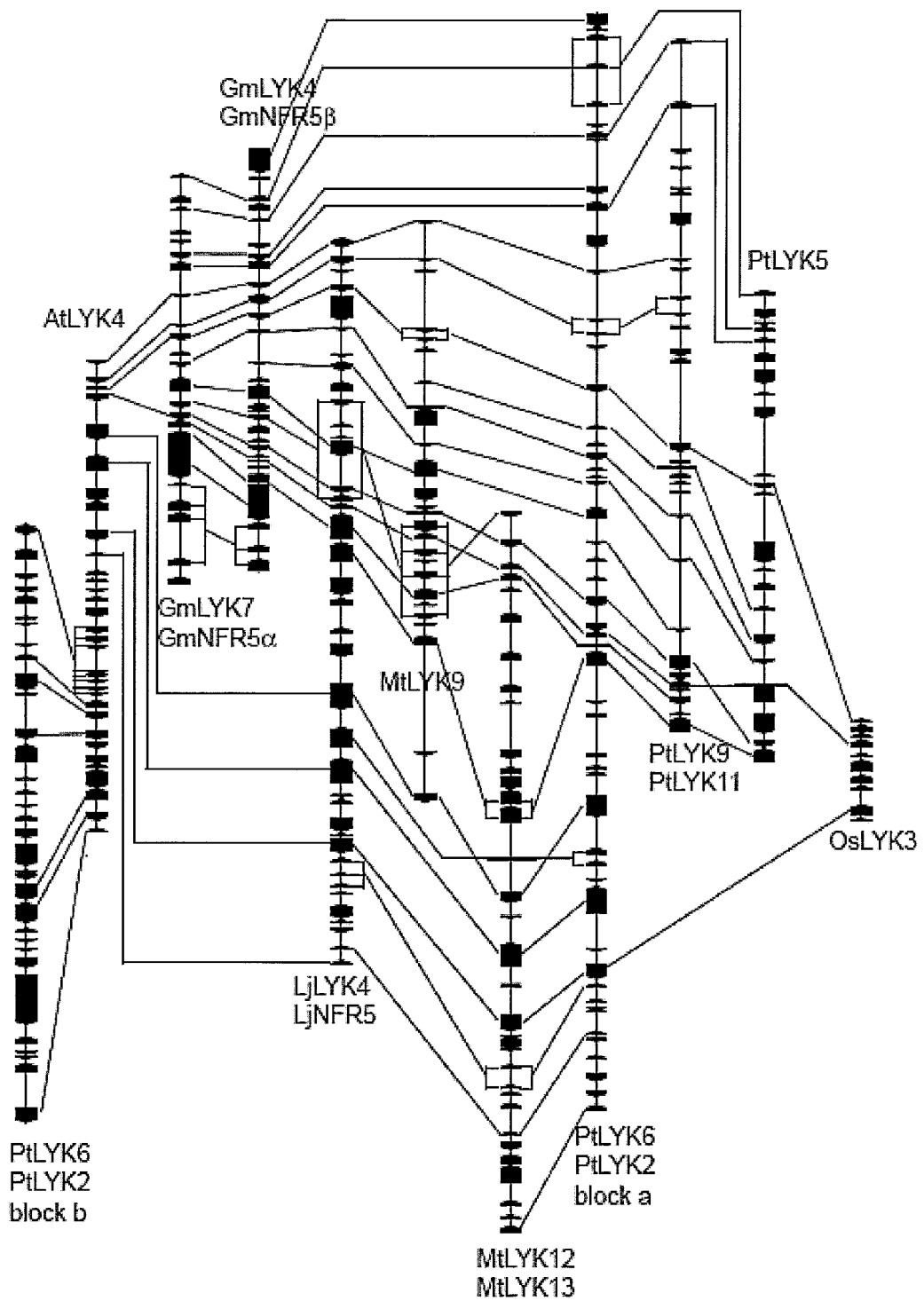

FIG. 18 shows similarity between the LysM receptor kinase-like genes in a variety of plants.

Figure 19:
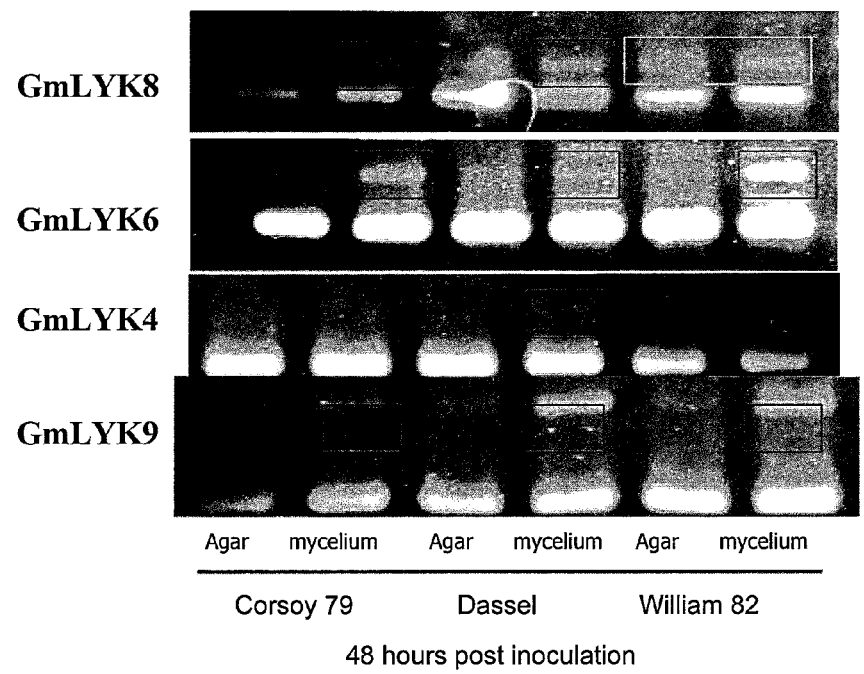

FIG. 19 shows the expression analysis of GmLysM receptor-like kinases in response to white-mold pathogen.

Figure 20:
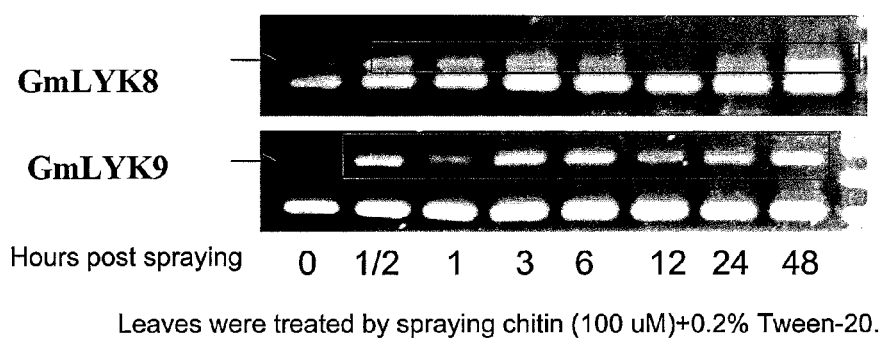

FIG. 20 shows the expression analysis of GmLysM receptor-like kinases in chitin-treated leaves.

Figure 21:
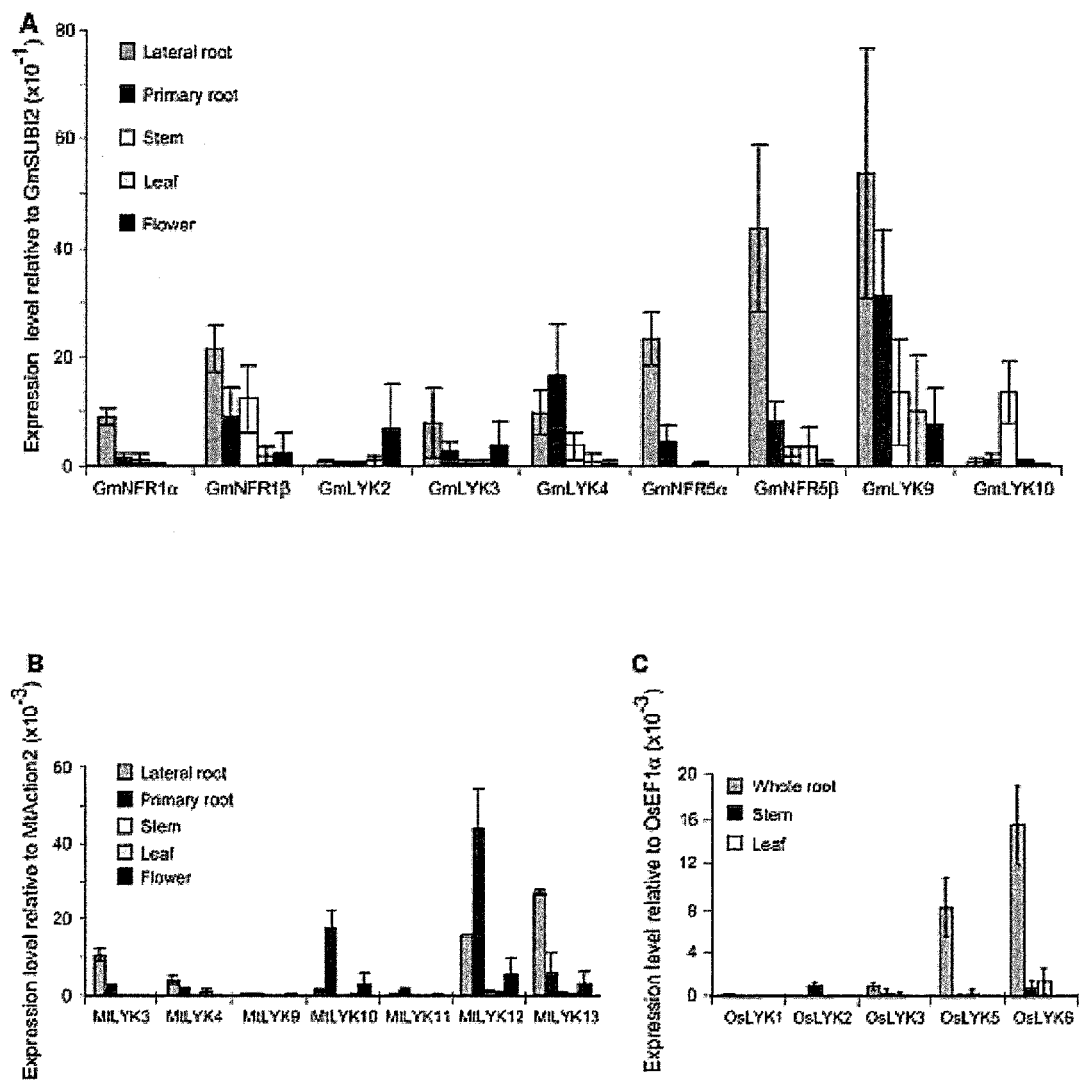

FIG. 21 shows the results of tissue-specific expression analysis of LysM receptor-like kinases in soybean, *M. truncatula*, and rice.

DETAILED DESCRIPTION

The following detailed description is provided to aid those skilled in the art in practicing the present instrumentalities. Even so, this detailed description should not be construed to unduly limit the present invention as modifications and variations in the embodiments discussed herein can be made by those of ordinary skill in the art without departing from the spirit or scope of the present inventive discovery.

LysM domain-containing receptor-like kinases ("LysM RLKs," "LYK" or "LysM receptor kinase family proteins"), such as NFR1 and NFR5 in legumes, have been shown to be critical for the perception of modified chitooligosaccharides—Nod signals—in the legume-rhizobial symbiotic nodulation process. See Limpens et al., 2003; Madsen et al., 2003; and Radutoiu et al., 2003. Similar LysM receptor kinase family genes (or LysM RLK genes) are also present in non-leguminous plants. Zhang et al., 2007. For example, five LysM RLK genes have been identified in the model plant *Arabidopsis thaliana*. LysM domain-containing proteins are also found in animals but LysM RLKs appear to be unique to plants. Zhang et al., 2007.

Figure 1A:
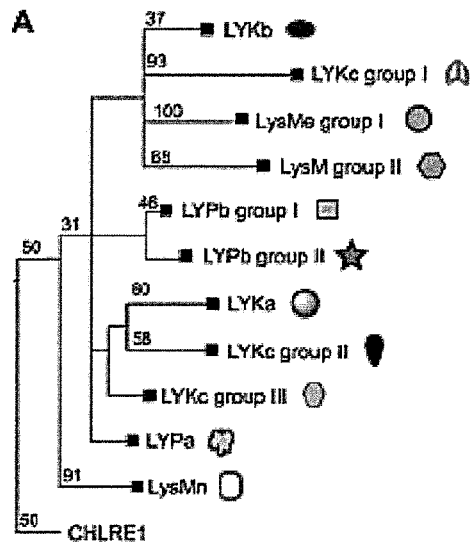
Figure 1B:
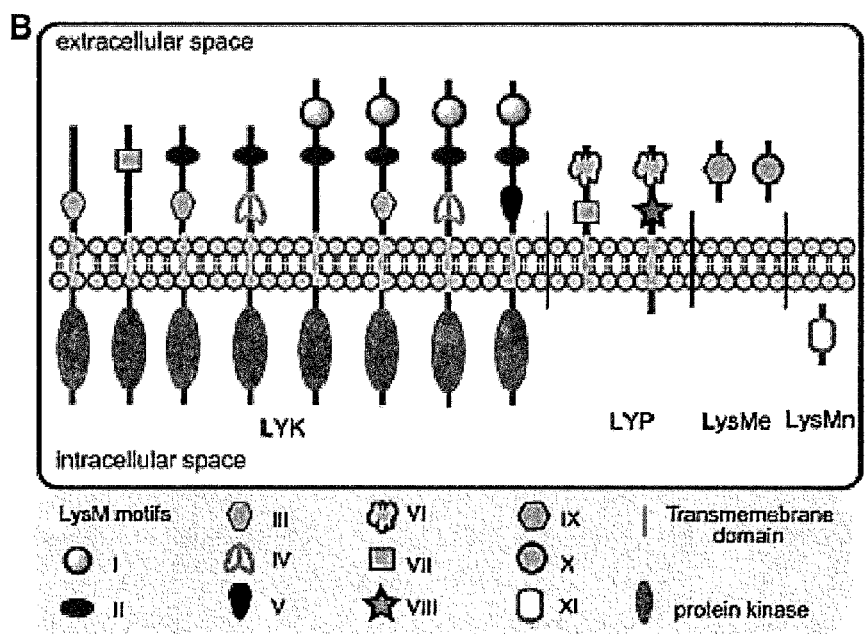
Figure 2A:
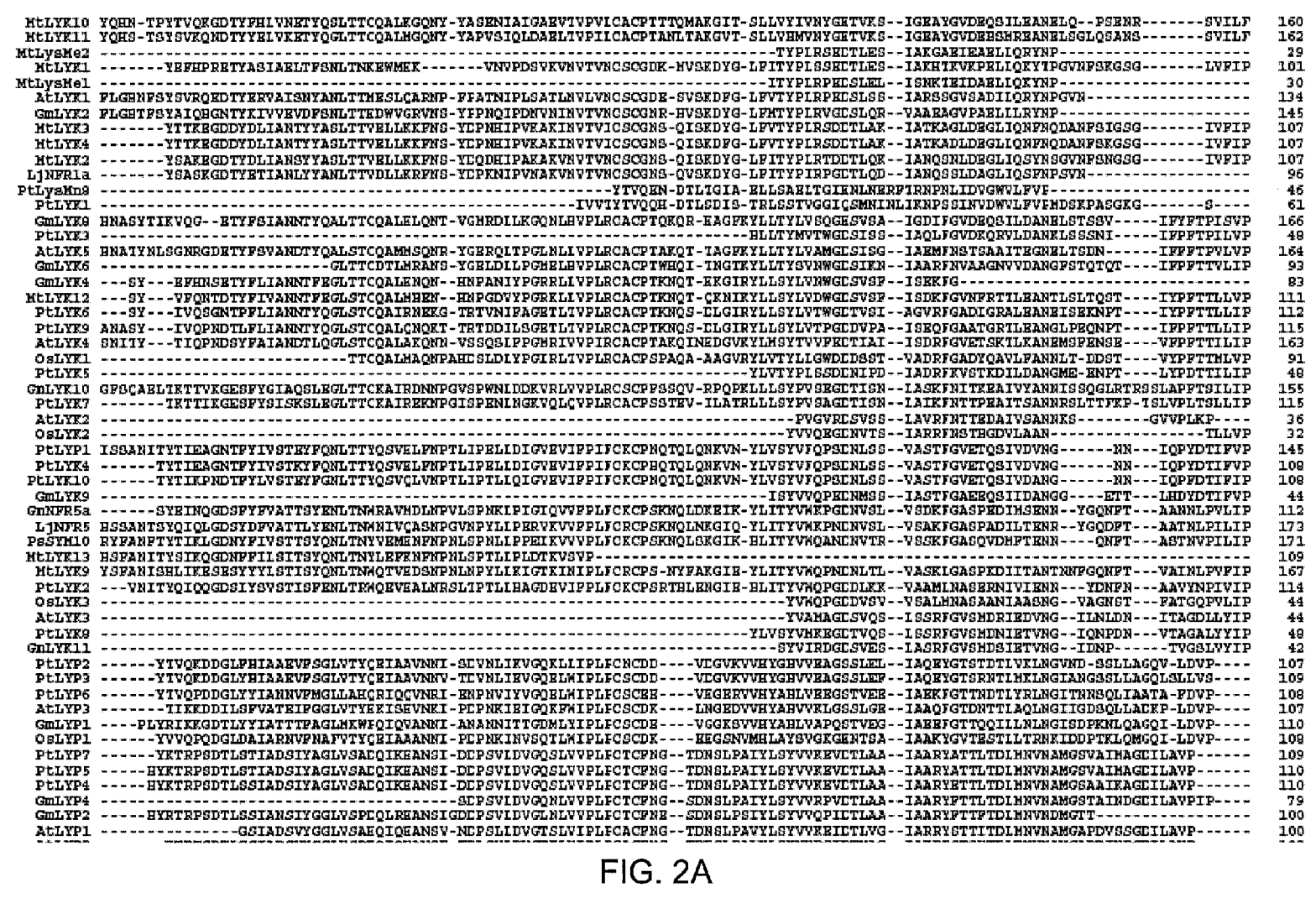
Figure 2A:
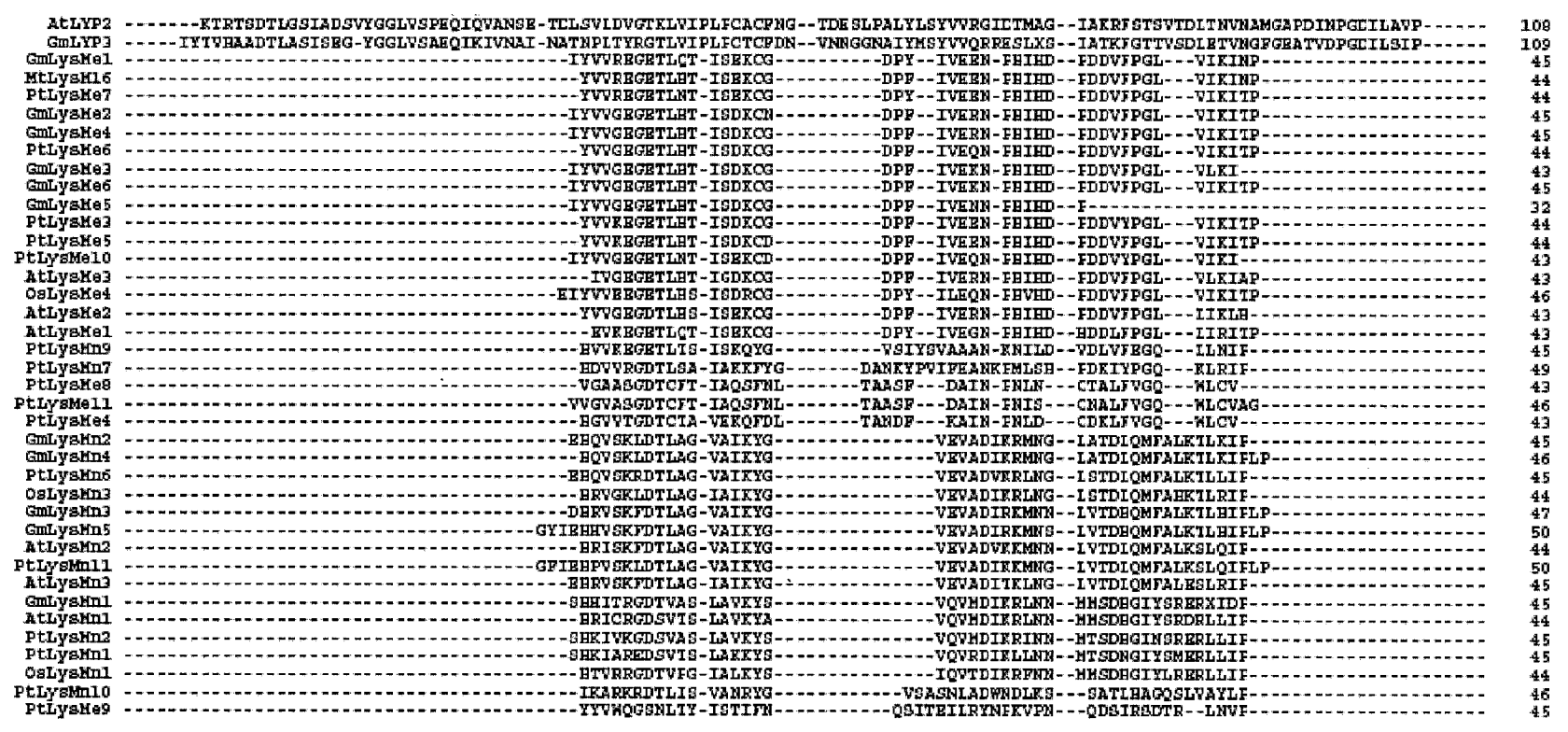
Figure 2C:
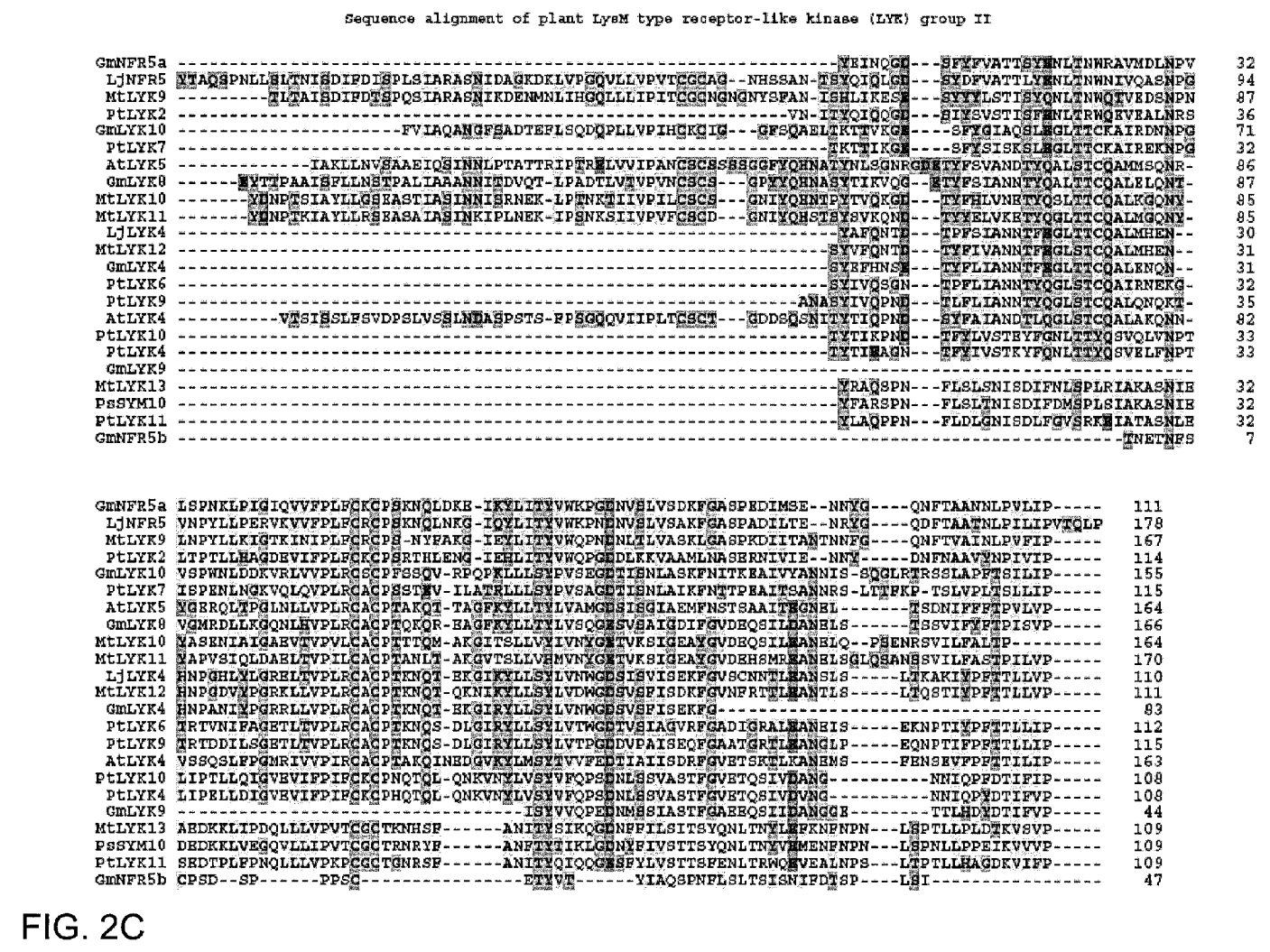
Figure 2E:
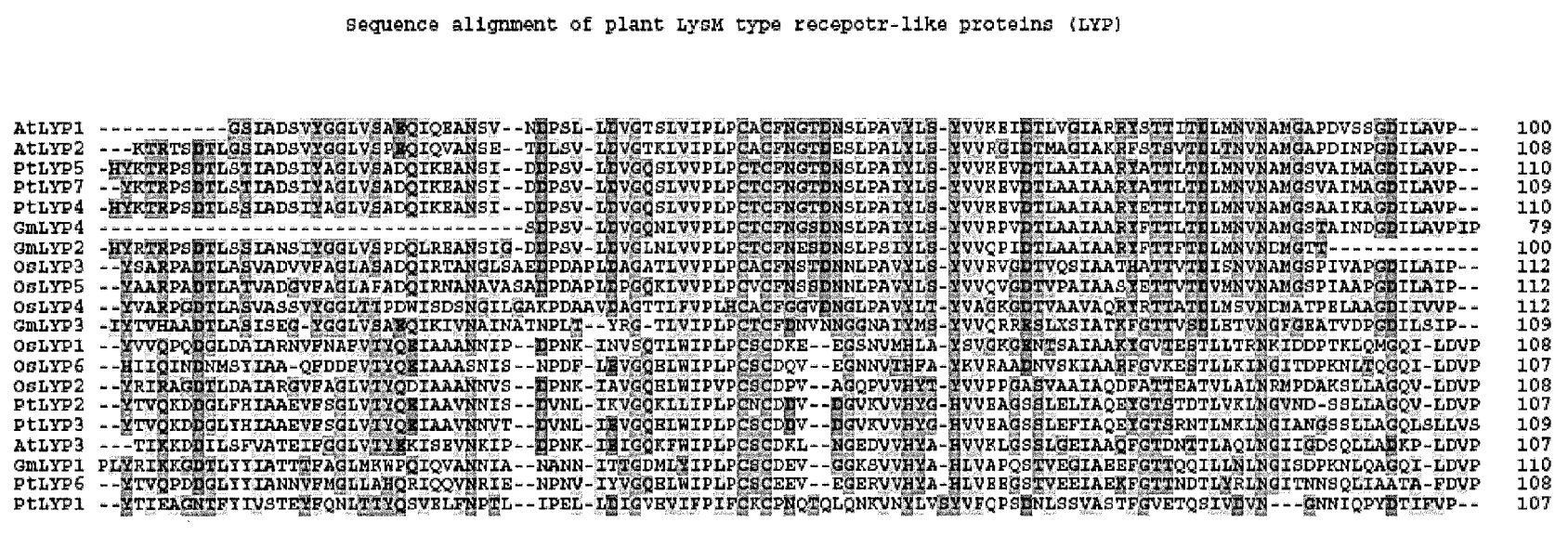

For purpose of this disclosure, a "LysM receptor kinase family gene" (LysM RLK gene) is any gene that encodes a protein with at least a Lysine motif (LysM) domain, a kinase domain and a transmembrane domain between the LysM and the kinase domain as shown in FIG. 1. In one aspect, the kinase domain is a serine/threonine kinase domain. A gene may be shown to belong to different subfamilies of LysM genes by sequence comparison with a known LysM gene, as exemplified by the sequence alignment of different LysM containing proteins in FIG. 2. This classification may be decided by a predetermined level of sequence identity in one or more functional domains of a known LysM receptor kinase, such as 70%, 80%, 90%, 95%, 96%, 97%, 98% 99% or 100% sequence identity with respect to a functional domain or an entire coding sequence.

Two sequences may be said to have "substantial sequence similarity" when they have a degree of sequence identity that persons of ordinary skill in the art may expect them to provide similar functionality; or in some cases, a person of skills in the art may expect individual domains within the sequences to possess similar functionality due to the sequence similarity. As measured by computer algorithms that are designed to quantitate sequence identity or similarity, this may be at least 70% identity, or more preferably, this may be any value from 90% and up, such as 95%, 96%, 97%, 98% or 99% identity, with 100% identity being an exact match. When two sequences are of different length, the sequence identity refers to cumulative sequence identity between those segments of both sequences that when aligned generate the best possible matches of individual residues throughout the full length of the sequences. In general, higher sequence similarity between two sequences indicates that the two sequences are more likely to perform similar, if not identical function.

The term CRGs (or CRG) refers to genes that may be activated upon perception of chitin or its derivatives by plant cells. Examples of CRGs may include MPK3, WRKY22, WRKY29, WRKY33, WRKY53 and any other genes whose expression levels may be up- or down-regulated when the cells are exposed to chitin or its derivatives. In one embodiment, genetic engineering may be used to render certain CRGs constitutively expressed, or, more preferably, expression of CRGs may be placed under control of certain regulatory elements such that CRG proteins may be expressed before fungi have been detected by the plant.

Under certain circumstances, it may be desirable to generate mutations in the coding sequence of certain genes, such as the LYK genes or CRGs. One of skills in the art may recognize that certain sequence variations may not significantly affect the functionality of a DNA or RNA molecule, or a protein. For instance, one may align and compare the sequences of the LYK family genes, as shown in FIG. 2, to determine which residues may be less conservative than others. The term "conservative" is used to depict those nucleotide or amino acid residues that have not undergone significant changes over the course of evolution. The conservative residues are typically shown as matching residues in a multi-sequence alignment. Guided by such an alignment, one may substitute those residues that are less conservative without compromising the functionality of the genes, RNAs, or proteins. Such manipulations of polynucleotide or polypeptide molecules are within the scope of this disclosure.

A "functional" LysM receptor kinase refers to a protein encoded by one of the LysM receptor kinase family genes that is capable of performing the full function that is typically performed by other LysM receptor kinase family proteins.

"Secretion sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

A "recombinant polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

"PCR" means polymerase chain reaction.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

"Sequence" means the linear order in which monomers occur in a polymer, for example, the order of amino acids in a polypeptide or the order of nucleotides in a polynucleotide.

"Peptide," "Protein" and "Polypeptide" are used interchangeably and mean a compound that consists of two or more amino acids that are linked by means of peptide bonds.

"Recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety, makes that gene unnatural for the purposes of this definition, and thus that gene cannot be "naturally" found in any cell.

A "non-immunoglobulin peptide" means a peptide which is not an immunoglobulin, a recognized region of an immunoglobulin, or contains a region of an immunoglobulin. For example, a single chain variable region of an immunoglobulin would be excluded from this definition.

"Substantially pure" or "substantially purified" means that the substance is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in even more preferred embodiments, at least 99% pure. The analysis may be weight or molar percentages, evaluated, e.g., by gel staining, spectrophotometry, or terminus labeling etc.

A "transgene" refers to a coding sequence that has been introduced into a host organism, which may be referred to as a transgenic organism, e.g., a transgenic animal, or a transgenic plant, when the transgene has been successfully introduced into said organism. Typically, a transgene is introduced into a host organism so that the coding sequence may be transcribed into RNA or, in most cases, be further expressed as a polypeptide. The introduction of a transgene into a host organism and subsequent expression of the transgene is generally known as a transgenic process. A transgenic plant may refer to a whole plant, or a tissue of a plant, such as a seed, that contains a transgene and has a potential to be grow into a plant.

A "mutation," as used herein, means a change in the nucleotide sequence of a polynucleotide molecule or a change in the amino acid sequence of a polypeptide. The molecule carrying such a change may be referred to as a mutant molecule, and the change is typically measured by comparing the sequence of the mutant molecule with that of the polynucleotide or polypeptide molecule from which the mutant molecule is derived. An organism with a mutation in one of its endogenous genes may be called a mutant.

A mutation in a gene may occur on either the coding region or the non-coding region of the gene. A mutated copy of a gene may be said to be "derived" from a endogenous copy of the same gene when one or more spontaneous or induced mutations occur on an endogenous gene, at which point the endogenous gene becomes a mutated gene because it is no longer the same as the original wild-type gene. The resultant organism may be called a mutant.

In one aspect, the polynucleotide sequences disclosed herein, including but not limited to LysM receptor kinase family genes and various CRGs, may be used to identify those mutants with mutations in one of the LysM receptor kinase family genes. For instance, a large number of mutants may be generated by either spontaneous or induced mutation. These mutants may be screened to identify those mutations that occur in one of the LysM receptor kinase family genes. Suitable methods for such a screening may include, for example, PCR, sequencing, or hybridization.

In another aspect, these polynucleotide sequences, including but not limited to LysM receptor kinase family genes and various CRGs, may also be used to design DNA construct for targeted insertion, deletion, or substitution of a specific LysM receptor kinase family gene. For instance, a DNA fragment may be first inserted into the coding region of a LysM receptor kinase family gene, the construct thus obtained may then be introduced into a host to create an insertional mutant by homologous recombination.

The traits of a plant may be modified. A modified plant may be coconsidered "fungal resistant" if the chance of a plant becoming infected by a specific fungal pathogen is at least 30% less than that of a wild-type plant from which the modified plant is derived.

A molecule is "endogenous" to an organism if the molecule exists or is encoded by a molecule that exists in the organism without requiring a transgenic process. For purpose of this disclosure, the terms "expression" and "express" refer to transcription of DNA into RNA, or translation of RNA into protein, or both.

Besides null mutation that renders a protein completely non-functional, a mutation may also render a protein dominant negative when it only abolishes partial function of a protein. The resultant partially functioning protein may act as a "dominant negative" protein when it continues to perform the remaining function. For example, a mutated protein may continue to bind a co-factor without activating that co-factor because the activation function has been lost. When such a mutated protein is expressed in a cell, it binds to many co-factors without activating them, thus rendering them unavailable for the wild-type protein. In this situation, the mutant protein is said to be acting in a dominant negative fashion.

The term "knocking out" or "knock out" means rendering a gene non-functional. "Knocking down" means lowering the expression levels of a gene or decrease the relative activity of the encoded protein. A gene can be knocked out or knocked down through deletion, insertion, substitution of a fragment or a residue in the coding region or in the regulatory regions of a gene.

Within the scope of the disclosed instrumentalities are recombinant oligonucleotides encoding peptides having antifungal activity. These recombinant oligonucleotides can be used to produce recombinant polynucleotides which are commonly used as cloning or expression vectors although other uses are possible. A cloning vector is a self-replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed and translated into a protein.

Both cloning and expression vectors may contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known to those skilled in the art and include, but are not limited to the pBR322 plasmid origin, the 2μ plasmid origin, and the SV40, polyoma, adenovirus, VSV and BPV viral origins. An expression vector may contain an origin of replication so that it can be replicated independently from the host's chromosome. More preferably, an expression vector carrying the transgene of interest may have a means by which the DNA fragment containing the transgene may be integrated onto a chromosome of the host plant and thus may be replicated along with the host chromosomes.

The polynucleotide sequences of the present disclosure may be used to produce antifungal peptides by the use of recombinant expression vectors containing the polynucleotide sequence disclosed herein. For purpose of this disclosure, antifungal peptides may mean polypeptides or fragments thereof that may help prevent fungal infection of a plant. Examples of antifungal peptides may include but not limited to polypeptides encoded by the LysM receptor kinase genes or the CRGs. In one embodiment, these antifungal peptide may be expressed in vitro and be applied onto a plant or be injected into a plant to achieve the desired antifungal effects. Suitable expression vectors include chromosomal, non-chromosomal and synthetic DNA sequences, for example, SV 40 derivatives; bacterial plasmids; phage DNA; baculovirus; yeast plasmids; vectors derived from combinations of plasmids and phage DNA; and viral DNA such as vaccinia, adenovirus, fowl pox virus, and pseudorabies. In addition, any other vector that is replicable and viable in the host may be used. Suitable host for in vitro expression may include bacterial, yeast, plant or insect cells, among others.

The nucleotide sequence of interest may be inserted into the vector by a variety of methods. In the most common method the sequence is inserted into an appropriate restriction endonuclease site(s) using procedures commonly known to those skilled in the art and detailed in, for example, Sambrook et al., *Molecular Cloning, A Laboratory Manual,* 2nd ed., Cold Spring Harbor Press, (1989) and Ausubel et al., *Short Protocols in Molecular Biology,* 2nd ed., John Wiley & Sons (1992).

In an expression vector, the sequence of interest may be operably linked to a suitable regulatory elements, including but not limited to a promoter or a enhancer, that may be recognized by the host cell to direct mRNA synthesis. Promoters generally refer to untranslated sequences located upstream from the start codon of a structural gene that regulate the transcription and translation of nucleic acid sequences under their control. Promoters may be classified as either inducible or constitutive promoters. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription.

A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual,* 2nd ed., Cold Spring Harbor Press, (1989) and Ausubel et al., *Short Protocols in Molecular Biology,* 2nd ed., John Wiley & Sons (1992).

Common promoters used in expression vectors include, but are not limited to, LTR or SV40 promoter, the *E. coli* lac or trp promoters, and the phage lambda PL promoter. Useful inducible plant promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651). Other promoters known to control the expression of genes in prokaryotic or eukaryotic cells can be used and are known to those skilled in the art. Expression vectors may also contain a ribosome binding site for translation initiation, and a transcription terminator. The vector may also contain sequences useful for the amplification of gene expression.

Expression and cloning vectors can, and usually do, contain a selection gene or selection marker. Typically, this gene encodes a protein necessary for the survival or growth of the host cell transformed with the vector. Examples of suitable markers include dihydrofolate reductase (DHFR) or neomycin resistance for eukaryotic cells and tetracycline or ampicillin resistance for *E. coli*. Selection markers in plants include resistance to bleomycin, gentamycin, glyphosate, hygromycin, kanamycin, methotrexate, phleomycin, phosphinotricin, spectinomycin, streptomycin, sulfonamide and sulfonylureas. Maliga et al., *Methods in Plant Molecular Biology*, Cold Spring Harbor Press, 1995, p. 39.

In addition, expression vectors can also contain marker sequences operatively linked to a nucleotide sequence for a protein that encode an additional protein used as a marker. The result is a hybrid or fusion protein comprising two linked and different proteins. The marker protein can provide, for example, an immunological or enzymatic marker for the recombinant protein produced by the expression vector. Suitable markers include, but are not limited to, alkaline phosphatase (AP), myc, hemagglutinin (HA), β-glucuronidase (GUS), luciferase, and green fluorescent protein (GFP).

The polynucleotide sequences of the present disclosure may also be part of an expression cassette that at a minimum comprises, operably linked in the 5' to 3' direction, a regulatory sequence such as a promoter, a polynucleotide encoding a peptide of the present disclosure, and a transcriptional termination signal sequence functional in a host cell. The promoter can be of any of the types discussed herein, for example, a tissue specific promoter, a developmentally regulated promoter, an organelle specific promoter, a seed specific promoter, a plastid specific promoter, etc. The expression cassette can further comprise an operably linked targeting, transit, or secretion peptide coding region capable of directing transport of the protein produced. The expression cassette can also further comprise a nucleotide sequence encoding a selectable marker and/or a purification moiety.

More particularly, the present disclosure includes recombinant constructs comprising an isolated polynucleotide sequence encoding the antifungal peptides of the present disclosure. The constructs can include a vector, such as a plasmid or viral vector, into which the sequence has been inserted, either in the forward or reverse orientation. The recombinant construct can further comprise regulatory sequences, including, for example, a promoter operatively linked to the sequence. Large numbers of suitable vectors and promoters are known to those skilled in the art and are commercially available.

Different domains from different LysM RLKs may be combined to obtain chimeric proteins. Such a chimeric protein may possess a number of desirable properties that are not otherwise exhibited by one single protein that naturally exist in plants. Such desirable properties may include but are not limited to increased sensibility to chitin and its derivatives, increased kinase activity or enhanced kinase specificity.

A further embodiment of the present disclosure relates to transformed host cells containing constructs comprising the oligonucleotide sequences of the present disclosure. For instance, various combination of the LysM RLK genes, in wild-type or mutated forms, may be introduced as transgenes into a host plant, such as soybean. In a preferred embodiment, the host plants is susceptible to fungal infection and the expression of the LysM RLK transgenes may confer certain degree of fungal resistance to the host. In addition to the LysM RLK genes, the transgenes may include other genes that may play a role in fungal defense, such as any of the CRGs whose forced expression may enhance the host's capability to defend against fungal pathogens.

The host cell can be a higher eukaryotic cell, such as a mammalian or plant cell, or a lower eukaryotic cell such as a yeast cell, or the host can be a prokaryotic cell such as a bacterial cell. Introduction of the construct into the host cell can be accomplished by a variety of methods including calcium phosphate transfection, DEAE-dextran mediated transfection, Polybrene, protoplast fusion, liposomes, direct microinjection into the nuclei, scrape loading, and electroporation. In plants, a variety of different methods can be employed to introduce transformation/expression vectors into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42: 205).

Peptides produced by expression of the polynucleotides of the present disclosure can be obtained by transforming a host cell by any of the previously described methods, growing the host cell under appropriate conditions, inducing expression of the polynucleotide and isolating the protein(s) of interest. If the protein in retained within the host cell, the protein can be obtained by lysis of the host cells, while if the protein is a secreted protein, it can be isolated from the culture medium. Several methods are available for purification of proteins and are known to those of ordinary skill in the art. These include precipitation by, for example, ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, high performance liquid chromatography (HPLC), electrophoresis under native or denaturing conditions, isoelectric focusing, and immunoprecipitation.

Alternatively, peptides encoded by the polynucleotides of the present disclosure can be produced by chemical synthesis using either solid-phase peptide synthesis or by classical solution peptide synthesis also known as liquid-phase peptide synthesis. In oligomer-supported liquid phase synthesis, the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, and eliminates tedious purification steps associated with traditional liquid phase synthesis. Oligomer-supported liquid phase synthesis has also been adapted to automatic liquid phase synthesis of peptides.

For solid-phase peptide synthesis, the procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. In a common method, an amino acid is bound to a resin particle, and the peptide generated in a stepwise manner by successive additions of protected amino acids to produce a chain of amino acids. Modifications of the technique described by Merrifield are commonly used (see, e.g., Merrifield, *J. Am. Chem. Soc.* 96: 2989-93, 1964). In an automated solid-phase method, peptides are synthesized by loading the carboxy-terminal amino acid onto an organic linker (e.g., PAM, 4-oxymethylphenylacetamidomethyl), which is covalently attached to an insoluble polystyrene resin cross-linked with divinyl benzene. The terminal amine is protected by blocking with t-butyloxycarbonyl. Hydroxyl- and carboxyl-groups are commonly protected by blocking with O-benzyl groups. Synthesis is accomplished in an automated peptide synthesizer, a number of which are commercially available. Following synthesis, the product may be removed from the resin. The blocking groups are removed typically by using hydrofluoric acid or trifluoromethyl sulfonic acid according to established methods (e.g., Bergot and McCurdy, *Applied Biosystems Bulletin,* 1987). Following cleavage and purification, a yield of approximately 60 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high-pressure liquid chromatography (e.g., using a C18 column with 0.1% trifluoroacetic acid and acetonitrile as solvents) if the molecular weight of the peptide is less than 500 daltons. Purified peptide may be lyophilized and stored in a dry state until use. Analysis of the resulting peptides may be accomplished using the common methods of analytical high pressure liquid chromatography (HPLC) and electrospray mass spectrometry (ES-MS).

In general, transgenic plants comprising cells containing polynucleotides of the present disclosure can be produced by any of the foregoing methods; selecting plant cells that have been transformed on a selective medium; regenerating plant cells that have been transformed to produce differentiated plants; and selecting a transformed plant that expresses the protein(s) encoded by the polynucleotides of the present disclosure at a desired level.

Specific methods for transforming a wide variety of dicots and obtaining transgenic plants are well documented in the literature (Gasser and Fraley, *Science* 244:1293, 1989; Fisk and Dandekar, *Scientia Horticulturae* 55:5, 1993; Dandekar and Fisk, Plant transformation: *agrobacterium*-mediated gene transfer. Methods Mol Biol. 2005; 286:35-46; Olhoft P M, Donovan C M, Somers D A, Soybean (*Glycine max*) transformation using mature cotyledonary node explants, Methods Mol Biol. 2006; 343:385-96; Ko T S, Korban S S, Somers D A, Soybean (*Glycine max*) transformation using immature cotyledon explants, Methods Mol Biol. 2006; 343: 397-405; and all references cited therein).

Successful transformation and plant regeneration have also been achieved in a variety of monocots. Specific examples are as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum* spp.; Bower and Birch (1992) *Plant J.* 2: 409); tall fescue (*Festuca arundinacea*;

Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299). All these references relate to transformation techniques in dicots or monocots and are hereby expressly incorporated into this disclosure by reference.

Various LysM RLK genes show tissue specific expression in plants. Tissue specific promoters or other regulatory elements may play a role in controlling these tissue specific expression patterns. DNA recombination utilizing these regulatory elements may be employed to manipulate the expression pattern and/or levels of the various LysM RLK genes, or other genes in general. For instance, expression construct containing a tissue specific promoter may be used to drive the expression of a LysM RLK which is not otherwise expressed in the particular tissue.

EXAMPLES

The following examples are intended to provide illustrations of the application of the present disclosure. The following examples are not intended to completely define or otherwise limit the scope of the invention.

Example 1

Plant LysM Domains are Highly Diversified

The sequences of NFR1 (SEQ ID No. 1) and NFR5 (SEQ ID No. 2) genes from *Lotus japonicus*, as reported by Radutoiu et al. (2003) were used to identify genes encoding LysM domain-containing proteins by searching public databases of *Arabidopsis*, rice, poplar, *M. truncatula*, and *L. japonicus*. Soybean LYK genes were identified by shotgun sequencing bacterial artificial chromosomes (BACs) with homologies to LysM-encoding ESTs. The resulting putative LYK protein sequences from all species were then searched against the Pfam server to verify LysM and kinase domains. Collectively, a total of 49 LYK genes were identified in the six plant genomes, namely, those of *Arabidopsis*, rice, poplar, *M. truncatula*, *L. japonicus* and soybean, as summarized in Table 2. The predicted amino acid sequences of these genes or fragments were obtained and compared by sequence alignment, with representative alignments shown in FIG. 2.

TABLE 2

LysM type receptor-like kinase genes from Arabidopsis, soybean, Lotus, Medicago, rice and poplar.

| Name (SEQ ID No.) | Alias name | Sources |
|---|---|---|
| AtLYK1 (SEQ ID No. 3) | At3g21630 | TAIR |
| AtLYK2 (SEQ ID No. 4) | At3g01840 | TAIR |
| AtLYK3 (SEQ ID No. 5) | At1g51940 | TAIR |
| AtLYK4 (SEQ ID No. 6) | At2g23770 | TAIR |
| AtLYK5 (SEQ ID No. 7) | At2g33580 | TAIR |
| GmNFR1α (SEQ ID 54) | GmW2098N11.16 | this study |
| GmNFR1β (SEQ ID 55) | GmW2098N15.9 | this study |
| GmLYK2 (SEQ ID 56) | GmW2098N11.15 | this study |
| GmLYK3 (SEQ ID 57) | GmW2026N19.18 | this study |
| GmLYK4 (SEQ ID 58) | GmW2095P01.22 | this study |
| GmNFR5α (SEQ ID 59) | GmW2035N07.17 | this study |
| GmNFR5β (SEQ ID 60) | GmW2095P01.23 | this study |
| GmLYK6 (SEQ ID 61) | GmW2075N23 | this study |
| GmLYK7 (SEQ ID 62) | GmW2035N07.16 | this study |
| GmLYK8 (SEQ ID 63) | GmW2098N11.2 | this study |
| GmLYK9 (SEQ ID 64) | GmW2069O12.22 | this study |
| GmLYK10 (SEQ ID 65) | GmW2080D08.12 | this study |
| GmLYK11 (SEQ ID 66) | GmW2042I24.15 | this study |
| LjNFR1 (SEQ ID 1) | AJ575248 | Gene Bank |
| LjLYK2 (SEQ ID 67) | TM0545.8 | Kazusa |
| LjLYK3 (SEQ ID 68) | TM0545.9 | Kazusa |
| LjLYK4 (SEQ ID 69) | TM0522.16 | Kazusa |
| LjNFR5 (SEQ ID 2) | AJ575255 | Gene Bank |

TABLE 2-continued

LysM type receptor-like kinase genes from Arabidopsis, soybean, Lotus, Medicago, rice and poplar.

| Name (SEQ ID No.) | Alias name | Sources |
|---|---|---|
| LjLYK6 (SEQ ID 70) | TM0076a.10 | Kazusa |
| MtLYK1 (SEQ ID 71) | CR936945.12 | Medicago truncatula sequencing resources |
| MtLYK3 (SEQ ID 72) | AY372402 | Gene Bank |
| MtLYK4 (SEQ ID 73) | AY372403 | Gene Bank |
| MtLYK9 (SEQ ID 74) | AC148241_11 | Medicago truncatula sequencing resources |
| MtLYK10 (SEQ ID 75) | AC148994_13 | Medicago truncatula sequencing resources |
| MtLYK11 (SEQ ID 76) | AC148994_15 | Medicago truncatula sequencing resources |
| MtLYK12 (SEQ ID 77) | AC126779_3 | Medicago truncatula sequencing resources |
| MtLYK13 (SEQ ID 78) | AC126779_4 | Medicago truncatula sequencing resources |
| OsLYK1 (SEQ ID 79) | LOC_Os01g36550 | TIGR |
| OsLYK2 (SEQ ID 80) | LOC_Os06g41980 | TIGR |
| OsLYK3 (SEQ ID 81) | LOC_Os06g41960 | TIGR |
| OsLYK4 (SEQ ID 82) | LOC_Os02g09960 | TIGR |
| OsLYK5 (SEQ ID 83) | LOC_Os03g13080 | TIGR |
| OsLYK6 (SEQ ID 84) | LOC_Os11g35330 | TIGR |
| PtLYK1 (SEQ ID 85) | FGENESH1_PG.C_LG_VIII001701 | DOE JGI |
| PtLYK2 (SEQ ID 86) | FGENESH1_PG.C_LG_VII000997 | DOE JGI |
| PtLYK3 (SEQ ID 87) | EUGENE3.00051645 | DOE JGI |
| PtLYK4 (SEQ ID 88) | EUGENE3.00081504 | DOE JGI |
| PtLYK5 (SEQ ID 89) | EUGENE3.00400189 | DOE JGI |
| PtLYK6 (SEQ ID 90) | GRAIL3.0019013601 | DOE JGI |
| PtLYK7 (SEQ ID 91) | GRAIL3.0017002501 | DOE JGI |
| PtLYK8 (SEQ ID 92) | FGENESH1_PM.C_LG_I000490 | DOE JGI |
| PtLYK9 (SEQ ID 93) | EUGENE3.00570233 | DOE JGI |
| PtLYK10 (SEQ ID 94) | EUGENE3.00100714 | DOE JGI |
| PtLYK11 (SEQ ID 95) | eugene3.00570235 | DOE JGI |

More specifically, plant LysM protein sequences were first searched using the key word LysM and BLASTp (1e-20) using the LysM domains of LjNFR1 (SEQ ID No. 1) and LjNFR5 (SEQ ID No. 2) against the following publicly available databases: Arabidopsis (Arabidopsis thaliana, database maintained by the Carnegie Institution of Washington Department of Plant Biology); rice (Oryza sativa, database maintained by the Institute for Genomic Research (TIGR)); poplar (Populus spp., database maintained by DOE's Joint Genome Institute); Medicago truncatula, database maintained by the lab of Nevin Young at the University of Minnesota); and Lotus japonicus (database maintained by the Kazusa DNA Research Institute in Japan. Domain structures of the resulting potential LysM proteins were analyzed with Pfam software and Inter-ProScan to identify LysM proteins. Soybean (Glycine max) LysM proteins were searched via tBLASTn (1e-5) using the same query sequences as above against two publicly available EST databases, one maintained by the Institute for Genomic Research, the other maintained by Monsanto.

Primers were designed based on the resulting soybean EST sequences to probe a six-dimensional BAC pool for LysM-containing BACs via a PCR-based approach. The probed LYK-containing BACs were verified and shotgun sequenced to either finished phase (phase 3) at the Arizona Genome Sequencing Center or prefinished phase (phase 2) at the Washington University Genome Sequencing Center. BAC sequences were annotated using the dicot species model and *Arabidopsis* matrix of FGENESH. Annotated proteins were similarly analyzed to screen for LYK proteins. Signal peptides and transmembrane domains were predicted with SignalP using both nearest-neighbor and hidden Markov model (HMM) algorithms and transmembrane HMM, respectively.

The GenBank accession numbers of soybean BACs are EF533702 for GMWb098N11; EF533695 for GMWb098N15; EF533696 for GMWb026N19; EF533701 for GMWb095P01; EF533697 for GMWb035N07; EF533699 for GMWb069O12; EF533700 for GMWb080D08; and EF533698 for GMWb042I24. LysM protein sequences from species spanning all kingdoms were extracted from Pfam and searched for LysM motifs at an E-value cutoff of 0.1.

Sequence alignments were performed using ClustalX 1.83 (Thompson et al., 1997) with PHYLIP output format and edited in Jalview (Clamp et al., 2004). The average identities across the alignments for LysMe (type X), LysMn (type XI), and LYPb (type VII) were calculated based on the exported annotations in Jalview. An HMM profile calculated using hmmer (Eddy, 1998) for each alignment was used to realign (hmmalign) sequences at matching states (-m) to identify and remove indel regions.

Parsimony trees were generated using the program protpars of PHYLIP (Felsenstein, 2000), with maximum-likelihood branch lengths calculated using TREE-PUZZLE (Schmidt et al., 2002). Distance trees were calculated using the program Protdist and Fitch of the PHYLIP package. Maximum-likelihood trees were calculated using the program proml of the PHYLIP package. Bootstrap values were calculated using the program seqboot of the PHYLIP package. Trees were viewed and rooted using A Tree Viewer (Zmasek and Eddy, 2001). For calculation of nucleotide substitution rates, codon-aligned nucleic acid sequences were created using CodonAlign 2.0. All insertions and deletions were removed except that a gap of more than 30 nucleotides was preferably retained to demonstrate the lack of the p loop and the activation loop in the kinase domains of LjNFR5 orthologs (Limpens et al., 2003; Madsen et al., 2003; Arrighi et al., 2006). Nucleotide substitution levels were calculated using the program codeml of the PAML package (Yang, 1997) with a user-defined parsimony tree.

To build microsynteny maps, genomic sequences surrounding each LYK gene, about 0.5 to 0.9 Mb in length, were extracted from the above databases and from soybean BAC sequences, which are about 100 to 170 kb in length. The genomic sequences were annotated using dicot species model and *Arabidopsis* matrix of FGENESH for the five dicot plants and monocot species model and rice matrix for rice. The annotated protein sequences were compiled together into a peptide sequence database. Repetitive sequences were excluded from the databases. BLASTp was used to compare proteins against the database with an E-value cutoff of 1e-20 and a percent identity cutoff of 35% between species and 40% within same species and legumes. BLASTp results were then filtered once to remove retroelements. The microsynteny maps were finally drawn in Adobe Illustrator 10.0.

Example 2

Induction of Gene Expression in *Arabidopsis* Treated with Chitin

A total of five LysM receptor-like kinase genes were identified in *Arabidopsis* from the studies described in Example 1. The Genbank numbers of these five genes are AtLYK1 (GenBank accession #At3g21630), AtLYK2 (GenBank accession # At3g01840), AtLYK3 (GenBank accession #At1g51940), AtLYK4 (GenBank accession # At2g23770), AtLYK5 (GenBank accession #At2g33580), and, which are designated as SEQ ID. Nos. 3-7, respectively. A DNA microarray experiment was performed by treating *Arabidopsis* plants with chitin. Leaves were treated by spraying with chitin (100 µM)+ 0.2% Tween-20. The Affymetrix 24K *Arabidopsis* genome chip was utilized according to the manufacturer's instructions for this test. The data obtained showed that transcription of 3 of the 5 *Arabidopsis* LysM RLK genes, At2g33580 (13-fold), At3g21630 (2-fold) and At2g23770 (2-fold), was significantly increased by treating the plants with chitin. The data implicate these genes in plant chitin response.

Example 3

LysM RLK Mutants in *Arabidopsis*

To test whether non-leguminous LysM RLKs may be involved in the perception of chitooligosaccharides and the subsequent induction of downstream genes that have been implicated in fungal defense, T-DNA insertion mutants were obtained for all five LysM RLK genes (i.e., At1g51940, At2g23770, At2g33580, At3g01840, and At3g21630) in *Arabidopsis*. The gene At3g21630 (SEQ ID. No. 3) is also termed AtLYK1 or AtLysM RLK1. Homozygous mutants were then treated with a purified chitooligosaccharide (chitooctaose) and the expression levels of known CRGs, such as MPK3 (At3g45640, SEQ ID. No. 8), WRKY22 (At4g01250, SEQ ID. No. 9), WRKY29 (At4g23550, SEQ ID. No. 10), WRKY33 (At2g38470, SEQ ID. No. 11), and WRKY53 (At4g23810, SEQ ID. No. 12), were measured.

More particularly, *Arabidopsis* seedlings were grown hydroponically as described by Ramonell et al., 2005. Fourteen-day old seedlings were treated with chitooctaose (Sigma, St. Louis, Mo., USA) at a concentration of 1 µM or with distilled water (as a control) for 30 minutes. To test flagellin-responsive genes, 14-day old seedlings were also treated with the flagellinderived flg22 peptide (dissolved in dimethyl sulfoxide, DMSO) at a final concentration of 10 µM or with an equivalent amount of DMSO (as a control) for 30 minutes. To test other defense pathways, *Arabidopsis* seedlings were also treated for 24 hours with 5 mM SA, 100 µM MeJA, and 0.5 mM ACC (all obtained from Sigma, St. Louis, Mo., USA) and dissolved in 0.1% ethanol. The control plants were similarly treated with an equivalent amount of ethanol. After treatment, the seedlings were collected and frozen in liquid nitrogen for RNA isolation.

Total RNA was isolated using the Trizol Reagent according to the manufacturer's instructions (Invitrogen, Carlsbad, Calif.). The isolated RNA was further purified using Qiagen RNeasy Mini Columns according to the manufacturer's instruction (Qiagen, Valencia, Calif., USA) and treated with Turbo™ DNase (Ambion, Austin, Tex., USA). For semi-quantitative RT-PCR or quantitative 17 PCR, cDNA was synthesized using M-MLV reverse transcriptase according to the manufacturer's instructions (Promega, Madison, Wis., USA).

Semi-Quantitative RT-PCR.

The gene-specific primer pairs (forward and reverse) for detecting the following selected chitooligosaccharide-responsive genes (CRGs) are:

```
For MPK3 (At3g45640):
5'-CTCACGGAGGACAGTTCATAAG-3'    (SEQ ID No. 13)
and

5'-GAGATCAGATTCTGTCGGTGTG-3'    (SEQ ID No. 14)

For WRKY22 (At4g01250):
5'-GTAAGCTCATCAGCTACTACCAC-3'   (SEQ ID No. 15)
and

5'-ACCGCTAGATGATCCTCAACAG-3'    (SEQ ID No. 16)

for WRKY29 (At4g23550):
5'-ATGGACGAAGGAGACCTAGAAG-3'    (SEQ ID No. 17)
and

5'-CCGCTTGGTGCGTACTCGTTTC-3'    (SEQ ID No. 18)

For WRKY33 (At2g38470):
5'-CTCCGACCACAACTACAACTAC-3'    (SEQ ID No. 19)
and

5'-GGCTCTCTCACTGTCTTGCTTC-3'    (SEQ ID No. 20)

For WRKY53 (At4g23810):
5'-CCTACGAGAGATCTCTTCTTCTG-3'   (SEQ ID No. 21)
and

5'-AGATCGGAGAACTCTCCACGTG-3'    (SEQ ID No. 22)
```

As an internal control, the following forward and reverse primers of actin-2 (At3g18780) were included in the same PCR reaction with each primer pair of the above genes:

```
5'-GACTAAGAGAGAAAGTAAGAGATAATCCAG-3' (SEQ ID No. 23)
and

5'-CAGCCTTTGATTTCAATTTGCATGTAAGAG-    (SEQ ID No. 24)
3'.
```

PCR reactions were conducted using Taq polymerase (Promega, Madison, Wis., USA) under the following conditions: 94° C., 3 minutes; 94° C., 30 seconds; 55° C., 30 seconds; 72° C., 1.5 minutes; 25 cycles; 72° C., 3 minutes. The corresponding CRG genes in *Lotus japonicus* were identified by blasting the cDNA sequences of the above *Arabidopsis* CRGs (and also actin-2) against the TIGR *Lotus japonicus* Gene Index. The closest hits were chosen and arbitrarily named after their *Arabidopsis* counterparts with the prefix Lj (standing for *Lotus japonicus*). The following primer pairs were designed to detect these genes:

```
For LjMPK3 (TC8079):
5'-CACCCTTGCGTAGAGAGTTTACTGATGTC-3', (SEQ ID No. 25)
and 5'-GTTGACGAGGATATTGAGGAAGTTGTCTG-3'; (SEQ ID No. 26)

For LjWRKY22 (AV423663):
5'-TCACCTTGCTGGTTCTGGTTCTGGTTCTG-3', (SEQ ID No. 27)
and 5'-TCTGATAGGGGTGCAACCCCATCTTCTTC-3'; (SEQ ID No. 28)

For LjWRKY33 (TC14849):
5'-AGTTGTGGTTCAGACCACCAGTGACATTG-3'  (SEQ ID No. 29)
and 5'-ACCCCATTGAGTTTCCAAACCCTGATGAG-3'  (SEQ ID No. 30)

For LjWRKY53 (TC9074):
5'-CCCATCAAAAGAACCAACCACAACAAGAG-3'  (SEQ ID No. 31)
and

5'-ATCCGCACGCACTTGAACCATGTATTGTG-3'; (SEQ ID No. 32)

For LjActin-2 (TC14247):
5'-AAGGTTCGTAAACGATGGCTGATGCTGAG-3'  (SEQ ID No. 33)
and 5'-ACCTTGATCTTCATGCTGCTAGGAGCAAG-3'. (SEQ ID No. 34)
```

LjActin-2 was used as an internal control.

Quantitative PCR.

To quantify gene expression using quantitative PCR, the forward and reverse primers of each gene were as follows:

```
For PR-1 (At2g14610, SEQ ID. No. 35):
                                    (SEQ ID No. 36)
5'-AACACGTGCAATGGAGTTTGTGGTCACT-3'
and (SEQ ID No. 37)
5'-ACCATTGTTACACCTCACTTTGGCACAT-3';

For PDF1.2 (At5g44420, SEQ ID. No. 38):
                                    (SEQ ID No. 39)
5'-AGTGCATTAACCTTGAAGGAGCCAAACAT-3'
and (SEQ ID No. 40)
5'-AACAGATACACTTGTGTGCTGGGAAGACA-3';

For MPK3 (At3g45640):
                                    (SEQ ID No. 41)
5'-TGGCCATTGATCTTGTTGACAGAATGTTGA-3'
and (SEQ ID No. 42)
5'-TCGTGCAATTTAGCAAGGTACTGGTGATT-3';

for WRKY53 (At4g23810):
                                    (SEQ ID No. 43)
5'-TTTAGGCGCCAAATTCCCAAGGAGTTATT-3'
and (SEQ ID No. 44)
5'-TCTGGACTTGTTTCGTTGCCCAACAGTTT-3';

For actin-2 (At3g18780):
                                    (SEQ ID No. 45)
5'-GGTATTCTTACCTTGAAGTATCCTATTG-3'
and (SEQ ID No. 46)
5'-CTCATTGTAGAAAGTGTGATGCCAGATC-3'.
```

Actin-2 was used as an internal control to normalize gene expression across different samples. The reactions were conducted on a 7500 Real-Time PCR System (Applied Biosystems, Foster City, Calif., USA) using the SYBR®Green Master Mix (Applied Biosystems, Foster City, Calif., USA) with the following PCR conditions: 95° C., 10 minutes; 95° C., 15 seconds; 60° C., 1 minute; 40 cycles; followed by the dissociation curve analysis to verify single amplicon. The fold change in the target gene, normalized to actin-2 and relative to the gene expression in the control sample, was calculated as described in Ramonell et al., 2002.

The AtLysM RLK1 insertion mutant (096F09) used in the current work was generated in the context of the GABI-Kat program and provided by Bernd Weisshaar (MPI for Plant Breeding Research, Cologne, Germany). See Shibuya et al., 2001. The homozygous plants were identified by genotyping using the following gene-specific primers:

```
5'-AGAATATATCCACGAGCACACGGTTCCAG-3'  (SEQ ID No. 47)
(forward),
and

5'-GACGAAAAGAGAGTGGATAAAGCAACCAC-3'  (SEQ ID No. 48)
(reverse)
``` together with the T-DNA left border primer:

```
5'-CCCATTTGGACGTGAATGTAGACAC-3'.  (SEQ ID No. 49)
```

These two primers were also used to detect the expression of the AtLysM RLK1 gene via RT-PCR. The other primers used to detect the transcript 5' of the insertion site were as follows:

```
5'-ATGAAGCTAAAGATTTCTCTAATCGCTC-3',  (SEQ ID No. 50)
and

5'-GAAATGCACCATTTGGATCTCTTCCAG-3'  (SEQ ID No. 51)
```

The mutants of the other 4 *Arabidopsis* LysM RLK genes were obtained from the SALK Institute and Syngenta Incorporation through the *Arabidopsis* Basic Research Center (ABRC) or from the Martienssen lab at the Cold Spring Harbor Laboratory.

Figures 3A, 3B:
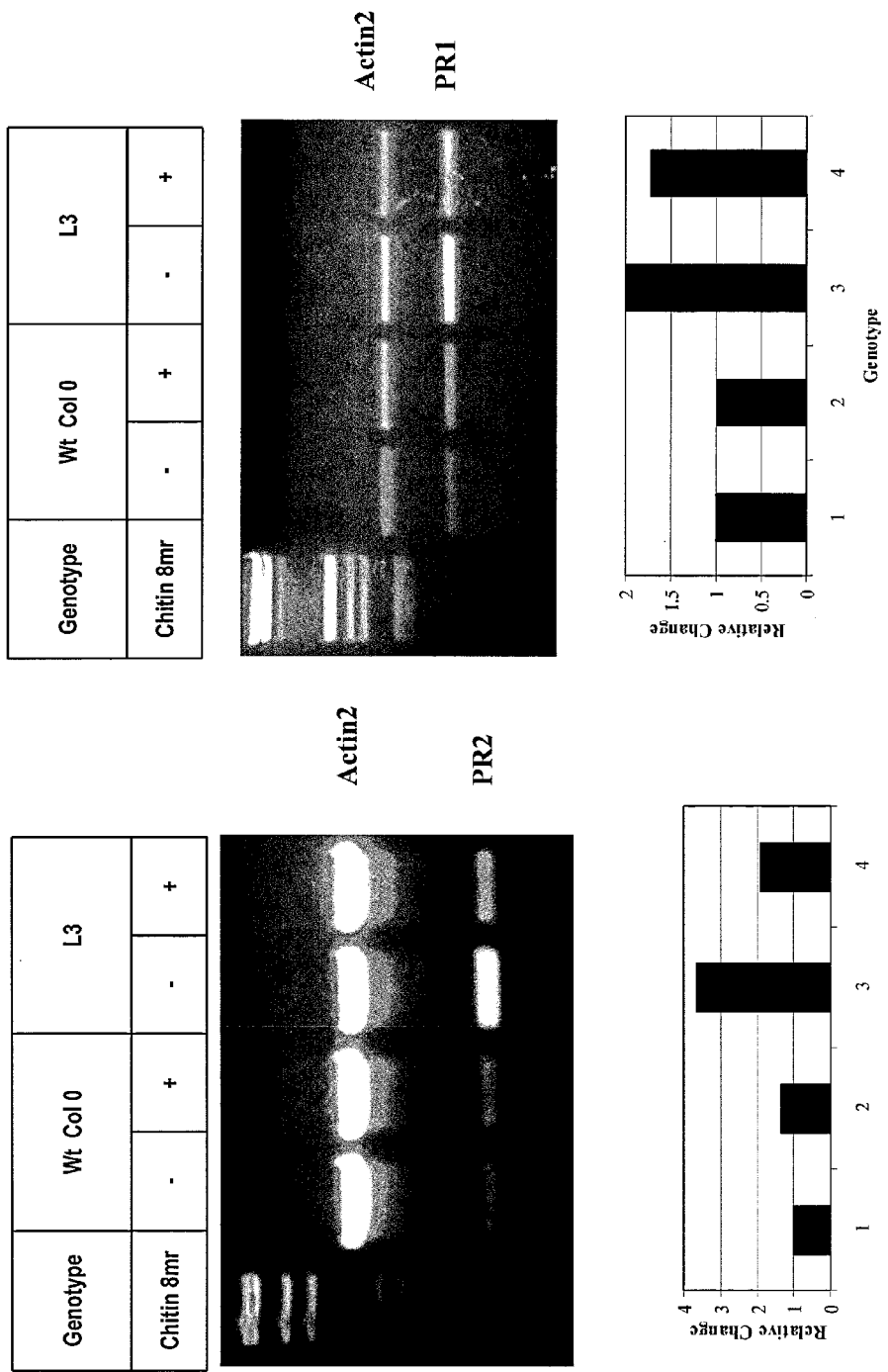
Figure 4A:
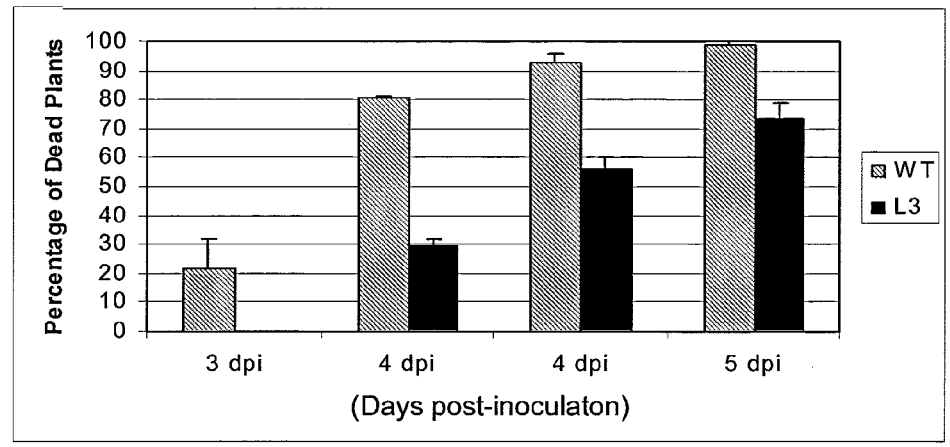
FIG. 4A shows an improved defense response of the L3 mutant to infection by the necotrophic fungus *Botrytis cinerea*.

One insertion mutant designated as L3 with an insertion in gene At1g51940 exhibited an interesting phenotype. This mutant showed enhanced expression of some defense-related genes, such as PR-2 and PR-1, as shown in FIG. 3. The PR-2 gene (AT3G57260, SEQ ID. No. 52) encodes a β-1,3-glucanase, which is an enzyme that degrades the fungal cell wall component glucan to inhibit fungal infection. PR-1 (SEQ ID. No. 35) has also been shown to be involved in plant defense against pathogens, especially bacterial pathogens. This enhanced expression of defense genes suggests that the mutant may be resistant to fungal pathogens. The test of this mutant with a fungal pathogen called *Botrytis cinerea* demonstrated that the mutant is resistant to this fungal pathogen, as shown in FIG. 4A. *B. cinerea* is a necrotrophic fungus, and dead plants were assessed as those having no remaining green, only yellowish leaves. The L3 mutant demonstrated increased resistance relative to the wild-type plant.

Figure 4B:
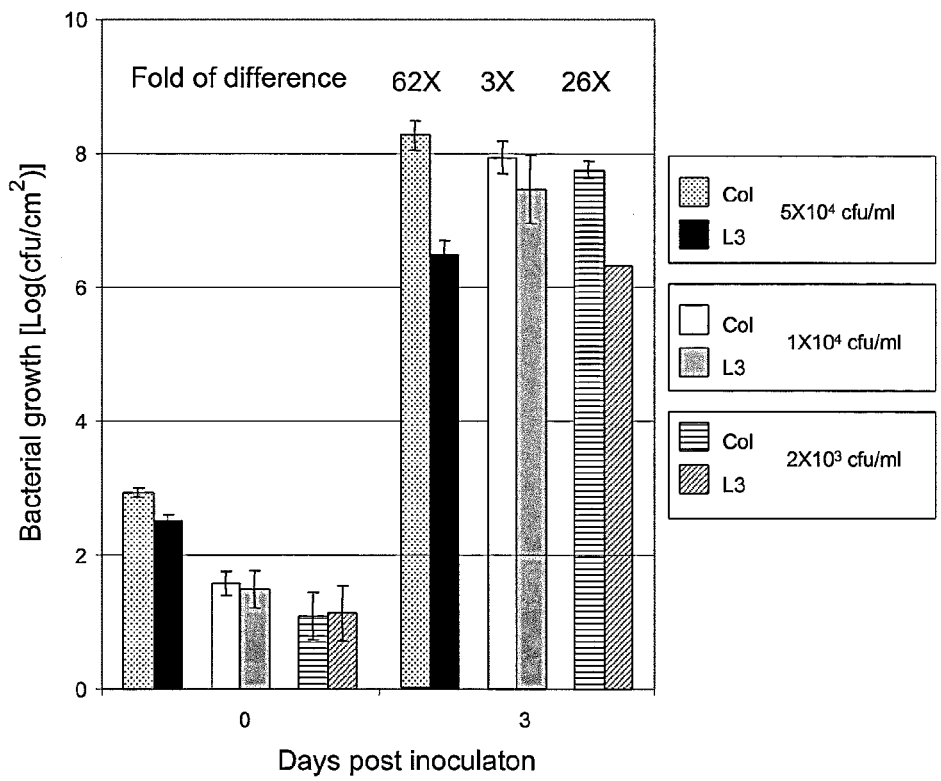
FIG. 4B shows an improved defense response of the L3 mutant to infection by *Pseudomonas syringae*.
Figure 5:
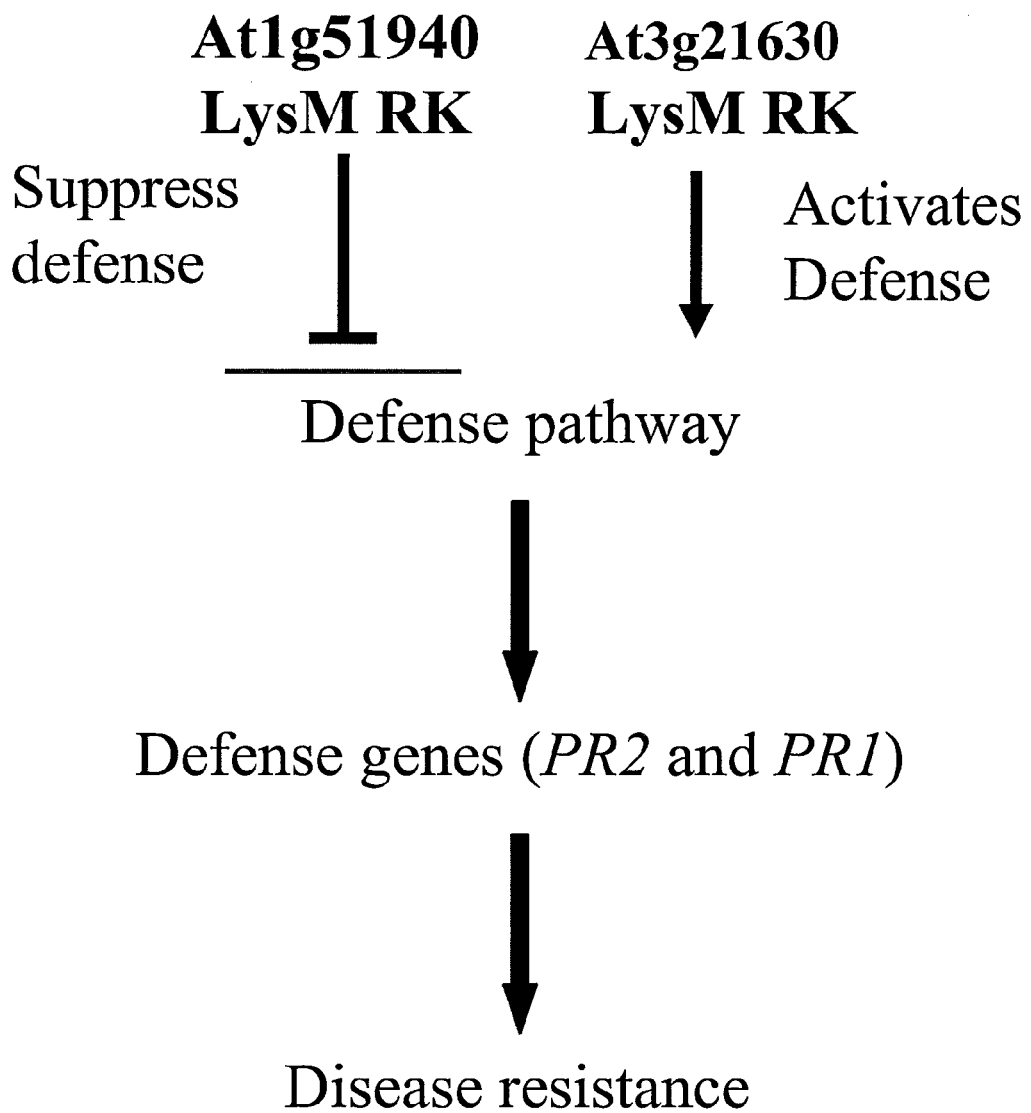
FIG. 5 shows a model of the involvement of the LysM receptor kinases in plant defense.

In addition, the L3 mutant showed decreased susceptibility to the bacterial pathogen *Pseudomonas syringae* strain DC3000, as shown in FIG. 4B. The enhanced resistance is likely due to the knockout of the specific LysM receptor kinase gene. Analysis of expression of the At1g51940 gene in the L3 mutant failed to detect the mRNA. Therefore, the lack of At1g51940 gene expression correlates with elevated PR1 expression and enhanced disease resistance. This suggests that At1g51940 may act normally to repress the disease resistance response according to a model pathway of the involvement of the LYSM RK in plant defense, as shown in FIG. 5. Therefore, it is possible to make plants more resistant to fungal pathogens by either knocking out or knocking down the expression of this gene. Furthermore, dominant negative forms of this protein may also be made and employed to modulate plant fungal resistance.

Figure 6A:
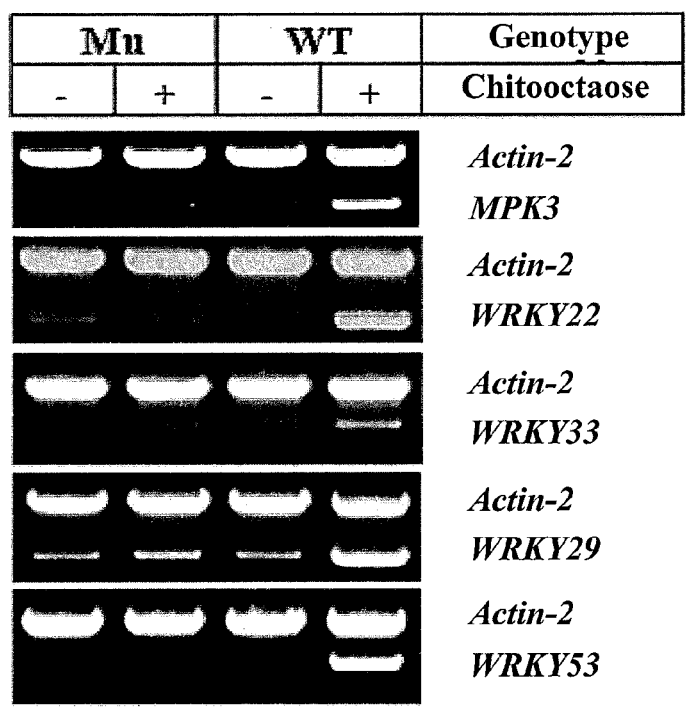
FIG. 6 shows that the knockout of the AtLysM RLK1 gene blocks the induction of the selected chitooligosaccharide-responsive genes (CRGs).

Another insertion mutant, corresponding to At3g21630, or AtLYK1 (designated hereafter as AtLysM RLK1), almost completely blocked the induction of all the selected CRGs (FIG. 6A), suggesting a critical role of AtLysM RLK1 in the perception of chitooligosaccharides. Both the mutant (Mu) and wildtype (WT) plants were treated with purified chitooctaose or water (as a control) for 30 minutes and gene expression of the selected CRGs was detected using semi-quantitative RT-PCR. Actin-2 was used as an internal control. The amplification of both actin-2 and a CRG was conducted in the same tube.

The AtLysM RLK1 gene (SEQ ID. No. 3) is 2988 nucleotides (nts) long, with 11 introns (FIG. 6B) and a coding sequence of 1854 nts. Square boxes represent exons. Solid lines between them are introns. The start codon (ATG) and stop codon (TAG) are included in the first and last exon, respectively. The two T-DNA insertions (T-DNA1 and 2) inserted in the 10th intron in the AtLysM RLK1 mutant are indicated above the gene. LB: left border; RB: right border. The AtLysM RLK1 gene encodes a LysM RLK of 617 amino acids (SEQ ID No. 53), with an extracellular domain (containing 3 predicted LysM motifs), a transmembrane domain (TM), and an intracellular serine/threonine kinase domain. FIG. 6C illustrates the predicted domain structure of AtLysM RLK1. S: signal peptide; LysM: LysM domain; TM: transmembrane domain; Ser/Thr Kinase: Serine/Threonine kinase domain. AtLysM RLK1 has been shown to be phylogenetically related to the Nod signal receptor NFR1. Zhang et al., 2007.

Figure 6B:
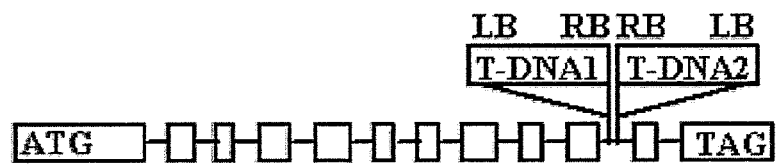
Figure 6C:

Two T-DNA insertions were identified in the AtLysM RLK1 mutant, separated by 4 nts, in the 10th intron (FIG. 6B). RT-PCR analysis using primers corresponding to the exon regions on the side of the 10th intron failed to detect mRNA expression in the AtLysM RLK1 mutant; however, a truncated transcript derived from the gene sequence before the intron was detected by RT-PCR (FIGS. 7A and 7B), suggesting the T-DNA insertions in the intron blocked full-length transcription of the gene.

To confirm that the observed changes in CRGs expression were caused by the mutation in the AtLysM RLK1 gene, the mutant was complemented with the full-length AtLysM RLK1 cDNA driven by the constitutive Cauliflower Mosaic Virus (CMV) 35S promoter. More specifically, the full-length CDS (1854 nucleotides long) was obtained by RT-PCR and cloned in the Eco RV site of the pBluescript vector. The confirmed sequence was further cloned into the modified binary 16 vector pCAMBIA1200 that contains a 35S promoter-Multiple Cloning Sites (MCS)-poly A signal, downstream of the 35S promoter. The final construct was electroporated into *Agrobacterium tumafaciens* EHA 105 according to the procedures described by Stacey and Shibuya, 1997. The resultant *A. tumafaciens* was then used to transform the homozygous AtLysM RLK1 mutant via floral dipping as described by Passarinho et al., 2002.

Multiple transgenic lines were obtained. The complemented plants were treated with chitooctaose or water (as a control) at a final concentration of 1 μM for 30 minutes. RT-PCR data show that the selected CRGs were induced to a level in the selected complemented plants (Com-1 and Com-2) similar to the level in the wild type (WT) plants (FIG. 8). Com-1 and Com-2 are two independent complemented lines and WT is wild-type Col-0 plants.

Thus, the complemented plants showed restored induction of those selected CRGs, confirming that it was the insertions in the AtLysM RLK1 gene that caused the observed change in gene expression. The complementation data also ruled out the possibility that a truncated protein translated from the observed truncated transcript may have affected the expression of the selected CRGs.

The expression pattern of the AtLysM RLK1 gene was also studied. RT-PCR data show that AtLysM RLK1 is expressed ubiquitously in the whole plant, in tissues such as root, rosette leaf, cauline leaf, stem, inflorescence, silique, flower bud, open flower, and pollen, with the lowest expression levels in pollen (FIG. 9). Interestingly, this gene was induced by chitooligosaccharides, but not by the flg22 peptide derived from flagellin, a PAMP (pathogen-associated molecular pattern) produced by pathogenic bacteria (FIG. 10) (Gomez-Gomez et al., 2000), suggesting a specific role of this gene in chitooligosaccharide signaling. More specifically, for experiment (A), fourteen-day-old, hydroponically grown seedlings were treated for 30 minutes with chitooctaose at a final concentration of 1 µM or with distilled water (as a control); for experiment (B), the seedlings were treated with flg22 (dissolved in DMSO) at a final concentration of 10 µM or with an equivalent amount of DMSO (as a control).

Figure 11A:
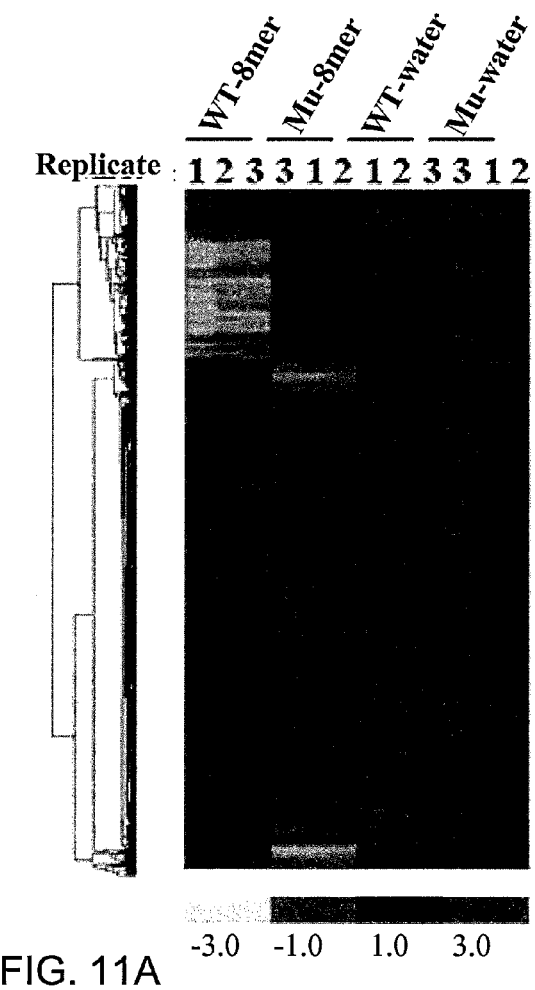

Gene expression profiles in the AtLysM RLK1 mutant in response to chitooctaose were studied using the Affymetrix *Arabidopsis* Whole Genome Array ATH1 (with ~22000 genes), with wild-type plants as a control. Data analysis showed that a total of 909 genes responded more than 1.5 fold (P<0.05) to chitooctaose elicitation in both the wild-type and mutant plants 30 minutes after the treatment (FIG. 11A). A row represents a gene and each column represents a sample. WT-8mer=wild-type Col-0 treated with chitooctaose; WT-water=wild-type Col-0 treated with distilled water; Mu-water=the AtLysM RLK1 mutant treated with distilled water; Mu-8mer=the AtLysM RLK1 mutant treated with chitooctaose. The color bar below the cluster picture: the red color indicates the expression level of a gene is above the mean expression of the gene across all samples; the green color indicates expression lower than the mean. These genes can be separated into two groups: up- and down-regulated by chitooctaose, as represented by the two large clusters in FIG. 11A.

Figure 11B:
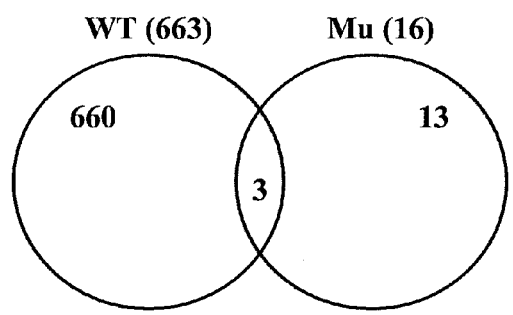
Figure 11C:
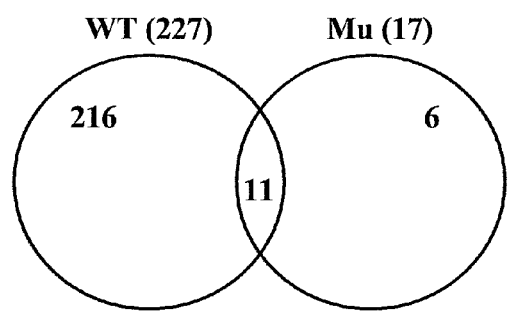

Out of the 909 genes tested, 890 showed a change in transcript levels in the wild-type plants in response to chitooctaose, with 663 up-regulated and 227 down-regulated (FIG. 11B, 11C and Table 3). Up-regulated genes: 1.5 fold, P<0.05. Down-regulated genes: 1.5 fold, P<0.05. By contrast, only 33 genes out of 909 were responsive in the mutant, with 16 up-regulated and 17 down-regulated (FIGS. 11B and 11C; Table 4). Among the 33 genes, 14 genes (3 up- and 11 down-regulated) were also similarly regulated in the wild-type plants (rows 1 to 15 in Table 4), leaving only 19 genes that appeared to be differentially regulated by chitooctaose in the mutant (rows 16-34 in Table 4). However, 13 of these genes showed a similar regulation trend (up- or down-regulation) in the wild-type plants to that in the mutant, although such a trend was not considered significant in the wild-type plants (rows 16 to 28 in Table 4).

TABLE 3

Genes that are Responsive to chitooctaose in Wild-type

| Probe set | Annotation | Accession | WT FC | Mu FC | WT P | Mu P |
|---|---|---|---|---|---|---|
| 245613_at | hypothetical protein | At4g14450 | 72.79 | −1.8 | 0.019018 | 0.836714 |
| 249197_at | putative protein contains similarity to calmodulin; supported by full-length cDNA: Ceres: 99348. | At5g42380 | 51.63 | 1.06 | 0.019359 | 0.866994 |
| 258947_at | hypothetical protein similar to calmodulin-like protein GB: CAB42906 [*Arabidopsis thaliana*]; Pfam HMM hit: EF hand; supported by full-length cDNA: Ceres: 7252. | At3g01830 | 43.33 | 1.58 | 0.012148 | 0.103554 |
| 260399_at | putative lipoxygenase similar to lipoxygenase GB: CAB56692 [*Arabidopsis thaliana*]; supported by cDNA: gi_15810254_gb_AY056166.1_ | At1g72520 | 41.48 | −1.11 | 0.009183 | 0.804844 |
| 257540_at | hypothetical protein | At3g21520 | 34.95 | 1.08 | 0.001687 | 0.921695 |
| 256526_at | disease resistance protein, putative similar to disease resistance protein RPP1-WsA [*Arabidopsis thaliana*] GI: 3860163; supported by full-length cDNA: Ceres: 93530. | At1g66090 | 33.68 | −1.13 | 0.01628 | 0.597847 |
| 250796_at | putative protein similar to unknown protein (gb\|AAF01528.1) | At5g05300 | 31.56 | 1.1 | 0.004167 | 0.773037 |
| 261474_at | anionic peroxidase, putative similar to anionic peroxidase GI: 170202 from [*Nicotiana sylvestris*] | At1g14540 | 30.96 | −1.02 | 0.001414 | 0.955549 |
| 245755_at | hypothetical protein predicted by genemark.hmm; supported by full-length cDNA: Ceres: 42217. | At1g35210 | 30.5 | −1.11 | 0.01789 | 0.881393 |
| 254231_at | putative protein AR411-*Arabidopsis thaliana* (thale cress), PID: g1669603; supported by cDNA: gi_13507100_gb_AF272748.1_AF272748 | At4g23810 | 28.21 | −1.25 | 0.018401 | 0.425568 |
| 248322_at | putative protein similar to unknown protein (emb\|CAA71173.1) | At5g52760 | 26.14 | 1.31 | 0.004693 | 0.152597 |
| 249770_at | unknown protein; supported by full-length cDNA: Ceres: 6469. | At5g24110 | 25.43 | −1.06 | 0.035483 | 0.869658 |
| 247215_at | Expressed protein; supported by full-length cDNA: Ceres: 3657. | At5g64905 | 24.84 | 1.24 | 0.04883 | 0.449026 |
| 265725_at | putative alanine acetyl transferase | At2g32030 | 23.73 | 1.08 | 0.027584 | 0.473742 |
| 266821_at | putative ethylene response element binding protein (EREBP); supported by full-length cDNA: Ceres: 6397. | At2g44840 | 23.69 | −1.22 | 0.019899 | 0.271281 |
| 248904_at | Expressed protein; supported by full-length cDNA: Ceres: 18973. | At5g46295 | 23.69 | −1.49 | 0.007953 | 0.428724 |
| 261648_at | salt-tolerance zinc finger protein identical to salt-tolerance zinc finger protein GB: CAA64820 GI: 1565227 from [*Arabidopsis thaliana*]; supported by cDNA: gi_14334649_gb_AY034998.1_ | At1g27730 | 22.71 | −1.09 | 0.016239 | 0.33423 |
| 262085_at | hypothetical protein predicted by genemark.hmm | At1g56060 | 22.37 | 1.36 | 0.001015 | 0.285112 |
| 261021_at | hypothetical protein similar to reticuline oxidase-like protein GB: CAB45850 GI: 5262224 from | At1g26380 | 22.2 | 2.37 | 0.004697 | 0.108353 |

TABLE 3-continued

Genes that are Responsive to chitooctaose in Wild-type

| Probe set | Annotation | Accession | WT FC | Mu FC | WT P | Mu P |
|---|---|---|---|---|---|---|
| | [*Arabidopsis thaliana*]; supported by cDNA: gi_13430839_gb_AF360332.1_AF360332 | | | | | |
| 263182_at | Expressed protein; supported by full-length cDNA: Ceres: 27081. | At1g05575 | 19.34 | −1.02 | 0.005652 | 0.804382 |
| 249417_at | calcium-binding protein-like cbp1 calcium-binding protein, *Lotus japonicus*, EMBL: LJA251808; supported by cDNA: gi_16648829_gb_AY058192.1_ | At5g39670 | 18.84 | −1.03 | 0.012777 | 0.874622 |
| 254120_at | putative mitochondrial uncoupling protein mitochondrial uncoupling protein, *Arabidopsis thaliana* (thale cress), PATX: E1316826; supported by full-length cDNA: Ceres: 119476. | At4g24570 | 18.47 | −1.26 | 0.006894 | 0.121685 |
| 264153_at | disease resistance protein RPS4, putative similar to disease resistance protein RPS4 GI: 5459305 from [*Arabidopsis thaliana*] | At1g65390 | 17.77 | −1.01 | 0.006757 | 0.837017 |
| 249264_s_at | disease resistance protein-like | At5g41740 | 17.16 | 1.01 | 0.016032 | 0.965149 |
| 246821_at | calmodulin-binding-like protein calmodulin-binding protein TCB60, *Nicotiana tabacum*, EMBL: U58971 | At5g26920 | 16.58 | −1.22 | 0.002033 | 0.305516 |
| 265327_at | unknown protein | At2g18210 | 16.02 | −1.08 | 0.007312 | 0.847704 |
| 252131_at | BCS1 protein-like protein *Homo sapiens* h-bcs1 (BCS1) mRNA, nuclear gene encoding mitochondrial protein which is involved in the expression of functional mitochondrial ubiquinol-cytochrome c reductase complex probably via the control of expression of Riesk | At3g50930 | 15.81 | 1.28 | 0.020727 | 0.19657 |
| 245840_at | hypothetical protein predicted by genemark.hmm; supported by full-length cDNA: Ceres: 124269. | At1g58420 | 15.76 | −1.16 | 0.001929 | 0.649675 |
| 245041_at | AR781, similar to yeast pheromone receptor identical to GB: D88743, corrected a frameshift found in the original record (at 69530 bp), sequence submitted has been verified from 10 sequence electropherograms. The translation now starts from an upstream ATG. | At2g26530 | 15.71 | −1.4 | 0.011514 | 0.105739 |
| 248799_at | ethylene responsive element binding factor 5 (ATERF5) (sp|O80341); supported by cDNA: gi_14326511_gb_AF385709.1_AF385709 | At5g47230 | 15.6 | −1.36 | 0.005208 | 0.117072 |
| 250149_at | cinnamoyl CoA reductase-like protein cinnamoyl CoA reductase, *Populus tremuloides*, EMBL: AF217958; supported by full-length cDNA: Ceres: 17229. | At5g14700 | 15.46 | −1.13 | 0.022877 | 0.554222 |
| 256306_at | lipase, putative contains Pfam profile: PF01764: Lipase | At1g30370 | 15.3 | 1.11 | 0.00866 | 0.751633 |
| 246777_at | RING-H2 zinc finger protein-like RING-H2 zinc finger protein ATL6-*Arabidopsis thaliana*, EMBL: AF132016; supported by full-length cDNA: Ceres: 106078. | At5g27420 | 14.67 | −1.44 | 0.011803 | 0.037951 |
| 263783_at | putative WRKY-type DNA binding protein; supported by cDNA: gi_15430276_gb_AY046275.1_ | At2g46400 | 14.41 | 1.26 | 0.005589 | 0.126494 |
| 245369_at | Expressed protein; supported by full-length cDNA: Ceres: 124835. | At4g15975 | 14.34 | 1.03 | 0.00366 | 0.920236 |
| 251336_at | putative protein hypothetical protein F4I18.26-*Arabidopsis thaliana*, PIR: T02471; supported by full-length cDNA: Ceres: 30454. | At3g61190 | 14.31 | 1.07 | 0.007665 | 0.724447 |
| 260046_at | Expressed protein; supported by cDNA: gi_16648699_gb_AY058126.1_ | At1g73800 | 13.55 | 1 | 0.010217 | 0.9771 |
| 260068_at | putative calmodulin-binding protein similar to calmodulin-binding protein GB: AAB37246 [*Nicotiana tabacum*] | At1g73805 | 13.35 | 1.16 | 0.007383 | 0.51944 |
| 266071_at | unknown protein | At2g18680 | 13.32 | 1.11 | 0.004216 | 0.713949 |
| 253643_at | hypothetical protein; supported by full-length cDNA: Ceres: 249769. | At4g29780 | 13.05 | −1.11 | 0.002383 | 0.344174 |
| 264213_at | hypothetical protein contains similarity to lectin polypeptide GI: 410436 from [*Cucurbita maxima*] | At1g65400 | 12.76 | −1.17 | 0.021498 | 0.255697 |
| 262382_at | virus resistance protein, putative similar to virus resistance protein GI: 558886 from [*Nicotiana glutinosa*] | At1g72920 | 12.68 | −1.4 | 0.003189 | 0.073493 |
| 247543_at | DNA binding protein-like DNA binding protein EREBP-4, *Nicotiana tabacum*, PIR: T02434; supported by full-length cDNA: Ceres: 92102. | At5g61600 | 12.31 | −1.31 | 0.014862 | 0.112814 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 256442_at | hypothetical protein predicted by genefinder; supported by full-length cDNA: Ceres: 12509. | At3g10930 | 11.62 | −1.07 | 0.025288 | 0.782271 |
| 253060_at | putative protein predicted protein, *Arabidopsis thaliana*; supported by full-length cDNA: Ceres: 207350. | At4g37710 | 11.56 | 1.34 | 0.005721 | 0.412461 |
| 253915_at | putative protein centrin, *Marsilea vestita*; supported by full-length cDNA: Ceres: 13072. | At4g27280 | 11.5 | −1.07 | 0.01185 | 0.333253 |
| 249928_at | CCR4-associated factor-like protein | At5g22250 | 11.41 | −1.17 | 0.009043 | 0.204172 |
| 245711_at | putative c2h2 zinc finger transcription factor | At5g04340 | 11.35 | −1.11 | 0.016673 | 0.392119 |
| 261892_at | transcription factor, putative similar to WRKY transcription factor GB: BAA87058 GI: 6472585 from [*Nicotiana tabacum*]; supported by full-length cDNA: Ceres: 6437. | At1g80840 | 11.27 | 1.09 | 0.006954 | 0.498704 |
| 261394_at | wall-associated kinase 2, putative similar to wall-associated kinase 2 GI: 4826399 from [*Arabidopsis thaliana*] | At1g79680 | 11.05 | 1.08 | 0.003074 | 0.819188 |
| 251774_at | nematode resistance protein-like protein Hs1pro-1 nematode resistance gene, Beta procumbens, EMBL: BPU79733; supported by full-length cDNA: Ceres: 149697. | At3g55840 | 11.02 | −1.37 | 0.007795 | 0.481526 |
| 265723_at | putative disease resistance protein | At2g32140 | 10.99 | 1.18 | 0.016981 | 0.537825 |
| 255339_at | hypothetical protein similar to *A. thaliana* hypothetical protein F1N20.130, GenBank accession number AL022140 | At4g04480 | 10.83 | 1.32 | 0.012367 | 0.514455 |
| 251054_at | receptor like protein kinase receptor like protein kinase-*Arabidopsis thaliana*, EMBL: ATLECGENE; supported by cDNA: gi_13605542_gb_AF361597.1_AF361597 | At5g01540 | 10.66 | −1.01 | 0.003949 | 0.917593 |
| 253827_at | Expressed protein; supported by cDNA: gi_15028040_gb_AY045877.1_ | At4g28085 | 10.37 | −1.09 | 0.010797 | 0.530514 |
| 255945_at | putative protein | At5g28610 | 10.06 | 1.21 | 0.010366 | 0.464865 |
| 249618_at | putative protein predicted proteins, *Arabidopsis thalina* | At5g37490 | 9.99 | −1.09 | 0.004719 | 0.814525 |
| 248934_at | serine/threonine protein kinase-like protein | At5g46080 | 9.94 | −1.17 | 0.007605 | 0.645509 |
| 261037_at | lipoxygenase identical to GB: CAB56692 from (*Arabidopsis thaliana*) | At1g17420 | 9.88 | −1.1 | 0.002351 | 0.775492 |
| 267623_at | unknown protein | At2g39650 | 9.87 | −1.12 | 0.006744 | 0.439834 |
| 259428_at | MAP kinase, putative similar to MAP kinase 5 GI: 4239889 from [*Zea mays*] | At1g01560 | 9.84 | 1.54 | 0.002458 | 0.135149 |
| 246927_s_at | nodulin-like protein nodulin, Glycine max, EMBL: AF065435 | At5g25260 | 9.74 | 1.6 | 0.004623 | 0.163075 |
| 264758_at | late embryogenesis abundant protein, putative similar to late embryogenesis abundant protein GI: 1350540 from [*Picea glauca*] | At1g61340 | 9.73 | 1.17 | 0.016626 | 0.389155 |
| 245329_at | Expressed protein; supported by full-length cDNA: Ceres: 37809. | At4g14365 | 9.7 | 1.42 | 0.002486 | 0.029582 |
| 262072_at | hypothetical protein predicted by genemark.hmm; supported by full-length cDNA: Ceres: 99553. | At1g59590 | 9.54 | −1.12 | 0.009452 | 0.599212 |
| 255844_at | putative protein kinase contains a protein kinase domain profile (PDOC00100) | At2g33580 | 9.42 | 1.11 | 0.006611 | 0.553845 |
| 253632_at | senescence-associated protein homolog senescence-associated protein 5-Hemerocallis hybrid cultivar, PID: g3551954; supported by full-length cDNA: Ceres: 122632. | At4g30430 | 9.29 | 1.22 | 0.004184 | 0.351697 |
| 257511_at | hypothetical protein | At1g43000 | 9.29 | −1.13 | 0.020984 | 0.846669 |
| 253999_at | 1-aminocyclopropane-1-carboxylate synthase-like protein ACC synthase, *Malus domestica*, U73816 | At4g26200 | 9.24 | −1.56 | 0.004129 | 0.115048 |
| 265920_s_at | unknown protein | At2g15120 | 9.13 | 1.33 | 0.001682 | 0.33404 |
| 263800_at | hypothetical protein predicted by genscan; supported by cDNA: gi_15810330_gb_AY056204.1_ | At2g24600 | 8.97 | 1.02 | 0.014457 | 0.769925 |
| 248164_at | putative protein similar to unknown protein (pir‖T05752); supported by full-length cDNA: Ceres: 109272. | At5g54490 | 8.97 | −1.17 | 0.008767 | 0.190232 |
| 265597_at | Expressed protein; supported by cDNA: gi_13605516_gb_AF361584.1_AF361584 | At2g20145 | 8.96 | −1 | 0.023429 | 0.965819 |
| 248327_at | putative protein similar to unknown protein (emb|CAA71173.1); supported by full-length cDNA: Ceres: 19542. | At5g52750 | 8.93 | −1.04 | 0.017097 | 0.808905 |
| 252908_at | putative protein | At4g39670 | 8.56 | 1.17 | 0.012661 | 0.466742 |
| 251400_at | putative protein prib5, *Ribes nigrum*, EMBL: RNI7578; supported by full-length cDNA: Ceres: 31361. | At3g60420 | 8.53 | 1.64 | 0.029245 | 0.023237 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 261475_at | anionic peroxidase, putative similar to anionic peroxidase GI: 170202 from [*Nicotiana sylvestris*] | At1g14550 | 8.51 | 1.41 | 0.01103 | 0.395333 |
| 256185_at | dof zinc finger protein identical to dof zinc finger protein [*Arabidopsis thaliana*] GI: 3608261; supported by cDNA: gi_3608260_dbj_AB017564.1_AB017564 | At1g51700 | 8.47 | −1.09 | 0.001565 | 0.51485 |
| 250493_at | putative protein various predicted proteins, *Arabidopsis thaliana* | At5g09800 | 8.28 | −1.06 | 0.010787 | 0.857557 |
| 252679_at | CCR4-associated factor 1-like protein CAF1_MOUSE CCR4-ASSOCIATED FACTOR 1-*Mus musculus*, SWISSPROT: CAF1_MOUSE; supported by cDNA: gi_15292828_gb_AY050848.1_ | At3g44260 | 8.27 | −1.27 | 0.000484 | 0.065446 |
| 265797_at | Expressed protein; supported by full-length cDNA: Ceres: 9996. | At2g35715 | 8.26 | −1.27 | 0.005817 | 0.60028 |
| 248448_at | putative protein contains similarity to ethylene responsive element binding factor; supported by full-length cDNA: Ceres: 2347. | At5g51190 | 8.25 | −1.1 | 0.009635 | 0.575899 |
| 255884_at | hypothetical protein predicted by genemark.hmm; supported by full-length cDNA: Ceres: 8562. | At1g20310 | 8.15 | −1.19 | 0.022852 | 0.204061 |
| 261449_at | putative ATPase similar to GB: AAF28353 from [*Fragaria* x *ananassa*] | At1g21120 | 7.97 | 1.46 | 0.004955 | 0.182958 |
| 265841_at | putative glycogenin | At2g35710 | 7.96 | −1.27 | 0.011587 | 0.280483 |
| 251895_at | class IV chitinase (CHIV) | At3g54420 | 7.95 | −1.09 | 0.003142 | 0.722712 |
| 263935_at | unknown protein | At2g35930 | 7.89 | −1.06 | 0.006185 | 0.342267 |
| 255502_at | contains similarity to a protein kinase domain (Pfam: pkinase.hmm, score: 166.20) and to legume lectins beta domain (Pfam: lectin_legB.hmm, score: 139.32) | At4g02410 | 7.89 | −1.07 | 0.003365 | 0.691648 |
| 258787_at | hypothetical protein predicted by genscan; supported by full-length cDNA: Ceres: 100676. | At3g11840 | 7.84 | −1.13 | 0.036463 | 0.37994 |
| 266658_at | Expressed protein; supported by full-length cDNA: Ceres: 7152. | At2g25735 | 7.71 | −1.47 | 0.003942 | 0.026409 |
| 245250_at | ethylene responsive element binding factor-like protein (AtERF6); supported by cDNA: gi_3298497_dbj_AB013301.1_AB013301 | At4g17490 | 7.54 | 1.06 | 0.008242 | 0.704323 |
| 247487_at | putative protein predicted protein, *Arabidopsis thaliana* | At5g62150 | 7.39 | 1.01 | 0.005388 | 0.945249 |
| 261470_at | ethylene-responsive element binding factor, putative similar to ethylene-responsive element binding factor GI: 8809573 from [*Nicotiana sylvestris*]; supported by full-length cDNA: Ceres: 27635. | At1g28370 | 7.33 | −1.17 | 0.005528 | 0.478834 |
| 262381_at | virus resistance protein, putative similar to virus resistance protein GI: 558886 from [*Nicotiana glutinosa*] | At1g72900 | 7.27 | −1.19 | 0.006528 | 0.311035 |
| 248123_at | putative protein similar to unknown protein (gb\|AAD32884.1) | At5g54720 | 7.23 | 1.29 | 0.006214 | 0.245803 |
| 263379_at | putative CCCH-type zinc finger protein also an ankyrin-repeat protein | At2g40140 | 7.21 | 1.01 | 0.004911 | 0.848966 |
| 263584_at | NAM (no apical meristem)-like protein similar to petunia NAM (X92205) and *A. thaliana* sequences ATAF1 (X74755) and ATAF2 (X74756); probable DNA-binding protein; supported by cDNA: gi_13605646_gb_AF361804.1_AF361804 | At2g17040 | 7.13 | −1.29 | 0.006099 | 0.12014 |
| 259566_at | hypothetical protein | At1g20520 | 7.04 | −1.14 | 0.024145 | 0.734624 |
| 267028_at | putative WRKY-type DNA binding protein | At2g38470 | 7.02 | −1.19 | 0.009642 | 0.27064 |
| 265008_at | Mlo protein, putative similar to Mlo protein GI: 1877220 from [*Hordeum vulgare*]; supported by cDNA: gi_14091581_gb_AF369567.1_AF369567 | At1g61560 | 6.99 | 1.2 | 0.00298 | 0.470024 |
| 247693_at | putative protein leucine zipper-containing protein, *Lycopersicon esculentum*, PIR: S21495; supported by cDNA: gi_14334437_gb_AY034910.1_ | At5g59730 | 6.97 | 1.01 | 0.004438 | 0.963142 |
| 257748_at | hypothetical protein predicted by genemark.hmm | At3g18710 | 6.82 | −1.16 | 0.009082 | 0.446456 |
| 258351_at | hypothetical protein contains similarity to ion channel protein from [*Arabidopsis thaliana*]; supported by cDNA: gi_8131897_gb_AF148541.1_AF148541 | At3g17700 | 6.78 | −1.02 | 0.004386 | 0.920019 |
| 251745_at | putative protein zinc finger transcription factor (PEI1), *Arabidopsis thaliana*, EMBL: AF050463; supported by cDNA: gi_15810486_gb_AY056282.1_ | At3g55980 | 6.71 | −1.36 | 0.001393 | 0.169064 |
| 257536_at | unknown protein | At3g02800 | 6.46 | 1.24 | 0.011172 | 0.244827 |
| 246108_at | putative protein retinal glutamic acid-rich protein, bovine, PIR: A40437; supported by full-length cDNA: Ceres: 24151. | At5g28630 | 6.43 | −1.14 | 0.017801 | 0.374617 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 256046_at | unknown protein | At1g07135 | 6.42 | −1.28 | 0.005287 | 0.339032 |
| 258436_at | putative RING zinc finger protein similar to RING-H2 zinc finger protein ATL6 GB: AAD33584 from [*Arabidopsis thaliana*]; supported by full-length cDNA: Ceres: 4581. | At3g16720 | 6.39 | −1.2 | 0.002525 | 0.290143 |
| 254255_at | serine/threonine kinase-like protein serine/threonine kinase, *Brassica oleracea*; supported by cDNA: gi_14423417_gb_AF386946.1_AF386946 | At4g23220 | 6.39 | 1.58 | 0.01157 | 0.225448 |
| 248686_at | 33 kDa secretory protein-like; supported by cDNA: gi_15292980_gb_AY050924.1_ | At5g48540 | 6.37 | 1.07 | 0.007302 | 0.530534 |
| 248726_at | RAS superfamily GTP-binding protein-like; supported by cDNA: gi_12004622_gb_AF218121.1_AF218121 | At5g47960 | 6.34 | −1 | 0.011505 | 0.996984 |
| 256633_at | unknown protein | At3g28340 | 6.32 | −1.23 | 0.013314 | 0.277616 |
| 256183_at | MAP kinase kinase 4 (ATMKK4) identical to MAP kinase kinase 4 [*Arabidopsis thaliana*]; supported by cDNA: gi_13265419_gb_AF324667.2_AF324667 | At1g51660 | 6.32 | 1.03 | 0.001255 | 0.842274 |
| 247949_at | cytochrome P450 | At5g57220 | 6.31 | −1.03 | 0.00798 | 0.740555 |
| 250098_at | putative protein; supported by full-length cDNA: Ceres: 1198. | At5g17350 | 6.21 | −1.09 | 0.005623 | 0.628534 |
| 255504_at | drought-induced-19-like 1 similar to drought-induced-19, GenBank accession number X78584 similar to F2P16.10, GenBank accession number 2191179 identical to T10M13.20 | At4g02200 | 6.14 | 1.1 | 0.002902 | 0.428306 |
| 253414_at | putative protein | At4g33050 | 6.08 | −1.1 | 0.002073 | 0.284317 |
| 262731_at | hypothetical protein similar to gb\|AF098458 latex-abundant protein (LAR) from *Hevea brasiliensis* | At1g16420 | 6.07 | 1.18 | 0.016528 | 0.727417 |
| 247848_at | resistance protein-like disease resistance protein RPP1-WsA, *Arabidopsis thaliana*, EMBL: AF098962 | At5g58120 | 6.07 | −1.04 | 0.01295 | 0.876046 |
| 254926_at | ACC synthase (AtACS-6); supported by cDNA: gi_16226285_gb_AF428292.1_AF428292 | At4g11280 | 6.04 | −1.17 | 0.005123 | 0.161176 |
| 249719_at | Expressed protein; supported by full-length cDNA: Ceres: 32450. | At5g35735 | 6.04 | −1.08 | 0.005081 | 0.233393 |
| 247208_at | nodulin-like; supported by full-length cDNA: Ceres: 142026. | At5g64870 | 6.04 | 1.22 | 0.001605 | 0.225756 |
| 257478_at | hypothetical protein similar to putative serine/threonine-specific protein kinase GI: 7270012 from [*Arabidopsis thaliana*] | At1g16130 | 5.96 | −1.23 | 0.008918 | 0.562604 |
| 246993_at | Cys2/His2-type zinc finger protein 1 (dbj\|BAA85108.1) | At5g67450 | 5.95 | −1.06 | 0.005299 | 0.855156 |
| 252060_at | putative protein other hypothetical proteins in *Arabidopsis thaliana*; supported by cDNA: gi_6457330_gb_AF188329.1_AF188329 | At3g52430 | 5.94 | 1.2 | 0.005073 | 0.34486 |
| 267381_at | unknown protein; supported by cDNA: gi_16930468_gb_AF419588.1_AF419588 | At2g26190 | 5.9 | −1.09 | 0.006528 | 0.587987 |
| 245038_at | similar to latex allergen from *Hevea brasiliensis*; supported by full-length cDNA: Ceres: 1999. | At2g26560 | 5.89 | −1.06 | 0.019374 | 0.83179 |
| 266800_at | hypothetical protein predicted by genefinder | At2g22880 | 5.86 | −1.01 | 0.003336 | 0.993661 |
| 259211_at | unknown protein identical to GB: AAD56318 (*Arabidopsis thaliana*) | At3g09020 | 5.82 | 1.08 | 0.00649 | 0.5476 |
| 253485_at | Expressed protein; supported by full-length cDNA: Ceres: 40692. | At4g31800 | 5.82 | −1.13 | 0.00494 | 0.428126 |
| 260211_at | hypothetical protein similar to YGL010w-like protein GB: AAC32136 [*Picea mariana*] | At1g74440 | 5.77 | 1.06 | 0.003351 | 0.730279 |
| 256093_at | predicted protein; supported by cDNA: gi_15027984_gb_AY045849.1_ | At1g20823 | 5.74 | −1.35 | 0.016068 | 0.107243 |
| 267451_at | putative AP2 domain transcription factor | At2g33710 | 5.72 | −1.17 | 0.015334 | 0.725714 |
| 260411_at | hypothetical protein similar to GB: AAB61488 [*Arabidopsis thaliana*]; supported by full-length cDNA: Ceres: 34864. | At1g69890 | 5.71 | −1.29 | 0.011204 | 0.168552 |
| 254592_at | heat shock transcription factor-like protein heat shock transcription factor, *Zea mays*, PIR2: S61448 | At4g18880 | 5.7 | −1.08 | 0.009829 | 0.552909 |
| 264000_at | putative mitochondrial dicarboxylate carrier protein; supported by full-length cDNA: Ceres: 20723. | At2g22500 | 5.68 | −1.18 | 0.004964 | 0.182153 |
| 263475_at | Expressed protein; supported by full-length cDNA: Ceres: 258917. | At2g31945 | 5.63 | 1 | 0.00655 | 0.971652 |
| 254408_at | serine/threonine kinase-like protein serine/threonine kinase BRLK, *Brassica oleracea*, gb: Y12531 | At4g21390 | 5.63 | 1.2 | 0.003477 | 0.605633 |
| 245209_at | putative protein similarity to predicted protein, *Arabidopsis thaliana* | At5g12340 | 5.63 | −1.23 | 0.004077 | 0.532051 |
| 259629_at | disease resistance protein contains domains associated with disease resistance genes in plants: TIR/NB-ARC/LRR | At1g56510 | 5.61 | −1.13 | 0.009583 | 0.608416 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 247655_at | zinc finger protein Zat12; supported by full-length cDNA: Ceres: 40576. | At5g59820 | 5.56 | 1.2 | 0.004335 | 0.099425 |
| 266834_s_at | putative protein phosphatase 2C | At2g30020 | 5.52 | −1.03 | 0.005778 | 0.730603 |
| 256181_at | light repressible receptor protein kinase, putative similar to light repressible receptor protein kinase GI: 1321686 from (*Arabidopsis thaliana*) | At1g51820 | 5.51 | −1.08 | 0.002365 | 0.605128 |
| 251705_at | DNA-binding protein-like DNA-binding protein 4 WRKY4-*Nicotiana tabacum*, EMBL: AF193771; supported by full-length cDNA: Ceres: 34847. | At3g56400 | 5.5 | −1.03 | 0.00667 | 0.83389 |
| 251097_at | receptor like protein kinase receptor like protein kinase-*Arabidopsis thaliana*, EMBL: ATLECGENE | At5g01560 | 5.48 | −1.09 | 0.00945 | 0.858858 |
| 248392_at | integral membrane protein-like | At5g52050 | 5.45 | −1.21 | 0.005162 | 0.477438 |
| 254158_at | putative protein dihydrofolate reductase-*Schizosaccharomyces pombe*, PID: e1320950; supported by full-length cDNA: Ceres: 27155. | At4g24380 | 5.44 | −1.17 | 0.013347 | 0.342417 |
| 260406_at | putative glutathione transferase similar to glutathione transferase GB: CAA09188 [*Alopecurus myosuroides*] | At1g69920 | 5.41 | 2.07 | 0.009635 | 0.082596 |
| 254241_at | serine/threonine kinase-like protein serine/threonine kinase, *Brassica oleracea* | At4g23190 | 5.37 | 1.09 | 0.001802 | 0.566443 |
| 265674_at | unknown protein; supported by full-length cDNA: Ceres: 40344. | At2g32190 | 5.3 | 1.24 | 0.013333 | 0.440285 |
| 264757_at | receptor protein kinase (IRK1), putative similar to receptor protein kinase (IRK1) GI: 836953 from [*Ipomoea trifida*] | At1g61360 | 5.28 | −1.05 | 0.002166 | 0.73136 |
| 248875_at | disease resistance protein-like | At5g46470 | 5.28 | −1.01 | 0.004999 | 0.943089 |
| 247708_at | putative protein COP1-interacting protein CIP8, *Arabidopsis thaliana*, EMBL: AF162150; supported by cDNA: gi_15450686_gb_AY052711.1_ | At5g59550 | 5.28 | −1.21 | 0.003861 | 0.156044 |
| 260239_at | putative receptor protein kinase similar to brassinosteroid insensitive 1 GB: AAC49810 (putative receptor protein kinase); contains Pfam profiles: PF00560 Leucine Rich Repeat (17 repeats), PF00069 Eukaryotic protein kinase domain; supported by cDNA: gi_158 | At1g74360 | 5.26 | 1.27 | 0.014165 | 0.212238 |
| 255549_at | predicted protein of unknown function | At4g01950 | 5.23 | −1.02 | 0.009729 | 0.893458 |
| 266992_at | similar to Mlo proteins from *H. vulgare*; supported by cDNA: gi_14091593_gb_AF369573.1_AF369573 | At2g39200 | 5.21 | −1.12 | 0.008101 | 0.282992 |
| 261973_at | hypothetical protein predicted by genemark.hmm | At1g64610 | 5.19 | −1.09 | 0.005786 | 0.674167 |
| 254242_at | serine/threonine kinase-like protein serine/threonine kinase, *Brassica oleracea* | At4g23200 | 5.19 | 1.03 | 0.007882 | 0.840853 |
| 260477_at | Ser/Thr protein kinase isolog | At1g11050 | 5.15 | −1.34 | 0.029135 | 0.243484 |
| 265670_s_at | unknown protein; supported by full-length cDNA: Ceres: 31665. | At2g32210 | 5.07 | 1.19 | 0.014682 | 0.138268 |
| 265199_s_at | putative glucosyl transferase | At2g36770 | 5.07 | 1.33 | 0.003771 | 0.194926 |
| 247493_at | copine-like protein copine I, *Homo sapiens*, EMBL: HSU83246; supported by full-length cDNA: Ceres: 146738. | At5g61900 | 5.07 | 1.04 | 0.003077 | 0.714944 |
| 265737_at | putative phosphatidic acid phosphatase; supported by full-length cDNA: Ceres: 19163. | At2g01180 | 5.04 | −1.05 | 0.00382 | 0.74519 |
| 260243_at | hypothetical protein similar to putative protein GB: CAA18164 [*Arabidopsis thaliana*]; supported by cDNA: gi_13878144_gb_AF370335.1_AF370335 | At1g63720 | 5.01 | 1.07 | 0.019639 | 0.772243 |
| 252045_at | putative protein arm repeat containing protein ARC1-*Brassica napus*, PID: g2558938 | At3g52450 | 5.01 | 1.25 | 0.012091 | 0.125673 |
| 250153_at | putative protein TMV response-related gene product, *Nicotiana tabacum*, EMBL: AB024510 | At5g15130 | 5 | 1.05 | 0.011689 | 0.809857 |
| 247047_at | putative protein contains similarity to unknown protein (gb AAC17084.1); supported by cDNA: gi_14596230_gb_AY042903.1_ | At5g66650 | 4.98 | −1.01 | 0.006647 | 0.888192 |
| 261476_at | hypothetical protein contains similarity to alpha-latroinsectotoxin precursor GI: 9537 from [*Latrodectus tredecimguttatus*] | At1g14480 | 4.97 | 1.14 | 0.02789 | 0.562278 |
| 247205_at | unknown protein; supported by full-length cDNA: Ceres: 9242. | At5g64890 | 4.96 | 1.59 | 0.010532 | 0.389292 |
| 261450_s_at | O-methyltransferase, putative similar to GB: AAF28353 from [*Fragaria x ananassa*] | At1g21110 | 4.95 | 1.5 | 0.02203 | 0.137219 |
| 252474_at | putative protein several hypothetical proteins-*Arabidopsis thaliana* | At3g46620 | 4.94 | −1.06 | 0.006633 | 0.705845 |
| 257840_at | protein kinase, putative contains Pfam profile: PF00069 Eukaryotic protein kinase domain | At3g25250 | 4.93 | 1.19 | 0.013824 | 0.496857 |
| 248964_at | cytochrome P450 | At5g45340 | 4.93 | −1.52 | 0.003815 | 0.013613 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 247071_at | putative protein similar to unknown protein (emb CAB16816.1) | At5g66640 | 4.92 | −1.02 | 0.010559 | 0.987089 |
| 246270_at | putative protein | At4g36500 | 4.92 | −1.2 | 0.002823 | 0.230335 |
| 261033_at | unknown protein; supported by full-length cDNA: Ceres: 37370. | At1g17380 | 4.84 | −1.01 | 0.017643 | 0.96188 |
| 260261_at | unknown protein | At1g68450 | 4.78 | −1.03 | 0.006946 | 0.882923 |
| 249485_at | receptor protein kinase-like protein receptor-protein kinase-like protein, *Arabidopsis thaliana*, PIR: T45786 | At5g39020 | 4.74 | 1.03 | 0.002268 | 0.823569 |
| 256487_at | disease resistance gene, putative similar to downy mildew resistance protein RPP5 [*Arabidopsis thaliana*] GI: 6449046 | At1g31540 | 4.73 | 1.14 | 0.01107 | 0.679977 |
| 249983_at | putative protein S-receptor kinase PK3 precursor, maize, PIR: T02753; supported by full-length cDNA: Ceres: 154037. | At5g18470 | 4.69 | 1.03 | 0.006021 | 0.801393 |
| 258682_at | putative ribosomal-protein S6 kinase (ATPK19) identical to putative ribosomal-protein S6 kinase (ATPK19) GB: D42061 [*Arabidopsis thaliana*] (FEBS Lett. 358 (2), 199-204 (1995)); supported by cDNA: gi_15292784_gb_AY050826.1_ | At3g08720 | 4.68 | 1.12 | 0.009464 | 0.260404 |
| 254487_at | calcium-binding protein-like calcium-binding protein, *Solanum tuberosum*, gb: L02830 | At4g20780 | 4.63 | −1.43 | 0.015022 | 0.176224 |
| 265728_at | hypothetical protein predicted by genscan | At2g31990 | 4.62 | −1.14 | 0.025876 | 0.616683 |
| 258792_at | hypothetical protein predicted by genefinder; supported by full-length cDNA: Ceres: 8992. | At3g04640 | 4.62 | −1.08 | 0.003809 | 0.521094 |
| 253535_at | putaive DNA-binding protein DNA-binding protein WRKY3-*Petroselinum crispum*, PIR2: S72445; supported by cDNA: Ceres: 11953. | At4g31550 | 4.62 | −1.17 | 0.001616 | 0.072643 |
| 257751_at | hypothetical protein predicted by genemark.hmm; supported by full-length cDNA: Ceres: 104278. | At3g18690 | 4.6 | −1.01 | 0.006195 | 0.939184 |
| 261367_at | protein kinase, putative similar to many predicted protein kinases | At1g53080 | 4.59 | 1.31 | 0.008723 | 0.439817 |
| 247240_at | putative protein strong similarity to unknown protein (emb|CAB89350.1) | At5g64660 | 4.57 | −1.08 | 0.004191 | 0.392312 |
| 261526_at | protein kinase identical to protein kinase GI: 2852447 from [*Arabidopsis thaliana*]; supported by cDNA: gi_2852446_dbj_D88206.1_D88206 | At1g14370 | 4.56 | −1.08 | 0.004758 | 0.475696 |
| 254948_at | putative protein various predicted proteins, *Arabidopsis thaliana* | At4g11000 | 4.55 | 1.03 | 0.020674 | 0.901116 |
| 245119_at | unknown protein; supported by cDNA: gi_16930450_gb_AF419579.1_AF419579 | At2g41640 | 4.54 | −1.2 | 0.013528 | 0.323955 |
| 248319_at | unknown protein | At5g52710 | 4.5 | −1.19 | 0.022646 | 0.498394 |
| 245765_at | hypothetical protein similar to putative disease resistance protein GB: AAC14512 GI: 2739389 from [*Arabidopsis thaliana*] | At1g33600 | 4.5 | −1.01 | 0.00753 | 0.943437 |
| 248821_at | protein serine threonine kinase-like | At5g47070 | 4.49 | 1.13 | 0.005807 | 0.220356 |
| 245272_at | hypothetical protein; supported by cDNA: gi_16323154_gb_AY057681.1_ | At4g17250 | 4.49 | −1 | 0.016447 | 0.969266 |
| 255595_at | putative chitinase similar to peanut type II chitinase, GenBank accession number X82329, E.C. 3.2.1.14 | At4g01700 | 4.48 | 1.09 | 0.009232 | 0.455046 |
| 249918_at | putative protein predicted protein, *Arabidopsis thaliana* | At5g19240 | 4.48 | 1.11 | 0.005605 | 0.490746 |
| 263565_at | unknown protein | At2g15390 | 4.45 | −1.28 | 0.011298 | 0.375612 |
| 261713_at | protein kinase, putative identical to bHLH protein GB: CAA67885 GI: 1465368 from [*Arabidopsis thaliana*]; supported by cDNA: gi_14335047_gb_AY037203.1_ | At1g32640 | 4.43 | 1.12 | 0.002007 | 0.392042 |
| 262772_at | puative calcium-transporting ATPase similar to gb|AF038007 FIC1 gene from *Homo sapiens* and is a member of the PF|00122 E1-E2 ATPase family. ESTs gb|T45045 and gb|AA394473 come from this gene | At1g13210 | 4.4 | −1.06 | 0.004192 | 0.641809 |
| 258364_at | unknown protein | At3g14225 | 4.4 | −1.49 | 0.013195 | 0.305266 |
| 257022_at | zinc finger protein, putative similar to Cys2/His2-type zinc finger protein 2 GB: BAA85107 from [*Arabidopsis thaliana*]; supported by cDNA: gi_15028256_gb_AY046043.1_ | At3g19580 | 4.39 | −1.04 | 0.01073 | 0.818188 |
| 252053_at | syntaxin-like protein synt4; supported by full-length cDNA: Ceres: 37248. | At3g52400 | 4.38 | 1.02 | 0.002866 | 0.837782 |
| 250695_at | lectin-like protein kinase | At5g06740 | 4.38 | −1.34 | 0.030543 | 0.436678 |
| 246293_at | SigA binding protein; supported by cDNA: gi_14596086_gb_AY042831.1_ | At3g56710 | 4.38 | −1.01 | 0.005488 | 0.98387 |

TABLE 3-continued

Genes that are Responsive to chitooctaose in Wild-type

| Probe set | Annotation | Accession | WT FC | Mu FC | WT P | Mu P |
| --- | --- | --- | --- | --- | --- | --- |
| 249032_at | putative protein contains similarity to disease resistance protein | At5g44910 | 4.37 | 1.06 | 0.010921 | 0.589391 |
| 265189_at | unknown protein; supported by cDNA: gi_14335017_gb_AY037188.1_ | At1g23840 | 4.34 | 1.12 | 0.020118 | 0.585186 |
| 265668_at | putative alanine acetyl transferase; supported by full-length cDNA: Ceres: 21201. | At2g32020 | 4.31 | 1.45 | 0.006627 | 0.053107 |
| 264232_at | putative protein kinase Pfam HMM hit: Eukaryotic protein kinase domain; identical to GB: AAC18787 (*Arabidopsis thaliana*) | At1g67470 | 4.3 | −1.07 | 0.003961 | 0.651045 |
| 263948_at | similar to harpin-induced protein hin1 from tobacco; supported by full-length cDNA: Ceres: 26418. | At2g35980 | 4.28 | 1.34 | 0.007735 | 0.319605 |
| 261748_at | hypothetical protein predicted by genemark.hmm; supported by full-length cDNA: Ceres: 39494. | At1g76070 | 4.27 | −1.05 | 0.034903 | 0.781675 |
| 252278_at | NAC2-like protein NAC2-*Arabidopsis thaliana*, EMBL: AF201456; supported by cDNA: gi_16604578_gb_AY059734.1_ | At3g49530 | 4.25 | −1.01 | 0.001287 | 0.915747 |
| 247137_at | calcium-dependent protein kinase; supported by full-length cDNA: Ceres: 18901. | At5g66210 | 4.23 | −1.01 | 0.004474 | 0.902625 |
| 255568_at | putative DNA-binding protein; supported by cDNA: gi_15028172_gb_AY045909.1_ | At4g01250 | 4.21 | −1.2 | 0.010495 | 0.218487 |
| 259479_at | Expressed protein; supported by full-length cDNA: Ceres: 31015. | At1g19020 | 4.2 | 1.23 | 0.002707 | 0.175614 |
| 245247_at | scarecrow-like 13 (SCL13); supported by cDNA: gi_16930432_gb_AF419570.1_AF419570 | At4g17230 | 4.2 | 1.06 | 0.010533 | 0.625637 |
| 252470_at | protein kinase 6-like protein protein kinase 6-*Glycine max*, PIR2: S29851 | At3g46930 | 4.19 | 1.13 | 0.012875 | 0.362838 |
| 256050_at | leucine zipper protein, putative similar to leucine zipper protein GI: 10177020 from [*Arabidopsis thaliana*] | At1g07000 | 4.16 | 1.04 | 0.018298 | 0.855313 |
| 261405_at | unknown protein; supported by full-length cDNA: Ceres: 40753. | At1g18740 | 4.15 | −1.11 | 0.00951 | 0.382476 |
| 267288_at | similar to cold acclimation protein WCOR413 [*Triticum aestivum*] | At2g23680 | 4.12 | 1.06 | 0.026303 | 0.758149 |
| 252592_at | mitogen-activated protein kinase 3; supported by cDNA: gi_14423447_gb_AF386961.1_AF386961 | At3g45640 | 4.12 | −1.15 | 0.004807 | 0.119458 |
| 247125_at | putative protein contains similarity to unknown protein (gb|AAF18680.1) | At5g66070 | 4.11 | 1 | 0.001239 | 0.979764 |
| 265184_at | unknown protein; supported by full-length cDNA: Ceres: 36437. | At1g23710 | 4.09 | −1.18 | 0.014497 | 0.24269 |
| 247773_at | putative protein | At5g58630 | 4.09 | −1.08 | 0.006176 | 0.825067 |
| 263478_at | putative receptor-like protein kinase; supported by cDNA: gi_16648754_gb_AY058153.1_ | At2g31880 | 4.08 | 1.14 | 0.00624 | 0.158364 |
| 251910_at | serine/threonine-specific kinase like protein serine/threonine-specific kinase (EC 2.7.1.—) precursor-*Arabidopsis thaliana*, PIR: S68589 | At3g53810 | 4.05 | −1.02 | 0.002869 | 0.843094 |
| 245662_at | hypothetical protein predicted by genemark.hmm | At1g28190 | 4.04 | −1.23 | 0.0328 | 0.44426 |
| 259997_at | unknown protein similar to N-acetylglucosaminyltransferase III GB: AAC53064 [*Mus musculus*] | At1g67880 | 4.03 | 1 | 0.005767 | 0.973619 |
| 252179_at | putative protein UDP-glucose: (glucosyl) LPS alpha1,3-glucosyltransferase WaaO, *E. coli*, EMBL: AF019746 | At3g50760 | 4.03 | −1.04 | 0.00304 | 0.802486 |
| 252928_at | putative protein more than 30 predicted proteins, *Arabidopsis*; supported by full-length cDNA: Ceres: 40069. | At4g38940 | 4.01 | 1.07 | 0.000729 | 0.325455 |
| 251832_at | putative protein tomato leucine zipper-containing protein, *Lycopersicon esculentum*, PIR: S21495 | At3g55150 | 4.01 | 1.41 | 0.010257 | 0.134388 |
| 266396_at | unknown protein | At2g38790 | 4 | 1.05 | 0.027395 | 0.850892 |
| 259400_at | receptor-like protein kinase, putative similar to receptor-like protein kinase INRPK1 GI: 1684913 from [*Ipomoea nil*] | At1g17750 | 3.97 | −1.02 | 0.042252 | 0.932069 |
| 255654_at | Similar to receptor kinase | At4g00970 | 3.97 | −1.11 | 0.010838 | 0.737951 |
| 254587_at | resistance protein RPP5-like downy mildew resistance protein RPP5, *Arabidopsis thaliana*, PATX: G2109275 | At4g19520 | 3.97 | −1.05 | 0.00768 | 0.89806 |
| 255753_at | myb factor, putative similar to myb factor GI: 1946266 from [*Oryza sativa*]; supported by cDNA: gi_3941465_gb_AF062887.1_AF062887 | At1g18570 | 3.95 | 1.03 | 0.004424 | 0.830522 |
| 246532_at | putative protein beta-glucan-elicitor receptor-*Glycine max*, EMBL: D78510 | At5g15870 | 3.94 | −1.02 | 0.015841 | 0.913394 |
| 246631_at | unknown protein; supported by full-length cDNA: Ceres: 34587. | At1g50740 | 3.93 | 1.04 | 0.006841 | 0.56351 |
| 252533_at | putative protein predicted proteins, *Arabidopsis thaliana* | At3g46110 | 3.9 | 1.02 | 0.017185 | 0.893955 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 267384_at | unknown protein highly similar to GP|2435515|AF024504 | At2g44370 | 3.88 | 1.08 | 0.005016 | 0.736235 |
| 258650_at | putative protein kinase similar to protein kinase (APK1A) GB: Q06548 [*Arabidopsis thaliana*]; contains Pfam profile: PF00069 Eukaryotic protein kinase domain | At3g09830 | 3.88 | 1.11 | 0.012936 | 0.571912 |
| 249339_at | putative protein similar to unknown protein (gb|AAB80666.1) | At5g41100 | 3.88 | −1.05 | 0.004061 | 0.72083 |
| 248794_at | ethylene responsive element binding factor 2 (ATERF2) (sp|O80338); supported by full-length cDNA: Ceres: 3012. | At5g47220 | 3.87 | −1.23 | 0.011156 | 0.098663 |
| 245457_s_at | disease resistance RPP5 like protein | At4g16960 | 3.86 | 1.18 | 0.010259 | 0.375561 |
| 248316_at | putative protein similar to unknown protein (emb|CAA71173.1) | At5g52670 | 3.84 | −1.03 | 0.006334 | 0.875191 |
| 253046_at | cytochrome P450-like protein cytochrome P450, *Glycyrrhiza echinata*, AB001379; supported by full-length cDNA: Ceres: 253698. | At4g37370 | 3.83 | 2.17 | 0.019261 | 0.016853 |
| 262374_s_at | flax rust resistance protein, putative similar to flax rust resistance protein GI: 4588066 from [*Linum usitatissimum*]; supported by full-length cDNA: Ceres: 2795. | At1g72930 | 3.81 | 1.03 | 0.004406 | 0.567071 |
| 258537_at | putative disease resistance protein similar to disease resistance protein RPP1-WsC GB: AAC72979 [*Arabidopsis thaliana*]; supported by cDNA: gi_15982829_gb_AY057522.1_ | At3g04210 | 3.81 | 1.09 | 0.005941 | 0.472196 |
| 252648_at | disease resistance protein homolog disease resistance protein RPP1-WsB-*Arabidopsis thaliana*, EMBL: AF098963 | At3g44630 | 3.81 | −1.23 | 0.007177 | 0.068548 |
| 247913_at | unknown protein | At5g57510 | 3.81 | 1.12 | 0.009476 | 0.608703 |
| 267411_at | putative disease resistance protein | At2g34930 | 3.8 | −1.06 | 0.015151 | 0.825604 |
| 265440_at | pEARLI 4 protein Same as GB: L43081; supported by cDNA: gi_871781_gb_L43081.1_ATHPEARA | At2g20960 | 3.8 | −1.08 | 0.001968 | 0.382136 |
| 245252_at | ethylene responsive element binding factor 1 (frameshift !); supported by cDNA: gi_3434966_dbj_AB008103.1_AB008103 | At4g17500 | 3.8 | −1.47 | 0.008058 | 0.087956 |
| 259033_at | putative pectinacetylesterase similar to pectinacetylesterase precursor GB: CAA67728 [*Vigna radiata*] | At3g09410 | 3.79 | 1.64 | 0.003796 | 0.052828 |
| 246233_at | putative protein | At4g36550 | 3.79 | −1.43 | 0.028755 | 0.228285 |
| 255599_at | cyclic nucleotide gated channel (CNGC4) like protein *Arabidopsis thaliana* cyclic nucleotide gated channel (CNGC4), PID: g4378659 | At4g01010 | 3.78 | −1.02 | 0.00606 | 0.91649 |
| 262901_at | hypothetical protein predicted by genemark.hmm | At1g59910 | 3.77 | −1.08 | 0.006294 | 0.540378 |
| 259952_at | putative disease resistance protein similar to Cf-4 GB: CAA05268 from (*Lycopersicon hirsutum*) | At1g71400 | 3.74 | 1.08 | 0.001393 | 0.408545 |
| 246858_at | receptor-like protein kinase-like receptor-like protein kinase 5, *Arabidopsis thaliana*, PIR: S27756 | At5g25930 | 3.73 | 1.02 | 0.015786 | 0.964753 |
| 250435_at | putative protein various predicted proteins, *Arabidopsis thaliana* | At5g10380 | 3.72 | 1.22 | 0.007856 | 0.106321 |
| 261650_at | envelope Ca2+-ATPase identical to envelope Ca2+-ATPase GB: AAD10212 GI: 516118 from (*Arabidopsis thaliana*); supported by cDNA: gi_493621_dbj_D13983.1_ATHRCECAA | At1g27770 | 3.71 | 1.05 | 0.00839 | 0.580228 |
| 252906_at | putative gamma-glutamyltransferase gamma-glutamyltransferase, *Arabidopsis thaliana*, PIR2: S58286 | At4g39640 | 3.71 | 1.07 | 0.012355 | 0.562612 |
| 251636_at | calcium-dependent protein kinase calcium-dependent protein kinase-*Fragaria* x *ananassa*, EMBL: AF035944 | At3g57530 | 3.71 | −1.26 | 0.016722 | 0.11982 |
| 247426_at | putative protein contains similarity to calmodulin-binding protein | At5g62570 | 3.67 | 1.02 | 0.018802 | 0.878551 |
| 266685_at | hypothetical protein | At2g19710 | 3.66 | −1 | 0.018487 | 0.952139 |
| 249903_at | disease resistance protein-like | At5g22690 | 3.65 | −1.04 | 0.010635 | 0.754135 |
| 247925_at | TCH4 protein (gb|AAA92363.1); supported by cDNA: gi_14194112_gb_AF367262.1_AF367262 | At5g57560 | 3.65 | −1.28 | 0.003003 | 0.132214 |
| 248611_at | putative protein contains similarity to WRKY-type DNA-binding protein | At5g49520 | 3.63 | −1.45 | 0.010966 | 0.13904 |
| 265221_s_at | putative glutamate decarboxylase; supported by cDNA: gi_13605709_gb_AF361836.1_AF361836 | At2g02010 | 3.62 | −1.12 | 0.01727 | 0.698419 |
| 259792_at | unknown protein; supported by cDNA: gi_15809819_gb_AY054177.1_ | At1g29690 | 3.62 | −1.05 | 0.013953 | 0.685925 |
| 256576_at | zinc finger protein (PMZ), putative identical to putative zinc finger protein (PMZ) GB: AAD37511 GI: 5006473 [*Arabidopsis thaliana*] | At3g28210 | 3.62 | 1.34 | 0.019514 | 0.107277 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 254784_at | growth factor like protein antisense basic fibroblast growth factor GFG-*Rattus norvegicus*, PID: g1518635; supported by full-length cDNA: Ceres: 148575. | At4g12720 | 3.62 | 1.06 | 0.012904 | 0.638871 |
| 247177_at | unknown protein; supported by cDNA: gi_13877834_gb_AF370180.1_AF370180 | At5g65300 | 3.62 | 1.1 | 0.004863 | 0.387978 |
| 245226_at | gene_id: K17E7.15~unknown protein | At3g29970 | 3.6 | 1.76 | 0.01017 | 0.066452 |
| 256756_at | ATPase II, putative similar to GB: AAD34706 from [*Homo sapiens*] (Biochem. Biophys. Res. Commun. 257 (2), 333-339 (1999)) | At3g25610 | 3.59 | −1.01 | 0.009255 | 0.929097 |
| 253140_at | RING-H2 finger protein RHA3b; supported by full-length cDNA: Ceres: 31493. | At4g35480 | 3.56 | −1.04 | 0.013391 | 0.651703 |
| 250289_at | putative protein; supported by full-length cDNA: Ceres: 5392. | At5g13190 | 3.56 | 1.18 | 0.000966 | 0.176346 |
| 247811_at | leucine zipper-containing protein leucine zipper-containing protein, *Lycopersicon esculentum*, PIR: S21495 | At5g58430 | 3.56 | −1.01 | 0.001344 | 0.933016 |
| 261899_at | cinnamoyl CoA reductase, putative similar to cinnamoyl CoA reductase GB: AAF43141 GI: 7239228 from [*Populus tremuloides*]; supported by full-length cDNA: Ceres: 32255. | At1g80820 | 3.55 | −1.11 | 0.01598 | 0.720481 |
| 245866_s_at | unknown protein | At1g57990 | 3.55 | −1.09 | 0.011056 | 0.501011 |
| 264867_at | unknown protein | At1g24150 | 3.53 | −1 | 0.030643 | 0.978236 |
| 261193_at | unknown protein; supported by cDNA: gi_15450636_gb_AY052686.1_ | At1g32920 | 3.53 | −1.12 | 0.009489 | 0.382199 |
| 261339_at | protein kinase, putative similar to many predicted protein kinases | At1g35710 | 3.51 | 1.32 | 0.013195 | 0.062019 |
| 267490_at | putative receptor-like protein kinase | At2g19130 | 3.5 | 1 | 0.015702 | 0.997521 |
| 259561_at | hypothetical protein; supported by cDNA: gi_14532585_gb_AY039917.1_ | At1g21250 | 3.49 | 1.52 | 0.005151 | 0.042781 |
| 263228_at | putative reticuline oxidase-like protein similar to GB: P30986 from [*Eschscholzia californica*] (berberine bridge-forming enzyme), ESTs gb|F19886, gb|Z30784 and gb|Z30785 come from this gene; supported by cDNA: gi_16930506_gb_AF419607.1_AF419607 | At1g30700 | 3.48 | 1.07 | 0.007823 | 0.648304 |
| 255627_at | Expressed protein; supported by full-length cDNA: Ceres: 93818. | At4g00955 | 3.48 | 1.08 | 0.009206 | 0.72176 |
| 254256_at | serine/threonine kinase-like protein serine/threonine kinase, *Brassica oleracea*; supported by cDNA: gi_13506744_gb_AF224705.1_AF224705 | At4g23180 | 3.45 | −1.2 | 0.002919 | 0.140829 |
| 260135_at | calmodulin-related protein similar to GB: P25070 from [*Arabidopsis thaliana*], contains Pfam profile: PF00036 EF hand (4 copies); supported by full-length cDNA: Ceres: 95959. | At1g66400 | 3.44 | −1.11 | 0.013883 | 0.371779 |
| 260206_at | putative protein kinase contains Pfam profile: PF00069 Eukaryotic protein kinase domain | At1g70740 | 3.43 | −1.12 | 0.012329 | 0.420329 |
| 259887_at | putative protein kinase similar to protein kinase (APK1A); contains Pfam profile: PF00069 Eukaryotic protein kinase domain | At1g76360 | 3.42 | 1.1 | 0.008975 | 0.501823 |
| 262383_at | disease resistance protein, putative similar to disease resistance protein GI: 9758876 from [*Arabidopsis thaliana*] | At1g72940 | 3.41 | 1.18 | 0.011942 | 0.230832 |
| 256177_at | protein kinase, putative contains Pfam profile: PF00069: Eukaryotic protein kinase domain | At1g51620 | 3.41 | 1.23 | 0.01444 | 0.359679 |
| 245777_at | unknown protein contains similarity to diphosphoinositol polyphosphate phosphohydrolase GI: 3978224 from [*Homo sapiens*] | At1g73540 | 3.41 | −1.25 | 0.026487 | 0.341823 |
| 249221_at | serine/threonine protein kinase-like protein | At5g42440 | 3.4 | −1.02 | 0.005295 | 0.883947 |
| 245448_at | disease resistance RPP5 like protein | At4g16860 | 3.4 | −1.15 | 0.027985 | 0.375642 |
| 254869_at | protein kinase-like protein KI domain interacting kinase 1-*Zea mays*, PIR2: T02053 | At4g11890 | 3.37 | 2.12 | 0.007665 | 0.003284 |
| 256755_at | calmodulin, putative similar to GB: P07463 from [*Paramecium tetraurelia*] (Cell 62 (1), 165-174 (1990)) | At3g25600 | 3.37 | −1.05 | 0.007284 | 0.663209 |
| 264107_s_at | putative receptor-like protein kinase | At2g13790 | 3.34 | 1.16 | 0.008131 | 0.293891 |
| 266017_at | unknown protein; supported by cDNA: gi_14517479_gb_AY039575.1_ | At2g18690 | 3.32 | 1.36 | 0.008527 | 0.108178 |
| 263776_s_at | putative cyclic nucleotide-regulated ion channel protein | At2g46440 | 3.32 | 1.21 | 0.026465 | 0.278033 |
| 245193_at | F12A21.6 hypothetical protein | At1g67810 | 3.32 | 1.17 | 0.00613 | 0.205789 |
| 256522_at | unknown protein; supported by full-length cDNA: Ceres: 35218. | At1g66160 | 3.3 | −1.22 | 0.004073 | 0.074994 |
| 248703_at | dermal glycoprotein precursor, extracellular-like | At5g48430 | 3.28 | 1.09 | 0.005001 | 0.574329 |
| 260434_at | hypothetical protein predicted by genscan+ | At1g68330 | 3.27 | −1.14 | 0.006128 | 0.614427 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 252652_at | putative chloroplast prephenate dehydratase similar to bacterial PheA gene products | At3g44720 | 3.23 | 1.08 | 0.004759 | 0.192206 |
| 260023_at | unknown protein | At1g30040 | 3.21 | 1.26 | 0.004354 | 0.301041 |
| 251640_at | putative protein; supported by full-length cDNA: Ceres: 12522. | At3g57450 | 3.21 | −1.03 | 0.002724 | 0.717428 |
| 264314_at | unknown protein; supported by cDNA: gi_15010575_gb_AY045589.1_ | At1g70420 | 3.18 | 1.24 | 0.00926 | 0.33473 |
| 262549_at | hypothetical protein similar to hypothetical protein GB: AAF24586 GI: 6692121 from [*Arabidopsis thaliana*] | At1g31290 | 3.18 | 1.36 | 0.017342 | 0.141779 |
| 261459_at | O-methyltransferase, putative similar to GB: AAF28353 from [*Fragaria* x *ananassa*]; supported by cDNA: gi_15982843_gb_AY057529.1_ | At1g21100 | 3.18 | 1.37 | 0.006504 | 0.199125 |
| 249139_at | Cys2/His2-type zinc finger protein 3 (dbj|BAA85109.1); supported by full-length cDNA: Ceres: 9878. | At5g43170 | 3.18 | −1.11 | 0.014619 | 0.403291 |
| 248980_at | putative protein similar to unknown protein (pir||T04765) | At5g45090 | 3.18 | −1.03 | 0.006572 | 0.837241 |
| 264660_at | putative glutamyl-tRNA reductase 2 precursor similar to GB: P49294 and to *A. thaliana* HEMA2 (gb|U27118) | At1g09940 | 3.17 | −1.02 | 0.009351 | 0.857849 |
| 254014_at | NPR1 like protein regulatory protein NPR1-*Arabidopsis thaliana*, PID: g1773295 | At4g26120 | 3.17 | 1.03 | 0.021113 | 0.898299 |
| 252126_at | putative disease resistance protein | At3g50950 | 3.17 | 1.08 | 0.00517 | 0.256863 |
| 262228_at | protein kinase, putative similar to protein kinase 1 GB: BAA94509 GI: 7573596 from [*Populus nigra*]; supported by cDNA: gi_14334805_gb_AY035076.1_ | At1g68690 | 3.16 | 1.18 | 0.018754 | 0.421396 |
| 259626_at | bZIP transcription factor, putative contains Pfam profile: PF00170: bZIP transcription factor; supported by cDNA: gi_15028322_gb_AY045964.1_ | At1g42990 | 3.15 | 1.08 | 0.006031 | 0.361959 |
| 254063_at | receptor kinase-like protein receptor-like protein kinase, RLK3-*Arabidopsis thaliana*, PID: e1363211 | At4g25390 | 3.15 | −1.09 | 0.021274 | 0.509081 |
| 259443_at | chitinase, putative similar to chitinase GI: 1237025 from [*Arachis hypogaea*] | At1g02360 | 3.14 | 1.33 | 0.010757 | 0.097826 |
| 266615_s_at | putative monooxygenase; supported by full-length cDNA: Ceres: 34214. | At2g29720 | 3.13 | −1 | 0.006073 | 0.993995 |
| 251507_at | putative protein CND41, chloroplast nucleoid DNA binding protein-*Nicotiana tabacum*, EMBL: D26015; supported by cDNA: gi_15983375_gb_AF424562.1_AF424562 | At3g59080 | 3.13 | −1.26 | 0.019246 | 0.076416 |
| 246870_at | ferrochelatase-I | At5g26030 | 3.12 | −1.03 | 0.007971 | 0.563075 |
| 261063_at | transcription factor scarecrow-like 14, putative similar to GB: AAD24412 from [*Arabidopsis thaliana*] (Plant J. 18 (1), 111-119 (1999)) | At1g07520 | 3.09 | 1.05 | 0.0041 | 0.648222 |
| 260296_at | putative disease resistance protein similar to disease resistance protein (RPP1-WsC) GB: AAC72979 [*Arabidopsis thaliana*] | At1g63750 | 3.07 | −1.24 | 0.035995 | 0.346342 |
| 248868_at | putative protein similar to unknown protein (gb|AAC61815.1); supported by full-length cDNA: Ceres: 254442. | At5g46780 | 3.07 | 1.08 | 0.012841 | 0.668687 |
| 267069_at | unknown protein | At2g41010 | 3.06 | −1 | 0.022932 | 0.942266 |
| 261143_at | unknown protein | At1g19770 | 3.06 | −1.07 | 0.003012 | 0.469481 |
| 255116_at | receptor protein kinase-like protein receptor protein kinase-like protein-*Arabidopsis thaliana*, PIR2: T05898 | At4g08850 | 3.06 | 1.13 | 0.013035 | 0.33618 |
| 253284_at | putative protein hydroxyproline-rich glycoprotein precursor, *Nicotiana tabacum*, PIR2: S06733; supported by cDNA: gi_15724315_gb_AF412098.1_AF412098 | At4g34150 | 3.05 | 1.01 | 0.004615 | 0.829133 |
| 252903_at | putative protein various predicted proteins, *Arabidopsis thaliana* | At4g39570 | 3.05 | −1.05 | 0.005467 | 0.697229 |
| 254847_at | putative phospholipase D-gamma phospholipase D-gamma-*Arabidopsis thaliana*, PID: g2653885; supported by cDNA: gi_2653884_gb_AF027408.1_AF027408 | At4g11850 | 3.04 | −1.01 | 0.014523 | 0.911568 |
| 251937_at | putative protein predicted protein, *Arabidopsis thaliana* | At3g53400 | 3.04 | 1.04 | 0.035806 | 0.858509 |
| 256366_at | protein kinase, putative contains Pfam profile: PF00069: Eukaryotic protein kinase domain | At1g66880 | 3.03 | 1.12 | 0.002701 | 0.411044 |
| 247393_at | unknown protein | At5g63130 | 3.03 | −1.65 | 0.018398 | 0.063566 |
| 260556_at | putative endochitinase | At2g43620 | 3.02 | 1.32 | 0.003455 | 0.0287 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 259445_at | dioxygenase, putative similar to dioxygenase GI: 1666096 from [*Marah macrocarpus*] | At1g02400 | 3.01 | 1.16 | 0.012122 | 0.130623 |
| 259298_at | putative disease resistance protein similar to Cf-2 disease resistance protein GB: AAC15780 from [*Lycopersicon pimpinellifolium*] | At3g05370 | 3.01 | −1.08 | 0.040444 | 0.621247 |
| 257644_at | unknown protein; supported by full-length cDNA: Ceres: 3457. | At3g25780 | 3.01 | 1.19 | 0.022772 | 0.336306 |
| 253628_at | xyloglucan endo-1,4-beta-D-glucanase-like protein xyloglucan endo-1,4-beta-D-glucanase (EC 3.2.1.—) XTR-3-*Arabidopsis thaliana*, PIR2: S71222; supported by full-length cDNA: Ceres: 142204. | At4g30280 | 3.01 | 1.29 | 0.005842 | 0.110446 |
| 249072_at | putative protein similar to unknown protein (gb\|AAD10670.1) | At5g44060 | 3.01 | 1.08 | 0.007698 | 0.56653 |
| 253257_at | extra-large G-protein-like extra-large G-protein, *Arabidopsis thaliana*, AF060942 | At4g34390 | 3 | −1.06 | 0.004333 | 0.352585 |
| 253124_at | putative protein unknown protein *Arabidopsis thaliana*, PATX: E248475 | At4g36030 | 3 | −1.07 | 0.016993 | 0.706449 |
| 250676_at | harpin-induced protein-like; supported by cDNA: gi_9502175_gb_AF264699.1_AF264699 | At5g06320 | 3 | 1.02 | 0.003772 | 0.798472 |
| 266037_at | putative protein kinase contains a protein kinase domain profile (PDOC00100); supported by cDNA: gi_15810412_gb_AY056245.1_ | At2g05940 | 2.99 | 1.03 | 0.011895 | 0.742301 |
| 254314_at | extensin-like protein hybrid proline-rich protein, *Zea mays*, PIR2: JQ1663 | At4g22470 | 2.98 | −1.04 | 0.013677 | 0.797081 |
| 252825_at | small GTP-binding protein-like SR1 Nt-rab6, *Nicotiana tabacum*, L29273; supported by cDNA: gi_14423429_gb_AF386952.1_AF386952 | At4g39890 | 2.97 | 1.25 | 0.014269 | 0.471148 |
| 260401_at | unknown protein similar to hypothetical protein GB: CAA10289 [*Cicer arietinum*] | At1g69840 | 2.96 | 1.19 | 0.013016 | 0.197702 |
| 250821_at | putative protein similar to unknown protein (emb\|CAB88044.1) | At5g05190 | 2.95 | −1.11 | 0.008801 | 0.532383 |
| 245265_at | hypothetical protein; supported by cDNA: gi_15810232_gb_AY056155.1_ | At4g14400 | 2.95 | 1.34 | 0.046774 | 0.092249 |
| 264289_at | hypothetical protein similar to hypothetical protein GI: 2894569 from [*Arabidopsis thaliana*]; supported by cDNA: gi_15028186_gb_AY045916.1_ | At1g61890 | 2.94 | 1.17 | 0.016735 | 0.217477 |
| 259410_at | hypothetical protein predicted by genemark.hmm | At1g13340 | 2.94 | 1.45 | 0.015002 | 0.097363 |
| 253958_at | putative protein RING zinc finger protein, *Gallus gallus* | At4g26400 | 2.94 | 1.06 | 0.002619 | 0.621194 |
| 249078_at | phytochelatin synthase (gb\|AAD41794.1); supported by cDNA: gi_14532653_gb_AY039951.1_ | At5g44070 | 2.94 | −1.02 | 0.008033 | 0.806261 |
| 267293_at | hypothetical protein | At2g23810 | 2.93 | −1.06 | 0.004637 | 0.578539 |
| 259992_at | putative heat shock transcription factor contains Pfam profile: PF00447 HSF-type DNA-binding domain; N-terminal portion similar to heat shock transcription factor proteins: GB: CAA74397 [*Arabidopsis thaliana*], GB: S25478 [*Lycopersicon esculentum*] | At1g67970 | 2.93 | −1.01 | 0.006051 | 0.910383 |
| 252862_at | putative L-ascorbate oxidase L-ascorbate oxidase, *Cucumis sativus*, PIR1: KSKVAO | At4g39830 | 2.93 | 1.13 | 0.009756 | 0.383415 |
| 249550_at | protein kinase-like protein wall-associated kinase 4 (wak4), *Arabidopsis thaliana*, EMBL: ATH9695 | At5g38210 | 2.93 | −1.13 | 0.00676 | 0.38925 |
| 247279_at | arabinogalactan-protein (gb\|AAC77823.1); supported by full-length cDNA: Ceres: 25423. | At5g64310 | 2.93 | −1.01 | 0.00661 | 0.937671 |
| 265450_at | hypothetical protein predicted by genefinder | At2g46620 | 2.92 | −1.03 | 0.014924 | 0.733991 |
| 251479_at | serine/threonine-specific kinase lecRK1 precursor, lectin receptor-like | At3g59700 | 2.91 | −1.08 | 0.008769 | 0.515335 |
| 249418_at | putative protein predicted protein, *Arabidopsis thaliana* | At5g39780 | 2.91 | 1.1 | 0.015458 | 0.521455 |
| 266247_at | hypothetical protein predicted by genscan | At2g27660 | 2.89 | −1.11 | 0.009688 | 0.350456 |
| 249252_at | putative protein contains similarity to unknown protein (gb\|AAF19687.1) | At5g42010 | 2.89 | −1.05 | 0.014073 | 0.747236 |
| 255291_at | putative calcium dependent protein kinase | At4g04700 | 2.88 | −1.04 | 0.023496 | 0.890022 |
| 253747_at | serine threonine-specific kinase like protein serine threonine-specific kinase lecRK1-*Arabidopsis thaliana*, PIR2: S68589 | At4g29050 | 2.87 | −1.09 | 0.011457 | 0.626019 |
| 250323_at | putative protein hydroxyproline-rich glycoprotein, kidney bean, PIR: A29356 | At5g12880 | 2.87 | 1.06 | 0.009216 | 0.469664 |
| 262801_at | unknown protein; supported by full-length cDNA: Ceres: 17521. | At1g21010 | 2.86 | 1.08 | 0.017653 | 0.443505 |
| 251061_at | putative protein hypothetical protein ARC1-*Brassica napus*, PIR: T08872 | At5g01830 | 2.86 | 1.18 | 0.015743 | 0.623238 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 265132_at | unknown protein; supported by cDNA: gi_16604403_gb_AY058100.1_ | At1g23830 | 2.84 | −1.07 | 0.017467 | 0.652241 |
| 260439_at | hypothetical protein predicted by genscan+; supported by full-length cDNA: Ceres: 3385. | At1g68340 | 2.84 | −1.04 | 0.003917 | 0.840841 |
| 260227_at | unknown protein similar to hypothetical proteins GB: AAD39276 [*Arabidopsis thaliana*], GB: CAB53491 [*Oryza sativa*]; supported by full-length cDNA: Ceres: 108193. | At1g74450 | 2.83 | −1.16 | 0.009649 | 0.269848 |
| 261453_at | O-methyltransferase, putative similar to GB: AAF28353 from [*Fragaria* x *ananassa*]; supported by full-length cDNA: Ceres: 101583. | At1g21130 | 2.82 | −1.15 | 0.010888 | 0.513201 |
| 254432_at | reticuline oxidase-like protein reticuline oxidase, *Eschscholzia californica*, PIR: A41533; supported by cDNA: gi_15983492_gb_AF424621.1_AF424621 | At4g20830 | 2.82 | 1.19 | 0.046062 | 0.572211 |
| 253971_at | fructose-bisphosphate aldolase-like protein fructose-bisphosphate aldolase, *Arabidopsis thaliana*, PIR1: ADMU; supported by full-length cDNA: Ceres: 34690. | At4g26530 | 2.82 | −1.02 | 0.016712 | 0.805977 |
| 262165_at | putative acyl-CoA: 1-acylglycerol-3-phosphate acyltransferase similar to acyl-CoA: 1-acylglycerol-3-phosphate acyltransferase GB: CAB09138 (*Brassica napus*); contains Pfam profile: PF01553 Acyltransferase; supported by full-length cDNA: Ceres: 115679. | At1g75020 | 2.81 | −1.13 | 0.010295 | 0.275107 |
| 258275_at | unknown protein; supported by full-length cDNA: Ceres: 8259. | At3g15760 | 2.81 | −1.09 | 0.002884 | 0.259472 |
| 255564_s_at | hypothetical protein T15B16.8 | At4g01750 | 2.81 | 1.28 | 0.004474 | 0.364426 |
| 253377_at | putative protein NBS/LRR disease resistance protein (RFL1)-*Arabidopsis thaliana*, PID: g3309619 | At4g33300 | 2.81 | 1.03 | 0.008788 | 0.64371 |
| 260220_at | putative MYB family transcription factor contains Pfam profile: PF00249 Myb-like DNA-binding domain | At1g74650 | 2.8 | −1.05 | 0.014801 | 0.787419 |
| 256583_at | hypothetical protein | At3g28850 | 2.8 | 1.08 | 0.009872 | 0.39554 |
| 252193_at | R2R3-MYB transcription factor; supported by cDNA: gi_15983427_gb_AF424588.1_AF424588 | At3g50060 | 2.8 | −1.67 | 0.007202 | 0.02821 |
| 247509_at | heat shock factor 6 | At5g62020 | 2.8 | 1.11 | 0.004718 | 0.497285 |
| 246368_at | light repressible receptor protein kinase, putative similar to light repressible receptor protein kinase GI: 1321686 from [*Arabidopsis thaliana*] | At1g51890 | 2.8 | 1.32 | 0.007014 | 0.17566 |
| 259507_at | unknown protein | At1g43910 | 2.79 | 1.41 | 0.005884 | 0.156323 |
| 251769_at | receptor kinase-like protein receptor kinase homolog CRINKLY4, maize, PIR: T04108 | At3g55950 | 2.79 | 1.02 | 0.037029 | 0.858886 |
| 250335_at | lysophospholipase-like protein lysophospholipase homolog LPL1, *Oryza sativa*, EMBL: AF039531; supported by full-length cDNA: Ceres: 15284. | At5g11650 | 2.78 | 1.07 | 0.004853 | 0.539031 |
| 248134_at | putative protein contains similarity to integral membrane protein | At5g54860 | 2.78 | 1.09 | 0.010767 | 0.465367 |
| 246988_at | putative protein strong similarity to unknown protein (pir\|\|T00518) | At5g67340 | 2.78 | 1.18 | 0.01807 | 0.609865 |
| 247707_at | scarecrow-like 11-like scarecrow-like 11, *Arabidopsis thaliana*, EMBL: AF036307; supported by cDNA: gi_14334655_gb_AY035001.1_ | At5g59450 | 2.76 | −1.06 | 0.028093 | 0.649019 |
| 256497_at | ORF1, putative similar to ORF1 GI: 457716 from (*Arabidopsis thaliana*); supported by cDNA: gi_16649160_gb_AY059950.1_ | At1g31580 | 2.75 | 1.39 | 0.004888 | 0.080053 |
| 264008_at | unknown protein | At2g21120 | 2.74 | −1.01 | 0.003042 | 0.876414 |
| 264716_at | matrix metalloproteinase, putative similar to matrix metalloproteinase GI: 7159629 from [*Cucumis sativus*] | At1g70170 | 2.73 | −1.02 | 0.005524 | 0.873758 |
| 261445_at | unknown protein; supported by cDNA: gi_16604598_gb_AY059744.1_ | At1g28380 | 2.73 | −1.06 | 0.02128 | 0.701956 |
| 256968_at | unknown protein | At3g21070 | 2.73 | −1.14 | 0.014315 | 0.494381 |
| 256763_at | unknown protein | At3g16860 | 2.73 | −1.06 | 0.01099 | 0.724699 |
| 255605_at | hypothetical protein | At4g01090 | 2.73 | −1.18 | 0.02941 | 0.263496 |
| 254652_at | DNA binding-like protein SPF1 protein, sweet protein, PIR2: S51529 and WRKY protein family, *Petroselinum crispum*, MNOS: S72443, MNOS: S72444, MNOS: S72445 | At4g18170 | 2.73 | 1.05 | 0.048645 | 0.839297 |
| 247532_at | putative protein disease resistance protein kinase Pto, *Lycopersiocon esculentum*, PIR: A49332 | At5g61560 | 2.73 | −1.03 | 0.020053 | 0.845513 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 264106_at | unknown protein | At2g13780 | 2.71 | 1.2 | 0.013998 | 0.074305 |
| 265075_at | hypothetical protein similar to embryo-abundant protein GB: L47672 GI: 1350530 from [*Picea glauca*]; supported by cDNA: gi_14335021_gb_AY037190.1_ | At1g55450 | 2.7 | −1.08 | 0.016743 | 0.546091 |
| 256793_at | unknown protein; supported by full-length cDNA: Ceres: 8081. | At3g22160 | 2.69 | −1.09 | 0.013465 | 0.391312 |
| 258551_at | hypothetical protein predicted by genscan+; supported by full-length cDNA: Ceres: 262487. | At3g06890 | 2.68 | −1.02 | 0.016594 | 0.966946 |
| 255740_at | wall-associated kinase, putative similar to wall-associated kinase 1 GI: 3549626 from [*Arabidopsis thaliana*]; supported by cDNA: gi_15529241_gb_AY052245.1_ | At1g25390 | 2.68 | −1.15 | 0.012139 | 0.281008 |
| 246099_at | blue copper binding protein; supported by full-length cDNA: Ceres: 7767. | At5g20230 | 2.67 | 1.7 | 0.008061 | 0.011289 |
| 264616_at | unknown protein | At2g17740 | 2.67 | 1 | 0.022917 | 0.884668 |
| 254042_at | xyloglucan endo-1,4-beta-D-glucanase (XTR-6); supported by cDNA: gi_1244757_gb_U43488.1_ATU43488 | At4g25810 | 2.66 | 1.07 | 0.002288 | 0.480301 |
| 246289_at | putative protein predicted protein At2g41010-*Arabidopsis thaliana*; EMBL: AC004261; supported by full-length cDNA: Ceres: 39584. | At3g56880 | 2.66 | −1.02 | 0.010884 | 0.82618 |
| 266792_at | putative sucrose/H+ symporter | At2g02860 | 2.65 | 1.05 | 0.005194 | 0.618209 |
| 265853_at | putative RING zinc finger protein | At2g42360 | 2.64 | 1.27 | 0.007875 | 0.101121 |
| 258786_at | putative syntaxin contains Pfam profile: PF00804 syntaxin; supported by full-length cDNA: Ceres: 38899. | At3g11820 | 2.64 | 1.16 | 0.005501 | 0.095192 |
| 247940_at | phosphatidylserine decarboxylase | At5g57190 | 2.64 | −1.08 | 0.02156 | 0.742477 |
| 257083_s_at | non-race specific disease resistance protein, putative contains non-consensus CT donor splice site at exon 1; potential pseudogene; similar to non-race specific disease resistance protein GB: AAB95208 [*Arabidopsis thaliana*] | At3g20590 | 2.63 | −1.1 | 0.022335 | 0.571353 |
| 264434_at | hypothetical protein predicted by genscan; supported by cDNA: gi_13937239_gb_AF372975.1_AF372975 | At1g10340 | 2.61 | 1.14 | 0.016538 | 0.421888 |
| 263804_at | putative protein kinase contains a protein kinase domain profile (PDOC00100); supported by full-length cDNA: Ceres: 123911. | At2g40270 | 2.61 | 1.02 | 0.002801 | 0.766513 |
| 249896_at | unknown protein; supported by cDNA: gi_14532613_gb_AY039931.1_ | At5g22530 | 2.61 | 1.12 | 0.01975 | 0.439704 |
| 249459_at | peroxidase ATP24a | At5g39580 | 2.61 | −1.24 | 0.011537 | 0.098646 |
| 247740_at | receptor-like protein kinase precursor-like receptor-like protein kinase precursor, Madagascar periwinkle, PIR: T10060 | At5g58940 | 2.61 | 1.11 | 0.013363 | 0.45095 |
| 246931_at | putative protein apoptosis-related protein PNAS-4, *Homo sapiens*, EMBL: AF229834; supported by full-length cDNA: Ceres: 263500. | At5g25170 | 2.6 | 1.01 | 0.003003 | 0.89146 |
| 265713_at | putative integral membrane protein | At2g03530 | 2.59 | −1.18 | 0.010284 | 0.275593 |
| 263931_at | unknown protein; supported by full-length cDNA: Ceres: 12251. | At2g36220 | 2.59 | 1.04 | 0.032332 | 0.640228 |
| 264834_at | unknown protein similar to ESTs gb\|AA605440 and gb\|H37232; supported by full-length cDNA: Ceres: 30716. | At1g03730 | 2.58 | 1.02 | 0.006042 | 0.863016 |
| 259852_at | disulfide bond formation protein, putative similar to GI: 6642925 from [*Mus musculus*] | At1g72280 | 2.58 | 1.24 | 0.014598 | 0.356183 |
| 252539_at | putative protein | At3g45730 | 2.58 | 1.3 | 0.009508 | 0.150314 |
| 252378_at | receptor kinase-like protein protein kinase Xa21-*Oryza sativa*, PIR: A57676; supported by cDNA: gi_15810450_gb_AY056264.1_ | At3g47570 | 2.58 | 1.12 | 0.02363 | 0.435178 |
| 251684_at | putative protein | At3g56410 | 2.57 | 1.08 | 0.023561 | 0.592162 |
| 261719_at | hypothetical protein similar to hypothetical protein GB: AAF25996 GI: 6714300 from [*Arabidopsis thaliana*] | At1g18380 | 2.56 | 1.36 | 0.016331 | 0.094821 |
| 254248_at | serine/threonine kinase serine/threonine kinase, *Brassica oleracea* | At4g23270 | 2.56 | −1.04 | 0.006144 | 0.687459 |
| 253204_at | GTP binding protein beta subunit; supported by cDNA: gi_15028006_gb_AY045860.1_ | At4g34460 | 2.56 | −1.01 | 0.007411 | 0.949586 |
| 249361_at | protein kinase-like protein protein kinase ATN1, *Arabidopsis thaliana*, PIR: S61766 | At5g40540 | 2.55 | −1 | 0.004647 | 0.984046 |
| 248665_at | Expressed protein; supported by full-length cDNA: Ceres: 12974. | At5g48655 | 2.55 | 1.02 | 0.009359 | 0.848153 |
| 253455_at | putative protein | At4g32020 | 2.54 | −1.01 | 0.00825 | 0.888496 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 248978_at | putative protein contains similarity to disease resistance protein | At5g45070 | 2.54 | −1.05 | 0.030143 | 0.671649 |
| 248870_at | putative protein similar to unknown protein (pir\|T05076); supported by full-length cDNA: Ceres: 42747. | At5g46710 | 2.54 | 1.03 | 0.004547 | 0.48662 |
| 252170_at | hypothetical protein; supported by cDNA: gi_13605735_gb_AF361849.1_AF361849 | At3g50480 | 2.53 | 1.09 | 0.00647 | 0.431092 |
| 264636_at | hypothetical protein predicted by genemark.hmm; supported by full-length cDNA: Ceres: 2118. | At1g65490 | 2.52 | 1.04 | 0.019945 | 0.653146 |
| 264400_at | glucose-6-phosphate/phosphate-translocator precursor, putative similar to glucose-6-phosphate/phosphate-translocator precursor GI: 2997591 from [*Pisum sativum*]; supported by cDNA: gi_14596172_gb_AY042874.1_ | At1g61800 | 2.51 | −1.13 | 0.035853 | 0.380949 |
| 245567_at | germin precursor oxalate oxidase | At4g14630 | 2.51 | −1.12 | 0.010395 | 0.322763 |
| 264083_at | ethylene reponse factor-like AP2 domain transcription factor | At2g31230 | 2.5 | −1.09 | 0.007348 | 0.596007 |
| 261220_at | ER lumen protein-retaining receptor similar to SP: O44017 from [*Entamoeba histolytica*] | At1g19970 | 2.5 | 1.11 | 0.01247 | 0.321046 |
| 259546_at | unknown protein | At1g35350 | 2.49 | −1.02 | 0.009622 | 0.86289 |
| 266101_at | unknown protein; supported by cDNA: gi_16604321_gb_AY058059.1_ | At2g37940 | 2.47 | 1.05 | 0.006689 | 0.366431 |
| 262384_at | disease resistance protein, putative similar to disease resistance protein GI: 9758876 from [*Arabidopsis thaliana*] | At1g72950 | 2.47 | −1.07 | 0.017043 | 0.63375 |
| 251423_at | regulatory protein-like regulatory protein preg, *Neurospora crassa*, PIR: S52974 | At3g60550 | 2.47 | 1.04 | 0.005454 | 0.86361 |
| 259312_at | putative RING-H2 zinc finger protein ATL6 similar to GB: AAD33584 from [*Arabidopsis thaliana*]; supported by cDNA: gi_4928402_gb_AF132016.1_AF132016 | At3g05200 | 2.46 | −1.11 | 0.020543 | 0.252889 |
| 267624_at | putative protein kinase | At2g39660 | 2.45 | −1.1 | 0.015362 | 0.313576 |
| 266230_at | hypothetical protein predicted by genscan and genefinder; supported by cDNA: gi_14334729_gb_AY035038.1_ | At2g28830 | 2.45 | 1.03 | 0.03586 | 0.739871 |
| 260656_at | hypothetical protein predicted by genemark.hmm | At1g19380 | 2.45 | 1.12 | 0.012154 | 0.152235 |
| 253664_at | NADPH-ferrihemoprotein reductase (ATR2) | At4g30210 | 2.45 | 1.06 | 0.014893 | 0.463357 |
| 251259_at | putative protein phosphoprotein phosphatase (EC 3.1.3.16) 1A-alpha-*Homo sapiens*, PIR: S22423; supported by full-length cDNA: Ceres: 20050. | At3g62260 | 2.45 | 1.09 | 0.008555 | 0.495561 |
| 267357_at | putative nematode-resistance protein; supported by full-length cDNA: Ceres: 35056. | At2g40000 | 2.44 | 1.16 | 0.031618 | 0.266241 |
| 254521_at | putative protein similar to unknown protein (gb\|AAC79139.1) | At5g44810 | 2.44 | −1.09 | 0.041638 | 0.416086 |
| 263419_at | putative protein kinase contains a protein kinase domain profile (PDOC00100); supported by full-length cDNA: Ceres: 13257. | At2g17220 | 2.43 | 1.09 | 0.008341 | 0.27009 |
| 253323_at | putative protein protein phosphatase Wip1, *Homo sapiens*, PID: g2218063; supported by full-length cDNA: Ceres: 40123. | At4g33920 | 2.43 | −1.13 | 0.025096 | 0.456412 |
| 258983_at | putative aminotransferase similar to beta-alanine-pyruvate aminotransferase GB: BAA19549 [*Rattus norvegicus*], alanine-glyoxylate aminotransferase GB: Q64565 [*Rattus norvegicus*]; Pfam HMM hit: Aminotransferases class-III pyridoxal-phosphate | At3g08860 | 2.42 | 1.14 | 0.006331 | 0.051755 |
| 249583_at | CALMODULIN-RELATED PROTEIN 2, TOUCH-INDUCED (TCH2); supported by full-length cDNA: Ceres: 25475. | At5g37770 | 2.42 | −1.17 | 0.006305 | 0.208762 |
| 258046_at | MAP kinase kinase 5 identical to GB: BAA28831 from [*Arabidopsis thaliana*]; supported by cDNA: gi_3219272_dbj_AB015316.1_AB015316 | At3g21220 | 2.41 | 1.13 | 0.013633 | 0.416118 |
| 250990_at | serine/threonine-specific protein kinase NAK; supported by full-length cDNA: Ceres: 27477. | At5g02290 | 2.41 | −1.12 | 0.012886 | 0.320809 |
| 249423_at | Expressed protein; supported by full-length cDNA: Ceres: 118847. | At5g39785 | 2.41 | −1.13 | 0.026115 | 0.657212 |
| 248814_at | putative protein similar to unknown protein (pir\|T06699) | At5g46910 | 2.4 | −1.03 | 0.007949 | 0.787827 |
| 254204_at | putative protein CGI-58 protein-*Homo sapiens*, PID: g4929585 | At4g24160 | 2.38 | −1.04 | 0.010591 | 0.590709 |
| 252485_at | disease resistance protein RPP13-like protein disease resistance protein RPP8-*Arabidopsis thaliana*, EMBL: AF089710; supported by cDNA: gi_14334999_gb_AY037179.1_ | At3g46530 | 2.37 | −1.05 | 0.012107 | 0.677972 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 265620_at | unknown protein | At2g27310 | 2.35 | −1.2 | 0.049206 | 0.345125 |
| 264756_at | receptor protein kinase (IRK1), putative similar to receptor protein kinase (IRK1) GI: 836953 from [*Ipomoea trifida*] | At1g61370 | 2.35 | −1.07 | 0.010494 | 0.634376 |
| 266993_at | nodulin-like protein; supported by cDNA: gi_16930478_gb_AF419593.1_AF419593 | At2g39210 | 2.33 | 1.12 | 0.017636 | 0.371447 |
| 256735_at | hypothetical protein predicted by genemark.hmm | At3g29400 | 2.33 | −1.12 | 0.006192 | 0.192654 |
| 256425_at | disease resistance protein, putative similar to disease resistance protein RPP1-WsB GB: BAB01321 GI: 9279731 from (*Arabidopsis thaliana*) | At1g33560 | 2.33 | 1.04 | 0.010206 | 0.488005 |
| 250829_at | disease resistance-like protein rpp8, *Arabidopsis thaliana*, EMBL: AF089711; supported by cDNA: gi_15292720_gb_AY050794.1_ | At5g04720 | 2.33 | −1.08 | 0.013721 | 0.38143 |
| 248698_at | receptor-like protein kinase; supported by cDNA: gi_13605826_gb_AF367312.1_AF367312 | At5g48380 | 2.33 | 1.13 | 0.021685 | 0.326459 |
| 247594_at | putative protein farnesylated protein GMFP5, *Glycine max*, EMBL: U64916 | At5g60800 | 2.33 | 1.37 | 0.027382 | 0.054007 |
| 266166_at | putative glucosyltransferase; supported by full-length cDNA: Ceres: 13761. | At2g28080 | 2.32 | −1.05 | 0.018474 | 0.764619 |
| 262745_at | lipase, putative contains Pfam profile: PF00657 Lipase/Acylhydrolase with GDSL-like motif; supported by full-length cDNA: Ceres: 37307. | At1g28600 | 2.32 | −1.12 | 0.015545 | 0.267784 |
| 257407_at | unknown protein | At1g27100 | 2.32 | −1.19 | 0.009875 | 0.068971 |
| 258282_at | unknown protein | At3g26910 | 2.31 | 1.14 | 0.003241 | 0.168885 |
| 252373_at | disease resistance protein EDS1; supported by cDNA: gi_15028150_gb_AY046025.1_ | At3g48090 | 2.31 | −1.07 | 0.011996 | 0.442811 |
| 250956_at | putative protein | At5g03210 | 2.31 | −1.02 | 0.03092 | 0.993512 |
| 248851_s_at | disease resistance protein-like; supported by cDNA: gi_16323098_gb_AY057653.1_ | At5g46490 | 2.3 | 1.09 | 0.009234 | 0.638209 |
| 254924_at | MAP kinase (ATMPK5) possible internal deletion at position 161, missing one A residue; reference GI: 457401; supported by cDNA: gi_457401_dbj_D21841.1_ATHATMPK5 | At4g11330 | 2.29 | −1.14 | 0.010478 | 0.330061 |
| 250279_at | ABA-responsive protein-like ABA-responsive protein, *Hordeum vulgare*, EMBL: AF026538 | At5g13200 | 2.29 | −1.11 | 0.021853 | 0.295383 |
| 263221_at | UDP-galactose 4-epimerase-like protein similar to proteins from many bacterial species including [*Bacillus subtilis*] and [*Methanobacterium thermoautotrophicum*] | At1g30620 | 2.28 | 1.23 | 0.015145 | 0.343241 |
| 261718_at | wall-associated kinase, putative similar to wall-associated kinase 2 GB: CAB42872 GI: 4826399 from [*Arabidopsis thaliana*] | At1g18390 | 2.28 | 1.07 | 0.008635 | 0.505026 |
| 250398_at | putative protein predicted proteins, *Arabidopsis thaliana*; supported by full-length cDNA: Ceres: 263168. | At5g11000 | 2.28 | 1.16 | 0.012015 | 0.299864 |
| 256922_at | hypothetical protein contains similarity to flavonol synthase (FLS) GB: Q41452 from [*Solanum tuberosum*], contains Pfam profile: PF00671 Iron/Ascorbate oxidoreductase family; supported by full-length cDNA: Ceres: 41506. | At3g19010 | 2.27 | −1.04 | 0.029488 | 0.80973 |
| 267530_at | putative receptor-like protein kinase | At2g41890 | 2.26 | −1.11 | 0.028311 | 0.389366 |
| 256627_at | unknown protein; supported by cDNA: gi_14532501_gb_AY039875.1_ | At3g19970 | 2.26 | 1.05 | 0.015238 | 0.715164 |
| 255880_at | hypothetical protein predicted by genscan+ | At1g67060 | 2.26 | −1.01 | 0.015412 | 0.926607 |
| 254660_at | receptor serine/threonine kinase-like protein receptor serine/threonine kinase PR5K, PATCHX: G1235680 | At4g18250 | 2.26 | −1.06 | 0.024187 | 0.802259 |
| 264528_at | hypothetical protein similar to Human XE169 protein (gi\|3033385); similar to EST gb\|T88128 | At1g30810 | 2.25 | 1.03 | 0.00644 | 0.758062 |
| 257784_at | geranylgeranylated protein, putative similar to ATGP4 GB: AAD00115 from [*Arabidopsis thaliana*] | At3g26970 | 2.25 | 1.17 | 0.00182 | 0.287058 |
| 255344_s_at | putative receptor-like protein kinase | At4g04540 | 2.25 | 1.01 | 0.022152 | 0.792265 |
| 255080_at | arabinogalactan-protein homolog arabinogalactan-protein-*Arabidopsis thaliana*, PID: g3883126; supported by cDNA: gi_10880496_gb_AF195891.1_AF195891 | At4g09030 | 2.25 | −1.04 | 0.036604 | 0.768432 |
| 259325_at | unknown protein | At3g05320 | 2.24 | −1.15 | 0.016669 | 0.38111 |
| 252851_at | putative protein CLATHRIN COAT ASSEMBLY PROTEIN AP180-*Mus musculus*, SWISSPROT: Q61548; supported by full-length cDNA: Ceres: 8970. | At4g40080 | 2.24 | −1.08 | 0.014274 | 0.543837 |
| 257071_at | unknown protein; supported by cDNA: gi_15810494_gb_AY056286.1_ | At3g28180 | 2.23 | 1.04 | 0.014928 | 0.697835 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 253476_at | S-receptor kinase-like protein serine/threonine-specific protein kinase PK10 precursor, *Oryza sativa*, PIR2: S50767 | At4g32300 | 2.23 | −1.04 | 0.009096 | 0.440827 |
| 254292_at | putative protein | At4g23030 | 2.22 | 1.13 | 0.007331 | 0.570308 |
| 249393_at | disease resistance-like protein resistance gene Cf-4, *Lycopersicon hirsutum*, EMBL: LHJ002235 | At5g40170 | 2.22 | −1.04 | 0.016127 | 0.647441 |
| 249320_at | disease resistance protein-like non-consensus TT donor splice site at exon 1 | At5g40910 | 2.22 | 1.13 | 0.049144 | 0.285783 |
| 246327_at | receptor-like serine/threonine kinase, putative similar to receptor-like serine/threonine kinase GI: 2465923 from [*Arabidopsis thaliana*]; supported by cDNA: gi_16649102_gb_AY059921.1_ | At1g16670 | 2.22 | 1.02 | 0.008469 | 0.775987 |
| 267537_at | putative guanylate kinase; supported by cDNA: gi_7861794_gb_AF204675.1_AF204675 | At2g41880 | 2.21 | −1.02 | 0.012268 | 0.883883 |
| 251987_at | CYTOCHROME P450 71B5; supported by cDNA: gi_3164131_dbj_D78601.1_D78601 | At3g53280 | 2.21 | −1.27 | 0.010305 | 0.155225 |
| 248981_at | regulatory protein NPR1-like; transcription factor inhibitor I kappa B-like | At5g45110 | 2.21 | 1.11 | 0.020899 | 0.556465 |
| 265611_at | unknown protein; supported by full-length cDNA: Ceres: 10730. | At2g25510 | 2.2 | −1.04 | 0.010382 | 0.533642 |
| 259071_at | unknown protein similar to hin1 GB: CAA68848 [*Nicotiana tabacum*]; supported by cDNA: gi_9502173_gb_AF264698.1_AF264698 | At3g11650 | 2.2 | −1.02 | 0.008823 | 0.776008 |
| 249029_at | disease resistance protein-like | At5g44870 | 2.2 | 1.01 | 0.033247 | 0.925701 |
| 265648_at | putative beta-1,3-glucanase; supported by full-length cDNA: Ceres: 1126. | At2g27500 | 2.19 | −1.07 | 0.015702 | 0.521836 |
| 252921_at | putative protein DNA damage-inducible protein-*Synechocystis* sp., PIR2: S77364 | At4g39030 | 2.19 | 1.57 | 0.026714 | 0.071711 |
| 266749_at | putative protein kinase contains a protein kinase domain profile (PDOC00100) | At2g47060 | 2.18 | −1.05 | 0.013372 | 0.636302 |
| 266231_at | putative protein kinase | At2g02220 | 2.18 | −1.01 | 0.008538 | 0.969684 |
| 254878_at | heat shock transcription factor-like protein heat shock transcription factor HSF29, *Glycine max*, PIR2: S59541 | At4g11660 | 2.18 | 1.15 | 0.015925 | 0.386918 |
| 258764_at | putative pectinesterase contains similarity to pectinesterase GB: AAB57671 [*Citrus sinensis*] | At3g10720 | 2.17 | −1 | 0.01345 | 0.975443 |
| 266975_at | hypothetical protein predicted by grail | At2g39380 | 2.16 | 1.09 | 0.019477 | 0.60417 |
| 254921_at | putative protein hypothetical protein F16G20.230-*Arabidopsis thaliana*, PIR2: T05391; supported by full-length cDNA: Ceres: 17771. | At4g11300 | 2.16 | −1.01 | 0.016335 | 0.995903 |
| 259937_s_at | putative ABC transporter contains Pfam profile: PF00005 ABC transporter | At1g71330 | 2.14 | 1.25 | 0.009288 | 0.060426 |
| 255524_at | hypothetical protein similar to pectinesterase | At4g02330 | 2.14 | −1.08 | 0.006633 | 0.352183 |
| 250018_at | putative protein similar to unknown protein (emb|CAB87627.1) | At5g18150 | 2.14 | −1.05 | 0.005427 | 0.652846 |
| 249987_at | putative protein predicted proteins, *Arabidopsis thaliana*; supported by full-length cDNA: Ceres: 32414. | At5g18490 | 2.14 | 1.03 | 0.016862 | 0.931777 |
| 265722_at | putative chlorophyll a/b binding protein; supported by full-length cDNA: Ceres: 6454. | At2g40100 | 2.13 | 1.35 | 0.029801 | 0.022089 |
| 262540_at | hypothetical protein predicted by genemark.hmm | At1g34260 | 2.13 | 1.1 | 0.022736 | 0.377889 |
| 264767_at | hypothetical protein similar to putative serine/threonine kinase GI: 4585880 from [*Arabidopsis thaliana*]; supported by full-length cDNA: Ceres: 13461. | At1g61380 | 2.12 | 1.15 | 0.012495 | 0.215443 |
| 251192_at | alpha galactosyltransferase-like protein alpha galactosyltransferase-*Trigonella foenum-graecum*, EMBL: TFO245478; supported by cDNA: gi_15983425_gb_AF424587.1_AF424587 | At3g62720 | 2.12 | −1.11 | 0.0119 | 0.381401 |
| 249984_at | putative protein rsc43, *Dictyostelium discoideum*, EMBL: AF011338; supported by full-length cDNA: Ceres: 6084. | At5g18400 | 2.12 | 1.05 | 0.006326 | 0.639984 |
| 249237_at | putative protein similar to unknown protein (sp|P37707); supported by full-length cDNA: Ceres: 6903. | At5g42050 | 2.12 | 1.01 | 0.019097 | 0.90689 |
| 249021_at | putative protein similar to unknown protein (pir||T04881) | At5g44820 | 2.12 | −1.03 | 0.014955 | 0.780757 |
| 266452_at | hypothetical protein predicted by genscan; supported by cDNA: gi_14517475_gb_AY039573.1_ | At2g43320 | 2.11 | 1.01 | 0.010229 | 0.93189 |
| 266168_at | putative protease inhibitor; supported by full-length cDNA: Ceres: 11662. | At2g38870 | 2.11 | 1.07 | 0.011954 | 0.24411 |
| 257264_at | hypothetical protein contains Pfam profile: PF01657 Domain of unknown function; supported by cDNA: gi_14334417_gb_AY034900.1_ | At3g22060 | 2.11 | 1.41 | 0.033325 | 0.224965 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 252133_at | hypothetical protein hypothetical protein-*Arabidopsis thaliana* chromosome 4 AP2 contig, PID: e353223; supported by full-length cDNA: Ceres: 10044. | At3g50900 | 2.11 | −1.16 | 0.048974 | 0.506058 |
| 248230_at | putative protein similar to unknown protein (gb\|AAF34839.1); supported by cDNA: gi_13926341_gb_AF372918.1_AF372918 | At5g53830 | 2.11 | −1.24 | 0.009004 | 0.419028 |
| 247571_at | snap25a; supported by full-length cDNA: Ceres: 14562. | At5g61210 | 2.11 | 1.1 | 0.033279 | 0.210386 |
| 253147_at | protein kinase-like protein serine/threonine-specific protein kinase APK1, *Arabidopsis thaliana*, PIR2: S28615 | At4g35600 | 2.1 | 1.1 | 0.007538 | 0.342113 |
| 252976_s_at | Phospholipase like protein *Arabidopsis thaliana* pEARLI 4 mRNA, PID: g871782 | At4g38550 | 2.1 | 1.02 | 0.005166 | 0.820109 |
| 260975_at | receptor-like serine/threonine kinase, putative similar to receptor-like serine/threonine kinase GB: AAC50043 GI: 2465923 from [*Arabidopsis thaliana*] | At1g53430 | 2.09 | −1.06 | 0.02462 | 0.698322 |
| 256799_at | unknown protein; supported by cDNA: gi_14190488_gb_AF380644.1_AF380644 | At3g18560 | 2.09 | 1.14 | 0.021195 | 0.61081 |
| 246529_at | serine/threonine-specific protein kinase-like protein serine/threonine-specific protein kinase NPK15-*Nicotiana tabacum*; supported by full-length cDNA: Ceres: 25636. | At5g15730 | 2.09 | 1.07 | 0.010794 | 0.454295 |
| 245731_at | MAP kinase, putative similar to MAP kinase kinase 5 GI: 3219273 from [*Arabidopsis thaliana*]; supported by full-length cDNA: Ceres: 112118. | At1g73500 | 2.09 | −1.17 | 0.002926 | 0.06007 |
| 257785_at | geranylgeranylated protein, putative similar to ATGP4 GB: AAD00115 from [*Arabidopsis thaliana*] | At3g26980 | 2.08 | 1.12 | 0.027564 | 0.130143 |
| 251248_at | P-glycoprotein-like proetin P-glycoprotein-2-*Arabidopsis thaliana*, EMBL: Y10228 | At3g62150 | 2.08 | 1.18 | 0.006349 | 0.219814 |
| 264841_at | putative protein kinase similar to (Z71703), cdc2-like protein kinase; similar to ESTs gb\|T20748, gb\|T20464, and emb\|Z17761; supported by cDNA: gi_14532735_gi_13430451 | At1g03740 | 2.07 | 1.03 | 0.009533 | 0.802311 |
| 262360_at | receptor protein kinase, putative similar to receptor protein kinase GI: 1389566 from [*Arabidopsis thaliana*] | At1g73080 | 2.07 | 1.07 | 0.049706 | 0.387954 |
| 249705_at | serine/threonine protein kinase-like | At5g35580 | 2.07 | 1.06 | 0.02776 | 0.584833 |
| 259876_at | putative DnaJ protein similar to dnaJ-like protein GB: CAA72705 [*Arabidopsis thaliana*]; Pfam HMM hit: DnaJ, prokaryotic heat shock protein | At1g76700 | 2.06 | 1.04 | 0.040672 | 0.74219 |
| 266316_at | unknown protein; supported by cDNA: gi_15450380_gb_AY052291.1_ | At2g27080 | 2.05 | 1.1 | 0.008877 | 0.282687 |
| 262183_at | unknown protein | At1g77900 | 2.05 | 1.11 | 0.020307 | 0.383917 |
| 260345_at | receptor protein kinase, putative similar to receptor protein kinase GI: 1389566 from (*Arabidopsis thaliana*); supported by cDNA: gi_4204848_gb_U55875.1_ATU55875 | At1g69270 | 2.05 | −1.16 | 0.02512 | 0.233028 |
| 260635_at | unknown protein | At1g62420 | 2.04 | −1.19 | 0.00958 | 0.160716 |
| 253780_at | protein phosphatase 2C-like protein protein phosphatase 2C-fission yeast, PIR2: S54297; supported by cDNA: gi_16604584_gb_AY059737.1_ | At4g28400 | 2.04 | 1.02 | 0.049077 | 0.837741 |
| 251218_at | CP12 protein precursor-like protein CP12 protein precursor, chloroplast-*Pisum sativum*, PIR: T06562; supported by full-length cDNA: Ceres: 2721. | At3g62410 | 2.04 | 1.05 | 0.005991 | 0.528908 |
| 245641_at | Expressed protein; supported by full-length cDNA: Ceres: 118770. | At1g25370 | 2.04 | −1.04 | 0.0479 | 0.829103 |
| 263915_at | hypothetical protein predicted by genscan and genefinder | At2g36430 | 2.03 | −1.26 | 0.020455 | 0.076673 |
| 254508_at | putative protein gene F4P9.34 chromosome II BAC F4P9, *Arabidopsis thaliana* | At4g20170 | 2.03 | −1.03 | 0.032001 | 0.79323 |
| 253292_at | Expressed protein; supported by full-length cDNA: Ceres: 9341. | At4g33985 | 2.03 | −1.02 | 0.00638 | 0.87138 |
| 265772_at | putative protein kinase contains a protein kinase domain profile (PDOC00100); supported by cDNA: gi_14335115_gb_AY037237.1_ | At2g48010 | 2.02 | 1.04 | 0.012695 | 0.802318 |
| 265375_at | unknown protein; supported by full-length cDNA: Ceres: 91878. | At2g06530 | 2.02 | 1.08 | 0.015552 | 0.48528 |
| 265208_at | putative giberellin beta-hydroxylase contains similarities to GA beta-20-hydroxylase from tobacco (GB: 3327245) and to ethylene forming enzyme from *Picea glauca* (GB: L42466) | At2g36690 | 2.01 | −1.35 | 0.006868 | 0.034666 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 264746_at | unknown protein similar to putative DNA-binding protein GI: 7268215 from [Arabidopsis thaliana]; supported by cDNA: gi_12658409_gb_AF331712.1_AF331712 | At1g62300 | 2.01 | 1.04 | 0.035415 | 0.469191 |
| 260312_at | putative disease resistance protein similar to disease resistance protein RPP1-WsC GB: AAC72979 [Arabidopsis thaliana] | At1g63880 | 2.01 | −1.17 | 0.018521 | 0.24588 |
| 258173_at | putative protein kinase similar to serine/threonine protein kinase Pto GB: AAB47421 [Lycopersicon esculentum] (Plant Cell 9 (1), 61-73 (1997)) | At3g21630 | 2.01 | 1.07 | 0.010988 | 0.529339 |
| 247617_at | receptor like protein kinase receptor like protein kinase, Arabidopsis thaliana, PIR: T47484 | At5g60270 | 2 | −1.35 | 0.002662 | 0.065021 |
| 259213_at | putative receptor ser/thr protein kinase similar to receptor kinase GB: S70769 [Arabidopsis thaliana]; supported by full-length cDNA: Ceres: 124301. | At3g09010 | 1.99 | 1.14 | 0.025161 | 0.261501 |
| 258544_at | disease resistance gene (RPM1) identical to disease resistance gene (RPM1) GB: X87851 [Arabidopsis thaliana] | At3g07040 | 1.99 | −1.35 | 0.036667 | 0.073823 |
| 249777_at | putative protein similar to unknown protein (gb AAD29063.1) | At5g24210 | 1.99 | −1.11 | 0.022053 | 0.175713 |
| 249208_at | allene oxide synthase (emb CAA73184.1); supported by cDNA: gi_6002956_gb_AF172727.1_AF172727 | At5g42650 | 1.99 | 1.18 | 0.018657 | 0.090962 |
| 248014_at | putative protein similar to unknown protein (pir\|\|T05064) | At5g56340 | 1.99 | −1.05 | 0.045301 | 0.723728 |
| 264223_s_at | receptor kinase, putative similar to receptor kinase 1 GI: 9294449 from [Arabidopsis thaliana] | At1g67520 | 1.98 | 1.1 | 0.021718 | 0.628018 |
| 262082_s_at | wall-associated kinase 2, putative similar to receptor-like serine/threonine kinase GB: AAC50043 GI: 2465923 from [Arabidopsis thaliana] | At1g56120 | 1.98 | 1.12 | 0.030141 | 0.183617 |
| 249835_s_at | putative protein similar to unknown protein (gb AAF01580.1) | At5g23510 | 1.98 | −1.08 | 0.01545 | 0.400133 |
| 245051_at | putative WRKY-type DNA-binding protein; supported by cDNA: gi_13506742_gb_AF224704.1_AF224704 | At2g23320 | 1.98 | 1.19 | 0.009782 | 0.0756 |
| 264351_at | unknown protein Contains similarity to gb\|AB011110 KIAA0538 protein from Homo sapiens brain and to phospholipid-binding domain C2 PF\|00168. ESTs gb\|AA585988 and gb\|T04384 come from this gene | At1g03370 | 1.97 | 1.02 | 0.026436 | 0.91627 |
| 262926_s_at | receptor kinase, putative similar to receptor kinase 1 [Brassica rapa] GB: BAA23676 | At1g65790 | 1.97 | −1.11 | 0.021308 | 0.451766 |
| 253326_at | putative protein polygalacturonase(EC 3.2.1.15) precursor-Erwinia carotovora, PID: g42330 | At4g33440 | 1.97 | −1.05 | 0.019179 | 0.7895 |
| 246305_at | putative protein protein At2g40060-Arabidopsis thaliana, EMBL: AF002109; supported by full-length cDNA: Ceres: 93427. | At3g51890 | 1.97 | 1.2 | 0.016172 | 0.125232 |
| 245219_at | viral resistance protein, putative similar to viral resistance protein GI: 7110565 from [Arabidopsis thaliana] | At1g59124 | 1.97 | −1.03 | 0.010527 | 0.805754 |
| 267393_at | similar to axi 1 protein from Nicotiana tabacum | At2g44500 | 1.96 | −1.24 | 0.025881 | 0.212221 |
| 259109_at | putative serine threonine protein phosphatase type one similar to GB: AAC39461 | At3g05580 | 1.96 | 1.08 | 0.029112 | 0.485226 |
| 252037_at | putative calmodulin calmodulin-Tetrahymena pyriformis (SGC5), PIR1: MCTE; supported by cDNA: gi_14190470_gb_AF380635.1_AF380635 | At3g51920 | 1.96 | 1.1 | 0.015438 | 0.170162 |
| 258176_at | B regulatory subunit of PP2A, putative similar to B regulatory subunit of PP2A GB: AAB58902 [Arabidopsis thaliana] | At3g21650 | 1.95 | −1.17 | 0.03792 | 0.249846 |
| 256169_at | receptor protein kinase, putative contains Pfam profiles: PF00069: Eukaryotic protein kinase domain, multiple PF00560: Leucine Rich Repeat | At1g51800 | 1.95 | 1.2 | 0.02536 | 0.076434 |
| 260974_at | receptor-like serine/threonine kinase, putative similar to receptor-like serine/threonine kinase GB: AAC50043 GI: 2465923 from [Arabidopsis thaliana] | At1g53440 | 1.94 | −1.02 | 0.009705 | 0.677274 |
| 252310_at | GTPase activating-like protein GTPase activating protein gyp7, Yarrowia lipolytica, EMBL: YLGYP7 | At3g49350 | 1.94 | −1 | 0.026703 | 0.921316 |
| 251790_at | elicitor responsive/phloem-like protein FIERG2 protein, Oryza sativa, PIR: T04363 | At3g55470 | 1.94 | 1.05 | 0.012047 | 0.64204 |
| 249480_s_at | protein kinase-like protein receptor-like protein kinase (EC 2.7.1.—) precursor, Madagascar periwinkle, PIR: T10060 | At5g38990 | 1.94 | −1.2 | 0.019593 | 0.193368 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 249364_at | putative protein predicted protein, *Arabidopsis thaliana* | At5g40590 | 1.94 | −1.06 | 0.023463 | 0.5486 |
| 265385_at | putative diacylglycerol kinase; supported by full-length cDNA: Ceres: 15863. | At2g20900 | 1.93 | 1.03 | 0.02312 | 0.814052 |
| 264580_at | unknown protein EST gb|ATTS0295 comes from this gene; supported by full-length cDNA: Ceres: 20380. | At1g05340 | 1.93 | 1.37 | 0.011774 | 0.077989 |
| 258608_at | unknown protein; supported by full-length cDNA: Ceres: 35949. | At3g03020 | 1.93 | 1.12 | 0.001615 | 0.228742 |
| 262868_at | unknown protein | At1g64980 | 1.92 | 1.03 | 0.010064 | 0.758096 |
| 260255_at | putative protein kinase similar to p58 protein kinase GB: AAB59449 (*Homo sapiens*); contains Pfam profile: PF00069 Eukaryotic protein kinase domain | At1g74330 | 1.92 | −1.02 | 0.036098 | 0.867257 |
| 257902_at | receptor kinase, putative similar to receptor kinase GB: AAD02501 from [*Arabidopsis thaliana*] | At3g28450 | 1.92 | 1.01 | 0.015158 | 0.903391 |
| 254211_at | phosphatase like protein phosphoprotein phosphatase (EC 3.1.3.16) PPT-rat | At4g23570 | 1.92 | 1.08 | 0.021478 | 0.429462 |
| 252009_at | zinc finger-like protein zinc finger protein 216, *Homo sapiens*, EMBL: AF062072; supported by cDNA: gi_14596166_gb_AY042871.1_ | At3g52800 | 1.92 | 1.01 | 0.025834 | 0.996803 |
| 265460_at | putative caltractin; supported by full-length cDNA: Ceres: 7802. | At2g46600 | 1.91 | −1.28 | 0.011693 | 0.060574 |
| 262455_at | Mlo protein, putative similar to Mlo protein GB: Z83834 GI: 1877220 from [*Hordeum vulgare*]; supported by full-length cDNA: Ceres: 259664. | At1g11310 | 1.91 | −1 | 0.011858 | 0.991742 |
| 262119_s_at | glutathione S-transferase, putative similar to glutathione S-transferase GI: 860955 from [*Hyoscyamus muticus*]; supported by cDNA: gi_15215607_gb_AY050332.1_ | At1g02930 | 1.91 | 1.13 | 0.011514 | 0.130465 |
| 257700_at | unknown protein similar to unknown protein GB: AAD25612 from [*Arabidopsis thaliana*]; supported by full-length cDNA: Ceres: 37019. | At3g12740 | 1.91 | 1.12 | 0.011076 | 0.18275 |
| 253534_at | cytochrome P450 monooxygenase; supported by full-length cDNA: Ceres: 13745. | At4g31500 | 1.91 | 1.1 | 0.008445 | 0.216603 |
| 248873_at | disease resistance protein-like | At5g46450 | 1.91 | 1.04 | 0.019311 | 0.616452 |
| 251071_at | putative protein receptor protein kinases | At5g01950 | 1.89 | −1.02 | 0.019672 | 0.77446 |
| 250419_at | RPP1 disease resistance protein-like disease resistance protein RPP1-WsC, *Arabidopsis thaliana*, EMBL: AF098964 | At5g11250 | 1.89 | −1.16 | 0.007043 | 0.23803 |
| 246018_at | Expressed protein; supported by full-length cDNA: Ceres: 103171. | At5g10695 | 1.88 | 1.11 | 0.007166 | 0.390262 |
| 245151_at | putative pectinesterase; supported by full-length cDNA: Ceres: 111254. | At2g47550 | 1.88 | 1.02 | 0.027515 | 0.828056 |
| 265499_at | putative glucosyltransferase | At2g15480 | 1.87 | −1.11 | 0.043677 | 0.508495 |
| 263797_at | putative WRKY-type DNA binding protein; supported by cDNA: gi_15991743_gb_AF425836.1_AF425836 | At2g24570 | 1.87 | 1.08 | 0.018452 | 0.267205 |
| 263731_at | metalloproteinase, putative similar to metalloproteinase GI: 3128477 from [*Arabidopsis thaliana*] | At1g59970 | 1.87 | −1.03 | 0.019632 | 0.713464 |
| 252076_at | LS1-like protein AT-LS1 product-*Arabidopsis thaliana*, EMBL: X58827; supported by full-length cDNA: Ceres: 107294. | At3g51660 | 1.87 | 1.38 | 0.021217 | 0.088589 |
| 258460_at | unknown protein | At3g17330 | 1.86 | 1.07 | 0.005904 | 0.601401 |
| 245254_at | ATP-sulfurylase; supported by cDNA: gi_459143_gb_U06275.1_ATU06275 | At4g14680 | 1.86 | −1.38 | 0.031698 | 0.050397 |
| 266536_at | hypothetical protein predicted by genefinder; supported by cDNA: gi_14532491_gb_AY039870.1_ | At2g16900 | 1.85 | −1.07 | 0.006846 | 0.487008 |
| 265479_at | hypothetical protein; supported by full-length cDNA: Ceres: 5. | At2g15760 | 1.85 | −1.04 | 0.048838 | 0.747296 |
| 262873_at | hypothetical protein predicted by genemark.hmm | At1g64700 | 1.85 | 1.2 | 0.006355 | 0.233681 |
| 258207_at | putative GTP pyrophosphokinase similar to GTP PYROPHOSPHOKINASE GB: O87331 from [*Corynebacterium glutamicum*]; supported by cDNA: gi_7141305_gb_AF225703.1_AF225703 | At3g14050 | 1.85 | −1.03 | 0.021111 | 0.736124 |
| 267335_s_at | putative beta-1,3-glucanase | At2g19440 | 1.84 | −1.28 | 0.025894 | 0.194876 |
| 245218_s_at | viral resistance protein, putative, 5 partial similar to viral resistance protein GI: 7110565 from [*Arabidopsis thaliana*] | At1g58842 | 1.84 | −1.02 | 0.034348 | 0.880456 |
| 264082_at | unknown protein; supported by full-length cDNA: Ceres: 36244. | At2g28570 | 1.83 | 1.16 | 0.032702 | 0.469306 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 260037_at | putative DNA-binding protein (RAV2-like) identical to residues 34-352 of RAV2 GB: BAA34251 (*Arabidopsis thaliana*); supported by full-length cDNA: Ceres: 19561. | At1g68840 | 1.83 | −1.21 | 0.029408 | 0.263089 |
| 258134_at | rubisco expression protein, putative similar to GB: O22034 from [*Cyanidium caldarium*] (J. Plant Res. 110, 235-245 (1997)); supported by full-length cDNA: Ceres: 148454. | At3g24530 | 1.83 | 1.06 | 0.014418 | 0.42968 |
| 260314_at | unknown protein similar to putative protein GB: CAA20468 [*Arabidopsis thaliana*] | At1g63830 | 1.82 | −1.01 | 0.00932 | 0.923314 |
| 258956_at | hypothetical protein predicted by genscan+; supported by full-length cDNA: Ceres: 13653. | At3g01440 | 1.82 | −1.19 | 0.013406 | 0.260869 |
| 262649_at | unknown protein contains similarity to xenotropic and polytropic retrovirus receptor GB: 4759334 | At1g14040 | 1.81 | 1.05 | 0.009938 | 0.587887 |
| 257972_at | putative protein kinase, ATN1 almost identical (1 amino acid) to GB: S61766 from [*Arabidopsis thaliana*]; supported by cDNA: gi_16604327_gb_AY058062.1_ | At3g27560 | 1.81 | −1.04 | 0.029115 | 0.724347 |
| 250575_at | putative protein | At5g08240 | 1.81 | 1.08 | 0.022224 | 0.516011 |
| 259826_at | arm repeat-containing protein, putative similar to GI: 2558938 from [*Brassica napus*] (Proc. Natl. Acad. Sci. U.S.A. 95 (1), 382-387 (1998)) | At1g29340 | 1.8 | 1.01 | 0.02957 | 0.88125 |
| 253364_at | F-box protein family, AtFBX13 cotains similarity to fimbriata GI: 547307 from [*Antirrhinum majus*] | At4g33160 | 1.8 | 1.01 | 0.015511 | 0.924255 |
| 248895_at | receptor protein kinase | At5g46330 | 1.8 | −1.03 | 0.014527 | 0.815519 |
| 263457_at | unknown protein | At2g22300 | 1.79 | 1.05 | 0.018298 | 0.6555 |
| 254553_at | TMV resistance protein N-like TMV resistance protein N, *Nicotiana glutinosa*, PIR2: A54810 | At4g19530 | 1.79 | −1.02 | 0.024648 | 0.800063 |
| 254331_s_at | cytochrome P450-like protein flavonoid 3,5-hydroxylase Hf1, *Petunia x hybrida*, PIR2: S38985 | At4g22710 | 1.79 | 1.04 | 0.011357 | 0.507737 |
| 245838_at | disease resistance protein, putative similar to disease resistance protein RPP8 GI: 8843900 from [*Arabidopsis thaliana*] | At1g58410 | 1.79 | 1.04 | 0.045241 | 0.800057 |
| 267392_at | putative beta-glucosidase | At2g44490 | 1.78 | −1.01 | 0.01293 | 0.768374 |
| 264879_at | cotton fiber expressed protein, putative similar to cotton fiber expressed protein 1 GI: 3264828 from [*Gossypium hirsutum*] | At1g61260 | 1.78 | −1.08 | 0.020899 | 0.6028 |
| 251804_at | beta-1,3-glucanase-like protein probable beta-1,3-glucanase, *Triticum aestivum*, PIR: T06268; supported by full-length cDNA: Ceres: 8980. | At3g55430 | 1.78 | −1.02 | 0.033278 | 0.91732 |
| 249314_at | receptor kinase-like protein | At5g41180 | 1.78 | 1.15 | 0.034221 | 0.348074 |
| 245456_at | disease resistance RPP5 like protein | At4g16950 | 1.78 | −1.02 | 0.014799 | 0.787739 |
| 267169_at | putative oxidoreductase | At2g37540 | 1.77 | 1.01 | 0.020016 | 0.912423 |
| 265079_at | hypothetical protein contains similarity to zinc finger protein rts2 GB: U16133 GI: 563244 from [*Saccharomyces cerevisiae*]; supported by cDNA: gi_13430439_gb_AF360132.1_AF360132 | At1g55460 | 1.76 | −1.02 | 0.015429 | 0.82749 |
| 259230_at | unknown protein; supported by cDNA: gi_15028084_gb_AY045899.1_ | At3g07780 | 1.76 | 1.13 | 0.012523 | 0.041915 |
| 250850_at | putative protein; supported by cDNA: gi_13605828_gb_AF367313.1_AF367313 | At5g04550 | 1.76 | −1.14 | 0.015093 | 0.108003 |
| 261506_at | choline kinase, putative similar to CHOLINE/ETHANOLAMINE KINASE GB: Q9Y259 from [*Homo sapiens*] | At1g71697 | 1.75 | 1.03 | 0.033638 | 0.818348 |
| 251028_at | putative protein putative hydrolase At2g32150-*Arabidopsis thaliana*, EMBL: AC006223; supported by full-length cDNA: Ceres: 36724. | At5g02230 | 1.75 | −1.06 | 0.019924 | 0.548891 |
| 258336_at | putative ethylene-inducible protein similar to ethylene-inducible protein GB: M88254 from [*Hevea brasiliensis*]; supported by cDNA: gi_4103951_gb_AF029980.1_AF029980 | At3g16050 | 1.74 | 1.13 | 0.019656 | 0.136759 |
| 253415_at | putative protein peptidyl-prolyl cis-trans isomerase, *Schizosaccharomyces pombe*, gb: SPBC16H5 | At4g33060 | 1.74 | 1.15 | 0.022933 | 0.090678 |
| 251643_at | guanylate kinase-like protein guanylate kinase-*Mus musculus*, TREMBL: MMU53514_1; supported by cDNA: gi_7861797_gb_AF204676.1_AF204676 | At3g57550 | 1.74 | 1.12 | 0.014659 | 0.125227 |
| 247384_at | protein kinase; supported by cDNA: gi_16974578_gb_AY060555.1_ | At5g63370 | 1.74 | 1.11 | 0.010852 | 0.400409 |
| 265269_at | hypothetical protein predicted by genscan | At2g42950 | 1.72 | 1.09 | 0.017878 | 0.365888 |
| 262571_at | hypothetical protein predicted by genscan+; supported by cDNA: gi_15293248_gb_AY051058.1_ | At1g15430 | 1.72 | 1.12 | 0.022912 | 0.305054 |
| 259466_at | response regulator 5, putative similar to response regulator 5 GI: 3953599 from [*Arabidopsis thaliana*]; | At1g19050 | 1.72 | −1.03 | 0.026729 | 0.64387 |

TABLE 3-continued

Genes that are Responsive to chitooctaose in Wild-type

| Probe set | Annotation | Accession | WT FC | Mu FC | WT P | Mu P |
|---|---|---|---|---|---|---|
| | supported by cDNA: gi_3953602_dbj_AB008490.1_AB008490 | | | | | |
| 254723_at | ammonium transport protein (AMT1); supported by cDNA: gi_14335079_gb_AY037219.1_ | At4g13510 | 1.72 | 1.08 | 0.011754 | 0.406577 |
| 253193_at | putative protein SEC7 protein, *Saccharomyces cerevisiae*, PIR2: S49764 | At4g35380 | 1.72 | 1.12 | 0.019937 | 0.504827 |
| 265461_at | unknown protein similarity to ubiquitin family of proteins; supported by cDNA: gi_16930424_gb_AF419566.1_AF419566 | At2g46500 | 1.71 | 1.18 | 0.019691 | 0.111325 |
| 253614_at | putative protein heat shock protein 101-*Triticum aestivum*, PID: g4558484 | At4g30350 | 1.71 | −1.07 | 0.030479 | 0.677967 |
| 247816_at | similar to unknown protein (pir\|S75584); supported by full-length cDNA: Ceres: 3488. | At5g58260 | 1.71 | −1.12 | 0.011236 | 0.191707 |
| 262457_at | hypothetical protein similar to hypothetical protein GB: CAB36801 GI: 4455265 from [*Arabidopsis thaliana*]; supported by full-length cDNA: Ceres: 40975. | At1g11200 | 1.7 | −1.03 | 0.017609 | 0.719233 |
| 255512_at | Expressed protein; supported by cDNA: gi_5059351_gb_AF154574.1_AF154574 | At4g02195 | 1.69 | 1.06 | 0.014636 | 0.692316 |
| 251516_s_at | putative protein hypothetical protein SPCC320.08-*Schizosaccharomyces pombe*, PIR: T41303 | At3g59310 | 1.69 | −1.06 | 0.017534 | 0.387516 |
| 254103_at | putative protein; supported by full-length cDNA: Ceres: 16463. | At4g25030 | 1.68 | 1.04 | 0.007754 | 0.433098 |
| 245757_at | phosphate-induced (phi-1) protein, putative similar to phi-1 GB: BAA33810 GI: 3759184 from [*Nicotiana tabacum*]; supported by full-length cDNA: Ceres: 118937. | At1g35140 | 1.68 | −1.51 | 0.004633 | 0.081204 |
| 253387_at | P-Protein-like protein P-Protein precursor, *Solanum tuberosum*, gb: Z99770; supported by cDNA: gi_14596024_gb_AY042800.1_ | At4g33010 | 1.66 | 1.04 | 0.019086 | 0.463263 |
| 247272_at | GTP cyclohydrolase II; 3,4-dihydroxy-2-butanone-4-phoshate synthase (emb\|CAA03884.1) supported by cDNA: gi_940382_dbj_D45165.1_ATHGTPCII | At5g64300 | 1.66 | 1 | 0.011375 | 0.888475 |
| 261788_at | unknown protein; supported by full-length cDNA: Ceres: 122986. | At1g15980 | 1.65 | −1.05 | 0.013373 | 0.66035 |
| 249010_at | unknown protein; supported by cDNA: gi_15027902_gb_AY045808.1_ | At5g44580 | 1.65 | 1.05 | 0.008905 | 0.282782 |
| 259074_at | putative protein kinase contains Pfam profile: Eukaryotic protein kinase domain | At3g02130 | 1.63 | −1.03 | 0.007959 | 0.571341 |
| 258394_at | unknown protein; supported by full-length cDNA: Ceres: 15303. | At3g15530 | 1.63 | 1.07 | 0.004284 | 0.548019 |
| 258665_at | thioredoxin-like protein similar to thioredoxin H-type GB: P29448 [*Arabidopsis thaliana*] | At3g08710 | 1.61 | 1.03 | 0.0083 | 0.731007 |
| 253317_at | putative protein | At4g33960 | −1.83 | −1.77 | 0.010341 | 0.022397 |
| 260126_at | putative hydroxymethyltransferase similar to serine hydroxymethyltranferage GB: P50433 from [*Solanum tuberosum*]; supported by full-length cDNA: Ceres: 122515. | At1g36370 | −1.93 | −1.86 | 0.005701 | 0.006964 |
| 246926_at | putative protein | At5g25240 | −2.09 | −2.21 | 0.019603 | 0.017979 |
| 258217_at | unknown protein contains Pfam profile PF00398 Ribosomal RNA adenine dimethylases | At3g17990 | −2.21 | −2.27 | 0.009887 | 0.0037 |
| 258218_at | methyltransferase, putative similar to methyltransferase GB: AAC01738 from [*Amycolatopsis mediterranei*] | At3g18000 | −2.21 | −2.29 | 0.00667 | 0.009294 |
| 254343_at | PRH26 protein; supported by full-length cDNA: Ceres: 36866. | At4g21990 | −2.22 | −1.83 | 0.012838 | 0.031291 |
| 265121_at | similar to flavin-containing monooxygenase (sp\|P36366); similar to ESTs gb\|R30018, gb\|H36886, gb\|N37822, and gb\|T88100 similar to flavin-containing monooxygenase GB: AAA21178 GI: 349534 from [*Oryctolagus cuniculus*]; supported by cDNA: gi_13877746_gb_AF37013 | At1g62560 | −2.37 | −1.87 | 0.020126 | 0.00922 |
| 251039_at | putative protein hypothetical protein T6H20.90-*Arabidopsis thaliana*, EMBL: AL096859; supported by cDNA: gi_16648747_gb_AY058150.1_ | At5g02020 | −3.73 | −1.91 | 0.001899 | 0.021967 |
| 259015_at | unknown protein similar to hypothetical protein GB: AAC17612 [*Arabidopsis thaliana*]; supported by full-length cDNA: Ceres: 251012. | At3g07350 | −3.79 | −1.81 | 0.001762 | 0.010373 |
| 248676_at | putative protein similar to unknown protein (gb\|AAC72543.1) | At5g48850 | −5.55 | −4.23 | 0.003428 | 0.003335 |
| 249752_at | putative protein similar to unknown protein (emb CAB62461.1); supported by full-length cDNA: Ceres: 268701. | At5g24660 | −5.87 | −2.27 | 0.002654 | 0.005949 |
| 246935_at | leucine-rich repeats containing protein grr1-*Glycine max*. EMBL: AF019910 | At5g25350 | −1.64 | −1.09 | 0.01077 | 0.205242 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 261957_at | methionine/cystathionine gamma lyase, putative similar to methionine gamma-lyase GB: CAA04124.1 GI: 2330885 from [*Trichomonas vaginalis*]; supported by cDNA: gi_15450931_gb_AY054546.1_ | At1g64660 | −1.66 | 1.1 | 0.017509 | 0.258584 |
| 263284_at | unknown protein | At2g36100 | −1.68 | 1.21 | 0.009385 | 0.046069 |
| 263064_at | putative bZIP transcription factor contains a bZIP transcription factor basic domain signature (PDOC00036); supported by cDNA: gi_14335073_gb_AY037216.1_ | At2g18160 | −1.68 | −1.04 | 0.003705 | 0.553739 |
| 265102_at | putative peroxidase similar to cationic peroxidase (gi|1232069); similar to EST gb|AI100412; supported by full-length cDNA: Ceres: 123968. | At1g30870 | −1.69 | 1.01 | 0.008534 | 0.760053 |
| 259773_at | auxin-induced protein, putative similar to SP: P33083 from [*Glycine max*] | At1g29500 | −1.69 | 1.03 | 0.017479 | 0.683467 |
| 258181_at | nitrate transporter identical to nitrate transporter GB: CAB38706 [*Arabidopsis thaliana*]; supported by full-length cDNA: Ceres: 111089. | At3g21670 | −1.7 | −1.68 | 0.013713 | 0.025046 |
| 252220_at | putative protein hypothetical protein-*Arabidopsis thaliana*, EMBL: CAB38293; supported by full-length cDNA: Ceres: 17840. | At3g49940 | −1.7 | −1.08 | 0.010242 | 0.277047 |
| 251524_at | 3-isopropylmalate dehydratase-like protein (small subunit) 3-isopropylmalate dehydratase, small subunit-*Thermotoga maritima*, PIR: A72363 | At3g58990 | −1.71 | −1.3 | 0.015617 | 0.116619 |
| 258008_at | putative late embryogenesis abundant protein similar to GB: AAB01570 from [*Picea glauca*] | At3g19430 | −1.72 | 1.26 | 0.007578 | 0.089324 |
| 263227_at | Expressed protein; supported by cDNA: gi_15292976_gb_AY050922.1_ | At1g30750 | −1.73 | 1.1 | 0.00931 | 0.284316 |
| 263118_at | putative 3-methylcrotonyl-CoA carboxylase ESTs gb|H35836, gb|AA651295 and gb|AA721862 come from this gene; supported by cDNA: gi_533706_gb_U12536.1_ATU12536 | At1g03090 | −1.73 | −1.22 | 0.009453 | 0.064506 |
| 248252_at | putative protein similar to unknown protein (emb|CAB71094.1) | At5g53250 | −1.73 | 1.16 | 0.005785 | 0.142465 |
| 256598_at | cytochrome P450 homolog, putative similar to cytochrome P450 homolog GB: U54770 GI: 1421740 from [*Lycopersicon esculentum*]; supported by full-length cDNA: Ceres: 11278. | At3g30180 | −1.74 | 1.01 | 0.019165 | 0.939678 |
| 256062_at | unknown protein; supported by full-length cDNA: Ceres: 28780. | At1g07090 | −1.75 | 1.03 | 0.007971 | 0.599694 |
| 263490_at | F-box protein ORE9, AtFBL7 identical to F-box containing protein ORE9 GI: 15420162 from [*Arabidopsis thaliana*] | At2g42620 | −1.76 | 1.14 | 0.014384 | 0.078788 |
| 247477_at | putative protein 21K protein precursor, *Medicago sativa*, PIR: T09390 | At5g62340 | −1.76 | 1.03 | 0.019734 | 0.869872 |
| 262399_at | unknown protein; supported by full-length cDNA: Ceres: 33047. | At1g49500 | −1.77 | −1.05 | 0.018923 | 0.609256 |
| 259856_at | unknown protein; supported by full-length cDNA: Ceres: 34166. | At1g68440 | −1.77 | −1.41 | 0.017035 | 0.048737 |
| 253510_at | hypothetical protein | At4g31730 | −1.77 | 1.29 | 0.034578 | 0.053073 |
| 251017_at | protein phosphatase-like protein protein phosphatase 2C homolog, *Mesembryanthemum crystallinum*, EMBL: AF097667 | At5g02760 | −1.77 | −1.04 | 0.007317 | 0.502031 |
| 248279_at | putative protein similar to unknown protein (pir||T13959) | At5g52910 | −1.77 | −1.28 | 0.016383 | 0.116964 |
| 266191_at | putative peroxidase | At2g39040 | −1.78 | 1.26 | 0.012061 | 0.114533 |
| 253217_at | actin depolymerizing factor-like protein actin depolymerizing factor1, *Arabidopsis thaliana*, PID: G1408471 | At4g34970 | −1.78 | 1.31 | 0.011164 | 0.086098 |
| 262717_s_at | putative cytochrome P450 similar to gb|AF069494 cytochrome P450 from *Sinapis alba* and is a member of the PF|00067 Cytochrome P450 family. EST gb|F14190 comes from this gene; supported by cDNA: gi_15208670_gb_AY035021.2_ | At1g16410 | −1.79 | −1.32 | 0.016905 | 0.014389 |
| 262517_at | putative glutathione transferase Second of three repeated putative glutathione transferases. 72% identical to glutathione transferase [*Arabidopsis thaliana*] (gi|4006934). Location of ests 191A10T7 (gb|R90188) and 171N13T7 (gb|R65532) | At1g17180 | −1.79 | 1.02 | 0.02066 | 0.906386 |
| 256926_at | hypothetical protein predicted by genemark.hmm | At3g22540 | −1.79 | 1.21 | 0.036851 | 0.289954 |
| 256252_at | glucosyl transferase, putative similar to zeatin O-xylosyltransferase SP: P56725 [*Phaseolus vulgaris* (Kidney bean) (French bean)] | At3g11340 | −1.79 | 1.59 | 0.019921 | 0.01385 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 261226_at | expansin S2 precursor, putative similar to GB: U30460 from [*Cucumis sativus*]; supported by full-length cDNA: Ceres: 11011. | At1g20190 | −1.8 | −1.05 | 0.012655 | 0.608442 |
| 251144_at | anthranilate N-benzoyltransferase-like protein anthranilate N-benzoyltransferase, clove pink, PIR: T10717; supported by cDNA: gi_15912268_gb_AY056412.1_ | At5g01210 | −1.8 | 1.11 | 0.008524 | 0.106988 |
| 265645_at | unknown protein | At2g27370 | −1.81 | 1.1 | 0.025976 | 0.504975 |
| 249923_at | conglutin gamma-like protein conglutin gamma precursor, *Lupinus angustifolius*, PIR: S21426; supported by cDNA: gi_15010797_gb_AY045700.1_ | At5g19120 | −1.81 | −1.05 | 0.007868 | 0.519593 |
| 247914_at | xyloglucan endotransglycosylase | At5g57540 | −1.81 | −1.03 | 0.026871 | 0.814009 |
| 265048_at | jasmonate inducible protein, putative similar to jasmonate inducible protein GI: 9279642 from [*Arabidopsis thaliana*] | At1g52050 | −1.82 | 1.15 | 0.022645 | 0.325821 |
| 252970_at | small auxin up RNA (SAUR-AC1); supported by full-length cDNA: Ceres: 14973. | At4g38850 | −1.82 | 1.19 | 0.007042 | 0.093178 |
| 249862_at | PGPD14 protein; supported by full-length cDNA: Ceres: 41666. | At5g22920 | −1.82 | −1.2 | 0.013335 | 0.024948 |
| 266820_at | putative AP2 domain transcription factor pFAM domain (PF00847)supported by full-length cDNA: Ceres: 31044. | At2g44940 | −1.84 | −1.27 | 0.027529 | 0.279728 |
| 258038_at | unknown protein; supported by full-length cDNA: Ceres: 260109. | At3g21260 | −1.84 | −1.25 | 0.024483 | 0.131574 |
| 252250_at | putative protein predicted protein, *Arabidopsis thaliana* | At3g49790 | −1.85 | −1.2 | 0.011715 | 0.131586 |
| 247337_at | putative protein similar to unknown protein (pir\|\|S51637) | At5g63660 | −1.85 | 1 | 0.021642 | 0.941607 |
| 260167_at | hypothetical protein predicted by genscan+ | At1g71970 | −1.86 | −1.06 | 0.02425 | 0.744455 |
| 257162_s_at | ammonium transporter, putative similar to GB: AAD54638 from [*Arabidopsis thaliana*] (Plant Cell (1999) 11 (5), 937-948) | At3g24290 | −1.86 | −1.03 | 0.01777 | 0.655292 |
| 246275_at | putative protein; supported by full-length cDNA: Ceres: 123997. | At4g36540 | −1.86 | 1.06 | 0.011645 | 0.640095 |
| 245586_at | hypothetical protein | At4g14980 | −1.86 | 1.16 | 0.037731 | 0.349881 |
| 245136_at | putative auxin-regulated protein | At2g45210 | −1.86 | 1.1 | 0.020869 | 0.28948 |
| 262850_at | signal response protein (GAI) identical to GAI GB: CAA75492 GI: 2569938 [*Arabidopsis thaliana*] (Genes Dev. In press); supported by cDNA: gi_16648833_gb_AY058194.1_ | At1g14920 | −1.87 | −1.05 | 0.012647 | 0.589803 |
| 258080_at | unknown protein; supported by full-length cDNA: Ceres: 2767. | At3g25930 | −1.87 | 1.11 | 0.025451 | 0.601329 |
| 253255_at | putative auxin-regulated protein auxin-induced protein X15, *Glycine max*, PIR2: JQ1097; supported by full-length cDNA: Ceres: 10510. | At4g34760 | −1.87 | −1.2 | 0.007683 | 0.154545 |
| 246996_at | putative protein similar to unknown protein (emb\|CAB62102.1); supported by full-length cDNA: Ceres: 40250. | At5g67420 | −1.87 | −1.17 | 0.029109 | 0.184764 |
| 265511_at | putative glycine-rich protein; supported by cDNA: gi_15215617_gb_AY050337.1_ | At2g05540 | −1.88 | −1.36 | 0.004653 | 0.037214 |
| 264957_at | F-box protein family, AtFBL5 contains similarity to F-box protein FBL2 GI: 6063090 from [*Homo sapiens*]; supported by full-length cDNA: Ceres: 3549. | At1g77000 | −1.88 | −1.06 | 0.021505 | 0.577258 |
| 264467_at | unknown protein similar to EST gb\|AA598098; supported by full-length cDNA: Ceres: 23916. | At1g10140 | −1.88 | 1.26 | 0.012415 | 0.023258 |
| 256828_at | unknown protein | At3g22970 | −1.88 | 1.18 | 0.017776 | 0.232803 |
| 248178_at | root cap protein 2-like protein | At5g54370 | −1.88 | 1.29 | 0.00898 | 0.087446 |
| 262396_at | unknown protein; supported by full-length cDNA: Ceres: 95546. | At1g49470 | −1.89 | −1.17 | 0.02115 | 0.065156 |
| 259976_at | hypothetical protein; supported by full-length cDNA: Ceres: 147838. | At1g76560 | −1.89 | −1.22 | 0.011496 | 0.142412 |
| 252834_at | putative protein RING-H2 zinc finger protein ATL6-*Arabidopsis thaliana*, PID: g4928403; supported by cDNA: gi_16930492_gb_AF419600.1_AF419600 | At4g40070 | −1.89 | 1.24 | 0.030751 | 0.235116 |
| 250860_at | amino acid transport-like protein amino acid transport protein AAT1, *Arabidopsis thaliana*, PIR: S51171; supported by full-length cDNA: Ceres: 158156. | At5g04770 | −1.89 | −1.19 | 0.02117 | 0.317647 |
| 265049_at | jasmonate inducible protein, putative similar to jasmonate inducible protein GI: 9279642 from [*Arabidopsis thaliana*] | At1g52060 | −1.9 | 1.31 | 0.010222 | 0.06857 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 265050_at | jasmonate inducible protein, putative similar to jasmonate inducible protein GI: 9279641 from [Arabidopsis thaliana] | At1g52070 | −1.91 | 1.32 | 0.019022 | 0.277021 |
| 252991_at | protein kinase like protein protein kinase 6 (EC 2.7.1.—)-soybean, PIR2: S29851 | At4g38470 | −1.91 | −1.43 | 0.022882 | 0.053733 |
| 250157_at | prx10 peroxidase-like protein prx10 peroxidase, Spinacia oleracea, EMBL: SOY16776 | At5g15180 | −1.91 | 1.05 | 0.009746 | 0.667075 |
| 267457_at | putative proline-rich protein | At2g33790 | −1.92 | 1.55 | 0.02688 | 0.053166 |
| 266882_at | unknown protein; supported by full-length cDNA: Ceres: 40641. | At2g44670 | −1.92 | −1.35 | 0.00935 | 0.103065 |
| 263208_at | zinc finger protein 5, ZFP5 possible transcription factor with C2H2 zinc finger; supported by full-length cDNA: Ceres: 23664. | At1g10480 | −1.93 | 1.06 | 0.009367 | 0.572822 |
| 253722_at | putative protein zinc finger transcription factor-Arabidopsis thaliana, PID: g2961542; supported by full-length cDNA: Ceres: 16432. | At4g29190 | −1.93 | 1.08 | 0.004592 | 0.184244 |
| 251356_at | putative protein hypothetical proteins-Arabidopsis thaliana; supported by cDNA: gi_14334587_gb_AY034967.1_ | At3g61060 | −1.93 | −1.13 | 0.007848 | 0.181064 |
| 245176_at | unknown protein similar to GP|2104534|AF001308 (T10M13.11) | At2g47440 | −1.93 | −1.64 | 0.031285 | 0.016259 |
| 262170_at | hypothetical protein predicted by genemark.hmm; supported by full-length cDNA: Ceres: 24864. | At1g74940 | −1.94 | 1.09 | 0.007492 | 0.34681 |
| 260900_s_at | branched-chain alpha keto-acid dehydrogenase, putative similar to branched-chain alpha keto-acid dehydrogenase GB: AAC69851 GI: 3822223 from [Arabidopsis thaliana] | At1g21400 | −1.94 | −1.33 | 0.003536 | 0.091842 |
| 260058_at | unknown protein; supported by cDNA: gi_15450975_gb_AY054568.1_ | At1g78100 | −1.94 | 1.22 | 0.026338 | 0.07061 |
| 259854_at | RING-H2 zinc finger protein ATL3, putative similar to GI: 4928397 from [Arabidopsis thaliana] (Plant Mol. Biol. 40 (4), 579-590 (1999)) | At1g72200 | −1.94 | 1.07 | 0.006318 | 0.364739 |
| 258145_at | integral membrane protein, putative similar to MtN21 (nodulation-induced gene) GB: CAA75575 [Medicago truncatula] | At3g18200 | −1.94 | 1.08 | 0.032913 | 0.537375 |
| 253763_at | xyloglucan endotransglycosylase-like protein xyloglucan endotransglycosylase 1, Fagus sylvatica, PID: e1354157 | At4g28850 | −1.94 | −1.07 | 0.010403 | 0.604484 |
| 249008_at | putative protein contains similarity to DNA-3-methyladenine glycosylase I; supported by full-length cDNA: Ceres: 29551. | At5g44680 | −1.94 | 1.04 | 0.019733 | 0.431852 |
| 261711_at | unknown protein similar to hypothetical protein GB: AAF25968 GI: 6714272 from [Arabidopsis thaliana]; supported by full-length cDNA: Ceres: 206224. | At1g32700 | −1.95 | −1.07 | 0.022252 | 0.357576 |
| 260887_at | ascorbate oxidase promoter-binding protein, putative similar to ascorbate oxidase promoter-binding protein GB: D45066 GI: 853689 from [Cucurbita maxima] | At1g29160 | −1.95 | −1.05 | 0.008773 | 0.547417 |
| 254718_at | putative protein disease resistance response protein 206-d, Pisum sativum, U11716 | At4g13580 | −1.95 | 1.13 | 0.008166 | 0.148335 |
| 253103_at | putative auxin-induced protein high similarity to auxin-induced protein 15A, soybean, PIR2: JQ1096; supported by cDNA: gi_13194817_gb_AF349524.1_AF349524 | At4g36110 | −1.95 | 1.24 | 0.007143 | 0.125412 |
| 245987_at | NAM-like protein hypothetical protein SENU5, senescence up-regulated-Lycopersicon esculentum, EMBL: Z75524; supported by cDNA: gi_14326559_gb_AF385734.1_AF385734 | At5g13180 | −1.95 | −1 | 0.030979 | 0.994604 |
| 264130_at | hypothetical protein predicted by genemark.hmm | At1g79160 | −1.96 | −1.01 | 0.007603 | 0.925019 |
| 257076_at | unknown protein | At3g19680 | −1.96 | −1.32 | 0.00642 | 0.015347 |
| 248564_at | putative protein contains similarity to AT-hook DNA-binding protein | At5g49700 | −1.96 | 1.11 | 0.017313 | 0.355178 |
| 246228_at | peroxidase like protein | At4g36430 | −1.96 | 1.3 | 0.014156 | 0.048404 |
| 245090_at | putative integral membrane protein nodulin | At2g40900 | −1.96 | 1.07 | 0.023157 | 0.443533 |
| 265031_at | serine/threonine protein kinase, putative similar to serine/threonine protein kinase GI: 1066501 from [Arabidopsis thaliana] | At1g61590 | −1.97 | 1.11 | 0.0313 | 0.357745 |
| 263981_at | unknown protein; supported by full-length cDNA: Ceres: 102453. | At2g42870 | −1.97 | −1.13 | 0.013425 | 0.350209 |
| 252570_at | isovaleryl-CoA-dehydrogenase precursor (IVD); supported by full-length cDNA: Ceres: 33674. | At3g45300 | −1.97 | −1.07 | 0.015973 | 0.428779 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 248432_at | putative protein similar to unknown protein (gb|AAB68039.1); supported by full-length cDNA: Ceres: 1076. | At5g51390 | −1.97 | −1.14 | 0.006297 | 0.177565 |
| 267628_at | unknown protein similar to GP|2262147|AC002330 | At2g42280 | −1.98 | 1.01 | 0.023113 | 0.929253 |
| 266941_at | peroxidase (ATP22a) identical to GB: Y08781 | At2g18980 | −1.98 | −1.16 | 0.014024 | 0.253565 |
| 266838_at | similar to jasmonate-inducible proteins from *Brassica napus* | At2g25980 | −1.98 | 1.03 | 0.013791 | 0.844383 |
| 263318_at | Expressed protein; supported by full-length cDNA: Ceres: 19631. | At2g24762 | −1.98 | 1.02 | 0.019425 | 0.816736 |
| 260081_at | unknown protein | At1g78170 | −1.98 | 1.1 | 0.010912 | 0.443013 |
| 257654_at | DnaJ protein, putative contains Pfam profile: PF00226 DnaJ domain; supported by full-length cDNA: Ceres: 31309. | At3g13310 | −1.98 | 1.19 | 0.018497 | 0.11787 |
| 257294_at | non-phototropic hypocotyl protein, putative similar to GB: AAF05914 from [*Arabidopsis thaliana*]; supported by full-length cDNA: Ceres: 118259. | At3g15570 | −1.98 | −1.4 | 0.017594 | 0.029437 |
| 254606_at | nodulin-26-like protein major intrinsic protein, *Oryza sativa*, PIR2: S52003; supported by full-length cDNA: Ceres: 109513. | At4g19030 | −1.98 | 1.03 | 0.008673 | 0.680712 |
| 264014_at | putative auxin-regulated protein | At2g21210 | −1.99 | −1.17 | 0.002926 | 0.036113 |
| 260770_at | RING-H2 finger protein RHA3a, putative similar to RING-H2 finger protein RHA3a GI: 3790573 from [*Arabidopsis thaliana*]; supported by cDNA: gi_14517431_gb_AY039551.1_ | At1g49200 | −1.99 | 1.24 | 0.024855 | 0.128926 |
| 260693_at | peptide transporter PTR2-B, putative similar to SP: P46032 from [*Arabidopsis thaliana*] | At1g32450 | −1.99 | −1 | 0.029791 | 0.955651 |
| 257448_s_at | putative protein various predicted proteins *Arabidopsis thaliana* | At3g45800 | −1.99 | −1.12 | 0.018199 | 0.206911 |
| 259328_at | putative lectin contains Pfam profile: PF01419 jacalin-like lectin domain; similar to jasmonate inducible protein GB: Y11483 (*Brassica napus*), myrosinase binding protein GB: BAA84545 (*Arabidopsis thaliana*); supported by cDNA: gi_6694742_gb_AF214573.1_AF2145 | At3g16440 | −2 | 1.24 | 0.010314 | 0.191237 |
| 263151_at | hypothetical protein predicted by genemark.hmm; supported by full-length cDNA: Ceres: 94743. | At1g54120 | −2.01 | −1.32 | 0.026676 | 0.072957 |
| 262427_s_at | thioglucosidase, putative similar to thioglucosidase GI: 871992 from [*Arabidopsis thaliana*] | At1g47600 | −2.01 | 1.2 | 0.008411 | 0.161898 |
| 261822_at | unknown protein; supported by full-length cDNA: Ceres: 113571. | At1g11380 | −2.01 | −1.42 | 0.035581 | 0.129626 |
| 265245_at | unknown protein | At2g43060 | −2.03 | −1.03 | 0.010559 | 0.598558 |
| 258511_at | unknown protein; supported by full-length cDNA: Ceres: 9391. | At3g06590 | −2.03 | −1.06 | 0.005721 | 0.306173 |
| 251072_at | putative protein wound-inducible protein wun1 protein-*Solanum tuberosum*, PIR: JQ0398; supported by full-length cDNA: Ceres: 248967. | At5g01740 | −2.03 | −1.26 | 0.023991 | 0.03577 |
| 267178_at | unknown protein; supported by full-length cDNA: Ceres: 28529. | At2g37750 | −2.04 | 1.3 | 0.011938 | 0.023415 |
| 262236_at | hypothetical protein similar to hypothetical protein GI: 9294146 from [*Arabidopsis thaliana*] | At1g48330 | −2.04 | −1.17 | 0.028943 | 0.116441 |
| 250717_at | putative protein similar to unknown protein (gb|AAF00668.1) | At5g06200 | −2.04 | 1.1 | 0.014766 | 0.475991 |
| 263265_at | hypothetical protein predicted by genscan and genefinder; supported by cDNA: gi_16649128_gb_AY059934.1_ | At2g38820 | −2.05 | −1.04 | 0.028413 | 0.735506 |
| 263150_at | heat-shock protein, putative similar to heat-shock protein GI: 472939 from [*Helianthus annuus*]; supported by full-length cDNA: Ceres: 97415. | At1g54050 | −2.05 | 1.3 | 0.019374 | 0.275131 |
| 254820_s_at | pEARLI 1-like protein *Arabidopsis thaliana* pEARLI 1 mRNA, completecds, PID: g871780 | At4g12510 | −2.05 | 1.07 | 0.00646 | 0.52646 |
| 251174_at | putative protein latex protein allergen Hev b 7-*Hevea brasiliensis*, EMBL: AF113546; supported by cDNA: gi_15912226_gb_AY056391.1_ | At3g63200 | −2.05 | −1.09 | 0.011679 | 0.253402 |
| 250469_at | pollen allergen-like protein SAH7 protein, *Arabidopsis thaliana*, EMBL: ATH133639 | At5g10130 | −2.05 | −1.05 | 0.021086 | 0.612309 |
| 249606_at | putative protein DNA-binding protein CCA1, *Arabidopsis thaliana*, PIR: T02684 | At5g37260 | −2.05 | 1.11 | 0.011138 | 0.453754 |
| 252368_at | cytochrome P450-like protein cytochrome P450 CYP94A1-*Vicia sativa*, PIR2: T08014 | At3g48520 | −2.06 | 1.18 | 0.017948 | 0.40172 |
| 245277_at | glucosyltransferase like protein; supported by cDNA: gi_2149126_gb_U81293.1_ATU81293 | At4g15550 | −2.07 | −1.21 | 0.004725 | 0.325423 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 260266_at | putative B-box zinc finger protein contains Pfam profile: PF00643 B-box zinc finger; supported by full-length cDNA: Ceres: 108109. | At1g68520 | −2.08 | −1.06 | 0.023551 | 0.259093 |
| 260741_at | hypothetical protein contains Pfam profile: PF00117 Glutamine amidotransferase class-I | At1g15045 | −2.09 | 1.12 | 0.016477 | 0.263068 |
| 257858_at | hypothetical protein predicted by genefinder; supported by full-length cDNA: Ceres: 924. | At3g12920 | −2.1 | 1 | 0.019142 | 0.98788 |
| 266372_at | putative two-component response regulator 3 protein identical to GB: AB010917, contains a response regulator receiver domain; supported by cDNA: gi_3273199_dbj_AB010917.1_AB010917 | At2g41310 | −2.11 | −1.24 | 0.013281 | 0.195422 |
| 266072_at | putative trehalose-6-phosphate synthase | At2g18700 | −2.11 | −1.08 | 0.005616 | 0.502618 |
| 255858_at | zinc finger protein (ZFP6) identical to zinc finger protein GI: 790683 from [*Arabidopsis thaliana*]; supported by cDNA: gi_15215716_gb_AY050387.1_ | At1g67030 | −2.11 | 1.3 | 0.017196 | 0.066902 |
| 247954_at | beta-galactosidase (emb|CAB64740.1); supported by cDNA: gi_15451017_gb_AY054589.1_ | At5g56870 | −2.12 | −1.36 | 0.01322 | 0.072012 |
| 252036_at | putative protein; supported by full-length cDNA: Ceres: 118329. | At3g52070 | −2.13 | −1.21 | 0.011681 | 0.137087 |
| 258497_at | putative flowering-time gene CONSTANS (COL2) identical to putative flowering-time gene CONSTANS (COL2) GB: AAB67879 GI: 1507699 (*Arabidopsis thaliana*); supported by full-length cDNA: Ceres: 949. | At3g02380 | −2.14 | −1.47 | 0.018979 | 0.03124 |
| 253829_at | *Medicago* nodulin N21-like protein MtN21 gene, *Medicago truncatula*, Y15293; supported by cDNA: gi_13899060_gb_AF370525.1_AF370525 | At4g28040 | −2.14 | −1.2 | 0.006927 | 0.185535 |
| 248801_at | homeobox-leucine zipper protein-like; supported by cDNA: gi_15450446_gb_AY052324.1_ | At5g47370 | −2.14 | 1.06 | 0.008347 | 0.456353 |
| 247921_at | CONSTANS-like B-box zinc finger protein-like; supported by full-length cDNA: Ceres: 6639. | At5g57660 | −2.14 | −1.13 | 0.003117 | 0.120344 |
| 257615_at | unknown protein | At3g26510 | −2.16 | −1.13 | 0.004838 | 0.273425 |
| 266140_at | nodulin-like protein; supported by cDNA: gi_16209713_gb_AY057618.1_ | At2g28120 | −2.17 | −1.3 | 0.008244 | 0.055633 |
| 257643_at | AP2 domain transcription factor contains Pfam profile: PF00847 AP2 domain; similar to RAV1 (DNA-binding protein) GB: BAA34250 [*Arabidopsis thaliana*] (Nucleic Acids Res. 27 (2), 470-478 (1999)); supported by full-length cDNA: Ceres: 39877. | At3g25730 | −2.17 | −1.32 | 0.038334 | 0.152701 |
| 248528_at | putative protein similar to unknown protein (emb|CAB86483.1) | At5g50760 | −2.18 | 1.01 | 0.008566 | 0.918675 |
| 264788_at | putative DnaJ protein; supported by full-length cDNA: Ceres: 22711. | At2g17880 | −2.19 | −1.25 | 0.011101 | 0.265694 |
| 253957_at | putative protein; supported by cDNA: gi_10880502_gb_AF195894.1_AF195894 | At4g26320 | −2.19 | −1.16 | 0.006508 | 0.414219 |
| 247199_at | DNA binding protein TGA1a homolog; supported by full-length cDNA: Ceres: 31032. | At5g65210 | −2.19 | 1.09 | 0.010073 | 0.256741 |
| 247170_at | putative protein contains similarity to lectin-like protein kinase | At5g65530 | −2.19 | 1.2 | 0.020752 | 0.326964 |
| 250099_at | unknown protein; supported by cDNA: gi_14190364_gb_AF378860.1_AF378860 | At5g17300 | −2.2 | 1.13 | 0.018091 | 0.37707 |
| 247474_at | putative protein predicted proteins, *Arabidopsis thaliana* | At5g62280 | −2.21 | −1.01 | 0.016382 | 0.887761 |
| 261768_at | gibberellin 3 beta-hydroxylase, putative similar to gibberellin 3 beta-hydroxylase GI: 3982753 from [*Arabidopsis thaliana*]; supported by cDNA: gi_1945343_gb_L37126.1_ATHGA4A | At1g15550 | −2.22 | 1.01 | 0.037882 | 0.920313 |
| 259264_at | putative aldose 1-epimerase shows similarity to aldose epimerases | At3g01260 | −2.22 | 1.22 | 0.023126 | 0.227322 |
| 253812_at | putative wound induced protein wound-induced protein-tomato (fragment), PIR2: S19773; supported by full-length cDNA: Ceres: 20161. | At4g28240 | −2.25 | −1.09 | 0.00548 | 0.137021 |
| 246917_at | serine-rich protein; supported by full-length cDNA: Ceres: 99323. | At5g25280 | −2.25 | 1.24 | 0.008947 | 0.039883 |
| 261265_at | hypothetical protein predicted by genscan+; supported by full-length cDNA: Ceres: 250127. | At1g26800 | −2.26 | 1.2 | 0.022793 | 0.218643 |
| 246229_at | pectinesterase like protein | At4g37160 | −2.26 | 1.07 | 0.01383 | 0.725863 |
| 250012_x_at | auxin-induced protein-like | At5g18060 | −2.27 | 1.11 | 0.022574 | 0.446969 |
| 259751_at | putative transcription factor similar to myb-related transcription factor 24 GB: S71287; supported by full-length cDNA: Ceres: 31592. | At1g71030 | −2.29 | −1.31 | 0.004307 | 0.051811 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 246932_at | ethylene-responsive element-like protein ethylene-responsive element binding protein homolog, *Stylosanthes hamata*, EMBL: U91857; supported by cDNA: gi_15010715_gb_AY045659.1_ | At5g25190 | −2.31 | −1.28 | 0.015246 | 0.042175 |
| 264463_at | unknown protein similar to ESTs gb|T20511, gb|T45308, gb|H36493, and gb|AA651176; supported by full-length cDNA: Ceres: 2558. | At1g10150 | −2.32 | −1.04 | 0.007428 | 0.701582 |
| 252178_at | putative protein various predicted proteins | At3g50750 | −2.33 | 1.17 | 0.016542 | 0.191688 |
| 247149_at | unknown protein; supported by full-length cDNA: Ceres: 25419. | At5g65660 | −2.33 | −1.03 | 0.011232 | 0.82378 |
| 260855_at | phosphatidylinositol-4-phosphate 5-kinase, putative similar to phosphatidylinositol-4-phosphate 5-kinase GB: CAB53377 GI: 5777366 from [*Arabidopsis thaliana*]; supported by full-length cDNA: Ceres: 37462. | At1g21920 | −2.34 | 1.02 | 0.010684 | 0.812177 |
| 256743_at | Expressed protein; supported by full-length cDNA: Ceres: 22461. | At3g29370 | −2.34 | 1.09 | 0.007379 | 0.34665 |
| 249065_at | putative protein similar to unknown protein (gb AAD10689.1); supported by cDNA: gi_14334449_gb_AY034916.1_ | At5g44260 | −2.34 | −1.05 | 0.002162 | 0.688129 |
| 264524_at | tat-binding protein, putative Highly Similar to branched-chain amino acid aminotransferase; Location of EST gb|T44177 and gb|AA395381; supported by cDNA: gi_15293208_gb_AY051038.1_ | At1g10070 | −2.35 | −1.06 | 0.006931 | 0.464612 |
| 264521_at | unknown protein Location of EST gb|T41885 and gb|AA395021 | At1g10020 | −2.37 | −1.37 | 0.002442 | 0.03961 |
| 258091_at | hypothetical protein predicted by genmark; supported by full-length cDNA: Ceres: 19279. | At3g14560 | −2.37 | 1.27 | 0.014798 | 0.126209 |
| 261480_at | phytochrome kinase substrate 1, putative similar to phytochrome kinase substrate 1 GI: 5020168 from [*Arabidopsis thaliana*]; supported by full-length cDNA: Ceres: 97569. | At1g14280 | −2.39 | 1.06 | 0.004881 | 0.498893 |
| 252040_at | putative protein hypothetical protein F10M6.70-*Arabidopsis thaliana*, PIR3: T05399; supported by cDNA: gi_15293266_gb_AY051067.1_ | At3g52060 | −2.39 | −1.02 | 0.011127 | 0.860596 |
| 246001_at | putative protein predicted protein, *Arabidopsis thaliana*; supported by full-length cDNA: Ceres: 267031. | At5g20790 | −2.39 | −1.63 | 0.007949 | 0.0182 |
| 258809_at | NAM-like protein (no apical meristem) similar to NAM GB: CAA63101 [*Petunia x hybrida*] | At3g04070 | −2.4 | −1.24 | 0.010367 | 0.050869 |
| 258362_at | unknown protein | At3g14280 | −2.41 | −1.2 | 0.007995 | 0.150833 |
| 249467_at | NAM/CUC2-like protein CUC2, *Arabidopsis thaliana*, EMBL: ATAB2560; supported by full-length cDNA: Ceres: 113779. | At5g39610 | −2.41 | −1.48 | 0.007479 | 0.036136 |
| 251665_at | responce reactor 4; supported by cDNA: gi_3273201_dbj_AB010918.1_AB010918 | At3g57040 | −2.42 | −1.1 | 0.008685 | 0.45678 |
| 263382_at | putative anthranilate N-hydroxycinnamoyl/benzoyltransferase; supported by full-length cDNA: Ceres: 105546. | At2g40230 | −2.45 | −1.06 | 0.018135 | 0.712794 |
| 246071_at | ids4-like protein ids-4 protein-*Hordeum vulgare*, PIR: T05905; supported by full-length cDNA: Ceres: 32843. | At5g20150 | −2.47 | −1.14 | 0.002464 | 0.214703 |
| 247585_at | putative protein predicted proteins, *Arabidopsis thaliana*; supported by full-length cDNA: Ceres: 16638. | At5g60680 | −2.5 | −1.09 | 0.002909 | 0.183267 |
| 264210_at | putative myb-related transcription factor Similar to myb-related transcription factor (THM27) gb|X95296 from *Solanum lycopersicum*. ESTs gb|T42000, gb|T04118, gb|AA598042, gb|AA394757 and gb|AA598046 come from this gene; supported by cDNA: gi_3941409_gb_AF | At1g22640 | −2.51 | 1.26 | 0.00562 | 0.068761 |
| 252965_at | putative auxin-induced protein auxin-induced protein 10A, Glycine max., PIR2: JQ1099 | At4g38860 | −2.53 | −1.12 | 0.006173 | 0.26078 |
| 253814_at | putative protein; supported by full-length cDNA: Ceres: 10077. | At4g28290 | −2.55 | −1.46 | 0.006294 | 0.044367 |
| 246523_at | CONSTANS-like 1 | At5g15850 | −2.55 | 1.01 | 0.013312 | 0.900077 |
| 263325_at | putative RING zinc finger protein; supported by cDNA: gi_13265496_gb_AF324691.2_AF324691 | At2g04240 | −2.56 | 1.18 | 0.004531 | 0.13068 |
| 265342_at | hypothetical protein predicted by genscan; supported by cDNA: gi_15724317_gb_AF412099.1_AF412099 | At2g18300 | −2.58 | 1.1 | 0.014912 | 0.315678 |
| 253872_at | putative protein *Arabidopsis thaliana* nap gene, PID: e1234813; supported by full-length cDNA: Ceres: 38344. | At4g27410 | −2.58 | 1.21 | 0.004591 | 0.057522 |

TABLE 3-continued

Genes that are Responsive to chitooctaose in Wild-type

| Probe set | Annotation | Accession | WT FC | Mu FC | WT P | Mu P |
| --- | --- | --- | --- | --- | --- | --- |
| 264783_at | putative calcium-dependent protein kinase (U90439) similar to ESTs gb|T46119, gb|H76837, and gb|H36948; supported by cDNA: gi_6318612_gb_AF162660.1_AF162660 | At1g08650 | −2.6 | −1.61 | 0.010263 | 0.046318 |
| 266363_at | hypothetical protein predicted by genscan and genefinder | At2g41250 | −2.64 | −1.63 | 0.002674 | 0.015646 |
| 260070_at | putative helix-loop-helix DNA-binding protein contains Pfam profile: PF00010 Helix-loop-helix DNA-binding domain | At1g73830 | −2.64 | −1.19 | 0.010198 | 0.127406 |
| 250844_at | putative protein; supported by full-length cDNA: Ceres: 13812. | At5g04470 | −2.64 | 1.22 | 0.009233 | 0.425631 |
| 256589_at | cytochrome P450, putative contains Pfam profile: PF00067 cytochrome P450; supported by cDNA: gi_15292830_gb_AY050849.1_ | At3g28740 | −2.66 | −1.69 | 0.010428 | 0.037959 |
| 265067_at | hypothetical protein predicted by genefinder; supported by full-length cDNA: Ceres: 271253. | At1g03850 | −2.7 | 1.37 | 0.004124 | 0.138732 |
| 256914_at | hypothetical protein | At3g23880 | −2.72 | 1.01 | 0.02091 | 0.915885 |
| 251169_at | putative protein putative protein At2g25690-Arabidopsis thaliana, EMBL: AC006053; supported by full-length cDNA: Ceres: 40080. | At3g63210 | −2.73 | 1.13 | 0.005839 | 0.38507 |
| 255934_at | cytochrome P450, putative similar to cytochrome P450 GI: 4176420 from [Arabidopsis thaliana] | At1g12740 | −2.74 | −1.11 | 0.010048 | 0.828407 |
| 266150_s_at | hypothetical protein | At2g12290 | −2.77 | 1.08 | 0.009686 | 0.668542 |
| 259502_at | unknown protein; supported by cDNA: gi_15146331_gb_AY049307.1_ | At1g15670 | −2.77 | −1.23 | 0.002226 | 0.019701 |
| 263283_at | hypothetical protein predicted by genscan and genefinder | At2g36090 | −2.79 | 1.26 | 0.004 | 0.034558 |
| 253125_at | DnaJ-like protein DnaJ-like protein, Phaseolus vulgaris, PATX: G1684851 | At4g36040 | −2.83 | 1.3 | 0.002096 | 0.029069 |
| 248208_at | unknown protein | At5g53980 | −2.83 | −1.12 | 0.002744 | 0.19142 |
| 264021_at | putative auxin-regulated protein; supported by full-length cDNA: Ceres: 7141. | At2g21200 | −2.85 | 1.14 | 0.01116 | 0.255677 |
| 249755_at | unknown protein; supported by full-length cDNA: Ceres: 6393. | At5g24580 | −2.87 | −1.02 | 0.01127 | 0.906115 |
| 255284_at | 5-adenylylsulfate reductase; supported by full-length cDNA: Ceres: 40330. | At4g04610 | −2.9 | −1.53 | 0.007861 | 0.08308 |
| 253207_at | putative protein small auxin up-regulated RNA, Malus domestica, gb: Z93766 | At4g34770 | −2.9 | −1.24 | 0.004842 | 0.041275 |
| 252118_at | putative protein various predicted proteins, Arabidopsis thaliana; supported by full-length cDNA: Ceres: 14797. | At3g51400 | −2.9 | −1.18 | 0.019242 | 0.328518 |
| 247540_at | ethylene responsive element binding factor-like ethylene responsive element binding factor 5, Arabidopsis thaliana, SWISSPROT: ERF5_ARATH; supported by full-length cDNA: Ceres: 19893. | At5g61590 | −2.99 | 1.03 | 0.003616 | 0.728822 |
| 264379_at | hypothetical protein predicted by grail | At2g25200 | −3 | −1.3 | 0.023213 | 0.145635 |
| 263688_at | unknown protein Location of EST 228A16T7A, gb|N65686; supported by full-length cDNA: Ceres: 24946. | At1g26920 | −3.05 | −1.22 | 0.00728 | 0.304232 |
| 246522_at | bZIP DNA-binding protein-like putative bZIP DNA-binding protein-Capsicum chinense, EMBL: AF127797 | At5g15830 | −3.09 | −1.46 | 0.010759 | 0.157233 |
| 258059_at | NAM-like protein (No Apical Meristem) similar to GB: CAA63101 from [Petunia x hybrida] (Cell 85 (2), 159-170 (1996)) | At3g29035 | −3.25 | 1.32 | 0.004473 | 0.140279 |
| 259982_at | putative RING zinc finger protein contains Pfam profile: PF00097 Zinc finger, C3HC4 type (RING finger); supported by full-length cDNA: Ceres: 27464. | At1g76410 | −3.31 | −1.01 | 0.011262 | 0.945494 |
| 262986_at | unknown protein similar to hypothetical protein GB: AAF27090 GI: 6730669 from (Arabidopsis thaliana); supported by full-length cDNA: Ceres: 101865. | At1g23390 | −3.44 | −1.22 | 0.008132 | 0.177105 |
| 260287_at | unknown protein contains two Kelch motifs; supported by full-length cDNA: Ceres: 32885. | At1g80440 | −3.57 | −1.18 | 0.008035 | 0.221837 |
| 247754_at | putative protein | At5g59080 | −3.77 | −1.55 | 0.004279 | 0.021198 |
| 267238_at | unknown protein; supported by full-length cDNA: Ceres: 6950. | At2g44130 | −3.86 | 1.18 | 0.003036 | 0.152629 |
| 266156_at | hypothetical protein predicted by genscan | At2g28110 | −3.99 | 1.1 | 0.004914 | 0.561885 |
| 266322_at | putative auxin-regulated protein | At2g46690 | −4 | −1.09 | 0.003394 | 0.327782 |
| 258367_at | putative protein kinase similar to protein kinase homolog GB: AAC78477 from [Arabidopsis | At3g14370 | −4.02 | −1.07 | 0.005242 | 0.532182 |

TABLE 3-continued

Genes that are Responsive to chitooctaose in Wild-type

| Probe set | Annotation | Accession | WT FC | Mu FC | WT P | Mu P |
|---|---|---|---|---|---|---|
| 253155_at | *thaliana*]; supported by full-length cDNA: Ceres: 96699. putative protein predicted protein, *Arabidopsis thaliana* | At4g35720 | −4.2 | −1.28 | 0.00697 | 0.318015 |
| 265573_at | putative zinc-finger protein similar to zinc-finger protein GB: AAC98446 | At2g28200 | −4.25 | −1.33 | 0.00752 | 0.040354 |
| 247696_at | MYB27 protein-like MYB27 protein, *Arabidopsis thaliana*, PIR: T46166; supported by cDNA: gi_3941479_gb_AF062894.1_AF062894 | At5g59780 | −4.32 | 1.37 | 0.003111 | 0.017905 |
| 250937_at | putative protein various predicted proteins, *Arabidopsis thaliana*; supported by cDNA: gi_13878024_gb_AF370275.1_AF370275 | At5g03230 | −4.33 | 1.47 | 0.010367 | 0.036447 |
| 251443_at | putative protein unknown protein At2g44130- *Arabidopsis thaliana*, EMBL: AC004005; supported by full-length cDNA: Ceres: 8014. | At3g59940 | −4.72 | 1.12 | 0.001814 | 0.186012 |
| 261177_at | hypothetical protein predicted by genemark.hmm | At1g04770 | −5.29 | −1.41 | 0.001922 | 0.031579 |
| 249454_at | expressed protein predicted protein, *Synechocystis* sp., PIR: S77152; supported by full-length cDNA: Ceres: 5331. | At5g39520 | −5.74 | −1.29 | 0.003609 | 0.135283 |
| 265387_at | unknown protein; supported by full-length cDNA: Ceres: 34827. | At2g20670 | −6.17 | −1.57 | 0.002564 | 0.056602 |
| 254265_s_at | serine threonine kinase-like protein KI domain interacting kinase 1 (KIK1), *Zea mays*; supported by cDNA: gi_13506746_gb_AF224706.1_AF224706 | At4g23140 | 2.94 | 1.76 | 0.151164 | 0.015078 |
| 263539_at | putative tyrosine aminotransferase; supported by full-length cDNA: Ceres: 14570. | At2g24850 | 2.01 | 2.2 | 0.066727 | 0.012756 |
| 265837_at | unknown protein | At2g14560 | 1.91 | 2.1 | 0.278938 | 0.013727 |
| 263402_at | hypothetical protein similar to hypothetical protein GB: AAC27412 | At2g04050 | 1.65 | 1.87 | 0.126971 | 0.028665 |
| 256766_at | Expressed protein; supported by cDNA: gi_14335055_gb_AY037207.1__ | At3g22231 | 1.62 | 1.87 | 0.168568 | 0.005967 |
| 263061_at | putative AAA-type ATPase | At2g18190 | 1.48 | 1.94 | 0.324983 | 0.049719 |
| 267024_s_at | putative aquaporin (plasma membrane intrinsic protein) | At2g34390 | 1.46 | 1.99 | 0.056378 | 0.04848 |
| 245035_at | unknown protein similar to GP\|2244827\|gnl\|PID\|e326818\|Z97336 | At2g26400 | 1.39 | 1.78 | 0.302025 | 0.044811 |
| 252746_at | sucrose synthase-like protein SUCROSE SYNTHASE (SUCROSE-UDP GLUCOSYLTRANSFERASE), *Arabidopsis thalina*, SWISSPROT: SUS1_ARATH; supported by cDNA: gi_14334569_gb_AY034958.1__ | At3g43190 | 1.35 | 2.67 | 0.11372 | 0.012763 |
| 263401_at | hypothetical protein similar to hypothetical protein GB: AAC27412 | At2g04070 | 1.22 | 2.22 | 0.734988 | 0.005027 |
| 245306_at | Expressed protein; supported by full-length cDNA: Ceres: 95834. | At4g14690 | 1.2 | 2.16 | 0.22188 | 0.009285 |
| 258277_at | putative cytochrome P450 similar to cytochrome P450 71B2 GB: O65788 [*Arabidopsis thaliana*] | At3g26830 | 1.04 | 2.61 | 0.754479 | 0.013858 |
| 252882_at | Expressed protein; supported by full-length cDNA: Ceres: 14423. | At4g39675 | −1.17 | 1.94 | 0.106839 | 0.012488 |
| 261913_at | flavin-containing monooxygenase FMO3, putative similar to flavin-containing monooxygenase FMO3 GI: 349533 from [*Oryctolagus cuniculus*] | At1g65860 | −1.63 | −1.85 | 0.058793 | 0.008577 |
| 249727_at | putative protein similar to unknown protein (gb\|AAB61527.1) | At5g35490 | −1.2 | −2.09 | 0.190584 | 0.008082 |
| 254474_at | putative protein predicted proteins, *Arabidopsis thaliana*; supported by full-length cDNA: Ceres: 248721. | At4g20390 | −1.06 | −1.71 | 0.572517 | 0.017439 |
| 260856_at | TINY-like protein similar to TINY GB: CAA64359 GI: 1246403 from [*Arabidopsis thaliana*]; supported by full-length cDNA: Ceres: 19721. | At1g21910 | 1.17 | −2.2 | 0.268116 | 0.009082 |
| 249215_at | dihydroflavonol 4-reductase | At5g42800 | 1.61 | −1.77 | 0.401965 | 0.048093 |
| 254283_s_at | anthocyanidin synthase-like protein putative leucoanthocyanidin dioxygenase, *Arabidopsis thaliana*, PID: g1575699 | At4g22870 | 2.09 | −1.98 | 0.161214 | 0.018458 |

TABLE 4

Genes that are Responsive to chitooctaose in the AtLysM RLK1 mutant

| Probe set | Annotation | Accession | WT FC | Mu FC | WT P | Mu P |
| --- | --- | --- | --- | --- | --- | --- |
| 253046_at | cytochrome P450—like protein cytochrome P450, *Glycyrrhiza echinata*, AB001379; supported by full-length cDNA: Ceres: 253698. | At4g37370 | 3.83 | 2.17 | 0.019261 | 0.016853 |
| 254869_at | protein kinase—like protein KI domain interacting kinase 1 -*Zea mays*, PIR2: T02053 | At4g11890 | 3.37 | 2.12 | 0.007665 | 0.003284 |
| 246099_at | blue copper binding protein; supported by full-length cDNA: Ceres: 7767. | At5g20230 | 2.67 | 1.7 | 0.008061 | 0.011289 |
| 253317_at | putative protein | At4g33960 | −1.83 | −1.77 | 0.010341 | 0.022397 |
| 260126_at | putative hydroxymethyltransferase similar to serine hydroxymethyltransferage GB: P50433 from [*Solanum tuberosum*]; supported by full-length cDNA: Ceres: 122515. | At1g36370 | −1.93 | −1.86 | 0.005701 | 0.006964 |
| 246926_at | putative protein | At5g25240 | −2.09 | −2.21 | 0.019603 | 0.017979 |
| 258217_at | unknown protein contains Pfam profile PF00398 Ribosomal RNA adenine dimethylases | At3g17990 | −2.21 | −2.27 | 0.009887 | 0.0037 |
| 258218_at | methyltransferase, putative similar to methyltransferase GB: AAC01738 from [*Amycolatopsis mediterranei*] | At3g18000 | −2.21 | −2.29 | 0.00667 | 0.009294 |
| 254343_at | PRH26 protein; supported by full-length cDNA: Ceres: 36866. | At4g21990 | −2.22 | −1.83 | 0.012838 | 0.031291 |
| 265121_at | similar to flavin-containing monooxygenase (sp|P36366); similar to ESTs gb|R30018, gb|H36886, gb|N37822, and gb|T88100 similar to flavin-containing monooxygenase GB: AAA21178 GI: 349534 from [*Oryctolagus cuniculus*]; supported by cDNA: gi_13877746_gb_AF37013 | At1g62560 | −2.37 | −1.87 | 0.020126 | 0.00922 |
| 251039_at | putative protein hypothetical protein T6H20.90 - *Arabidopsis thaliana*, EMBL: AL096859; supported by cDNA: gi_16648747_gb_AY058150.1_ | At5g02020 | −3.73 | −1.91 | 0.001899 | 0.021967 |
| 259015_at | unknown protein similar to hypothetical protein GB: AAC17612 [*Arabidopsis thaliana*]; supported by full-length cDNA: Ceres: 251012. | At3g07350 | −3.79 | −1.81 | 0.001762 | 0.010373 |
| 248676_at | putative protein similar to unknown protein (gb|AAC72543.1) | At5g48850 | −5.55 | −4.23 | 0.003428 | 0.003335 |
| 249752_at | putative protein similar to unknown protein (emb CAB62461.1); supported by full-length cDNA: Ceres: 268701. | At5g24660 | −5.87 | −2.27 | 0.002654 | 0.005949 |
| 254265_s_at | serine threonine kinase—like protein KI domain interacting kinase 1 (KIK1), *Zea mays*; supported by cDNA: gi_13506746_gb_AF224706.1_AF224706 | At4g23140 | 2.94 | 1.76 | 0.151164 | 0.015078 |
| 263539_at | putative tyrosine aminotransferase; supported by full-length cDNA: Ceres: 14570. | At2g24850 | 2.01 | 2.2 | 0.066727 | 0.012756 |
| 265837_at | unknown protein | At2g14560 | 1.91 | 2.1 | 0.278938 | 0.013727 |
| 263402_at | hypothetical protein similar to hypothetical protein GB: AAC27412 | At2g04050 | 1.65 | 1.87 | 0.126971 | 0.028665 |
| 256766_at | Expressed protein; supported by cDNA: gi_14335055_gb_AY037207.1_ | At3g22231 | 1.62 | 1.87 | 0.168568 | 0.005967 |
| 263061_at | putative AAA-type ATPase | At2g18190 | 1.48 | 1.94 | 0.324983 | 0.049719 |
| 267024_s_at | putative aquaporin (plasma membrane intrinsic protein) | At2g34390 | 1.46 | 1.99 | 0.056378 | 0.04848 |
| 245035_at | unknown protein similar to GP|2244827|gn1|PID|e326818|Z97336 | At2g26400 | 1.39 | 1.78 | 0.302025 | 0.044811 |
| 252746_at | sucrose synthase—like protein SUCROSE SYNTHASE (SUCROSE-UDP GLUCOSYLTRANSFERASE), *Arabidopsis thalina*, SWISSPROT: SUS1_ARATH; supported by cDNA: gi_14334569_gb_AY034958.1_ | At3g43190 | 1.35 | 2.67 | 0.11372 | 0.012763 |
| 263401_at | hypothetical protein similar to hypothetical protein GB: AAC27412 | At2g04070 | 1.22 | 2.22 | 0.734988 | 0.005027 |
| 245306_at | Expressed protein; supported by full-length cDNA: Ceres: 95834. | At4g14690 | 1.2 | 2.16 | 0.22188 | 0.009285 |
| 261913_at | flavin-containing monooxygenase FMO3, putative similar to flavin-containing monooxygenase FMO3 GI: 349533 from [*Oryctolagus cuniculus*] | At1g65860 | −1.63 | −1.85 | 0.058793 | 0.008577 |
| 249727_at | putative protein similar to unknown protein (gb|AAB61527.1) | At5g35490 | −1.2 | −2.09 | 0.190584 | 0.008082 |
| 258277_at | putative cytochrome P450 similar to cytochrome P450 71B2 GB: O65788 [*Arabidopsis thaliana*] | At3g26830 | 1.04 | 2.61 | 0.754479 | 0.013858 |
| 252882_at | Expressed protein; supported by full-length cDNA: Ceres: 14423. | At4g39675 | −1.17 | 1.94 | 0.106839 | 0.012488 |
| 254474_at | putative protein predicted proteins, *Arabidopsis thaliana*; supported by full-length cDNA: Ceres: 248721. | At4g20390 | −1.06 | −1.71 | 0.572517 | 0.017439 |

TABLE 4-continued

Genes that are Responsive to chitooctaose in the AtLysM RLK1 mutant

| Probe set | Annotation | Accession | WT FC | Mu FC | WT P | Mu P |
|---|---|---|---|---|---|---|
| 260856_at | TINY—like protein similar to TINY GB: CAA64359 GI: 1246403 from [Arabidopsis thaliana]; supported by full-length cDNA: Ceres: 19721. | At1g21910 | 1.17 | −2.2 | 0.268116 | 0.009082 |
| 249215_at | dihydroflavonol 4-reductase | At5g42800 | 1.61 | −1.77 | 0.401965 | 0.048093 |
| 254283_s_at | anthocyanidin synthase—like protein putative leucoanthocyanidin dioxygenase, Arabidopsis thaliana, PID: g1575699 | At4g22870 | 2.09 | −1.98 | 0.161214 | 0.018458 |

The similar regulation patterns for this small number of genes in both the mutant and wild-type plants may be due to some redundant function provided by one of the other four LysM RLKs in the mutant. Eventually, only 6 genes appeared to behave differentially in both the mutant and wild-type (last 6 rows in Table 4). The cause of such a discrepancy is not clear. Since these few genes were only weakly to moderately regulated (−1.7 to 2.6 fold), experimental variation is a possible cause.

To determine the functional classification of the 909 genes described above, information of these genes were input into the TAIR web-based GO annotation software. The output shows that the CRGs disclosed here include many defense-related genes (such as genes encoding pathogenesis-related proteins and disease resistance proteins) and signal transduction-related genes (such as various kinases and transcription factors) (FIG. 12), suggesting a potential relationship between gene induction and plant defense mediated by chitooligosaccharides.

Since the mutation in the AtLysM RLK1 gene blocked the regulation of almost all CRGs (~98%) by the chitooligosaccharide, AtLysM RLK1 is very likely the chitin receptor (or part of the receptor complex) that is responsible for perceiving the chitooligosaccharide elicitor and initiating cellular signaling leading to downstream gene expression. This notion is also indirectly supported by its structural features and the findings that LysM RLKs NFR1 and NFR5 in the legume Lotus japonicus serve as the receptors for the lipo-chitin Nod signal. See Limpens et al., 2003; Madsen et al., 2003; Radutoiu et al., 2003.

Because many receptor kinases form heterodimers, it has been suggested that the legume NFR1 and NFR5 may function as a heterodimer complex. See e.g., Goring et al., 2004. It is likely that AtLysRLK1 may require a partner protein, either another LysM RLK or a protein similar to the rice CEBiP. Kaku et al., 2006. However, since mutations in the other four AtLysM RLK genes had no obvious effect on the expression of selected CRGs, it seems unlikely that the products of these four genes are essential for the receptor function. There are three CEBiP-like proteins in Arabidopsis, which are encoded by At1g21880, At1g77630 and At2g17120, respectively.

If chitooligosaccharide recognition is an integral part of the response pathway by which plants defend against fungal pathogens, mutations in the AtLysM RLK1 gene should affect plant resistance to fungal pathogens. To test this hypothesis, three week-old mutant and wild-type plants were inoculated with the biotrophic powdery mildew fungal pathogen Erysiphe cichoracearum. Ten days later, the mutant plants appeared to support more fungal growth than the wild-type plants.

The susceptibility appeared to be less than that observed in NahG plants, which express salicylate hydrolase, preventing the accumulation of salicylic acid, and are therefore very susceptible to the fungal pathogen (FIG. 13A). Trypan blue staining of the infected leaves also showed the AtLysM RLK1 mutant supported more hyphal growth and production of conidiophores earlier than the wild-type plants (FIG. 13B). Arrows indicate sites where conidiophores are forming. All photographs were taken six days after inoculation. Bar=0.1 mm. 4-week-old plants were also inoculated with the necrotrophic fungus Alternaria brassicicola. Three days after inoculation, the mutant developed slightly bigger lesions than the wild-type plants, as measured by average diameter of the lesions (FIGS. 13C and 13D). In agreement with this, the mutant plants also produced more spores per lesion than the wild-type plants (FIG. 13E).

To test the specificity of AtLysM RLK1 in fungal disease resistance, the response of the mutant to the bacterial pathogen Pseudomonas syringae pv. Tomato DC3000 was also examined. After infiltration with the pathogen, both the mutant and wild-type plants supported a similar bacterial growth three days after inoculation (FIG. 13F), indicating that defense against bacterial infection was not affected by the mutation. WT=wild-type Col-0; Mu=the AtLysM RLK1 mutant. CSC=crab shell chitin, 8mer=chitooctaose, and water=distilled water. Empty columns=WT Col-0 and solid black columns=the AtLysM RLK1 mutant. Asterisks indicate statistically significant differences between the mutant and wild-type plants (P<0.05). Error bars=standard error. Each experiment was repeated at least twice with similar results.

The mutation in the AtLysM RLK1 gene led to only moderate susceptibility to fungal pathogens, suggesting that AtLysM RLK1 plays a role in mediating basal or general resistance to fungal pathogens through the recognition of the chitooligosaccharide PAMP derived from fungal cell walls. This result is not surprising because it is well documented that fungal pathogens produce multiple elicitors that induce plant innate immunity. See e.g., Chisholm et al., 2006. Thus, blocking the chitin response pathway would not be expected to completely block all defense responses mounted by the plant against the fungal pathogen.

This notion is supported by the observation that chitin-responsive defense genes (e.g., MPK3 and WRKY53) were still induced by the fungal pathogen A. brassicicola in the mutant, albeit to a lower level compared with that in wild-type plants (FIG. 14). The gene induction by the fungal pathogen is monitored by quantitative RT-PCR at different time points after inoculation. Each data point is the average of the relative gene expression (fold change, normalized to actin-2 and relative to the time 0 sample) from three replicates. Error bar=standard error. WT=wild-type Col-0; Mu=the AtLysM RLK1 mutant. This low level expression of some defense genes in the mutant may explain why the mutant was only moderately susceptible to the fungal pathogens as compared to the wild-type plants.

Pretreatment of rice plants by chitooligosaccharide has been shown to enhance fungal resistance in rice. Tanabe et al., 2006. It is shown here that pretreatment of wild-type plants with chitooligosaccharides reduced disease symptoms upon inoculation with the fungal pathogen *A. brassicicola*, as evidenced by reduced lesion size and spore production (FIGS. 13C, 13D and 13E). Pretreatment also inhibited the growth of the bacterial pathogen *P. syringae* pv. tomato DC3000 (FIG. 13F), reflecting a general induction of plant innate immunity. In contrast, similar pretreatment of the AtLysM RLK1 mutant plants did not enhance resistance. These data further support the critical role for AtLysM RLK1 in mediating the perception of chitooligosaccharides by plants.

Chitin is present in the cell walls of all true fungi, but not in plants. Fungal pathogens with defects in chitin synthesis are significantly less virulent on susceptible hosts, including both plants and animals. See Bulawa et al., 1995; and Soulie et al., 2006. As disclosed herein, AtLysM RLK1 is likely a receptor for chitin PAMP of fungal pathogen. AtLysM RLK1 is only the third pattern recognition receptor (PRR) identified in plants. The other two PRRs are both leucine-rich repeat receptor-like kinases (LRR RLKs). Nürnberger et al., 2006. Therefore, this finding adds a new class of proteins to the family of plant PRRs.

LysM RLK NFR1 and NFR5 Nod signal receptors specifically recognize a lipochitin molecule with a back-bone of 4-5 units of N-acetyl-D-glucosamine. For review, see Stacey et al. 2006. This specificity is supported by the findings that mutations in either of the NFR1 and NFR5 genes in *L. japonicus* did not block the induction of the selected CRGs in this plant (FIG. 15). In more details, both the wild type (Gifu) and the Nod signal receptor mutants nfr1-1 and nfr5-1 were treated with chitooctaose for 30 minutes at a concentration of 1 μM or with water (as a control). The selected CRGS were detected using semi-quantitative RT-PCR. LjActin-2 was used as an internal control.

However, previous results suggested that both the legume NFR genes and AtLysM RLK1 are under negative selection, implying the functional conservation between legume NFR and AtLysM RLK1 genes. Zhang et al., 2007. Perhaps, the discrepancy in substrate specificity lies in the difference in their extracellular LysM domains, since legume NFR proteins have two LysM motifs while AtLysM RLK1 has three. Zhang et al., 2007.

To determine whether the AtLysM RLK1 mutation affects other defense-related pathways, such as the salicylic acid (SA) and jasmonic acid/ethylene (JA/ETH) responsive pathways, the AtLysM RLK1 mutant and wild-type plants were treated with SA, methyl jasmonic acid (MeJA), and 1-aminocyclopropane-1-carboxylic acid (ACC), respectively, and expression of the pathway hallmark genes, PR-1 (the SA pathway) and PDF1.2 (the JA/ETH pathway) was examined.

Quantitative RT-PCR data demonstrated that both the mutant and wild-type plants showed similar induction of PR-1 by SA and of PDF1.2 by MeJA or ACC, indicating that the mutation did not affect these defense pathways (FIG. 16). In addition, the mutant plants were fully responsive to another typical PAMP, the flagellin-derived peptide flg22 (FIG. 16). Each data point is the average of the relative gene expression (fold change, normalized to actin-2 and relative to the control sample) from three replicates. Error bar=standard error. No statistically significant differences are found between the mutant and wild type in the induction of the above genes.

Interestingly, as shown by FIG. 17, the AtLysM RLK1 mutation does not block the induction of flagellin-responsive genes. Collectively, the data indicate that AtLysM RLK1 is the primary, specific receptor for recognition of the chitooligosaccharide PAMP derived from fungal pathogen cell walls. This recognition is a crucial step in the elicitation of protective innate immunity responses in the plant.

Example 4

Forced Expression of Certain LYSM RLK Genes Enhanced Fungal Resistance in Plants Over-expression of one LysM RLK gene, At2g33580, under a strong cauliflower mosaic virus (CMV) 35S promoter in transgenic plants, resulted in enhanced disease resistance. Therefore, this gene may function in a positive way to elevate disease resistance, similar to the mechanism of the At3g21630 gene, as shown in FIG. 5. Together with the data in Example 3 showing that forced expression of AtLysM RLK1 gene can restore induction of CRGs in a AtLysM RLK1 insertion mutant, these data confirm that the expression of specific LysM RLK genes in transgenic plants may confer enhanced disease resistance.

Example 5

Induction of Gene Expression by Chitin or its Derivatives

Based on the genome-wide gene expression studies using microarrays, quantitative reverse transcriptase-polymerase chain reaction (qRT-PCR) was conducted to identify over 120 different transcription factors in *Arabidopsis thaliana* whose expression is enhanced by chitin treatment. Many of these transcription factors are known to be involved in fungal pathogen response. This again shows the correlation of chitin response to disease resistance. Each of these transcription factors is a potential target for genetic manipulation in order to enhance disease resistance. The results of this study are described in greater details in Libault et al., 2007, which is hereby expressly incorporated by reference.

Some of the genes disclosed herein, including the LysM RLK genes, the CRGs such as the transcription factors described above, may play a positive role in plant fungal defense. Such genes may be called positive regulators. Transgenic plants may be generated wherein these positive regulators are expressed at an elevated level to increase the expression of transcription factors or other downstream genes. Some of the genes, on the other hand, may inhibit a plant's fungal defense capability. Such genes may be called negative regulators (also called "negative regulatory genes"). Deletion mutants of such genes that play a negative role in fungal defense may be created to obtain plants with enhanced fungal defense capability. Alternatively, dominant negative mutants of the negative regulatory genes may be introduced into a wild-type plant to inhibit the function of negative factors. Host plants may include any plants that may be susceptible to fungal infection, such as *Arabidopsis thaliana*, soybean, and others.

Example 6

LYSM Containing Proteins in Soybean

Utilizing the gene sequences from *Arabidopsis*, as described above, a total of 13 LysM RLK genes were identified in the soybean genome by searching the dbEST sequence database maintained by the Institute of Genomic Research. These 13 soybean LysM RLKs are: GmNFR1α (also referred to as GmNFR1a in this disclosure), GmNFR1β (also referred to as GmNFR1b in this disclosure), GmLYK2, GmLYK3, GmLYK4 (previously known as GmLysM17), GmNFR5α (also referred to as GmNFR5a in this disclosure), GmNFR5β (also referred to as GmNFR1b in this disclosure), GmLYK6 (previously known as GmLysM14), GmLYK7, GmLYK8 (previously known as GmLysM4), GmLYK9 (previously known as GmLysM16), GmLYK10, GmLYK11, and are designated as SEQ ID Nos. 54-66, respectively.

In addition, an additional fifteen soybean genes were identified that appear to have a LysM domain, but no associated kinase domain. PCR primers were developed for several of these genes, and their location on the soybean bacterial artificial chromosome (BAC)-based physical map was determined by probing pools of individual BAC clones. In this way, BAC clones encoding the various LysM domain proteins were identified. At this time, twelve BACs have been sequenced and the genomic sequences, including the regulatory regions, have been obtained for several LysM RLK genes.

Sequence comparisons between the soybean BAC sequences and other plant species showed examples where gene order (microsynteny) was well conserved. For example, FIG. 18 shows microsynteny between the soybean GmNFR5 and LysM17 (GmLYK4) gene-encoding regions and corresponding regions in poplar (Pt), *Lotus japonicus* (Lj), and *Medicago trancatula* (Mt) *Arabidopsis thaliana* (At) and rice (Os). These regions of microsynteny may be expanded by use of these methods to other plant species. Thus, knowledge of the genomic location in soybean can allow for the identification of the likely functional orthologue in other plant species, or vice versa.

In some cases, mapping the gene to the physical map also gave a genetic map location, due to genetic markers associated with the BAC clones. Table 5 shows examples of such regions that are in proximity to LysM RLK encoding regions. The locations of these genes were correlated with known quantitative trait loci (QTLs) associated with fungal resistance, i.e., *Sclerotina* white mold, Asian soybean rust and sudden death syndrome. In each case, a close correlation existed between the location of the LysM RLK and a known QTL for disease resistance. Thus, mapping of the LysM RLK may aid in the localization of disease resistance QTLs in soybean. The sequence of the LysM RLK gene can also be used to define better genetic markers for fine mapping of the associated QTLs. For instance, soybean mutants may be generated and selected for fungal resistant phenotypes. The close genetic link between certain QTLs and some LysM RLK genes may allow one to use the LysM RLK gene sequences to trace segregation of the QTLs. For example, molecular markers in the form of PCR primers, oligonucleotide probes, single nucleotide polymorphisms, restriction fragment polymorphisms, among others, derived from the DNA sequence of the LYK genes could be very useful in following a specific QTL in a breeding process.

TABLE 5

Associations of GmLysM-RLKs with known fungal resistance QTLs

| Soybean LysM-RLKs | Genetic marker | Linkage Group | Genetic position (cM) |
|---|---|---|---|
| *Sclerotinia sclerotiorum* QTL | Satt172 | D1b | 100.89 |
| *Sclerotinia sclerotiorum* QTL | Satt459 | D1b | 118.62 |
| | K411_1 | D1b | 119.34 |
| GmLysM4, GmLysM26, GmNFR1a | A343_2 | D1b | 120.97 |

TABLE 5-continued

Associations of GmLysM-RLKs with known fungal resistance QTLs

| Soybean LysM-RLKs | Genetic marker | Linkage Group | Genetic position (cM) |
|---|---|---|---|
| *Sclerotinia sclerotiorum* QTL | Satt143 | L | 30.19 |
| GmLysM23 | Sat_388 | L | 30.86 |
| *Sclerotinia sclerotiorum* QTL | Satt481 | L | 54.57 |
| GmLysM25 | Sat_402 | C2 | 103.33 |
| Asian soybean rust QTL | Satt460 | C2 | 117.77 |
| *Fusarium solani* f. sp glycines (SDS) QTL | Satt307 | C2 | 121.27 |

More particularly, all or a fragment of the polynucleotides of the instant disclosure may be used as probes for genetically and physically mapping the genes of which they are a part, and can be further used as markers for traits linked to those genes. Such information may be useful in plant breeding in order to develop lines with desired phenotypes. For example, the instant nucleic acid fragments may be used as restriction fragment length polymorphism (RFLP) markers. Southern blots of restriction-digested plant genomic DNA may be probed with the nucleic acid fragments of the instant disclosure. The resulting banding patterns may then be subjected to genetic analyses using computer programs such as Map-Maker (Lander et al. (1987) Genomics 1:174-181) in order to construct a genetic map. In addition, the nucleic acid fragments of the instant disclosure may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: Non mammalian Genomic Analysis: A Practical Guide, Academic press 1996, pp. 319-346, and references cited therein). In another embodiment, nucleic acid probes derived from the instant nucleic acid sequences may be used in direct fluorescence in sits hybridization (FISH) mapping (Trask (1991) Trends Genet. 7:149-154). Although current methods of FISH mapping favor use of large clones ranging from a few Kb to several hundred Kb; see Laan et al. (1995) Genome Res. 5:13-20), improvements in sensitivity may allow performance of FISH mapping using shorter probes.

A variety of nucleic acid amplification-based methods of genetic and physical mapping may be carried out using the nucleic acid sequences of the instant disclosure. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241: 1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Soybean genotypes used for mapping of soybean QTLs for white mold resistance included Corsoy 79 and Dassel. As shown in FIG. 19, treatment of leaves of these plants, as well as Williams 82 as a control, resulted in strong induction of three of the LysM RLK genes out of a total of six such genes tested. These genes are, therefore, excellent targets for genetic manipulation using the methods demonstrated in *Arabidopsis* to create soybean plants with decreased disease susceptibility. Finally, as was the case with *Arabidopsis*, some of the soybean LysM RLK genes are induced upon treatment of soybean with chitin, as confirmed by the results shown in FIG. 20. Leaves were treated by spraying with chitin (100 µM)+0.2% Tween-20.

Example 7

Tissue Specific Expression of LYSM-Containing Proteins in Soybean and Other Plants Other experiments examined the expression of the various LysM domain-containing genes under various conditions. For the six plant species in this study, tissue expression levels of LYK genes have only been reported for *M. truncatula* (Limpens et al., 2003; Arrighi et al., 2006) and *Arabidopsis*. Therefore, LYK gene expression was measured using quantitative reverse transcription (RT)-PCR in different tissues of soybean, *M. truncatula*, and rice plants.

More particularly, Soybean, *M. truncatula*, and rice plants were grown in the greenhouse at 28° C. to 30° C. with a 16-h light/8-h dark cycle. Roots and vegetative tissues were sampled about 3 weeks after planting and flowers were sampled about 3 months after planting. Total RNAs were extracted using Trizol (Invitrogen) followed by Turbo DNase (Ambion) treatment to remove genomic DNA contamination. First-strand cDNAs were synthesized using Moloney murine leukemia virus reverse transcriptase (Promega). Quantitative RT-PCR was performed using a 7500 real-time PCR system (Applied Biosystems) following standard procedures. The primer sequences are listed in Table 6. q-RT-PCR of GmSubi2, MtActin2, OsEF1α are used to normalize the expression data of all of the other genes in the respective species.

TABLE 6

| Plant LYK primers for qRT-PCR (5' to 3' from left to right) | | | | |
|---|---|---|---|---|
| Genes | Forward | SEQ ID No. | Reverse | SEQ ID No. |
| GmSubi2 | AGCTATTCGCAGTTCCCAAAT | 96 | CAGAGACGAACCTTGAGGAGA | 97 |
| GmNFR1a | AAGAACATCCGTGGAAAGGTT | 98 | AATGTTCCCACAAGACGAGTG | 99 |
| GmNFR1b | TGACATATGCCAATCTCACCA | 100 | GTGACATTAACCGTGGCATTT | 101 |
| GmLYK2 | GATCCACAACAACGTCCAAAT | 102 | ATGGAAGCAATATCCCAATCC | 103 |
| GmLYK3 | TAACGGTGACGTTGATGTTCA | 104 | GTTGTCGAGGTTGATTTCTCG | 105 |
| GmLYK4 | AGATGTGCTTGTCCCACAAAG | 106 | CAGAATCACCCCAGTTTACCA | 107 |
| GmNFR5a | ACCGCTCTTTTGCCAATATCT | 108 | AACGGGGTTTAAATCCATCAC | 109 |
| GmNFR5b | CATGGCCAGAACTTTTACCAA | 110 | GTTGTCATGGCTTTCCTACCA | 111 |
| GmLYK9 | TGATCTCCTACGTCGTCCAAC | 112 | GCGTCAATGATGGACTGTTCT | 113 |
| GmLYK10 | CCTCTCTCTCCAACCTCACCT | 114 | CTGATCCTGGGAGAGGAACTC | 115 |
| GmLYK11 | TTCGGTTCCTGGTGAGTCTTA | 116 | TCATGGGTACATGAGCTTTC | 117 |
| MtActin2 | TGGCATCACTCAGTACCTTTCAACAG | 118 | ACCCAAAGCATCAAATAATAAGTCAACC | 119 |
| MtLYK1 | CATGAGCATTCAGTGCCTGT | 120 | TGCAGAATCAGTAAGCCTGGT | 121 |
| MtLYK3 | TGCTAAGGGTTCAGCTGTTGGTA | 122 | AAATGCCCTAGAAGTTTGTGGAAG | 123 |
| MtLYK4 | CGCAAGATGGATGTGTATGC | 124 | CATGGCTCTCGAACTCGTTT | 125 |
| MtLYK9 | CACTCATATTCTTTTCTGCCACCCA | 126 | TGCAATGGATTGAGGACTGGTGT | 127 |
| MtLYK10 | GGAAATGGAGAAATGGCAAA | 128 | CGCCTTGACCAAGAAACCTA | 129 |
| MtLYK11 | GGCATTGATGGGTCAGAACT | 130 | TGCAAAGAGGATCACACTGC | 131 |
| MtLYK12 | CTCTTCTTCTTCTTCGTCAGCA | 132 | GGTATGCTTGGCATGTTTGAGTTT | 133 |
| MtLYK13 | GGTTGTTCTCGGAATCTTCG | 134 | ATGCATGTATTGCAGACCGA | 135 |

TABLE 6-continued

Plant LYK primers for qRT-PCR (5' to 3' from left to right)

| Genes | Forward | SEQ ID No. | Reverse | SEQ ID No. |
|---|---|---|---|---|
| OsEF1α | TTTCACTCTTGGTGTGAAGCAGAT | 136 | GACTTCCTTCACGATTTCATCGTAA | 137 |
| OsLYK1 | ATGGCGATATGGGTGACATT | 138 | TCCACATGGAAGGTGAATGA | 139 |
| OsLYK2 | GTTCTTGCGTCTGGTGCTCT | 140 | CTCCTTATCCGGAGCCAAC | 141 |
| OsLYK3 | ATGGAGGAGGTGTTCGTCAC | 142 | CCGAGGACCATAGAAGCTGA | 143 |
| OsLYK4 | CATGGTCACCTACCTCGTCA | 144 | TATGATGGAGCTCTCGGTGA | 145 |
| OsLYK5 | GTTCATCGACAAACCGATCA | 146 | TAATACGAGCTGCCGAGCTT | 147 |
| OsLYK6 | GTGACGAGGAGAATGGAGGA | 148 | CTCGATCAGCTTCACCATCA | 149 |

The data agree well with previous results on MtLYK expression levels (Limpens et al., 2003; Arrighi et al., 2006). It was also found that plant LYK expression was generally tissue specific and that most plant LYK genes were expressed predominantly in the root in soybean (FIG. 21A), *M. truncatula* (FIG. 21B), rice (FIG. 21C), *L. japonicus* (Madsen et al., 2003; Radutoiu et al., 2003), and *Arabidopsis*, although a few genes were expressed in stems and leaves. Expression levels of each LYK gene were displayed in artificial scales relative to particular housekeeping genes. Data were collected from three biological replicates. Error bars represent SDs.

As predicted from their orthologous relationships (Zhang et al, 2007), GmNFR1, GmNFR1, MtLYK3, and LjNFR1 (Radutoiu et al., 2003) showed similar patterns of root-specific expression. Similarly, GmNFR5, GmNFR5, MtLYK13, OsLYK5, and LjNFR5 (Madsen et al., 2003) showed root-specific expression. These results are reasonable, from a biological perspective, because these receptors need to efficiently contact Nod factors secreted by soilborne symbiotic bacteria.

Additionally, the following sets of orthologous genes also exhibit similar expression patterns: GmLYK4 and MtLYK12; GmLYK10 and AtLYK2; GmLYK8 (data not shown); and AtLYK5. Interestingly, several duplicated genes displayed different expression patterns. For example, GmLYK2 and MtLYK11 expression is dramatically different from duplicated partners, GmNFR1 and MtLYK10, respectively. MtLYK9, paralogous to MtLYK13, is expressed differently from the latter. These data suggest the functional diversification of LYK genes after duplications.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

Moreover, while most of the examples provided use *Arabidopsis* or soybean as the host plant, it is to be understood that the transgenic and plant breeding procedures described herein are broadly applicable to other plant species as well. These other plants may include but are not limited to: Rice, Wheat, Barley, poplar, *M. truncatula, L. japonicus* and many other crops, vegetables, and trees. Although transformation and breeding procedures differ from one plant species to another, it is within the skills of an ordinary artisan to modify the teaching of this disclosure for use in other plants. The methodology for conferring fungal resistance upon a plant or for selecting for a fungal resistant plant may be applicable to a broad spectrum of fungi, such as *Fusarium*, Powdery mildew, and the variety of fungi that cause soybean rust, among others.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

REFERENCES

Full citations of references that are not fully cited in the text are listed below. All references, including those that are not listed below but are fully cited in the text, are hereby incorporated by reference to the same extent as though fully disclosed herein:

1. Arrighi J, Barre A, Ben Amor B, Bersoult A, Soriano L, Mirabella R, Carvalho-Niebel F, Journet E, Gherardi M, Huguet T, et al (2006) The *Medicago truncatula* lysine motif-receptor-like kinase gene family includes NFP and new nodule-expressed genes. Plant Physiol 142: 265-279.
2. Bulawa, C. E., D. W. Miller, L. K. Henry, J. M. Becker, Proc. Natl. Acad. Sci. U.S.A. 92, 10570-10574 (1995).
3. Chisholm, S. T., G. Coaker, B. Day, B. J. Staskawicz, Cell 124, 803-814 (2006).
4. Clamp M, Cuff J, Searle S M, Barton G J (2004) The Jalview Java alignment editor. Bioinformatics 20: 426-427.
5. Day, R. B. et al., Plant Physiol. 126, 1162-1173 (2001).
6. Eddy S R (1998) Profile hidden Markov models. Bioinformatics 14: 755-763.
7. Felsenstein J (2000) PHYLIP (Phylogeny Inference Package), Ed 3.6. University of Washington, Seattle.
8. Gomez-Gomez, L., T. Boller, Mol. Cell 5, 1003-1011 (2000).

9. D. R. Goring, J. C. Walker, Science 303, 1474-1475 (2004).
10. Ito, Y., H. Kaku, N. Shibuya, Plant J. 12, 347-356 (1997).
11. Joris, B., FEMS Microbiol. Lett. 70, 257-264 (1992).
12. Kaku, H. et al., Proc. Natl. Acad. Sci. U.S.A. 103, 11086-11091 (2006).
13. Limpens et al., Science 302, 630-633 (2003).
14. Libault, M., J. Wan, T. Czechowski, M. Udvardi, G. Stacey, Mol. Plant-Microbe Interact. (in press) (2007).
15. Libault M, Wan J, Joshi T, Zhang X, Czechowski T, Xu D, Udvardi M, Stacey G (2006) The regulation of *Arabidopsis* transcription factor and ubiquitin-ligase genes by chitin allows the identification of a G-box motif highly represented in their promoter sequences. Plant Physiol. (submitted).
16. Libault, M., J. Wan, T. Czechowski, M. Udvardi, and G. Stacey, Identification of 118 *Arabidopsis* Transcription Factor and 30 Ubiquitin-Ligase Genes Responding to Chitin, a Plant-Defense Elicitor. Molecular Plant-Microbe Interactions, Vol. 20, No. 8, 2007, pp. 900-911.
17. Madsen, E B; Madsen, L H; Radutoiu, S; Olbryt, M; Rakwalska, M; Szczyglowski, K; Sato, S; Kaneko, T; Tabata, S; Sandal, N; Stougaard, J. 2003. A receptor kinase gene of the LysM type is involved in legume perception of rhizobial signals. Nature 425 (6958): 637-640.
18. Nürnberger, T., B. Kemmerling, Trends Plant Sci. 11, 519-522 (2006).
19. Okada, M. and M. Matsumura, Y. Ito, N. Shibuya, Plant Cell Physiol. 43, 505-512 (2002).
20. Passarinho, P., S. C. de Vries, In: The *Arabidopsis* Book, American Society of Plant Biologists (2002).
21. Radutoiu, S; Madsen, L H; Madsen, E B; Felle, H H; Umehara, Y; Gronlund, M; Sato, S; Nakamura, Y; Tabata, S; Sandal, N; Stougaard, J. 2003. Plant recognition of symbiotic bacteria requires two LysM receptor-like kinases. Nature 425 (6958): 585-592.
22. Ramonell, K., B. Zhang, R. Ewing, Y. Chen, D. Xu, G. Stacey, and S. Somerville. 2002 Microarray analysis of chitin elicitation in *Arabidopsis thaliana*. Mol. Plant Pathol. 3 (1): 301-311.
23. Ramonell K, Berrocal-Lobo M, Koh S, Wan J, Edwards H, Stacey G and Somerville S. 2005. Loss-of-function mutations in four chitin responsive genes show increased susceptibility to the powdery mildew pathogen, *Erysiphe cichoracearum*. Plant Physiol. 138: 1027-1036
24. Schmidt H A, Strimmer K, Vingron M, von Haeseler A (2002) TREE-PUZZLE: maximum likelihood phylogenetic analysis using quartets and parallel computing. Bioinformatics 18: 502-504.
25. Shibuya, N., E. Minami, Physiol. Mol. Plant Pathol. 59, 223-233 (2001).
26. Soulie, M. C. et al., Cell Microbiol. 8, 1310-1321 (2006).
27. Stacey, G. and N. Shibuya. 1997. Chitin recognition in rice and legumes. Plant and Soil 194: 161-169.
28. G. Stacey, M. Libault, L. Brechenmacher, J. Wan, G. D. May, Curr. Opin. Plant. Biol. 9, 110-121 (2006).
29. Tanabe, S., et al., Biosci. Biotechnol. Biochem. 70, 1599-1605 (2006).
30. Thompson J D, Gibson T J, Plewniak F, Jeanmougin F, Higgins D G (1997) The Clustal-X windows interface—flexible strategies for multiple sequence alignment aided by quality analysis tools. Nucleic Acids Res 25: 4876-4882
31. Wan, Jinrong, Shuqun Zhang, and Gary Stacey. 2004. Activation of a potential mitogen-activated protein kinase pathway in *Arabidopsis* by chitin. Mol. Plant Pathol. 5(1): 125-135.
32. Yang Z (1997) PAML: a program package for phylogenetic analysis by maximum likelihood. Comput Appl Biosci 13: 555-556.
33. Zhang, B., K. Ramonell, S. Somerville, and G. Stacey. 2002. Characterization of Early, Chitin-Induced Gene Expression in *Arabidopsis* Mol. Plant-Microbe Int. 15: 963-970.
34. Zhang, X.-C. et al., Plant Physiol. 144, 623-636 (2007).
35. Zmasek C M, Eddy S R (2001) ATV: display and manipulation of annotated phylogenetic trees. Bioinformatics 17: 383-384.

What is claimed is:

1. A transgenic plant comprising a transgene, said transgene having at least 98% sequence identity to a LysM receptor kinase family gene having the sequence of SEQ ID No. 7, wherein the transgenic plant is derived from a host plant that is susceptible to fungal infection, and wherein the expression of said transgene renders the transgenic plant less susceptible to fungal infection as compared to said host plant.

2. The transgenic plant according to claim 1, wherein the transgene has at least 99% sequence identity to a LysM receptor kinase family gene having the sequence of SEQ ID No. 7.

3. The transgenic plant according to claim 1, wherein the transgene has 100% sequence identity to a LysM receptor kinase family gene having the sequence of SEQ ID No. 7.

4. The transgenic plant according to claim 1, wherein the plant is soybean.

5. The transgenic plant according to claim 1, wherein the plant is *Arabidopsis thaliana*.

6. The transgenic plant according to claim 1 wherein the LysM receptor kinase family gene encodes a functional LysM receptor kinase.

7. The transgenic plant according to claim 1, further comprising at least one regulatory sequence operably linked to said LysM receptor kinase family gene, said regulatory sequence controlling the expression level of the LysM receptor kinase family gene.

8. A transgenic plant comprising a LysM receptor kinase family gene having at least one mutation, said mutated gene being derived from an endogenous wild-type LysM receptor kinase family gene having at least 98% sequence identity to SEQ ID No. 7.

9. The transgenic plant of claim 8, wherein the mutated LysM receptor kinase family gene encodes a LysM receptor kinase with a mutation selected from the group consisting of amino acid substitution, deletion and insertion.

10. The transgenic plant of claim 8, wherein the mutation of the LysM receptor kinase family gene alters the expression level of the encoded LysM receptor kinase in said plant.

11. A method for protecting a plant from fungal infection, comprising the step of introducing into said plant a transgene, said transgene having at least 95% sequence identity to a LysM receptor kinase family gene having the sequence of SEQ ID No. 7.

12. The method of claim 11, further comprising the step of expressing a LysM receptor kinase encoded by said transgene.

13. The method of claim 11, wherein the LysM receptor kinase family gene is at least 98% identical to SEQ ID No. 7.

14. A method for protecting a plant from fungal infection, comprising the step of generating in said plant at least one mutation in a LysM receptor kinase family gene, said LysM receptor kinase family gene being endogenous to said plant, wherein said LysM receptor kinase family gene has at least 95% sequence identity to the polynucleotide having the sequence of SEQ ID No. 7.

15. The method according to claim 14 wherein the plant is soybean.

16. The method according to claim 14 wherein the plant is *Arabidopsis thaliana*.

* * * * *